United States Patent
Anderson et al.

(10) Patent No.: US 10,519,483 B2
(45) Date of Patent: Dec. 31, 2019

(54) METHODS AND SYSTEMS FOR RAPID DETECTION OF MICROORGANISMS USING INFECTIOUS AGENTS

(71) Applicant: Laboratory Corporation of America Holdings, Burlington, NC (US)

(72) Inventors: Dwight Lyman Anderson, Minneapolis, MN (US); Jose S. Gil, Winnetka, CA (US); Ben Barrett Hopkins, Sherman Oaks, CA (US); Stephen Erickson, White Bear Township, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 274 days.

(21) Appl. No.: 14/625,481

(22) Filed: Feb. 18, 2015

(65) Prior Publication Data
US 2015/0218616 A1    Aug. 6, 2015

Related U.S. Application Data

(63) Continuation of application No. 13/773,339, filed on Feb. 21, 2013, now Pat. No. 9,482,668.
(Continued)

(51) Int. Cl.
*C12Q 1/66* (2006.01)
*G01N 33/569* (2006.01)
(Continued)

(52) U.S. Cl.
CPC .......... *C12Q 1/66* (2013.01); *C12N 15/86* (2013.01); *G01N 33/569* (2013.01);
(Continued)

(58) Field of Classification Search
None
See application file for complete search history.

(56) References Cited

U.S. PATENT DOCUMENTS

| 5,824,468 A | 10/1998 | Scherer et al. |
| 5,837,465 A | 11/1998 | Squirrel et al. |
| (Continued) | | |

FOREIGN PATENT DOCUMENTS

| EP | 0743366 | 11/1996 |
| JP | 2005-524394 A | 8/2005 |
| (Continued) | | |

OTHER PUBLICATIONS

Tanji et al. *Escherichia coli* detection by GFP-labeled lysozyme-inactivated T4 bacteriophage. Journal of Biotechnology 114 (2004) 11-20.*

(Continued)

*Primary Examiner* — Michelle S Horning
(74) *Attorney, Agent, or Firm* — Kilpatrick Townsend & Stockton LLP

(57) ABSTRACT

Disclosed herein are methods and systems for rapid detection of microorganisms in a sample, without culturing for enrichment of the microorganism. A modified bacteriophage is also disclosed which comprises a non-native indicator gene in the late gene region. The indicator product is not a fusion protein. The specificity of infectious agents allows a specific microorganism to be targeted, and an indicator signal may be amplified to optimize assay sensitivity.

30 Claims, 18 Drawing Sheets
Specification includes a Sequence Listing.

Related U.S. Application Data

(60) Provisional application No. 61/940,959, filed on Feb. 18, 2014, provisional application No. 61/601,231, filed on Feb. 21, 2012.

(51) Int. Cl.
  *G01N 33/58* (2006.01)
  *C12N 15/86* (2006.01)

(52) U.S. Cl.
  CPC ..... *G01N 33/56911* (2013.01); *G01N 33/581* (2013.01); *C12N 2795/10121* (2013.01); *C12N 2795/10131* (2013.01); *C12N 2795/10143* (2013.01); *C12N 2795/10221* (2013.01); *C12N 2795/10231* (2013.01); *C12N 2795/10243* (2013.01)

(56) References Cited

U.S. PATENT DOCUMENTS

| | | | |
|---|---|---|---|
| 6,225,066 B1 | 5/2001 | Jacobs, Jr. et al. | |
| 7,252,996 B2 | 8/2007 | Boccaccio et al. | |
| 8,318,474 B1* | 11/2012 | Smolke | C12N 15/81 |
| | | | 435/254.2 |
| 8,557,970 B2 | 10/2013 | Encell et al. | |
| 9,482,668 B2 | 11/2016 | Anderson et al. | |
| 2004/0137430 A1 | 7/2004 | Anderson et al. | |
| 2005/0003346 A1 | 1/2005 | Voorhees et al. | |
| 2009/0155768 A1* | 6/2009 | Scholl | C12N 15/70 |
| | | | 435/5 |
| 2009/0246752 A1 | 10/2009 | Voorhees et al. | |
| 2010/0291541 A1 | 11/2010 | Evoy et al. | |
| 2011/0201013 A1 | 8/2011 | Moore | |
| 2013/0216997 A1 | 2/2013 | Anderson et al. | |
| 2013/0122549 A1 | 5/2013 | Lu et al. | |

FOREIGN PATENT DOCUMENTS

| | | |
|---|---|---|
| JP | 2007523628 A | 8/2007 |
| JP | 2010-507371 A | 3/2010 |
| WO | WO 99/45396 | 9/1999 |
| WO | 03035889 A2 | 5/2003 |
| WO | 2005001475 A2 | 1/2005 |
| WO | 2007055737 | 5/2007 |
| WO | 2008124119 A1 | 10/2008 |
| WO | 2013126584 A1 | 8/2013 |
| WO | 2015126966 A2 | 8/2015 |
| WO | 2017127434 A1 | 7/2017 |

OTHER PUBLICATIONS

Macdonald and Mosig. Regulation of a new bacteriophage T4 gene, 69, that spans an origin of DNA replication. The EMBO Journal vol. 3 No. 12 pp. 2863-2871, 1984.*

Miyanaga et al. Detection of *Escherichia coli* in the sewage influent by fluorescent labeled T4 phage. Biochemical Engineering Journal, vol. 29, Issues 1-2, Apr. 1, 2006, pp. 119-124.*

State Intellectual Property Office of the Peoples Republic of China, Notification of the Second Office Action, Application No. 201380019483 dated Feb. 4, 2016.

Bague, J., Detection of Recombinant Human Erythropoietin and Analogues through Immunorecognition and N-Giycolyi-Neuraminic Acid Identification, Doctoral Thesis Pompeu Fabra University, Department of Experimental and Health Sciences, 2011, Retrieved from http://www.tesisenred/bitstream/handle/10803/31969/tjm.pdf?sequence=1 as available via the Internet and printed Mar. 27, 2013.

He, Y. et al., Monoclonal antibodies for detection of the H7 antigen of *Escherichia coli*, Appl. Environ Microbiol., 1996, 62(9):3325-32.

Inouye, S. et al., Overexpression, purification and characterization of the catalytic component of Oplophorus luciferase in the deep-sea shrimp, *Oplophorus gracilirostris*. Protein Expr. Purif., 2007, 56(2): 261-8.

Kodikara, C. et al., Near on-line detection of enteric bacteria using lux recombinant bacteriophage, FEMS Microbiol. Lett., 1991, 67(3):261-5.

Loessner, M. et al., Construction of luciferase reporter bacteriophage A511::luxAB for rapid and sensitive detection of viable Listeria cells, Appl. Environ. Microbiol., 1996, 62(4):1133-40.

Lu, T. et al., Advancing bacteriophage-based microbial diagnostics with synthetic biology, Trends Biotechnol., 2013, 31(6):325-7.

Patent Cooperation Treaty, International Search Report and Written Opinion, International Application No. PCT/US13/27155, dated May 6, 2013.

Rees C., The Use of Phage of Diagnostic Systems, Division of Food Sciences, School of Biosciences, University of Nottingham, Sutton Bonington Campus Loughborough, Leicestershire LE12 5RD, UK; The Bacteriophages, 2nd edition (2006) Richard Calendar—Oxford University Press.

Schofield, D. et al., Phage-based platforms for the clinical detection of human bacterial pathogens, Bacteriophage, 2012, 2(2):105-283.

Restriction Requirement dated Jun. 23, 2014 for U.S. Appl. No. 13/773,339.

Non-Final Office Action dated Oct. 31, 2014 for U.S. Appl. No. 13/773,339.

Final Office Action dated Jun. 9, 2015 for U.S. Appl. No. 13/773,339.

European Patent Office, Extended European Search Report, European Application No. 13751965 dated Sep. 30, 2015.

Edgar, R. et al., High-sensitivity bacterial detection using biotin-tagged phage and quantum-dot nanocomplexes, Proc. Natl. Acad. Sci. USA, 2006, 103(13):4841-5. Epub Mar. 20, 2006.

Goodridge, L. et al., Reporter bacteriophage assays as a means to detect foodborne pathogenic bacteria, Food research International, 2002, 35:863-870.

Hagens, S. et al., Reporter bacteriophage A511::celB transduces a hyperthermostable glycosidase from Pyrococcus furiosus for rapid and simple detection of viable Listeria cells, Bacteriophage, 2011, 1(3):143-151. Epub May 1, 2011.

Hagens, S. et al., Bacteriophage for Biocontrol of foodborne pathogens: calculations and considerations, Curr. Pharm. Biotechnol., 2010, 11(1):58-68.

Loessner, M. et al., Evaluation of luciferase reporter bacteriophage A511::luxAB for detection of Listeria monocytogenes in contaminated foods, Appl. Environ. Microbiol., 1997, 63(8):2961-5.

Noguera, P. et al., Carbon nanoparticles in lateral flow methods to detect genes encoding virulence factors of Shiga toxin-producing, Anal Bioanal. Chem., 2011, 399(2): 831-838.

Rees, C. et al., Chapter 14—The use of phage detection, antibiotic sensitivity testing and enumeration, In: Understanding Tuberculosis—Global Experiences and Innovative Approaches to the Diagnosis, 2012, Intech, Edited by Dr. Pere-Joan Cardona.

Smietana, M. et al., Detection of bacteria using bacteriophages as recognition elements immobilized on long-period fiber gratings, Opt Express., 2011, 19(9):7971-8.

Ulitzur, N. et al., New rapid and simple methods for detection of bacteria and determination of their antibiotic susceptibility by using phage mutants, Appl. Environ. Microbiol., 2006, 72(12 ):7455-7459.

Wu, L. et al., Trace detection of specific viable bacteria using tetracysteine-tagged bacteriophages, Anal Chem. 2014, 86(1):907-12. Epub Dec. 10, 2013.

Patent Cooperation Treaty, International Search Report and Written Opinion, International Application No. PCT/US2015/016415, dated Jun. 22, 2015.

State Intellectual Property Office of the Peoples Republic of China, Notification of the First Office Action, Application No. 201380019483, dated Jul. 7, 2015.

State Intellectual Property Office of the Peoples Republic of China, Notification of the Third Office Action, Application No. 201380019483 dated Jul. 18, 2016.

Japanese Patent Office, Notice of Reasons for Rejection, Application No. 2014-558827 dated Nov. 1, 2016.

U.S. Appl. No. 13/773,339, Non-Final Office Action dated Mar. 3, 2016, 26 pages.

(56) References Cited

OTHER PUBLICATIONS

Australian Patent Office Application No. 2013222411, First Examination Report dated Nov. 2, 2017, 4 pages.
European Patent Office Application No. 13751965.8, Communication Pursuant to Article 94(3) EPC dated Apr. 11, 2017, 6 pages.
European Patent Office Application No. 13751965.8, Communication Pursuant to Article 94(3) EPC dated Jan. 30, 2018, 6 pages.
Japanese Patent Office Application No. 2017-016551, Notice of Reasons for Rejection dated Jan. 19, 2018, 5 pages.
Mexican Patent Office Application No. MX/A/2014/010069, Office Action dated Apr. 25, 2017, 2 pages.
Elena et al., "Expression of codon optimized genes in microbial systems: current industrial applications and perspectives. Art. 21", Frontiers in Microbiology, vol. 5, Feb. 1, 2014, pp. 1-8.
JP2017-016551 , "Office Action", dated Dec. 21, 2018, 12 pages.
Kutter et al., "Characterization of a Vil-like Phage 11-20 Specific to *Escherichia coli* 0157:H7", Virology Journal, Biomed Central, London, GB, vol. 8, No. 1, Sep. 7, 2011, pp. 430.
PCT/US2017/013955 , "International Preliminary Report on Patentability", dated Aug. 2, 2018, 9 pages.
PCT/US2017/013955 , "International Search Report and Written Opinion", dated May 15, 2017, 16 pages.
PCT/US2017/013955 , "Invitation to Pay Additional Fees and Partial Search Report", dated Mar. 20, 2017, 7 pages.
U.S. Appl. No. 15/263,619 , "Non-Final Office Action", dated May 13, 2019, 21 pages.
Canadian Patent Application No. CA2,865,308 , "Office Action", dated Jun. 4, 2019, 3 pages.
Chinese Patent Application No. CN201710263366.1 , "Office Action", dated Jul. 31, 2019, 10 pages.
European Patent Application No. EP19152164.0 , "Extended European Search Report", dated Jul. 10, 2019, 6 pages.

\* cited by examiner

__US 10,519,483 B2__

METHODS AND SYSTEMS FOR RAPID DETECTION OF MICROORGANISMS USING INFECTIOUS AGENTS

RELATED APPLICATIONS

The present application is a Continuation-in-Part application of pending U.S. patent application Ser. No. 13/773,339, filed Feb. 21, 2013, entitled "Methods and Systems for Detection of Microorganisms," which claims priority under 35 USC 119(e) to U.S. Provisional Patent Application No. 61/601,231, filed Feb. 21, 2012. The present application also claims priority under 35 USC 119(e) to U.S. Provisional Patent Application No. 61/940,959, filed Feb. 18, 2014. The disclosures of U.S. Provisional Patent Application Nos. 61/601,231 and 61/940,959 and U.S. patent application Ser. No. 13/773,339 are incorporated by reference in their entireties herein.

REFERENCE TO A SEQUENCE LISTING

The Sequence Listing written in file 57618-929957_SUBSEQTXT_ST25.txt, created on Mar. 18, 2015, 243,361 bytes, machine format IBM-PC, MS-Windows operating system, is hereby incorporated by reference in its entirety for all purposes.

FIELD OF THE INVENTION

This invention relates to methods and systems for the detection of microorganisms using infectious agents.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Also, detection of microorganisms is a high priority for the Food and Drug Administration (FDA) and Centers for Disease Control (CDC) given outbreaks of life-threatening or fatal illness caused by ingestion of food contaminated with certain microorganisms, e.g., *Escherichia coli* or *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an enrichment step in order to obtain adequate sensitivity. Polymerase chain reaction (PCR) tests also include an amplification step and therefore are capable of both very high sensitivity and selectivity; however, the sample size that can be economically subjected to PCR testing is limited. With dilute bacterial suspensions, most small subsamples will be free of cells and therefore purification and/or enrichment steps are still required.

The time required for traditional biological enrichment is dictated by the growth rate of the target bacterial population of the sample, by the effect of the sample matrix, and by the required sensitivity. For instance, a magnetic-capture PCR system for verotoxigenic *E. coli* can require about 5, 7 and 10 hours of culturing for enrichment to detect 1000, 100, and 1 colony forming unit per milliliter (CFU/mL), respectively, in a model system, and 15 hours of culturing for enrichment to detect 1 CFU per gram (g) in ground beef. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water (or other product) may have already made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple and sensitive detection and identification of microorganisms, such as bacteria, viruses, and other potentially pathogenic microorganisms.

SUMMARY

Embodiments of the invention comprise compositions, methods, systems and kits for the detection of microorganisms. The invention may be embodied in a variety of ways.

In some aspects, the invention comprises a recombinant bacteriophage comprising an indicator gene inserted into a late gene region of the bacteriophage.

In some embodiments, the invention comprises a method for detecting a microorganism of interest in a sample comprising the steps of incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product, and detecting the indicator protein product, wherein positive detection of the indicator protein product indicates that the microorganism of interest is present in the sample.

In other embodiments, the invention comprises a system for rapid detection of a microorganism of interest in a sample, comprising a component for incubating the sample with an infectious agent specific for the microorganism of interest, wherein the infectious agent comprises an indicator moiety, and a component for detecting the indicator moiety.

In still other embodiments, the invention comprises non-transient computer readable media for use with methods or systems according to the invention.

BRIEF DESCRIPTION OF THE FIGURES

The present invention may be better understood by referring to the following non-limiting figures.

DETAILED DESCRIPTION OF THE INVENTION

Figure 1:
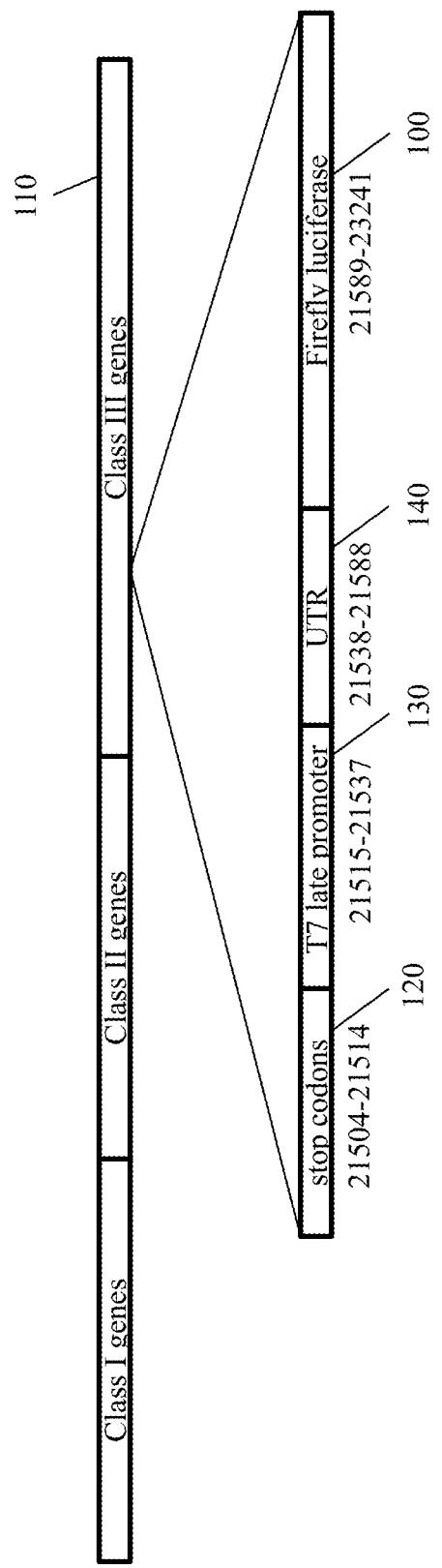
FIG. 1 depicts an indicator phage construct according to an embodiment of the invention illustrating insertion of a genetic construct comprising Firefly luciferase gene and a T7 late promoter inserted into the late (class III) region of a bacteriophage. Also depicted is a sequence comprising stop codons in all three reading frames to prevent read-through and an untranslated region (UTR).

Disclosed herein are compositions, methods and systems that demonstrate surprising sensitivity for detection of a microorganism of interest in test samples (e.g., biological, food, water, and clinical samples). Detection can be achieved in a shorter timeframe than was previously thought possible using genetically modified infectious agents in assays performed without any culturing for enrichment, or in some embodiments with minimal incubation times during which microorganisms could potentially multiply. Also surprising is the success of using high multiplicity of infection (MOI), or high concentrations of plaque forming units (PFU), for incubation with a test sample. Such high phage concentrations (PFU/mL) were previously purported to be detrimental to microorganism detection assays, as they were purported to cause "lysis from without."

The compositions, methods, systems and kits of the invention may comprise infectious agents for use in detection of such microorganisms. In certain embodiments, the invention may comprise a composition comprising a recombinant bacteriophage having an indicator gene inserted into a late gene region of the bacteriophage. In certain embodiments, expression of the indicator gene during bacteriophage replication following infection of a host bacterium results in a soluble indicator protein product. In certain embodiments, the indicator gene may be inserted into a late gene (i.e., class III) region of the bacteriophage. The bacteriophage may be derived from T7, T4, JG04, or another natural bacteriophage.

In some aspects, the invention comprises a method for detecting a microorganism of interest. The method may use an infectious agent for detection of the microorganism of interest. For example, in certain embodiments, the microorganism of interest is a bacterium and the infectious agent is a bacteriophage. Thus, in certain embodiments, the method may comprise detection of a microorganism of interest in a sample by incubating the sample with a recombinant bacteriophage that infects the microorganism of interest. In certain embodiments, the recombinant bacteriophage comprises an indicator gene. The indicator gene may, in certain embodiments, be inserted into a late gene region of the bacteriophage such that expression of the indicator gene during bacteriophage replication following infection of host bacteria results in a soluble indicator protein product. The method may comprise detecting the indicator protein product, wherein positive detection of the indicator protein product indicates that the microorganism of interest is present in the sample.

In certain embodiments, the invention may comprise a system. The system may contain at least some of the compositions of the invention. Also, the system may comprise at least some of the components for performing the method. In certain embodiments, the system is formulated as a kit. Thus, in certain embodiments, the invention may comprise a system for rapid detection of a microorganism of interest in a sample, comprising: a component for incubating the sample with an infectious agent specific for the microorganism of interest, wherein the infectious agent comprises an indicator moiety; and a component for detecting the indicator moiety. In yet other embodiments, the invention comprises software for use with the methods or systems.

Thus, some embodiments of the present invention solve a need by using infectious agent-based methods for amplifying a detectable signal indicating the presence of bacteria. In certain embodiments as little as a single bacterium is detected. The principles applied herein can be applied to the detection of a variety of microorganisms. Because of numerous binding sites for an infectious agent on the surface of a microorganism, the capacity to produce one hundred or more agent progeny during infection, and the potential for high level expression of an encoded indicator moiety, the infectious agent or an indicator moiety can be more readily detectable than the microorganism itself. In this way, embodiments of the present invention can achieve tremendous signal amplification from even a single infected cell.

Aspects of the present invention utilize the high specificity of binding agents that can bind to particular microorganisms, such as the binding component of infectious agents, as a means to detect and/or quantify the specific microorganism in a sample. In some embodiments, the present invention utilizes the high specificity of infectious agents such as bacteriophage.

In some embodiments, detection is achieved through an indicator moiety associated with the binding agent specific for the microorganism of interest. For example, an infectious agent may comprise an indicator moiety. In some embodiments the indicator may be encoded by the infectious agent, such as a bacteriophage, and the bacteriophage is designated an indicator phage.

Some embodiments of the invention disclosed and described herein utilize the discovery that a single microorganism is capable of binding specific recognition agents, such as phage. Following infection and replication of the phage, progeny phage may be detected via an indicator moiety expressed during phage replication. This principle allows amplification of indicator signal from one or a few cells based on specific recognition of microorganism surface receptors. For example, by exposing even a single cell of a microorganism to a plurality of phage, thereafter allowing amplification of the phage and high-level expression of an encoded indicator gene product during replication, the indicator signal is amplified such that the single microorganism is detectable.

Embodiments of the methods and systems of the invention can be applied to detection and quantification of a variety of microorganisms (e.g., bacteria, fungi, yeast) in a variety of circumstances, including but not limited to detection of pathogens from food, water, clinical and commercial samples. The methods of the present invention provide high detection sensitivity and specificity rapidly and without the need for traditional biological enrichment (e.g., culturing for enrichment), which is a surprising aspect as all available methods require culturing. In some embodiments detection is possible within 1-2 replication cycles of the bacteriophage or virus, which goes against conventional wisdom, as it doesn't take advantage of the phage's natural ability to amplify itself and the luciferase signal.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings.

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate or lateral flow strip).

The term "antibody" includes monoclonal antibodies, polyclonal antibodies, synthetic antibodies and chimeric antibodies, e.g., generated by combinatorial mutagenesis and phage display. The term "antibody" also includes mimetics or peptidomimetics of antibodies. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. Fragments of antibodies may serve in place of antibodies in some embodiments. "Surface-specific antibodies" as used herein bind to molecules exposed on the outer surface of a specific microorganism.

As used herein, the term "free antibodies" refers to antibodies which are in solution and may move freely through a liquid; i.e., they are not initially bound to a solid support or otherwise constrained.

As used herein, "affinity-purified" or "affinity-purification" refers to a series of steps used to prepare and treat antibodies such that they exhibit optimal specificity and sensitivity, including minimal cross-reactivity with undesired epitopes. For example, removal of undesired lipids and proteins from antiserum may first be achieved by salt precipitation steps. Further positive selection (also called "affinity-purification") and/or negative selection (also called "reverse-purification") may be achieved by passing the remaining antibodies over a support (e.g., agarose columns) comprising surface antigens designed to retain antibodies with particular epitope affinities. In some examples, where the starting antiserum is polyclonal, the purified antibodies that remain after these selection steps are able to recognize many different epitopes on the surface of the microorganism of interest, but they do not recognize the surface epitopes of other microorganisms.

The term "binding agent" refers to a molecule that can specifically and selectively bind to a second (i.e., different) molecule of interest. The interaction may be non-covalent, for example, as a result of hydrogen-bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator moiety" refers to a molecule that can be measured in a quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III) are transcribed in T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for very short periods of time may be employed in some embodiments of methods described herein, but is not necessary and is for a much shorter period of time than traditional culturing for enrichment, if it is used at all.

As used herein "recombinant" refers to genetic (i.e., nucleic acid) modifications as usually performed in a laboratory to bring together genetic material that would not otherwise be found. This term is used interchangeably with the term "modified" herein.

Samples

Each of the embodiments of the methods and systems of the invention can allow for the rapid detection and quantification of microbes in a sample. For example, methods according to the present invention can be performed, most preferably, in about two hours or less.

Microbes detected by the methods and systems of the present invention include pathogens that are of commercial, medical or veterinary concern. Such pathogens include Gram-negative bacteria, Gram-positive bacteria, mycoplasmas and viruses. Any microbe for which an infectious agent that is specific for the particular microbe has been identified can be detected by the methods of the present invention. Those skilled in the art will appreciate that there is no limit to the application of the present methods other than the availability of the necessary specific infectious agent/microbe pairs.

Bacterial cells detectable by the present invention include, but are not limited to, bacterial cells that are food or water borne pathogens. Bacterial cells detectable by the present invention include, but are not limited to, all species of Salmonella, all strains of Escherichia coli, including, but not limited to E. coli O157:H7, all species of Listeria, including, but not limited to L. monocytogenes, and all species of Campylobacter. Bacterial cells detectable by the present invention include, but are not limited to, bacterial cells that are pathogens of medical or veterinary significance. Such pathogens include, but are not limited to, Bacillus spp., Bordetella pertussis, Camplyobacter jejuni, Chlamydia pneumoniae, Clostridium perfringens, Enterobacter spp., Klebsiella pneumoniae, Mycoplasma pneumoniae, Salmonella typhi, Shigella sonnei, Staphylococcus aureus, and Streptococcus spp.

The sample may be environmental or food or water samples and medical or veterinary samples. Samples may be liquid, solid, or semi-solid. Samples may be swabs of solid surfaces. Samples may include environmental materials, such as the water samples, or the filters from air samples or aerosol samples from cyclone collectors. Samples may be of meat, poultry, processed foods, milk, cheese, or other dairy products. Medical or veterinary samples include, but are not limited to, blood, sputum, cerebrospinal fluid, and fecal samples and different types of swabs.

Samples may be used directly in the detection methods of the present invention, without preparation, concentration, or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to Na$^+$, Mg$^{2+}$, and K$^+$. Preferably a sample is maintained at a temperature that maintains the viability of any pathogen cells contained within the sample.

Preferably throughout detection assays, the sample is maintained at a temperature that maintains the viability of any pathogen cell present in the sample. During steps in which bacteriophages are attaching to bacterial cells, it is preferable to maintain the sample at a temperature that facilitates bacteriophage attachment. During steps in which bacteriophages are replicating within an infected bacterial cell or lysing such an infected cell, it is preferable to maintain the sample at a temperature that promotes bacteriophage replication and lysis of the host. Such temperatures are at least about 25 degrees Celsius (C.), more preferably no greater than about 45 degrees C., most preferably about 37 degrees C. It is also preferred that the samples be subjected to gentle mixing or shaking during bacteriophage attachment, replication and cell lysis.

Assays may include various appropriate control samples. For example, control samples containing no bacteriophages or control samples containing bacteriophages without bacteria may be assayed as controls for background signal levels.

Indicator Infectious Agents

As described in more detail herein, the compositions, methods, systems and kits of the invention may comprise infectious agents for use in detection of such microorganisms. In certain embodiments, the invention may comprise a composition comprising a recombinant bacteriophage having an indicator gene inserted into a late gene region of the bacteriophage. As described in more detail below, in certain embodiments of the infectious agent, the indicator gene does not encode a fusion protein. For example, in certain embodiments, expression of the indicator gene during bacteriophage replication following infection of a host bacterium results in a soluble indicator protein product. In certain embodiments, the indicator gene may be inserted into a late gene region of the bacteriophage. In a recombinant bacteriophage the late gene region may be a class III gene region.

In some embodiments, the indicator phage is derived from T7, T4 or another phage. An indicator bacteriophage may also be derived from T7-like, T4-like, JG04, JG04-like, or any other bacteriophage having a genome with at least 99, 98, 97, 96, 95, 94, 93, 92, 91 90, 89, 88, 87, 86, 85, 84, 83, 82, 81, 80, 79, 78, 77, 76, 75, 74, 73, 72, 71, or 70% homology to T7, T7-like, T4, T4-like, JG04, or JG04-like phages. In some embodiments, the indicator phage is derived from a natural phage isolated from the environment, such as JG04 phage, a T4-like phage isolated as described in the Examples. The genetic modifications may avoid deletions of wild-type genes and thus remain more similar to the wild-type infectious agent than many commercially available phage, e.g. T7SELECT®415. Such naturally derived bacteriophage may be more specific for bacteria that are found in the environment than bacteriophage that are commercially available and as such, genetically distinct from phage found in the environment.

Moreover, phage genes thought to be nonessential may have unrecognized function. For example, an apparently nonessential gene may have an important function in elevating burst size with subtle cutting, fitting, or trimming functions in assembly. As such, deleting genes to insert an indicator may be detrimental. Most phages can package a DNA that is a few percent larger than their natural genome. With this consideration, a smaller indicator gene may be a more appropriate choice for modifying a bacteriophage, especially one with a smaller genome. OpLuc and NANO-LUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp.

In some indicator phage embodiments, the indicator gene may be inserted into an untranslated region to avoid disruption of functional genes, leaving wild-type phage genes intact, which may lead to greater fitness when infecting non-laboratory strain bacteria. Additionally, stop codons at all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various type of luciferase may be used. In alternate embodiments, and as described in more detail herein, the luciferase is one of Oplophorus luciferase, Firefly luciferase, or an engineered luciferase.

Thus, in some embodiments, the present invention comprises a modified bacteriophage comprising a non-bacteriophage indicator gene in the late (class III) gene region. In some embodiments, the non-native indicator gene is under the control of a late promoter. Using a viral late gene promoter insures the reporter gene (luciferase) is not only expressed at high levels, like viral capsid proteins, but also does not shut down like endogenous bacterial genes or even early viral genes.

In some embodiments, the late promoter is a T4- or T7-like promoter, or another phage promoter similar to that found in the natural phage without genetic modification. The late gene region may be a class III gene region, and the bacteriophage may be derived from T7, T4, T4-like, JG04, or another natural bacteriophage having a genome with at least 90% homology to T7, T4 or T4-like phages. In preferred embodiments, the indicator gene does not encode a fusion protein.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. In some embodiments, the non-native indicator gene is not part of a fusion protein. That is, in some embodiments, a genetic modification may be configured such that the indicator protein product does not comprise polypeptides of the natural bacteriophage. In some embodiments, the indicator protein product is soluble. In some embodiments, the invention comprises a method for detecting a microorganism of interest comprising the step of incubating a test sample with such a modified bacteriophage.

In some embodiments, the non-native indicator gene is not contiguous with a gene encoding a structural phage protein and therefore does not yield a fusion protein. In some embodiments, expression of the indicator gene in progeny bacteriophage following infection of host bacteria results in a soluble protein product.

Unlike systems which employ a fusion of a detection moiety to the capsid protein (i.e., a fusion protein), some embodiments of the present invention express a soluble luciferase. This may greatly increase the sensitivity of the assay (down to a single bacterium), and simplifies the assay, allowing the assay to be completed in less than an hour for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate.

Furthermore, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the detection moiety (e.g., luciferase) than can fit on the bacteriophage. Additionally, large fusion proteins, such as a capsid-luciferase fusion, may inhibit assembly of the bacteriophage particle, thus yielding fewer bacteriophage progeny. Thus a soluble, non-fusion indicator gene product may be preferable.

In some embodiments, the indicator phage encodes a detectable enzyme. The indicator may emit light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

Also, the use of a soluble detection moiety eliminates the need to isolate contaminating parental phage from the lysate of the infected sample cells. With a fusion protein system, any bacteriophage used to infect sample cells would have the detection moiety attached, and would be indistinguishable from the daughter bacteriophage also containing the detection moiety. As detection of sample bacteria relies on the detection of newly created (de novo synthesized) detection moiety, using fusion constructs requires additional steps to separate old (parental) moieties from newly created (daughter bacteriophage) moieties. This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by streptavidin-coated sepharose beads). However, even with all these attempts at isolation, parental phage typically remain when a high multiplicity of infection (MOI) is used to assure infection of a low number of sample cells, creating background signal that may obscure detection of signal from infected cell progeny phage.

By contrast, with the soluble detection moiety expressed in some embodiments of the present invention, purification of the parental phage from the final lysate is unnecessary, as the parental phage will not have any detection moiety attached. Thus any detection moiety present after infection must have been created de novo, indicating the presence of an infected bacterium or bacteria. To take advantage of this benefit, the production and preparation of parental phage may include purification of the phage from any free detection moiety produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). The Examples herein describe the use cesium chloride isopycnic ultracentrifugation as part of the preparation of recombinant phage of the invention so as to separate parental phage particles from contaminating luciferase protein produced upon propagation of the phage in the bacteria stock. In this way, the recombinant bacteriophage of the invention is substantially free of any luciferase generated during production of the bacteria. Removal of residual luciferase present in the phage stock can substantially reduce background signal seen when the recombinant bacteriophage are incubated with a test sample.

In some embodiments of modified bacteriophage, the late promoter (class III promoter, e.g., from T7 or T4) has high affinity for RNA polymerase of the same native bacteriophage (e.g., T7 or T4, respectively) that transcribes genes for structural proteins assembled into the bacteriophage particle. These proteins are the most abundant proteins made by the phage, as each bacteriophage particle comprises dozens or hundreds of copies of these molecules. The use of a viral late promoter can ensure optimally high level of expression of the luciferase detection moiety. The use of a late viral promoter derived from, specific to, or active under the original wild-type bacteriophage the Indicator Phage is derived from (e.g., the T4 or T7 late promoter with a T4- or T7-based system) can further ensure optimal expression of the detection moiety. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator moiety, which does not limit expression to the number of subunits of a phage structural component.

Embodiments employing modified bacteriophage of the invention may allow rapid detection of specific bacterial strains, with total assay times as fast as 45 minutes-1.5 hours. The amount of time required may be somewhat shorter or longer depending on the strain of bacteriophage and the strain of bacteria to be detected in the assay.

The strategy of using indicator phage that produce soluble luciferase employs phage (e.g., T4 phage) engineered to express a soluble luciferase during replication instead of a capsid protein-luciferase fusion. Expression of luciferase is driven by a viral capsid promoter (e.g., the Soc promoter in T4 bacteriophage), yielding high expression. Parental phage will be free of luciferase, so any luciferase detected in the assay must come from replication of progeny phage released from the bacterial cells. Thus, there is no need to separate out the parental phage and the progeny phage.

In some embodiments, at least part of the sample comprising the bacteria to be quantified is spin filtered to remove the media and an appropriate multiplicity of biotinylated T4 phage that express luciferase are added. The parental and progeny phage in the filtrate from the infected bacteria may then be collected, e.g., by centrifugation and the level of luciferase quantified using a luminometer.

FIG. 1 depicts a schematic representation of the genomic structure of a recombinant bacteriophage of the invention, Indicator Phage T7SELECT®415-Luc. For the embodiment depicted in FIG. 1, the detection moiety is encoded by a Firefly luciferase gene 100 inserted within the late (class III) gene region 110, which is expressed late in the viral life cycle. Late genes are generally expressed at higher levels than other phage genes, as they code for structural proteins. Thus, in the embodiment of the recombinant phage depicted by FIG. 1, the indicator gene (i.e., Firefly luciferase) is inserted into the late gene region, just after gene 10B (major capsid protein), and is a construct comprising the Firefly luciferase gene 100. The construct depicted in FIG. 1 was designed to include stop codons 120 in all 3 reading frames to ensure luciferase is not incorporated into the gene 10B product. Also as depicted by FIG. 1, the construct may comprise the consensus T7 late promoter 130 to drive transcription and expression of the luciferase gene. The construct may also comprise a composite untranslated region synthesized from several T7 UTRs 140. This construct ensures soluble Firefly luciferase is produced such that expression is not limited to the number of capsid proteins inherent in the phage display system.

As noted herein, in certain embodiments, it may be preferred to utilize infectious agents that have been isolated from the environment for production of the infectious agents of the invention. In this way, infectious agents that are specific to naturally derived microorganisms may be generated.

Figure 2:
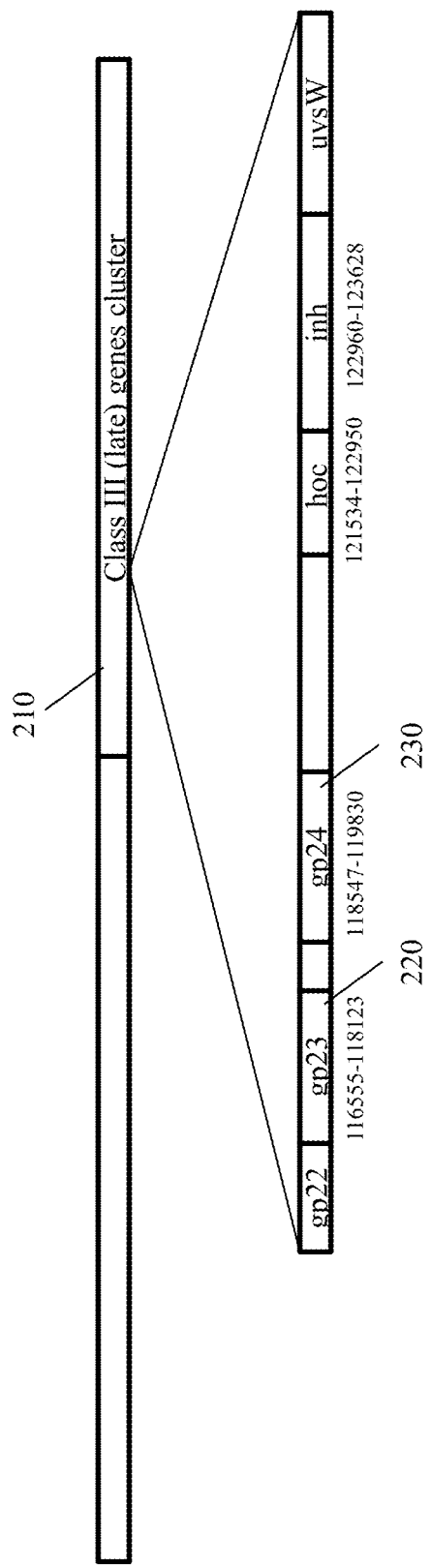
FIG. 2 shows the genome of bacteriophage JG04, a T4-like bacteriophage which was isolated from sewage treatment plant samples and shares ~98% homology with T4-like phage RB69. Capsid proteins gp23 and gp24 are within the late gene region, consisting of structural genes, which code for virion proteins. As these virion proteins are expressed at a very high level, any genes inserted into this region can be expected to have similar expression levels, as long as late gene promoters and/or other similar control elements are used.

For example, FIG. 2 shows the genome of bacteriophage JG04, a natural phage having about 98% sequence homology to a T4-like bacteriophage, RB69. Isolation of the JG04 bacteriophage from a sewage treatment plant sample is described with particularity in the Examples herein. As discussed in the Examples, the capsid proteins, gp23 (220) and gp24 (230) are within the late gene region (210), consisting of structural genes, which code for virion proteins. As these virion proteins are expressed at a very high level, any genes inserted into this region can be expected to have similar expression levels, as long as late gene promoters and/or other similar control elements are used. The bacteriophage construct depicted in FIG. 2 has the sequence as set forth in SEQ ID NO: 3.

Figure 3:
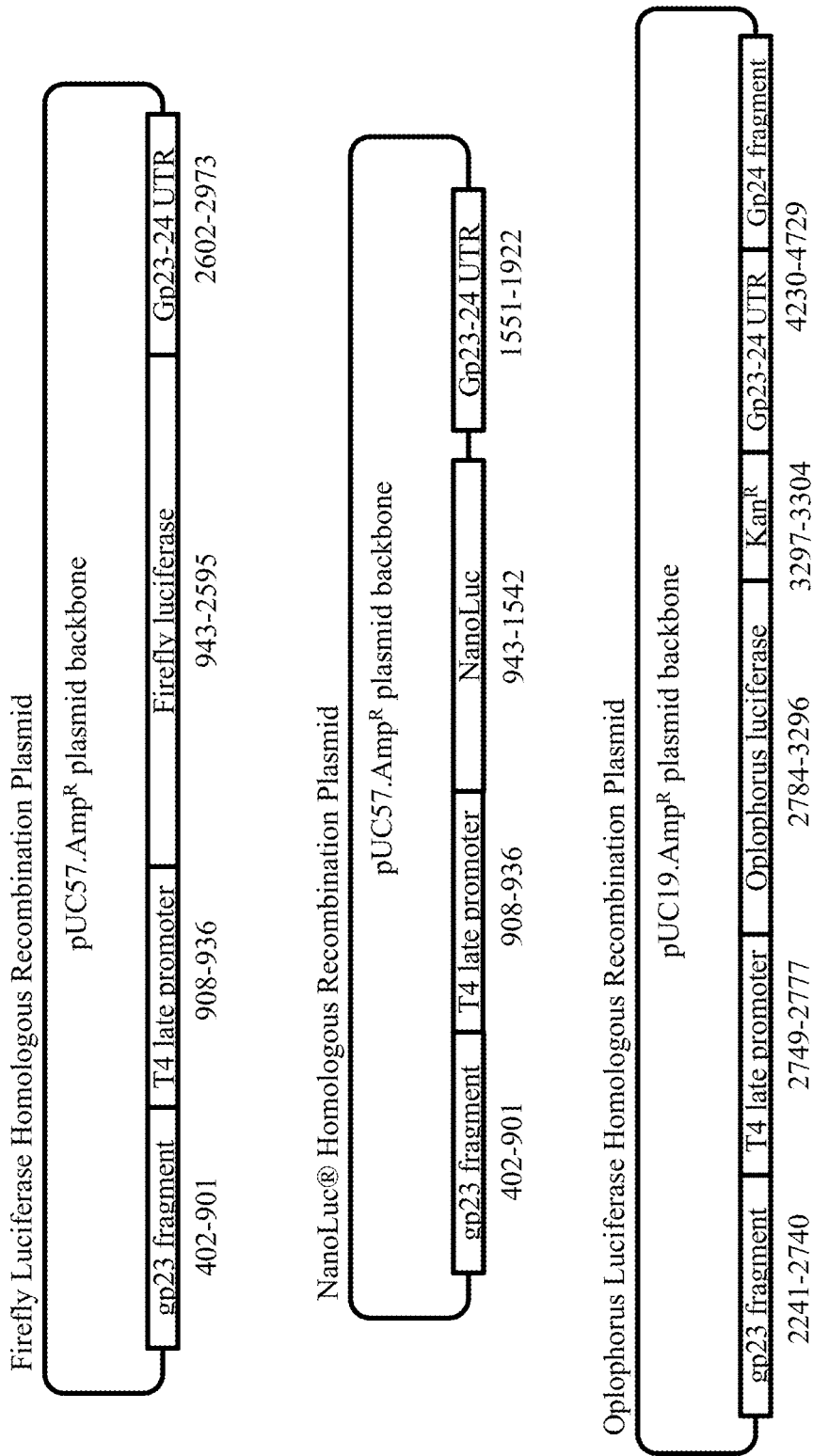
FIG. 3 shows three homologous recombination plasmid constructs carrying three different luciferase genes. Firefly luciferase, NANOLUC® luciferase, and Oplophorus luciferase genes are each inserted into a pUC57.Amp$^R$ plasmid backbone. In each construct, a fragment of the gp23 capsid protein gene is followed by a T4 late promoter, the respective luciferase gene, and a gp23-24 untranslated region. The Oplophorus construct additionally comprises a fragment of the gp24 gene downstream of the untranslated region.

The compositions of the invention may comprise various infectious agents and/or indicator genes. For example, FIG. 3 shows three homologous recombination plasmid constructs carrying three different luciferase genes. Three constructs were made and used in recombination with JG04 to generate recombinant bacteriophage of the invention. Thus, the top construct in FIG. 3 shows a recombination plasmid having Firefly luciferase construct used for homologous recombination insertion of the Firefly luciferase into JG04: homologous recombination plasmid pUC57.HR.Fluc, corresponding to SEQ ID NO. 5. The middle construct in FIG. 3 shows a recombination plasmid used for homologous recombination insertion of the NANOLUC® luciferase into JG04: homologous recombination plasmid pUC57.HR.NANOLUC® corresponding to SEQ ID NO. 6; and the lower construct in FIG. 3 shows a recombination plasmid used for homologous recombination insertion of the Oplophorus luciferase into JG04: homologous recombination plasmid pUC19.HR.OpLuc.KanR, corresponding to SEQ ID NO. 7.

In some embodiments, indicator phage according to the invention comprise JG04 genetically engineered to comprise any one of the three constructs shown in FIG. 3. That is, an indicator phage comprising the sequence of SEQ ID NO. 3, further comprising additional sequence inserted between nucleotides 116,555 and 119,830 of SEQ ID NO. 3 corresponding to nucleotides 402-2,973 of SEQ ID NO. 5 (or a portion thereof); or nucleotides 402-1,922 of SEQ ID NO. 6 (or a portion thereof), also called JG04-NANOLUC® Indicator Phage in Examples 6 and 11 herein; or nucleotides 2,241-4,729 of SEQ ID NO. 7 (or a portion thereof), also called JG04-OpLuc Indicator Phage in Examples 7-9 herein. For example, a portion thereof may comprise the luciferase portion only (i.e., nucleotides 943-2,595 of SEQ ID NO. 5; or nucleotides 943-1,542 of SEQ ID NO. 6; or nucleotides 2,784-3,296 of SEQ ID NO. 7). A portion thereof may further comprise the T4 late promoter (i.e., nucleotides 908-936 of either SEQ ID NO. 5 or NO. 6, or nucleotides 2,749-2,777 of SEQ ID NO. 7). In other embodiments, such indicator phage are comprised in systems or kits according to the invention. Methods described herein may also utilize such indicator phage.

Figure 4:
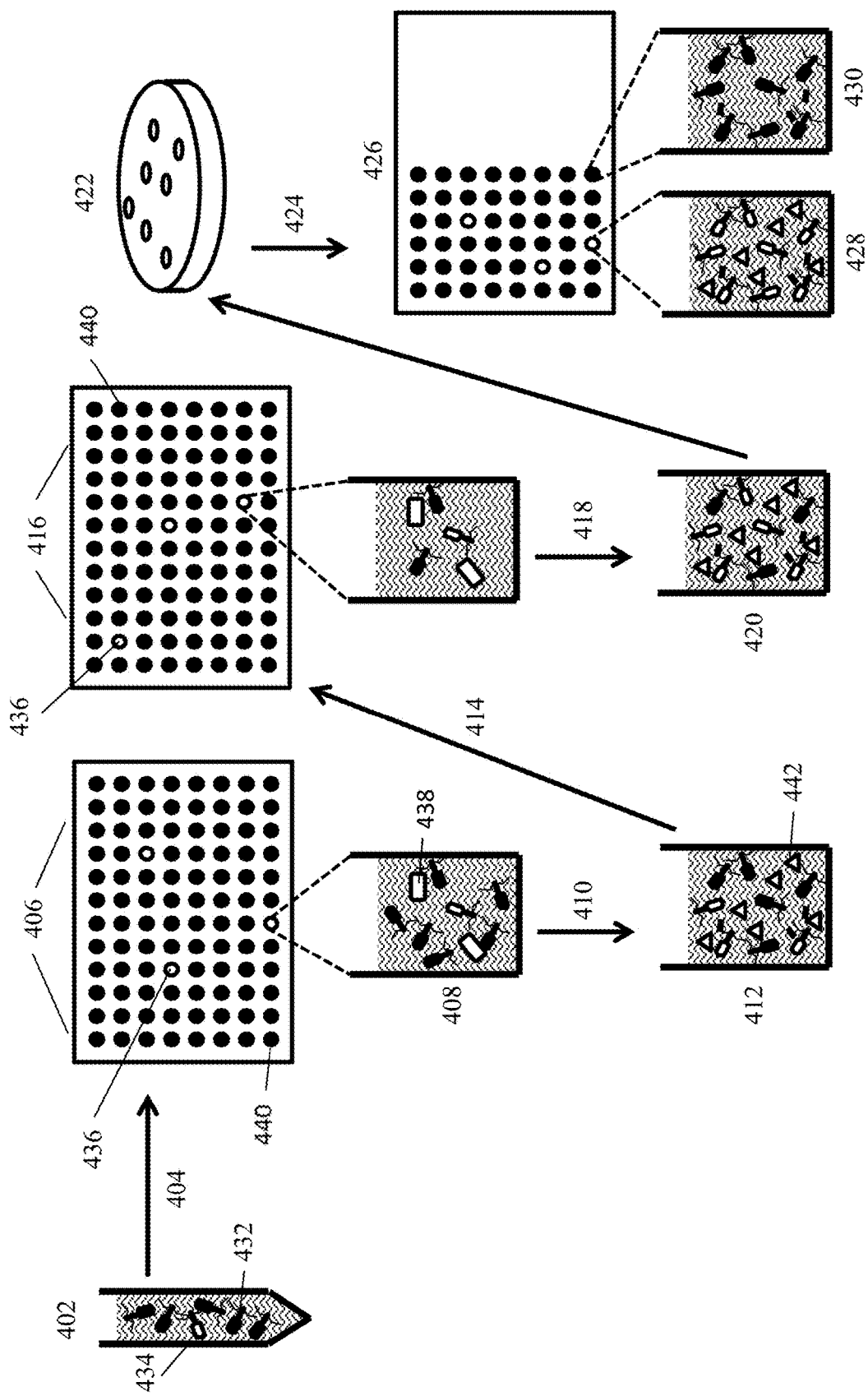
FIG. 4 depicts the isolation of recombinant phage from modifications of JG04 bacteriophage using the plasmid constructs such as those shown in FIG. 3 using a series of sequential infection and dilution steps to identify recombinant phage that express an indicator gene.

FIG. 4 depicts the isolation of recombinant phage from modifications of JG04 bacteriophage using the plasmid constructs shown in FIG. 3 and described in Example 6.

In the first step 402, bacteria transformed with homologous recombination plasmid are infected with bacteriophage, resulting in progeny phage with a mixture of parental and recombinant phage with a ratio of approximately 20,000 wild-type 432:1 recombinant phage 434. The resulting recombinant phage mix is diluted 404 into 96-well plates 406 to give an average of 3 recombinant transducing units (TU) per plate, which corresponds to about 625 infectious units (IU) of mostly wild-type phage per well. The 96-well plate is assayed for luciferase activity to identify wells 436 containing recombinant phage as compared to wells 440 containing wild-type bacteriophage. Bacteria 438 are added 408; for example, each well may contain about 50 μL of turbid *E. coli* O157:H7. This allows the phage to replicate and produce the luciferase enzyme 442. After 2 hours of incubation at 37° C. shown in 410, wells may be screened for the presence of luciferase 442. Any positive wells are likely to have been inoculated with a single recombinant phage, and at this stage the mixture may contain a ratio of approximately 600 wild-type phage:1 recombinant, an enrichment over the original 20,000:1 ratio. In one embodiment, soluble luciferase and phage were present at approximate ratio of 625 wild-type:1 recombinant. Progeny from this enriched culture 412 may be subjected to additional limiting dilution assay(s) 414 to verify the ratio and determine the actual concentration of recombinant phage transducing units. For example, about 3 recombinant TU per 96-well plate 416 may be aliquoted 414 from the first purification stock, leading to an approximate inoculation of ~20 mostly wild-type phage per well of a second dilution assay plate 420. Any positive luciferase wells are likely to have been inoculated with a single recombinant along with ~20 wild-type phage. These wells may be analyzed for presence of luciferase 442.

After addition of bacteria and incubation (e.g., 37° C. for 2 hours) 418, soluble luciferase and phage are present at approximately 20 wild-type:1 recombinant 420. Finally, a plaque assay may be performed 422 to screen for recombinants that express luciferase 446. A small number of individual (e.g., n=48) plaques may be individually picked and screened on a third multiwell plate 426 for luciferase activity 436. In an embodiment, this approach should insure that about 3 recombinants would be in the mix of plaques being screened. One plaque may be removed from the plate to each well of a 96-well plate 424 and a luciferase assay performed 426 to determine which wells contained phage exhibiting luciferase activity 442. Wells 428 demonstrating luciferase activity represent pure recombinant phage 434, while wells without luciferase activity 430 represent pure wild-type phage 432.

Individual plaques may then be suspended in buffer or media (e.g., 100 μL TMS), and an aliquot (e.g., about 5 μL) added to a well containing a turbid *E. coli* O157:H7 culture, and assayed after incubation (e.g., about 45 minutes to 1 hour at 37° C.). Positive wells are expected to contain a pure culture of recombinant phage. Still, it may be preferred, in certain embodiments to include an additional round of plaque purification.

Thus, as exemplified by FIG. 4, recombinant phage generated by homologous recombination of the appropriate recombination plasmid with JG04 can be isolated from a mixture comprising 0.005% of total phage. Following isolation, large scale production may be performed to obtain high titer stocks appropriate for use in the *E. coli* O157:H7 detection assay. For example, as described in more detail in the Examples herein, cesium chloride isopycnic density gradient centrifugation may be used to separate phage particles from contaminating luciferase protein to reduce background.

In this way, and as described in more detail in the Examples below, recombinant bacteriophage having the luciferase gene of interest (e.g., Firefly, Oplophorus or an engineered luciferase such as NANOLUC®) inserted into a bacteriophage derived from the environment may be generated.

Methods of Using Infectious Agents for Detecting Microorganisms

As noted herein, in certain embodiments, the invention may comprise methods of using infectious particles for detecting microorganisms. The methods of the invention may be embodied in a variety of ways.

Thus, the methods of the present invention utilizes the high specificity of binding agents that recognize and bind to a particular microorganism of interest as a means to amplify a signal and thereby detect low levels of a microorganism (e.g., a single microorganism) present in a sample. For example, infectious agents (e.g., bacteriophage) specifically recognize surface receptors of particular microorganisms and thus specifically infect those microorganisms. As such, these infectious agents may be appropriate binding agents for targeting a microorganism of interest. Some embodiments of the invention utilize the specificity of binding and high-level genetic expression capacity of infectious agents for rapid and sensitive targeting to infect and facilitate detection of a microorganism of interest.

Thus, in an embodiment, the invention may comprise a method for detecting a microorganism of interest in a sample comprising the steps of: incubating the sample with an infectious agent that infects the microorganism of interest, wherein the infectious agent comprises an indicator gene such that expression of the indicator gene during bacteriophage replication following infection of microorganism of interest results in a soluble indicator protein product; and detecting the indicator protein product, wherein positive detection of the indicator protein product indicates that the microorganism of interest is present in the sample.

A variety of infectious agents may be used. In alternate embodiments, bacteriophages, phages, mycobacteriophages (such as for TB and paraTB), mycophages (such as for fungi), mycoplasma phages, and any other virus that can invade living bacteria, fungi, mycoplasma, protozoa, yeasts, and other microscopic living organisms can be employed to target a microorganism of interest. For example, in an embodiment, where the microorganism of interest is a bacterium, the infectious agent may comprise a bacteriophage. As discussed herein, such bacteriophage may replicate inside of the bacteria to generate hundreds of progeny bacteria. Detection of the indicator gene inserted into the bacteriophage can be used as a measure of the bacteria in the sample. For example, well-studied phages of *E. coli* include T1, T2, T3, T4, T5, T7, and lambda; other *E. coli* phages available in the ATCC collection, for example, include phiX174, S13, Ox6, MS2, phiV1, fd, PR772, and ZIK1. Alternatively, natural bacteriophage may be isolated from a variety of environmental sources. A source for phage isolation may be selected based on the location where a microorganism of interest is expected to be found. Thus, in some embodiments, the indicator bacteriophage comprises an indicator moiety and infection of a single *E. coli* cell may be detected in an amplified signal generated via the indicator moiety. Thus the method may comprise detecting an indicator moiety produced during phage replication, wherein detection of the indicator indicates that the bacterium of interest is present in the sample.

In an embodiment, the invention may comprise a method for detecting a bacteria of interest in a sample comprising the steps of: incubating the sample with a recombinant bacteriophage that infects the bacteria of interest, wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that the bacteria of interest is present in the sample. In an embodiment, and as described in detail herein, the amount of indicator moiety detected corresponds to the amount of the bacteria of interest present in the sample.

In an embodiment, the late gene region is a class III gene region. As described in more detail herein, insertion of the indicator gene into the late class III gene region may ensure that the indicator gene is expressed in high quantities upon replication in the bacterium.

As described above for the compositions of the invention, the bacteriophage is derived from T7, T4, T4-like, JG04, or another natural bacteriophage having a genome with at least 90% homology to T7, T4 or other T4-like phage.

Also, in certain embodiments, the indicator gene does not encode a fusion protein. Thus, in certain embodiments, expression of the indicator gene during bacteriophage replication following infection of host bacteria results in a soluble indicator protein product.

A variety of indicator moieties may be used. In certain embodiments, the indicator gene may encode a luciferase enzyme. For example, the luciferase may be one of Oplophorus luciferase, Firefly luciferase, or an engineered luciferase.

As described in more detail herein, the methods and systems of the invention may utilize a variety of multiplicities of infection (MOI). In certain embodiments, the MOI is higher that standard assays. Such a relatively high MOI may allow for infection of microorganisms that are present at very low amounts in the sample. For example, in certain embodiments, the bacteriophage concentration for the incubating step is greater than $1\times10^7$ PFU/mL.

In certain embodiments, the recombinant infectious agent may be purified so as to be free of any residual indicator protein that may be generated upon production of the infectious agent stock. Thus, in certain embodiments, and as described in more detail herein, the recombinant bacteriophage may be purified using cesium chloride isopycnic density gradient centrifugation prior to incubation with the sample. When the infectious agent is a bacteriophage, this purification may have the added benefit of removing bacteriophage that do not have DNA (i.e., empty phage).

As described further below, in certain embodiments, the method may employ a step whereby the microorganism of interest is concentrated or captured from a large volume of sample. Thus, in certain embodiments, the method may comprise a step for capturing the microorganism from the sample on a solid support before the incubating step.

In some embodiments, the method may include contacting a microorganism captured on a solid support (e.g., a magnetic bead or a filter substrate) with a plurality of the specific infectious agent (e.g., indicator bacteriophage) and allowing the bacteriophage to bind and infect the bacteria. In other embodiments, capture of the microorganism is not necessary for detection. A variety of solid supports may be used. In certain embodiments, the solid support may comprise a multi-well plate, a filter, a bead, or a lateral flow strip, a filter strip, filter disc, or filter paper, or thin films designed for culturing cells (e.g., PetriFilm by 3M). Other solid supports may also be appropriate.

The microorganism of interest may be purified from the sample by using a binding agent. For example, in certain embodiments, the capturing step further comprises binding microorganism with a capture antibody. The antibody may be used in conjunction with the solid support. For example, in certain embodiments, the capture antibody facilitates binding of the microorganism to the solid support.

The method of the invention may comprise various steps to increase sensitivity. For example, as discussed in more detail herein, the method may comprise a step for washing the captured and infected microorganism, after adding the bacteriophage but before incubating, to remove excess parental bacteriophage and/or luciferase or other reporter protein contaminating the bacteriophage preparation.

In contrast to assays known in the art, detection of the microorganism of interest may be completed without the need for culturing the sample as a way to increase the population of the microorganisms. Thus, in certain embodiments, detection of the microorganism of interest is completed in less time than a time period required for increasing the number of microorganisms by 4-fold or 10-fold using culturing for enrichment. For example, in certain embodiments the total time required for detection is less than 6.0 hours, 5.0 hours, 4.0 hours, 3.0 hours, 2.5 hours, 2.0 hours, 1.5 hours, 1.0 hour, 45 minutes, or less than 30 minutes.

Also, in contrast to assays known in the art, the method of the invention can detect individual microorganisms. Thus, in certain embodiments, the method may detect ≤10 cells of the microorganism (i.e., 1, 2, 3, 4, 5, 6, 7, 8, 9 microorganisms) present in a sample.

Thus, aspects of the present invention provide methods for detection of microorganisms in a test sample via an indicator moiety. In some embodiments, where the microorganism of interest is a bacteria, the indicator moiety may be associated with an infectious agent such as an indicator bacteriophage. The indicator moiety may react with a substrate to emit a detectable signal or may emit an intrinsic signal (e.g., fluorescent protein). In some embodiments, the detection sensitivity can reveal the presence of as few as 50, 20, 10, 9, 8, 7, 6, 5, 4, 3, or 2 cells of the microorganism of interest in a test sample. In some embodiments, even a single cell of the microorganism of interest may yield a detectable signal.

In some embodiments, the indicator moiety associated with the infectious agent may be detectable during or after replication of the infectious agent. Many different types of detectable biomolecules suitable for use as indicator moieties are known in the art, and many are commercially available. In some embodiments the indicator phage comprises an enzyme, which serves as the indicator moiety. In some embodiments, the genome of the indicator phage is modified to encode a soluble protein. In some embodiments, the indicator phage encodes a detectable enzyme. The indicator may emit light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

Detecting the indicator may include detecting emissions of light. In some embodiments, a luminometer may be used to detect the indicator (e.g., luciferase). However, other machines or devices may also be used. For example, a spectrophotometer, CCD camera, or CMOS camera may detect color changes and other light emissions.

In some embodiments, indicator phage is genetically engineered to contain the gene for an enzyme, such as a luciferase, which is only produced upon infection of bacteria that the phage specifically recognizes and infects. In some embodiments, the indicator moiety is expressed late in the viral life cycle. In some embodiments, as described herein, the indicator is a soluble protein (e.g., soluble luciferase) and is not fused with a phage structural protein that limits its copy number.

In various embodiments of the methods of the invention, the microorganism may be detected without any purification of the microorganisms from a sample. For example, in certain embodiments, a sample containing one or a few microorganisms of interest may be applied directly to an assay container such as a spin column, an microtiter well, or a filter and the assay is conducted in that assay container. Various embodiments of such assays are disclosed herein.

For example, aliquots of a test sample comprising bacteria may be applied to a spin column and after infection with a recombinant bacteriophage and an optional washing to remove any excess bacteriophage, the amount of soluble indicator detected will be proportional to the amount of bacteriophage that are produced by infected bacteria. Example 4 describes such an assay.

Or, aliquots of a test sample may be distributed directly into wells of a multi-well plate, indicator phage may be added, and after a period of time sufficient for infection, a lysis buffer may be added as well as a substrate for the indicator moiety (e.g., luciferase substrate for a luciferase indicator) and assayed for detection of the indicator signal. Examples 5-6 describe embodiments of the method performed on filter plates. Examples 7-9 herein describe assay variations called the "No concentration assay."

For example, in many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Thus in some embodiments utilizing indicator phage, the invention comprises a method for detecting a microorganism of interest comprising the steps of capturing at least one sample microorganism; incubating the at least one microorganism with a plurality of indicator phage; allowing time for infection and replication to generate progeny phage and express soluble indicator moiety; and detecting the progeny phage, or preferably the indicator, wherein detection of the indicator demonstrates that the microorganism is present in the sample.

For example, in some embodiments the test sample microorganism may be captured by binding to the surface of a plate, or by filtering the sample through a bacteriological filter (e.g., 0.45 µm pore size spin filter or plate filter). In an embodiment, the infectious agent (e.g., indicator phage) is added in a minimal volume to the captured sample directly on the filter. In an embodiment, the microorganism captured on the filter or plate surface is subsequently washed one or more times to remove excess unbound infectious agent. In an embodiment, media (e.g., Luria-Bertani also called LB broth herein) is added for further incubation time, to allow replication of phage and high-level expression of the gene encoding the indicator moiety. However, a surprising aspect of embodiments of the assays is that the incubation step only needs to be long enough for a single phage life cycle. The amplification power of using bacteriophage was previously thought to require more time, such that the phage would replicate for several cycles. A single replication of indicator phage is sufficient to facilitate sensitive and rapid detection according to some embodiments of the present invention.

Soluble indicator (e.g., luciferase) is released into the surrounding liquid upon lysis of the bacteria, which may then be measured and quantified. In an embodiment, the solution is then spun through the filter, and the filtrate collected for assay by addition of a substrate for the indicator enzyme (e.g., luciferase substrate). The filtrate may thus be removed from the capture solid support and analyzed in a new receptacle (e.g., in a luminometer), or the indicator signal may be measured directly on the filter.

In various embodiments, the purified parental indicator phage does not comprise the detectable indicator itself, because the parental phage may be purified before it is used for incubation with a test sample. Expression of late (Class III) genes occurs late in the viral life cycle. In some embodiments of the present invention, parental phage may be purified to exclude any existing indicator protein (e.g., luciferase). In some embodiments, expression of the indicator gene during progeny bacteriophage replication following infection of host bacteria results in a soluble indicator protein product. Thus, in many embodiments, it is not necessary to separate parental from progeny phage in the detecting step. In an embodiment, the microorganism is a bacterium and the indicator phage is a bacteriophage. In an embodiment, the indicator moiety is soluble luciferase, which is released upon lysis of the host microorganism.

Thus, in an alternate embodiment, the indicator substrate may be incubated with the portion of the sample that remains bound to a filter or bound to a plate surface. Accordingly, in some embodiments the solid support is a 96-well filter plate (or regular 96-well plate), and the substrate reaction may be detected by placing the plate directly in the luminometer.

For example, in an embodiment, the invention may comprise a method for detecting *E. coli* O157:H7 comprising the steps of: infecting cells captured on a 96-well filter plate with a plurality of parental indicator phage capable of expressing luciferase upon infection; washing excess phage away; adding LB broth and allowing time for phage to replicate and lyse the specific *E. coli* target (e.g., 30-90 minutes); and detecting the indicator luciferase by adding luciferase substrate and measuring luciferase activity directly in the 96-well plate, wherein detection of luciferase activity indicates that the *E. coli* O157:H7 is present in the sample.

In another embodiment, the invention may comprise a method for detecting E. coli O157:H7 comprising the steps of: infecting cells in liquid solution or suspension in a 96-well plate with a plurality of parental indicator phage capable of expressing luciferase upon infection; allowing time for phage to replicate and lyse the specific E. coli target (e.g., 30-90 minutes); and detecting the indicator luciferase by adding luciferase substrate and measuring luciferase activity directly in the 96-well plate, wherein detection of luciferase activity indicates that the E. coli O157:H7 is present in the sample. In such an embodiment no capturing step is necessary. In some embodiments, the liquid solution or suspension may be a consumable test sample, such as a vegetable wash. In some embodiments, the liquid solution or suspension may be vegetable wash fortified with concentrated LB broth or Nutrient Broth. In some embodiments, the liquid solution or suspension may be bacteria diluted in LB Broth.

In some embodiments, lysis of the microorganism may occur before, during, or after the detection step. Experiments suggest that infected unlysed cells may be detectable upon addition of luciferase substrate in some embodiments. Presumably, luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with sample in solution or suspension, where the original plate full of intact and lysed cells is directly assayed in the luminometer, lysis is not necessary for detection.

In some embodiments, the reaction of indicator moiety (e.g., luciferase) with substrate may continue for 30 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of phage utilized for infecting test samples (i.e., high MOI) have successfully achieved detection of very low numbers of target microorganism in a very short timeframe. The incubation of phage with a test sample in some embodiments need only be long enough for a single phage life cycle. In some embodiments, the bacteriophage concentration for this incubating step is greater than $7\times10^6$, $8\times10^6$, $9\times10^6$, $1.0\times10^7$, $1.1\times10^7$, $1.2\times10^7$, $1.3\times10^7$, $1.4\times10^7$, $1.5\times10^7$, $1.6\times10^7$, $1.7\times10^7$, $1.8\times10^7$, $1.9\times10^7$, $2.0\times10^7$, $3.0\times10^7$, $4.0\times10^7$, $5.0\times10^7$, $6.0\times10^7$, $7.0\times10^7$, $8.0\times10^7$, $9.0\times10^7$, or $1.0\times10^8$ PFU/mL.

Success with such high concentrations of phage is surprising because the large numbers of phage were previously associated with "lysis from without," which killed target cells and thereby prevented generation of useful signal from earlier phage assays. It is possible that the clean-up of prepared phage stock described herein helps to alleviate this problem (e.g., clean-up by cesium chloride isopycnic density gradient ultracentrifugation), because in addition to removing any contaminating luciferase associated with the phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude JG04 lysate (i.e., before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a very clean phage prep allows the assay to be performed with no wash steps, which makes the No Concentration assay possible.

Spin Column Assays

Figure 5:
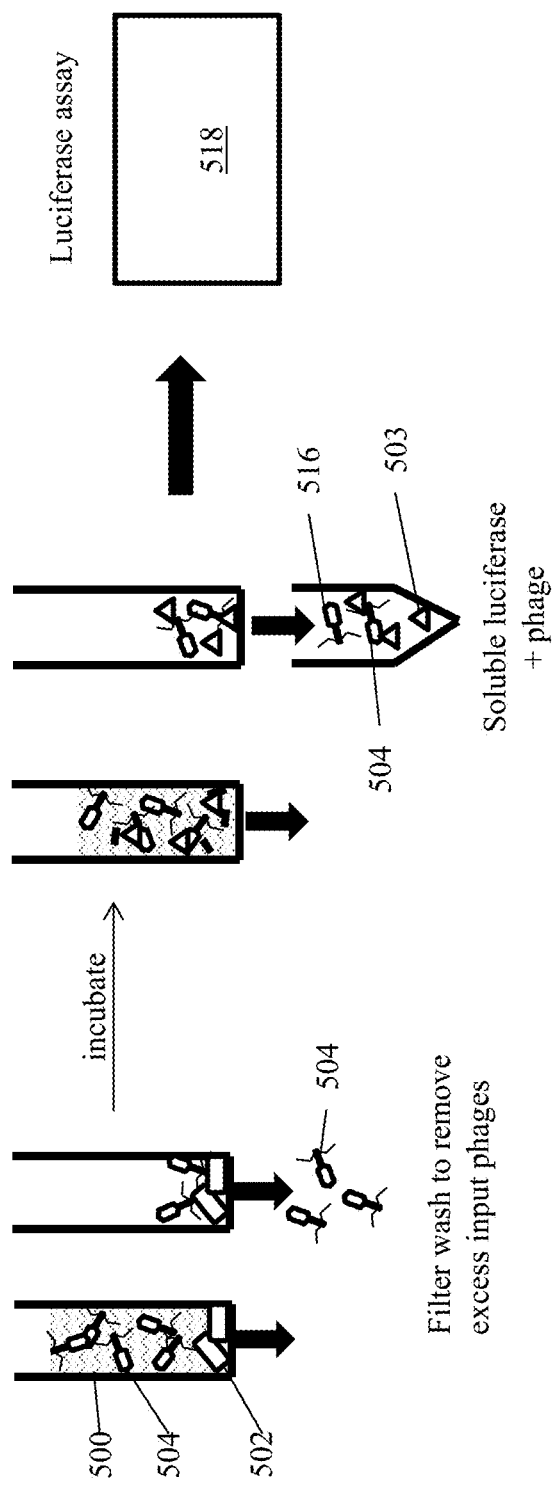
FIG. 5 depicts the use of indicator phage encoding a soluble luciferase to detect bacterial cells via detection of luciferase generated from replication of progeny phage during infection of the bacterial cells, according to an embodiment of the invention FIG. 6 demonstrates sensitivity for detection of target bacteria using indicator phage with spin columns, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

FIG. 5 shows a strategy of using indicator phage that produce soluble luciferase according to an embodiment of the invention. In this method, the phage (e.g., T7, T4, or JG04 phage) may be engineered to express a soluble luciferase during replication of the phage. Expression of luciferase is driven by a viral capsid promoter (e.g., the bacteriophage T7 or T4 late promoter), yielding high expression. Parental phage will be free of luciferase, so the luciferase detected in the assay must come from replication of progeny phage during infection of the bacterial cells. Thus, there is generally no need to separate out the parental phage from the progeny phage.

In these experiments, at least part of the sample 500 comprising the E. coli bacteria 502 to be quantified is placed in a spin column filter and centrifuged to remove the LB broth, and an appropriate multiplicity of T7 phage 504 genetically engineered to express soluble luciferase 503 are added. The infected cells may be incubated for a time sufficient for replication of progeny phage and cell lysis to occur (e.g., 30-90 minutes at 37° C.). The parental 504 and progeny phage 516 plus free luciferase 503 in the lysate may then be collected, e.g., by centrifugation, and the level of luciferase in the filtrate quantified using a luminometer 518. Alternatively, a high through-put method may be employed where bacterial samples are applied to a 96-well filter plate, and after all manipulations listed above are performed, may be directly assayed for luciferase in the original 96-well filter plate without a final centrifugation step.

Data from example experiments of embodiments of the invention are shown in FIGS. 6-9. The results demonstrate alternative embodiments of the invention utilizing indicator phage to assay sample bacteria via detection of soluble luciferase produced by the infection of bacteria with indicator phage. Indicator detection level calibrated as relative light units (RLU) is plotted against cell concentrations determined from the standard overnight colony forming unit (CFU) assay and expressed as "cells per assay," thus demonstrating similar sensitivity. Increasing luciferase signal corresponds to increasing input sample cells, demonstrating a dose-dependent response.

Figure 6:
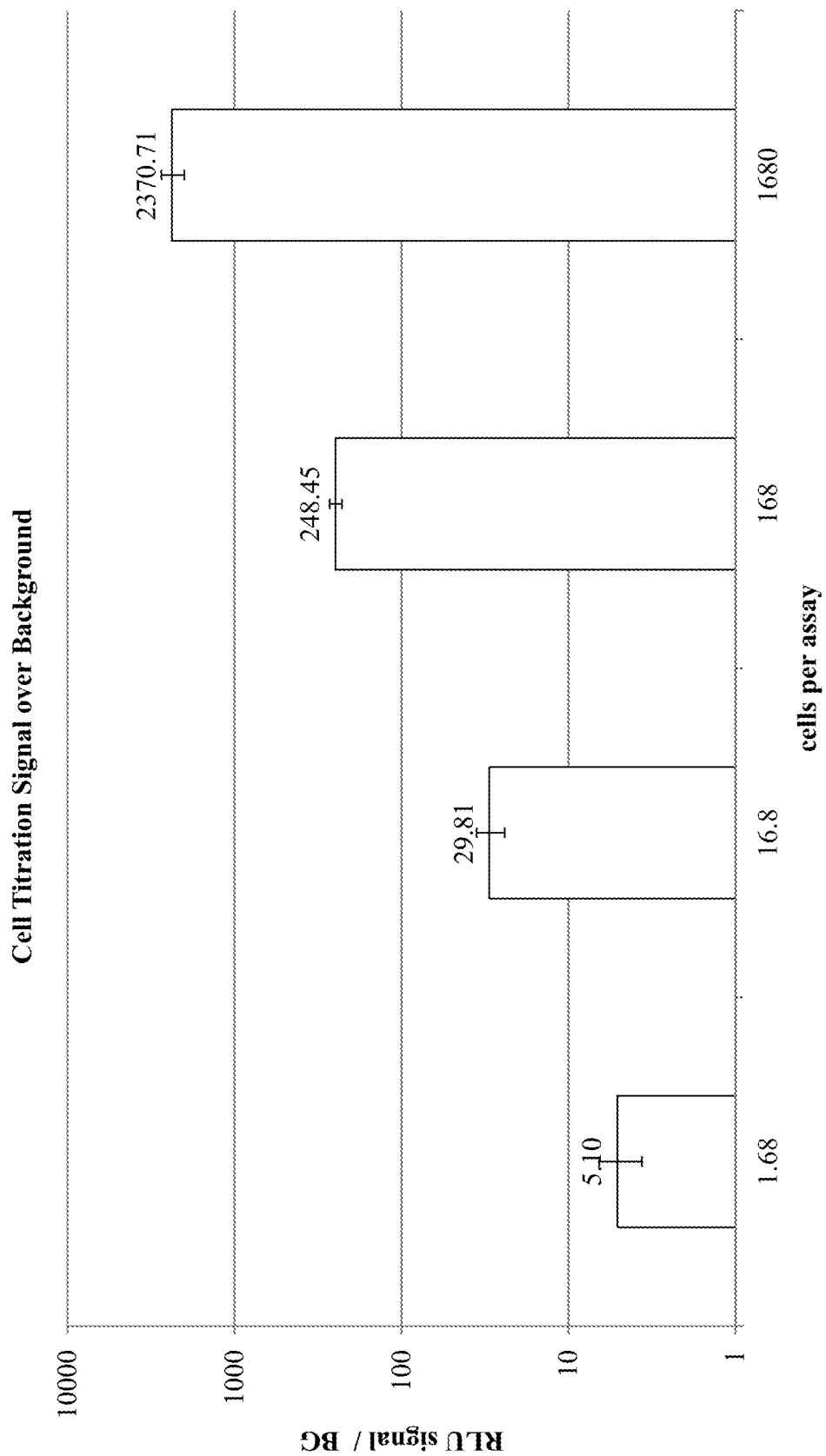

As shown in FIG. 6 the method of the invention may demonstrate high sensitivity for detection of target bacteria using indicator phage with spin column filters. In this assay, a test sample may be collected on a spin filter by centrifugation and incubated with indicator phage comprising a gene for soluble luciferase (e.g., as shown in FIG. 1). Following incubation for a time sufficient for infection (e.g., 10 minutes at room temperature), the filter may be washed and spun to remove excess input phage. Media (e.g., LB broth) may be added and incubated (e.g., for 30 minutes at 37° C.) to allow replication of progeny phage and lysis of bacteria. Filters may be spun again to remove the filtrate, which may be transferred to a luminometer plate, and a luciferase assay was performed (e.g., using a Promega® luminometer with injection of Luciferase Assay Reagent, Promega, Inc.). The cell count may be corrected according to the number of colonies in the parallel CFU assay.

As shown in FIG. 6, approximately 1,700 bacterial cells may be detected in the original sample, and further assay of serial dilutions may demonstrate detection down to an average of 1.7 cells, corresponding to actual detection of 1 or 2 cells. This shows that infection of as few as 1 to 3 *E. coli* cells can provide a measurable signal, via luciferase activity. This also shows statistical significance for the presence or absence of even a single cell over background (p value=0.018).

Figure 7:
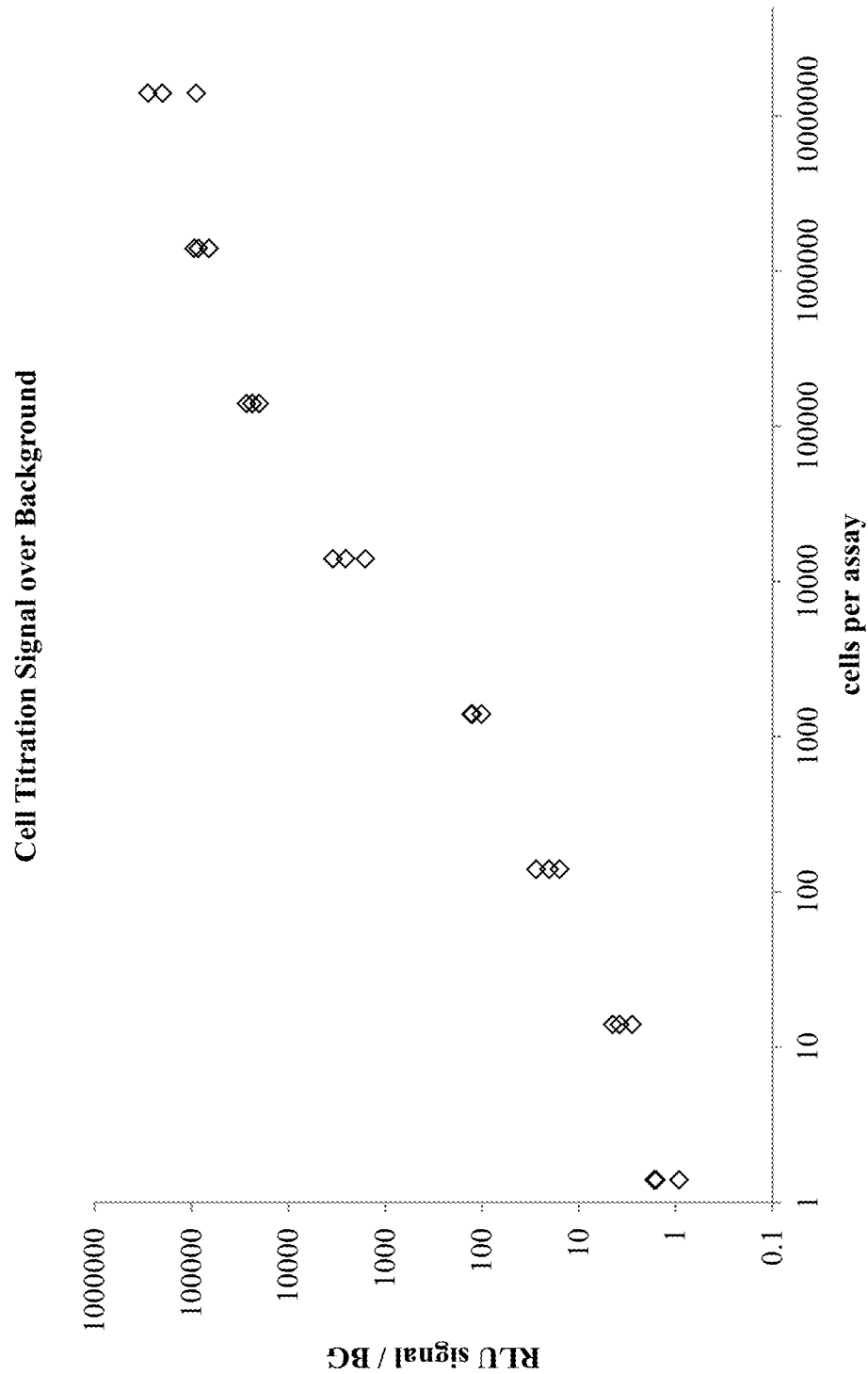
FIG. 7 demonstrates detection of target bacteria over a range of titers using indicator phage with spin columns, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

FIG. 7 demonstrates the very large detection range of the same method described for the assay of FIG. 5 using serial dilutions across a broader range of cell numbers. This shows detection may range from an average of 1.4 cells to 14 million cells.

Filter Plate Assays

Figure 8:
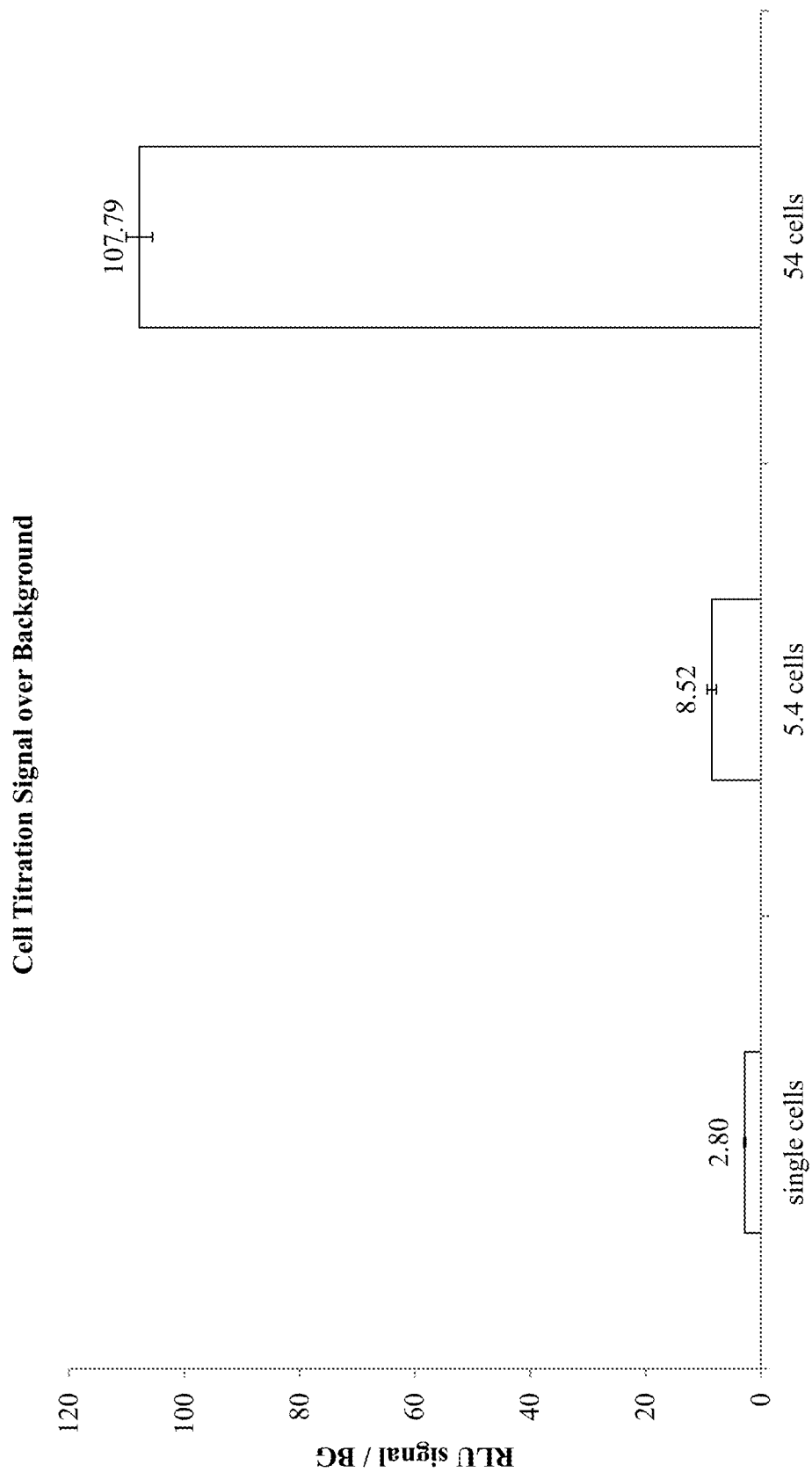
FIG. 8 demonstrates sensitivity for detection of target bacteria using indicator phage with 96-well filter plates, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

As noted above, in certain embodiments, the assay may be conducted directly in the well of a microtiter assay plate. For example, FIG. 8 demonstrates the use of indicator phage with a 96-well filter plate for capture and detection. The method is the same as described above for FIG. 5, except that the entire assay is performed in a 96-well filter plate, including the luciferase reaction. This embodiment reduces manipulations and materials compared to the spin filter method. The reduced manipulations and use of a 96-well filter plate is amenable to a high throughput assay situation, and may be adapted for use with a liquid handling robot according to embodiments of the invention. FIG. 8 shows that in this embodiment, a 96-well filter plate may be used to detect single *E. coli* cells (0.5 cells average assayed, confirming that about one-half of the wells received single cells), 5.4 and 54 cells.

Figure 9:
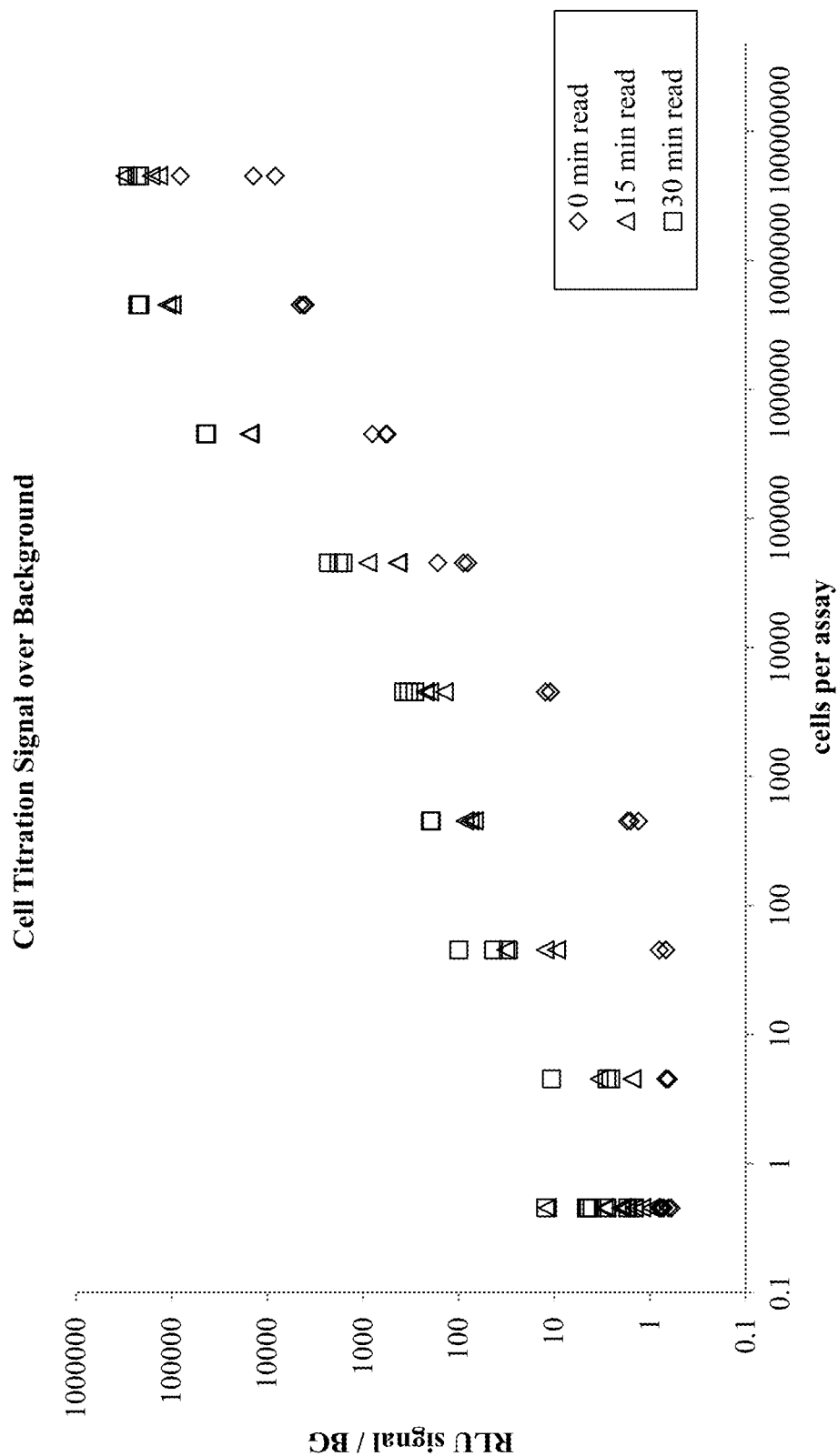
FIG. 9 demonstrates detection of target bacteria over a range of titers using indicator phage with 96-well filter plates, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG). The detection of luciferase activity may be continued for an extended period of time. Here, reading ◇ represents 0 time (i.e., a baseline control); Δ after 15 minutes (min); and □ after 30 minutes.

FIG. 9 demonstrates that in certain embodiments, a very large detection range of cell concentrations may be achieved for the same assay, using the 96-well system, from less than 1 cell per assay on average (single cells) to at least 14 million cells per assay. Multiple reads at different time points after addition of the luciferase substrate may demonstrate varied sensitivity. Sensitivity for detecting <10 cells was achieved with a 15 minute read, and sensitivity down to single cell levels may be achieved at the 30 minute read. Thus time may be saved if tens of cells or less need not be detected. Note signal increases in response to increased number of input sample cells in both experiments, again demonstrating a dose-dependent response.

Figure 10:
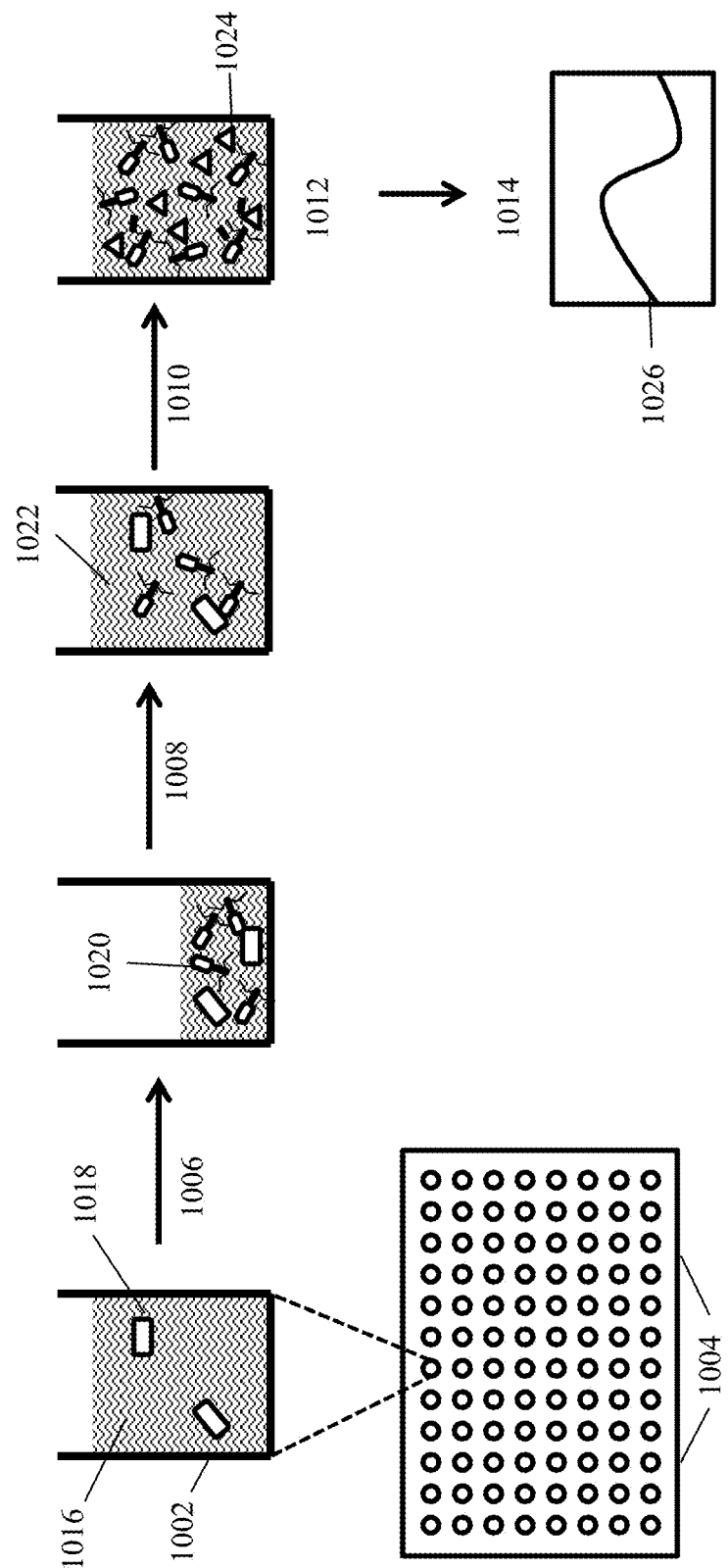
FIG. 10 depicts a filter plate assay for detecting bacteria of interest using a modified bacteriophage according to an embodiment of the invention where bacteria and recombinant phage are incubated on filter plates and after generation of progeny bacteriophage the indicator protein is detected directly without removal of the incubation medium.
Figure 11:
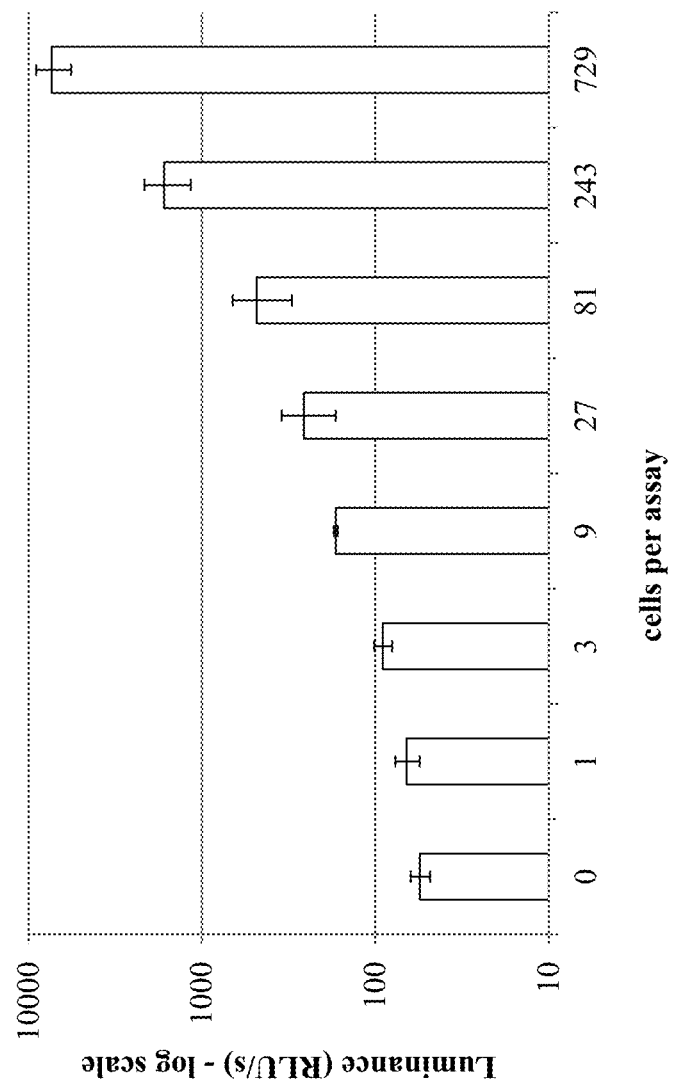
FIG. 11 shows results from a filter plate assay using JG04-NANOLUC® phage to detect E. coli O157:H7 cells in samples with known cell numbers. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

FIG. 10 depicts a filter plate assay for detecting bacteria of interest using a modified bacteriophage according to an embodiment of the invention. An actual experiment utilizing this assay is described in Example 6. Briefly, samples 1016 that include a bacterium of interest 1018 may be added to wells 1002 of a multi-well filter plate 1004 and spun 1006 to concentrate the samples by removal of liquid from the sample. Genetically modified phage 1020 are added to wells and incubated with additional media added for enough time sufficient for adsorption 1008 followed by infection of target bacteria and advancement of the phage life cycle 1010 (e.g., ~45 minutes). Finally, luciferase substrate is added and reacts with any luciferase present 1024. The resulting emission is measured in a luminometer 1014 which detects luciferase activity 1026. FIG. 11 shows results from a filter plate assay as described in FIG. 10, using JG04-NANO-LUC® phage to detect *E. coli* O157:H7 cells in samples with known cell numbers. Student's t-Test showed a p value of 0.034 between 0 cells and 1 cell per assay, demonstrating statistical significance.

Figure 12:
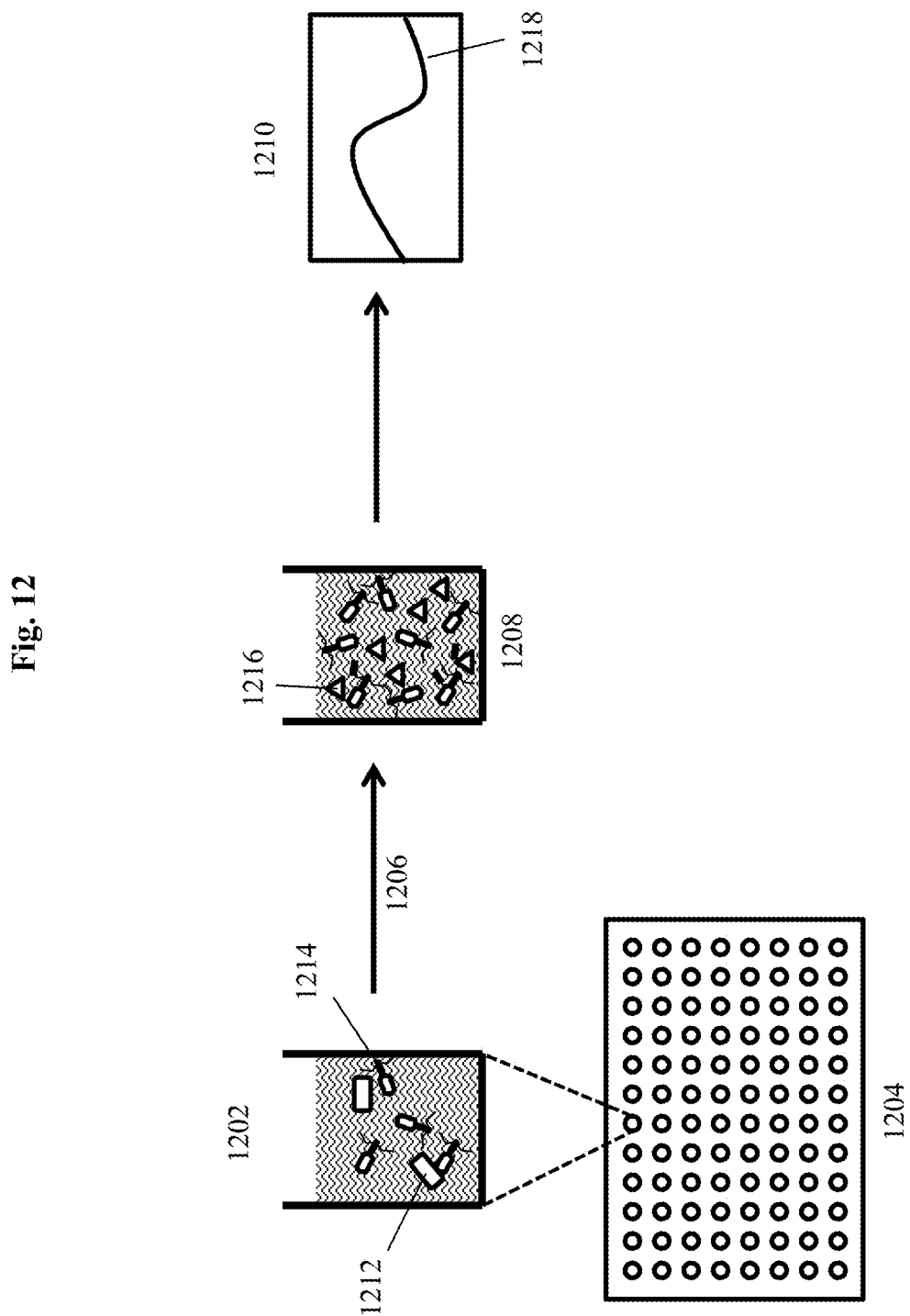
FIG. 12 depicts a "No Concentration Assay" for detecting a bacterium of interest using a modified bacteriophage according to an embodiment of the invention.

In certain embodiments, the assay may be performed without concentrating the bacterium on or near the capture surface. FIG. 12 illustrates a "No Concentration Assay" for detecting a bacterium of interest using a modified bacteriophage according to an embodiment of the invention. Aliquots of indicator phage 1214 are distributed to the individual wells 1202 of a multi-well plate 1204, and then test sample aliquots containing bacteria 1212 are added and incubated 1206 (e.g., 45 minutes at 37° C.) for a period of time sufficient for phage to replicate and generate soluble indicator 1216 (e.g., luciferase). The plate wells 1208 containing soluble indicator and phage may then be assayed 1210 to measure the indicator activity on the plate 1218 (e.g., luciferase assay). Actual experiments utilizing this method are described in Examples 7-9. In this embodiment, the test samples are not concentrated (e.g., by centrifugation) but are simply incubated directly with indicator phage for a period of time and subsequently assayed for luciferase activity.

Figure 13:
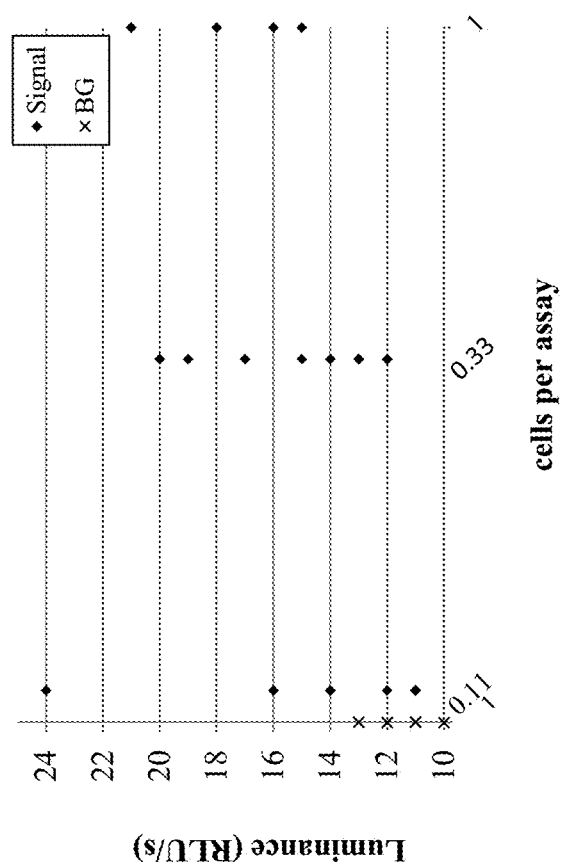
FIG. 13 shows results from a No Concentration Assay using JG04-OpLuc phage to detect E. coli O157:H7 cells in samples with known cell numbers in the low number range. The approximate number of E. coli O157:H7 cells in each assay is indicated on the X-axis. The signal provided by the soluble luciferase produced upon infection of the bacteria is shown on the Y-axis as relative luminal units (RLU) as compared to background (X) signal (i.e., no cells).

FIG. 13 shows results from a No Concentration Assay type assay as depicted in FIG. 12 using JG04-OpLuc phage to detect *E. coli* O157:H7 cells in samples with known cell numbers in the low number range (i.e., very diluted cell samples). This experiment, as described in Example 7, demonstrates that statistically significant differences can be seen between the signal from 0 cells and 1 cell per assay (p value=0.0024 by ANOVA test), demonstrating the ability to detect single cells. Thus the assay is surprisingly sensitive. Samples with fewer than 1 cell per well appear to show a proportional number of wells above the background signal.

Figure 14:
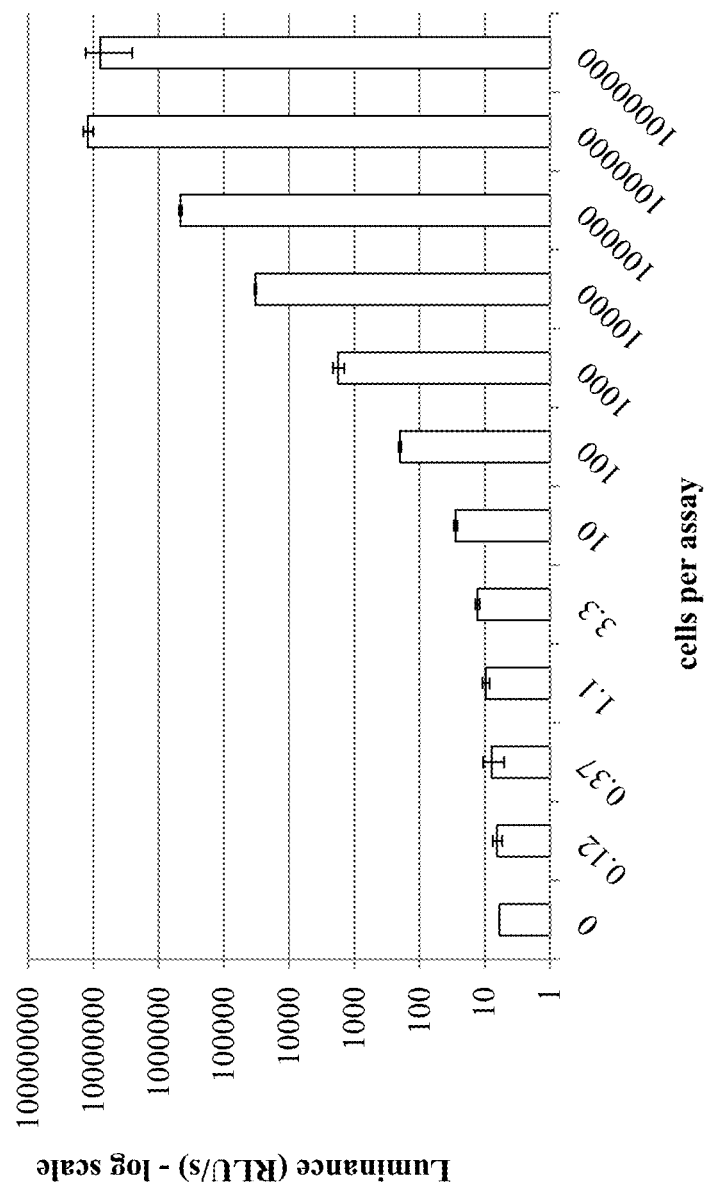
FIG. 14 shows results from a No Concentration Assay using JG04-OpLuc phage to detect E. coli O157:H7 cells in samples with known cell numbers in the low to high number range. The approximate number of E. coli O157:H7 cells in each assay is indicated on the X-axis. The signal provided by the soluble luciferase produced upon infection of the bacteria is shown on the Y-axis as relative luminal units (RLU).

FIG. 14 shows results from a No Concentration Assay using JG04-OpLuc phage to detect *E. coli* O157:H7 cells in samples with known cell numbers in the very low to very high number range (i.e., samples containing less than 1 cell per assay to millions of cells). This experiment, as described in Example 8, demonstrates statistically significant differences between the signal from 0 cells and 1.1 cell per assay (p value=0.000702 by Student's t-Test), demonstrating the ability to detect single cells. More bacterial cells per assay show increasing signal in a dose dependent manner, up to at least $10^6$ bacterial cells/assay, surprisingly demonstrating a very wide range of detection.

Figure 15:
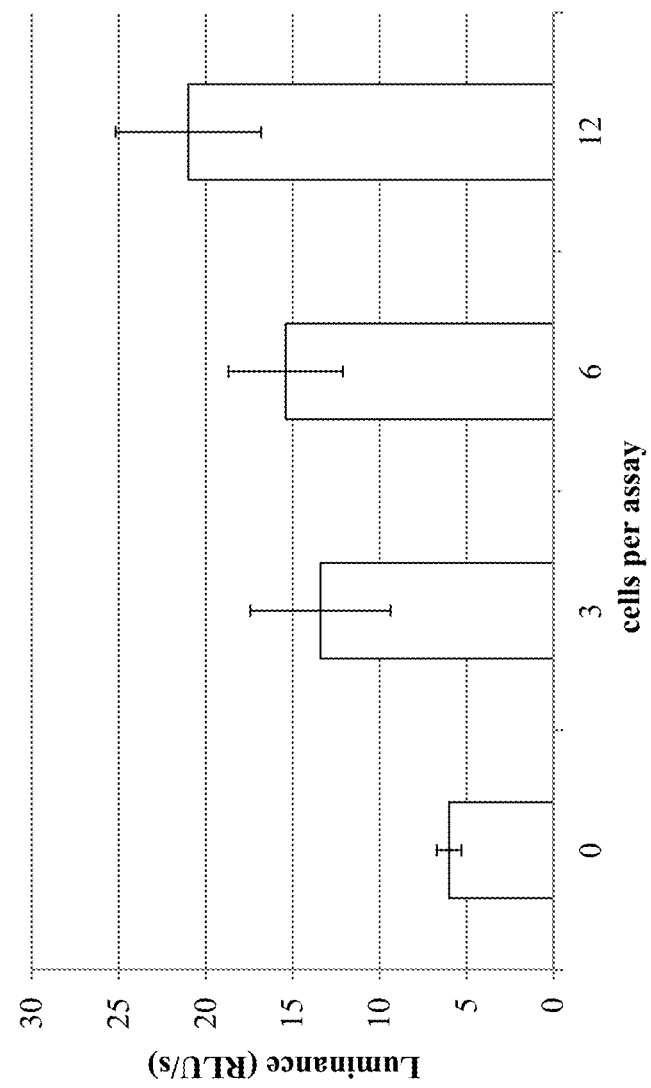
FIG. 15 shows results from a No Concentration Assay using JG04-OpLuc phage to detect E. coli O157:H7 cells in Vegetable Wash samples with known cell numbers. The approximate number of E. coli O157:H7 cells in each assay is indicated on the X-axis. The signal provided by the soluble luciferase produced upon infection of the bacteria is shown on the Y-axis as relative luminal units (RLU).

FIG. 15 shows results from a No Concentration Assay using JG04-OpLuc phage to detect *E. coli* O157:H7 cells in Vegetable Wash samples with known cell numbers, as described in Example 9.

To prepare the vegetable wash, vegetable leaves (e.g., spinach or lettuce) may be weighed and added to a clean plastic bag. One mL of LB (+/−0.01-0.05% TWEEN® 20 (Polysorbate)) was 10 added per each gram (g) of vegetable. Leaves and solution are mixed manually for a few minutes. Liquid is then extracted from the plastic bag and used as the "vegetable wash." Using this method, ~1 million bacteria were found to reside on a single spinach leaf (1-2 g).

The assay is quantitative in that the signal detected is proportional to the amount of the microorganism of interest in the sample. For example, in the experiment depicted in FIG. 15, known numbers of *E. coli* O157:H7 cells were added to vegetable wash samples to simulate contamination of vegetables with pathogenic bacteria. The experiment using vegetable wash samples demonstrates marked differences between the signal from 0 cells and 3 cells per assay, demonstrating the ability to detect single-digit cell numbers in vegetable wash. Using more bacterial cells per assay shows increasing signal in a dose dependent manner. The vegetable wash contains about $10^6$ non-target bacteria/mL, corresponding to at least $10^5$ non-target bacteria per sample in this assay (including the 0 cells *E. coli* O157:H7 control). The ability to discern as few as 3 target bacterial cells from $10^5$ non-target bacteria is surprising and again demonstrates the specificity of the assay.

Capture of the Microorganism Prior to Exposure to Infectious Agent

In some embodiments, the present invention comprises methods and systems that do not require a step for capturing microorganisms. Other embodiments allow physical isolation of bacterial cells from a sample. Methods described herein may serve as means to facilitate detection of low levels of a microorganism (e.g., a single microorganism) present in a sample. A capturing step may be based on a specific binding agent, such as an antibody that recognizes the microorganism of interest, or it may be based on selection for other features of the microorganism, such as size fractionation.

In some embodiments, a microorganism is captured based on physical features other than molecular specificity (e.g., size). In some embodiments, the present invention utilizes the physical size of the microorganism to capture it on a solid support. In some embodiments, the solid support is a filter. For example, filtering a sample through a bacteriological filter (e.g., 0.45 μm pore size spin filter) allows smaller substances to pass through while retaining intact bacteria. Alternatively, a plate filter may be used to capture a microorganism, or a variety of other filter devices may be used (e.g., 96-well filter plate).

For example, the method may include the step of collecting the microorganism on a solid support, such as for example by filtering a sample through a bacteriological filter. After size-based capture, any binding agent that specifically targets the microorganism of interest may be employed. For example, an infectious agent may be incubated with the captured microorganism, in order to specifically target and identify the microorganism of interest. Other methods of isolating the microorganisms in the sample may be used. In some embodiments, detection steps may be performed before, simultaneously with, or after such capture steps.

In some embodiments, binding agents with high specificity for a microorganism of interest may be employed as a means to facilitate specific capture of low levels of a microorganism (e.g., a single microorganism) present in a sample. In some embodiments, a large volume of liquid sample to be tested may need to be effectively concentrated before further testing.

For example, a single bacterium, which may have a volume of about one cubic micrometer, can be isolated from a one-milliliter sample having a volume of $10^{12}$ cubic micrometers. In such embodiments the capturing step may comprise contacting the sample with a plurality (an excess) of affinity-purified capture antibodies or antibody fragments.

Some embodiments utilize affinity-purified and/or reverse-purified surface-specific antibodies or antibody fragments generated against antigenic molecules found on the surface of a specific microorganism of interest. Such antibodies or antibody fragments can specifically identify a microorganism for capture or detection purposes or both. Antibodies demonstrating specific recognition of surface antigens on a wide variety of bacteria or other microorganisms are available commercially from a number of sources, such as Kirkegaard & Perry Laboratories, Inc. (KPL) or Abcam.

In some embodiments of the invention, affinity-purified and/or reverse-purified surface-specific antibodies that recognize the microbial surface antigens of a particular microorganism (e.g., *E. coli* O157:H7) do not recognize other similar microorganisms (e.g., *E. coli* B). In some embodiments, antibodies specific to, e.g., *E. coli* B or *E. coli* O157:H7 do not recognize cells of *Salmonella typhimurium* or *Staphylococcus epidermidis*. This represents another surprising discovery, as many bacteria have, e.g., surface lipopolysaccharide (Gram-negative bacteria) or lipoteichoic acid (Gram-positive bacteria) molecules that were previously believed to be highly similar, especially between closely related species.

Methods for antibody-based capture disclosed herein may be adapted to any bacterium or other microorganism of interest (e.g. pathogenic microorganisms) for which surface-specific antibodies are available which do not cross-react with other microorganisms.

For example, in some embodiments, a capturing step of the invention may use capture antibodies or antibody fragments that are specific for the microorganism to facilitate capture of the microorganism. In some embodiments, capture antibodies may be conjugated to a chemical moiety that binds with another binding agent attached to a solid support (e.g. beads or a plate surface). For example, in some embodiments, the capture antibody may be biotinylated to facilitate binding to streptavidin bound to a solid support. In some embodiments, the solid support comprises magnetic beads. In other embodiments, a solid support comprises a plate surface or the surfaces of a multi-well plate (e.g., an ELISA plate). For example, an ELISA plate may be coated with an antibody that specifically recognizes the microorganism of interest.

In certain embodiments, the microorganism may be isolated from other components of the sample through binding of the microorganism to a free capture antibody or antibody fragment that subsequently binds to a solid support. In some embodiments, the capture antibody or antibody fragment comprises a binding agent (e.g., biotin) that binds to a second agent (e.g., streptavidin) bound to a solid support.

In some embodiments, e.g., if the capture antibody is labeled with biotin, the method may further comprise contacting the sample with a plurality of magnetic streptavidin-coated beads to bind the bacterium-antibody complex, and sequestering the bead-antibody-bacterium complex with a magnet to isolate the bacteria. Or, other methods of purifying the biotin-antibody: bacterium complex may be used. With such embodiments, a bacterium in a one-milliliter sample can be concentrated to about one microliter (~1000-fold), facilitating further detection and/or quantification by methods described herein.

Thus, in some embodiments, the invention comprises a method for detecting a microorganism of interest wherein the capture step comprises specifically isolating the microorganism from other components in the sample.

Alternatively, in some embodiments the capturing step may be based on other features of the microorganism of interest, such as size. In embodiments utilizing size-based capture, the solid support may be a spin column filter. In some embodiments, the solid support comprises a 96-well filter plate. Or, the solid support for capture may be a location on an array, or a mobile support, such as a bead.

Thus, in some embodiments, a target microorganism may be captured and isolated from a large volume before detection using the methods described above. For example, the microorganism may be specifically isolated using attributes of a capture antibody or antibody fragment. In some embodiments, the capture antibody is biotinylated such that it facilitates subsequent binding of cell-antibody complexes to magnetic streptavidin beads. The biotin on the antibody can bind tightly to the streptavidin on the magnetic bead. Or the capture antibody may be conjugated to another protein or other molecule, which facilitates capture on beads or another solid support. Such embodiments may provide increased sensitivity, particularly where the initial sample volume is large. Thus, the method may comprise the steps of attaching a plurality of binding agents that can specifically bind to a surface antigen on the microorganism of interest, which thereby facilitates binding to a capture solid support.

Alternatively, another chemical moiety that binds the anti-bacterium antibody may be used to coat magnetic beads. For example, a bead coated with a secondary antibody that recognizes or binds the anti-bacterium antibody may be used. The bacteria bound to the beads may then be isolated. In an embodiment, the efficiency of capture may be quantified by plating the bacteria bound to the beads and the unbound supernatant fraction and counting the resultant colonies (CFU). In other embodiments, the signal generated by reaction with substrate (i.e., substrate reagent for the indicator moiety) is measured for detection.

In some embodiments, the specificity of antibodies is demonstrated using specific capture on a solid support. A method of the invention may comprise the step of retrieving and concentrating a microorganism (e.g., a bacterium) from a sample by the use of a substrate with a binding agent specific for the microorganism. In an embodiment, the binding agent is immobilized on a solid support (e.g. magnetic beads) or is free and subsequently immobilized on a solid support. The immobilized microorganism may then be removed from the sample (e.g., by aspiration, decanting, magnetic force, or other appropriate isolation techniques) and detected by a variety of techniques.

Figure 16:
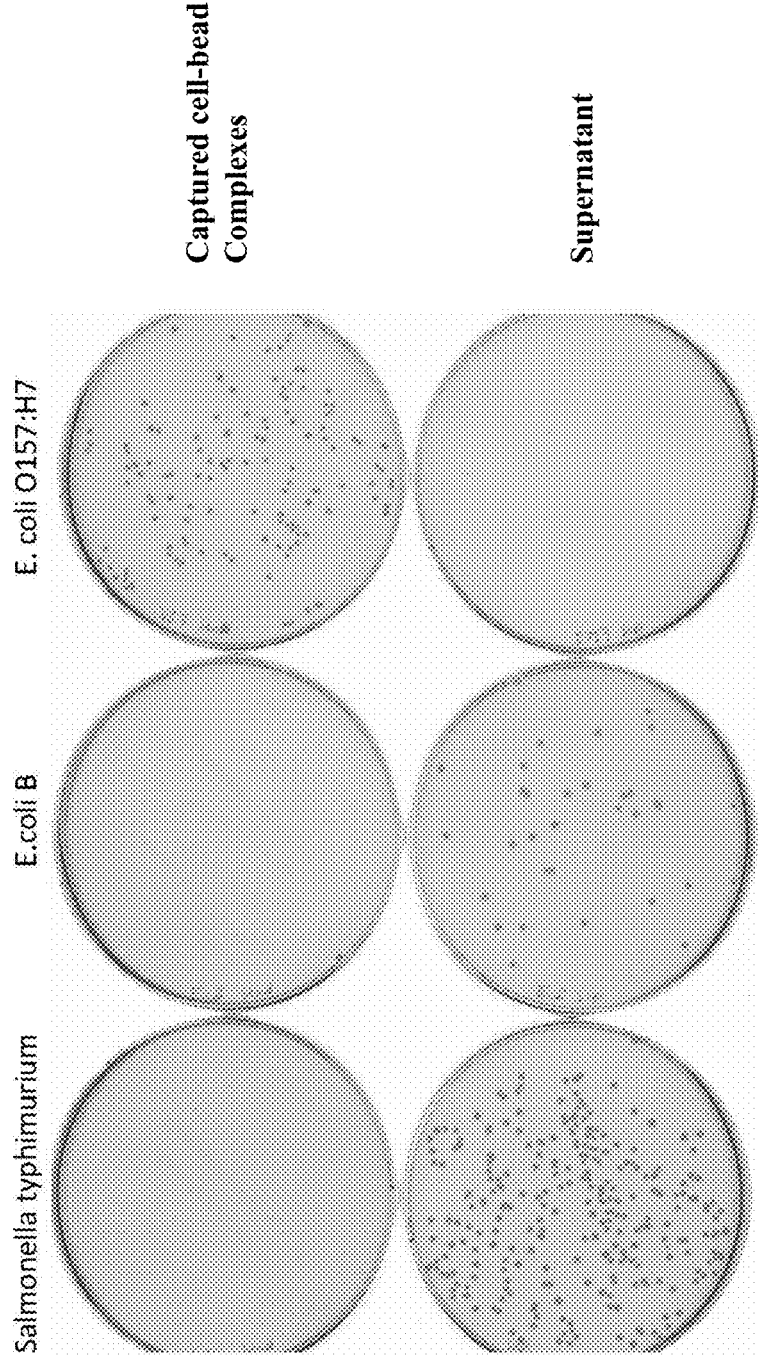
FIG. 16 demonstrates specific and quantitative capture of E. coli O157:H7 using affinity-purified, surface-specific antibodies, according to an embodiment of the invention.

FIG. 16 depicts an example embodiment of specific capture of $E.$ $coli$ O157:H7 but not $E.$ $coli$ B or $S.$ $typhimurium$ from samples by the use of antibodies produced against intact $E.$ $coli$ O157:H7. Thus, in certain embodiments magnetic beads coated with streptavidin may be used to isolate $E.$ $coli$ O157:H7 preincubated with free biotinylated polyclonal antibodies (KPL), affinity-purified and reverse-purified to minimize cross-reactivity with other microbial species. In certain embodiments, the $E.$ $coli$ O157:H7 will only be present in the captured fraction (i.e., bead fraction) when specific $E.$ $coli$ O157:H7 antibodies were used, and no bacteria will be recovered in the supernatant (unbound) fraction. In certain embodiments, $E.$ $coli$ B and $S.$ $typhimurium$ cells are found only in the supernatant fraction when $E.$ $coli$ O157:H7-specific antibodies are used, illustrating the remarkable specificity of these antibodies. In the absence of antibody, all three types of bacteria were found in the supernatant fraction.

Hybrid Immuno-Phage (HIP) Assay

In certain embodiments, the methods of the present invention combine the use of a binding agent (e.g., antibody) to purify and/or concentrate a microorganism of interest from the sample in addition to detection with an infectious agent. For example, in certain embodiments, the present invention comprises a method for detecting a microorganism of interest in a sample comprising the steps of: capturing the microorganism from the sample on a prior support using a capture antibody specific to the microorganism of interest; incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that the microorganism of interest is present in the sample.

Figure 17:
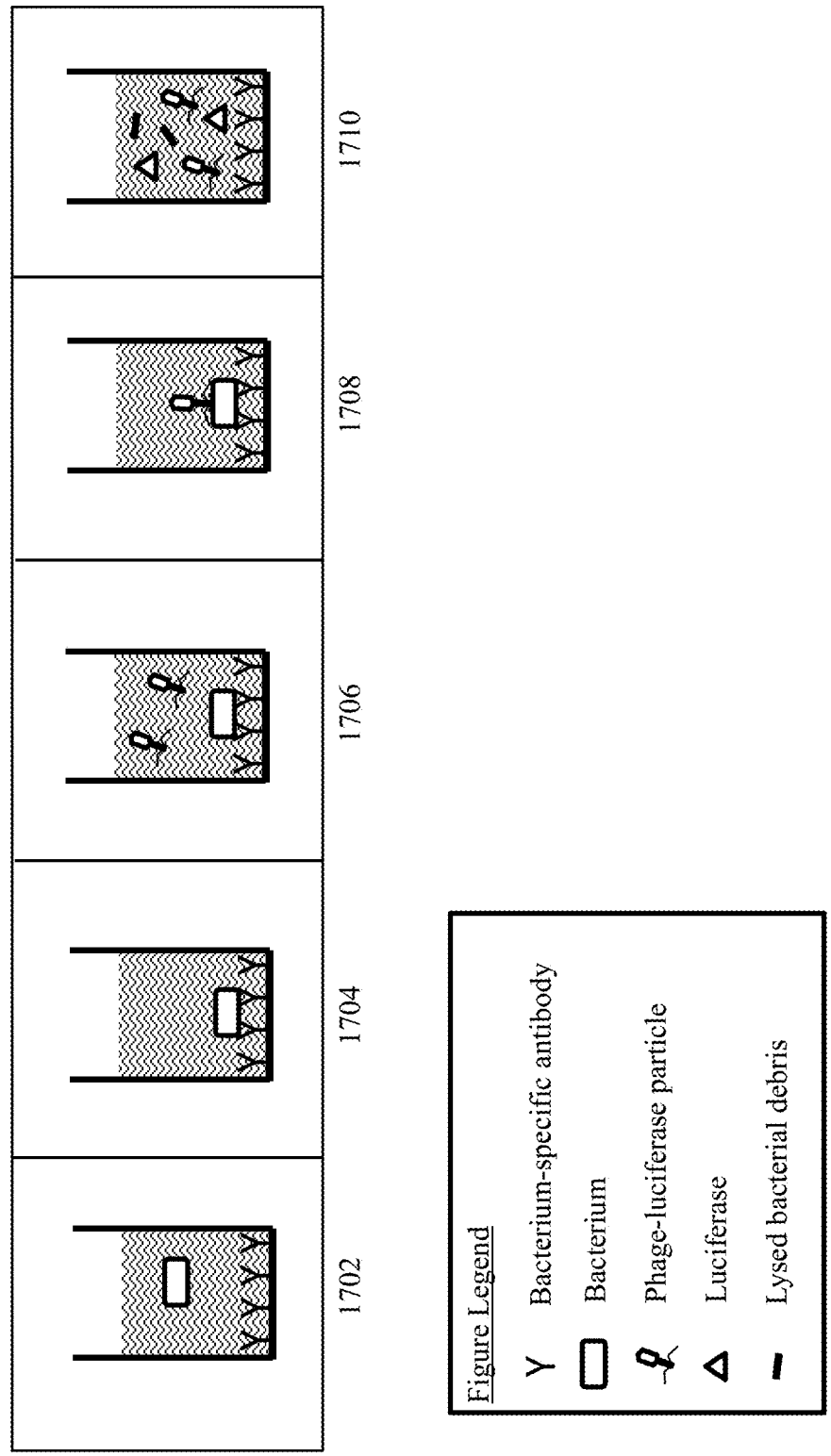
FIG. 17 depicts a Hybrid Immuno-Phage (HIP) Assay for detecting a bacterium of interest using a modified bacteriophage according to an embodiment of the invention wherein antibodies to the microorganism of interest are used to capture the microorganism on the surface of the assay well prior to incubation with a recombinant infectious agent having an indicator gene.

For example, FIG. 17 depicts a Hybrid Immuno-Phage (HIP) Assay for detecting a bacterium of interest using a modified bacteriophage according to an embodiment of the invention. The sample is first applied to the microtiter plate well coated with bacterium-specific antibodies 1702. The plate is then centrifuged to facilitate binding of the bacterium to the capture antibodies 1704. Following sufficient time to allow for complete bacteria capture, a solution containing bacterium-specific NANOLUC®-phage is added to each sample 1706. Incubation with the phage results in the binding and attachment of a single or multiple phages to the captured bacterium 1708. Finally, the sample is incubated to facilitate phage replication and luciferase expression, which leads to cell lysis and release of soluble luciferase 1710.

Figure 18:
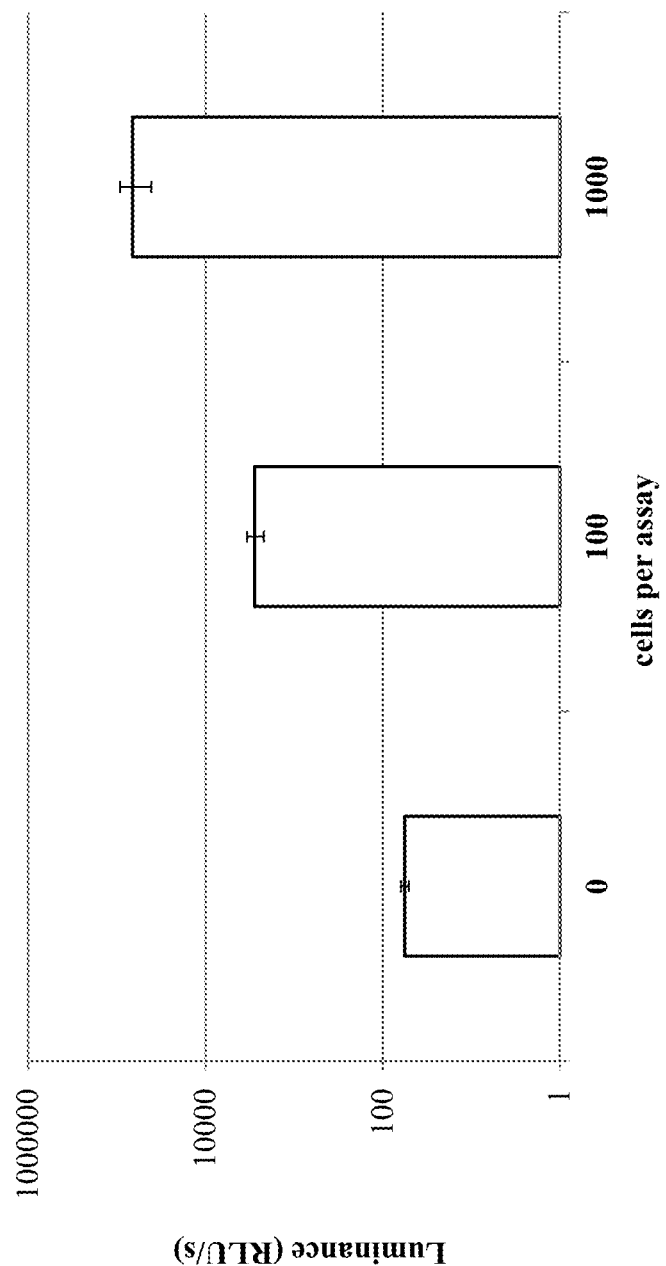
FIG. 18 shows results from a HIP assay using JG04-NANOLUC® phage to detect E. coli O157:H7 cells in samples with known cell numbers, on a logarithmic scale. The approximate number of E. coli O157:H7 cells in each assay is indicated on the X-axis. The signal provided by the soluble luciferase produced upon infection of the bacteria is shown on the Y-axis as relative luminal units (RLU).

FIG. 18 shows results from a HIP assay using JG04-NANOLUC® phage to detect $E.$ $coli$ O157:H7 cells in samples with known cell numbers, as described in Example 11, on a log scale. The HIP assay was able to detect 100 and 1,000 $E.$ $coli$ O157:H7 cells in LB media with approximately $2 \times 10^6$ PFU JG04-NANOLUC® phage. The average signal over a no-cell sample ranged from approximately 50-fold for the 100 cell sample to over 1,000-fold for the 1,000 cell sample.

In some embodiments, the incubating step of the methods described herein comprises a final bacteriophage concentration of greater than $7 \times 10^6$, $8 \times 10^6$, $9 \times 10^6$, $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $3.0 \times 10^7$, $4.0 \times 10^7$, $5.0 \times 10^7$, $6.0 \times 10^7$, $7.0 \times 10^7$, $8.0 \times 10^7$, $9.0 \times 10^7$, or $1.0 \times 10^8$ PFU/mL. This high phage concentration was previously purported to be detrimental to such an assay, and thus yields surprising results. In some embodiments, the methods of the invention require less than 3 hours, less than 2.5 hours, less than 2 hours, less than 1.5 hours, or less than 1 hour for detection of a microorganism of interest. In some embodiments, the methods can detect as few as 100, 50, 20, 10, 9, 8, 7, 6, 5, 4, 3, or 2 cells of the microorganism of interest. These are shorter timeframes than were previously thought possible. In some embodiments, even a single cell of the microorganism is detectable. In additional embodiments, the invention comprises systems (e.g., computer systems, automated systems or kits) comprising components for performing the methods disclosed herein, and/or using the modified infectious agents described herein.

Systems and Kits of the Invention

In some embodiments, the invention comprises systems (e.g., automated systems or kits) comprising components for performing the methods disclosed herein. Some embodiments described herein are particularly suitable for automation or kits, given the minimal amount of reagents and materials required to perform the methods. In certain embodiments, each of the components of the a kit may comprise a self-contained unit that is deliverable from a first site to a second site.

In some embodiments, the invention comprises a systems or kits for rapid detection of a microorganism of interest in a sample. The systems or kits may in certain embodiments comprise a component for incubating the sample with an infectious agent specific for the microorganism of interest, wherein the infectious agent comprises an indicator moiety and a component for detecting the indicator moiety. In some embodiments of both the systems and the kits of the invention, the infectious agent is a recombinant bacteriophage that infects the microorganism of interest, and the recombinant bacteriophage comprises an indicator gene inserted into a late gene region of the bacteriophage as the indicator moiety such that expression of the indicator gene during bacteriophage replication following infection of host bacteria results in a soluble indicator protein product. Some systems further comprise a component for capturing the microorganism of interest on a solid support.

In certain embodiments, the systems and/or kits may further comprise a component for washing the captured microorganism sample. Additionally or alternatively, the systems and/or kits may further comprise a component for determining amount of the indicator moiety, wherein the amount of indicator moiety detected corresponds to the amount of microorganism in the sample. For example, in certain embodiments, the system or kit may comprise a luminometer or other device for measuring a luciferase enzyme activity.

In some systems and/or kits, the same component may be used for multiple steps. In some systems and/or kits, the steps are automated or controlled by the user via computer input and/or wherein a liquid-handling robot performs at least one step.

Thus in certain embodiments, the invention may comprise a system for rapid detection of a microorganism of interest in a sample, the system comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism in the sample. Such systems can include various embodiments and subembodiments analogous to those described above for methods of rapid detection of microorganisms. In an embodiment, the microorganism is a bacterium and the infectious agent is a bacteriophage. In a computerized system, the system may be fully automated, semi-automated, or directed by the user through a computer (or some combination thereof).

In some embodiments, the system may comprise a component for isolated the microorganism of interest from the other components in the sample.

In an embodiment, the invention comprises a system comprising components for detecting a microorganism of interest comprising: a component for isolating at least one microorganism from other components in the sample; a component for infecting the at least one microorganism with a plurality of a parental infectious agent; a component for lysing the at least one infected microorganism to release progeny infectious agents present in the microorganism; and a component for detecting the progeny infectious agents, or a constituent of the progeny infectious agents, wherein detection of the infectious agent or a constituent of the infectious agent, indicates that the microorganism is present in the sample.

The systems may comprise a variety of components for detection of progeny infectious agents. For example, in an embodiment, the progeny infectious agent (e.g., bacteriophage) may comprise an indicator moiety. In an embodiment, the indicator moiety in the progeny infectious agent (e.g., bacteriophage) may be a detectable moiety that is expressed during replication, such as a soluble luciferase protein.

In other embodiments, the invention may comprise a kit for rapid detection of a microorganism of interest in a sample, the system comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism in the sample. Such kits can include various embodiments and subembodiments analogous to those described above for methods of rapid detection of microorganisms. In an embodiment, the microorganism is a bacterium and the infectious agent is a bacteriophage.

In some embodiments, the kit may comprise a component for isolated the microorganism of interest from the other components in the sample.

In an embodiment, the invention comprises a kit comprising components for detecting a microorganism of interest comprising: a component for isolating at least one microorganism from other components in the sample; a component for infecting the at least one microorganism with a plurality of a parental infectious agent; a component for lysing the at least one infected microorganism to release progeny infectious agents present in the microorganism; and a component for detecting the progeny infectious agents, or a constituent of the progeny infectious agents, wherein detection of the infectious agent or a constituent of the infectious agent, indicates that the microorganism is present in the sample.

The kits may comprise a variety of components for detection of progeny infectious agents. For example, in an embodiment, the progeny infectious agent (e.g., bacteriophage) may comprise an indicator moiety. In an embodiment, the indicator moiety in the progeny infectious agent (e.g., bacteriophage) may be a detectable moiety that is expressed during replication, such as a soluble luciferase protein.

These systems and kits of the invention include various components. As used herein, the term "component" is broadly defined and includes any suitable apparatus or collections of apparatuses suitable for carrying out the recited method. The components need not be integrally connected or situated with respect to each other in any particular way. The invention includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

Some of the embodiments of the technology described herein can be defined according to any of the following numbered paragraphs:

(1) A recombinant bacteriophage comprising an indicator gene inserted into a late gene region of the bacteriophage, and optionally wherein the late gene region is a class III gene region, and optionally wherein transcription of the indicator gene is controlled by a bacteriophage class III or "late" promoter.

(2) The recombinant bacteriophage of paragraph 1, wherein the bacteriophage is derived from T7, T4, T4-like, JG04, or another natural bacteriophage having a genome with at least 90% homology to T7, JG04, T4, or other T4-like phage; and/or wherein the amount of indicator moiety detected corresponds to the amount of the microorganism of interest present in the sample.

(3) The bacteriophage of any of paragraphs 1-2, wherein the indicator gene does not encode a fusion protein and/or wherein the indicator gene is adjacent to a major capsid gene, and optionally wherein expression of the indicator gene during bacteriophage replication following infection of a host bacterium results in a soluble indicator protein product.

(4) The bacteriophage of any of paragraphs 1-3, wherein the indicator gene encodes a luciferase enzyme, and optionally wherein the luciferase is one of Oplophorus luciferase, Firefly luciferase, or an engineered luciferase.

(5) A method for detecting a microorganism of interest in a sample comprising the steps of: incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that the microorganism of interest is present in the sample.

(6) The method of paragraph 5, wherein the late gene region is a class III gene region, and optionally wherein transcription of the indicator gene is controlled by a bacteriophage class III promoter.

(7) The method of paragraph 5 or 6, wherein the bacteriophage is derived from T7, T4, T4-like, JG04, or another natural bacteriophage having a genome with at least 90% homology to T7, T4 or other T4-like phage, and/or wherein the amount of indicator moiety detected corresponds to the amount of the microorganism of interest present in the sample.

(8) The method of any of paragraphs 5-7, wherein the indicator gene does not encode a fusion protein and/or wherein the indicator gene is adjacent to a major capsid gene, and optionally wherein expression of the indicator gene during bacteriophage replication following infection of a host bacterium results in a soluble indicator protein product.

(9) The method of any of paragraphs 5-8, wherein the indicator gene encodes a luciferase enzyme, and optionally wherein the luciferase is one of Oplophorus luciferase, Firefly luciferase, or an engineered luciferase.

(10) The method of any of paragraphs 5-9, wherein the bacteriophage concentration for the incubating step is greater than $1 \times 10^7$ PFU/mL, and optionally wherein the recombinant bacteriophage is purified using cesium chloride isopycnic density gradient centrifugation prior to incubation with the sample.

(11) The method of any of paragraphs 5-10, further comprising a step for capturing the microorganism from the sample on a solid support before the incubating step; and optionally wherein the solid support comprises a multi-well plate or a filter; and optionally wherein the capturing step further comprises binding microorganism with a capture antibody; and optionally wherein the capture antibody facilitates binding of the microorganism to the solid support; and optionally wherein the method further comprises a step for washing the captured and infected microorganism, after adding the bacteriophage but before incubating, to remove excess bacteriophage and/or contaminating reporter protein, such as luciferase.

(12) The method of any of paragraphs 5-11, wherein detection of the microorganism of interest is completed in less time than a time period required for increasing the number of microorganisms by 4-fold or 10-fold using culturing for enrichment; and optionally wherein the method can detect ≤10 cells of the microorganism in the sample; and optionally wherein the total time required for detection is less than 2 hours.

(13) A system for rapid detection of a microorganism of interest in a sample, comprising: a component for incubating the sample with an infectious agent specific for the microorganism of interest, wherein the infectious agent comprises an indicator moiety; and a component for detecting the indicator moiety; and optionally further comprising a component for determining amount of the microorganism of interest in the sample, wherein the amount of indicator moiety detected corresponds to the amount of microorganism in the sample; and optionally further comprising a component for capturing the microorganism of interest on a solid support, and/or further comprising a component for washing the captured microorganism sample, and optionally wherein the same component may be used for multiple steps.

(14) The system of paragraph 13, wherein the infectious agent is a recombinant bacteriophage that infects the microorganism of interest, wherein the recombinant bacteriophage comprises an indicator gene inserted into a late gene region of the bacteriophage as the indicator moiety such that expression of the indicator gene during bacteriophage replication following infection of host bacteria results in a soluble indicator protein product; and optionally wherein the steps are automated or controlled by the user via computer input and/or wherein a liquid-handling robot performs at least one step; or wherein the system comprises a kit.

(15) Non-transient computer readable media for use with the method of any of paragraphs 5-12 and/or the system of any of paragraphs 13-14.

EXAMPLES

Results depicted in the following examples, except for example 11, were obtained without culturing for enrichment or without incubation of the sample to achieve replication of sample cells. Further, in the "no concentration assay," indicator phage added directly to a sample, without concentrating the cells, could infect and detect a low number of cells, even a single bacterium.

Example 1

Creation of Indicator Phage

Indicator Phage were created using the T7SELECT®415-1 phage display system from Millipore, Inc. Briefly, purified T7SELECT® DNA was purchased and digested with DNA restriction enzymes EcoRI and HindIII (New England Biolabs), and the cut DNA was subsequently purified. The gene for wild-type Firefly luciferase (from the common Eastern firefly, *Photinus pyralis*) was synthesized with a bacteriophage T7 upstream region including the late T7 promoter, to ensure high levels of expression of the luciferase gene.

The synthesized luciferase gene is designated SEQ ID NO. 1. This gene was amplified by PCR to include compatible restriction enzyme recognition sites for EcoRI and HindIII to ensure the new gene could be inserted into the T7SELECT®415-1 genome, using the following primers:

```
TATCTGAATTCTAAGTAACTGATAATACGACTCACTATAGGGAGACCA
CAAC, designated SEQ ID NO. 2,
and AATGA AAGCTT TTACAATTTGGACTTTCCGCCCTTCTTGG,
designated SEQ ID NO. 3.
```

Additionally, stop codons in all 3 reading frames were added upstream of the luciferase start site, to terminate production of the bacteriophage major capsid protein, the gene 10B 25 product. The T7SELECT®415-1 phage display system is designed to create a fusion product of the gene 10B major capsid protein and any small protein inserted downstream of it. The addition of the stop codons ensures no fusion product is made, and allows the relatively large luciferase gene to be expressed in soluble form. The PCR product was digested with EcoR1 and HindIII, purified, and ligated into the T7SELECT®415-1. The ligation product was inserted into MegaX DH10B electrocompetent cells (Invitrogen) using a BIORAD® MicroPulser electroporation system, and the culture plated on *E. coli* for plaques. Plaques were picked, and phage were grown in *E. coli* DH10B and purified via sucrose density gradient centrifugation for use as Indicator Phage, T7SELECT®415-Luc.

FIG. 1 depicts the genomic structure of an example Indicator Phage, T7SELECT0415-Luc. The detectable indicator moiety is encoded by the Firefly luciferase gene inserted within the Class III gene region, expressed late in the viral life cycle and at higher levels than other phage genes. The construct contains stop codons to ensure the luciferase is not incorporated into a native gene product, such as the capsid protein gene 10B, and is thus also not a fusion protein. Thus this construct allows progeny phage to express soluble Firefly luciferase as the indicator to be detected.

Example 2

Isolation and Purification of *E. coli* O157:H7 Specific Bacteriophage from the Environment Samples from the Hyperion Sewage Treatment Plant were obtained along with water samples from the neighboring Ballona wetlands. The samples were mixed with powdered Nutrient Broth (Gibco, Inc.) to 1× and inoculated with *E. coli* O157:H7 (ATCC 43888) from 3 mL of turbid culture. The sample was incubated for 3 hours @ 37° C. with shaking to enrich for phage that infect *E. coli* O157:H7, lysed with 120 μL chloroform, vortexed for 15 seconds, and a 1 mL sample was centrifuged for 2 minutes at 6800 g. The supernatants were filtered (0.45 μm filter) and plated for plaques on *E. coli* O157:H7. This sample was plated out in plaque assays in various dilutions to obtain well isolated plaques. Individual plaques were stabbed with disposable pipette tips and resuspended in 100 μL TMS buffer (50 mM Tris-HCl, pH 7.4, 10 mM $MgCl_2$, and 100 mM NaCl).

Aliquots of 5 μL of resuspended plaques were spot-tested in overlay agar on *E. coli* strains O157:H7, B, and DH10B, and on a strain of *Salmonella*. Phage that only cleared O157:H7 were amplified in *E. coli* O157:H7, the lysates clarified by centrifugation, and the particles put into TMS buffer using ZEBA® Buffer Exchange columns.

Eight closely related phage isolates were grown on *E. coli* O157:H7, purified, and the genomes isolated and sequenced. Three genomic types all showed 98% homology to the T4-like phage RB69. The late genes were mapped based on this homology, and phage JG04 was selected for further study. FIG. 2 shows JG04, and the genome of JG04 is designated SEQ ID NO. 4.

Example 3

Creation and Purification of Recombinant Indicator Phage

Based on sequence analysis and location of the late gene region, homologous recombination sequences were synthesized with inserts for various reporter genes, consisting of different luciferase proteins, as shown in FIG. 3. Specifically, three constructs were used: Firefly luciferase homologous recombination plasmid, pUC57.HR.Fluc, corresponding to SEQ ID NO. 5; NANOLUC® Homologous Recombination Plasmid, pUC57.HR.NANOLUC® corresponding to SEQ ID NO. 6; and Oplophorus Luciferase Homologous Recombination Plasmid, pUC19.HR.OpLuc.KanR, corresponding to SEQ ID NO. 7.

Luciferase genes were inserted with an upstream T4 late gene promoter, to ensure expression during the viral late stage. In some cases, a kanamycin resistance marker was also inserted to allow for selection of infected cells under the kanamycin antibiotic. These regions were flanked with up to 500 bp of sequence matching the capsid proteins, gp23 and gp24. These synthesized sequences were carried by the Ampicillin resistant pUC57 or pUC19 plasmid.

Plasmids containing the synthesized sequences were transformed into electroporation competent *E. coli* O157:H7 using a BIORAD® Gene Pulser II electroporator, conferring resistance to Ampicillin. Colonies were screened for positive transformation by assaying with the appropriate luciferase substrate (D-luciferin for Firefly luciferase, coelenterazine for Oplophorus luciferase, and either coelenterazine or NANOGLO® for NANOLUC®). *E. coli* O157:H7 harboring a plasmid with luc flanked by sequences homologous with phage JG04 were grown in Ampicillin-containing LB broth bacterial cultures were grown in Ampicillin containing LB broth to approximately $10^7$ cells/mL. Cultures were then infected with phage JG04 at an MOI of 1 and incubated for 45 minutes at 37° C. with shaking to lyse cells. Lysates contained a mixture of mostly wild-type phage with a minority of recombinant phage created by homologous recombination of the wild-type phage genome with the homologous recombination plasmid.

In order to determine the ratio of recombinant to wild-type phage, limiting dilution assays based on the TCID50 (tissue culture infectious dose 50%) were used to both determine the concentration of infectious units (IU/mL), akin to number of virus particles or plaque forming units, and to determine the number of luciferase transducing units (TU/mL). In these assays, the sample was serially diluted, with each dilution aliquoted into replicates wells with *E. coli* O157:H7 bacteria. Any wells that show luciferase activity must have been infected with at least one recombinant phage. Any wells that showed cell lysis had been infected by at least one phage. Based on the highest dilution where each of these cases occurred, the original concentrations were back-calculated. These initial phage mixtures from transformed cells typically yielded a ratio of 20,000 wild-type IU for each recombinant phage TU. Steps were then taken to isolate and amplify the recombinant phage.

As illustrated in FIG. 4, recombinant phage were isolated from a mixture comprising 0.005% of total phage. The phage mixtures were diluted into 96 well plates to give an average of 3 recombinant TU per plate, which breaks down to about 625 IU of mostly wild-type phage per well. Each well contained 50 μL of turbid *E. coli* O157:H7. After 2 hours of incubation at 37° C., wells were sampled and screened for the presence of luciferase. Any positive wells would likely have been inoculated with a single recombinant phage, and ~600 wild-type phage, which is an enrichment over the original 20,000:1 ratio. Progeny from this enriched culture was subjected to another limiting dilution assay to verify the ratio and determine the actual concentration of recombinant phage transducing units.

Again, 3 recombinant TU per 96-well plate were aliquoted from this stock, leading to an approximate inoculation of ~20 mostly wild-type phage per well. Any positive luciferase wells were likely to have been inoculated with a single recombinant along with ~20 wild-type phage. These wells were analyzed for luciferase activity, and any positive wells were subjected to the limiting dilution assay to determine the ratio of TU to IU, then to plaque assay to obtain well-isolated plaques.

At this point, the expected ratio of wild-type to recombinants was about 20:1. 48 plaques were individually picked and screened for luciferase transducing ability, insuring about 3 recombinants were in the mix of plaques being screened. Each plaque was suspended in 100 μL TMS, and 5 μL was added to a well containing a turbid *E. coli* O157:H7 culture, and wells were assayed after incubation for 45 minutes to 1 hour at 37° C.

Positive wells were expected to contain a pure culture of recombinant phage, but an additional round of plaque purification was standard procedure. Large scale production was performed to obtain high titer stocks appropriate for use in the *E. coli* O157:H7 detection assay. Cesium chloride isopycnic density gradient centrifugation was used to separate phage particles from contaminating luciferase protein to reduce background.

Example 4

Bacterial Detection Via Indicator Phage Using Spin Column Filters

FIG. 5 illustrates use of indicator phage and spin column filters for bacterial detection, according to an embodiment of the invention. In an example experiment, *E. coli* DH10B was grown in Luria-Bertani broth (LB) at 37° C. with shaking T7SELECT® 415-Luc phage were diluted to $10^8$ PFU/40 μL ($2.5 \times 10^9$ PFU/mL). Cells were counted and diluted to 3000, 300, 30 and 3 cells/mL. A CFU assay was performed in parallel with the following luciferase assay to determine the actual number of input cells per assay.

For each cell dilution, 0.1 mL was added to filters in triplicate. Filters were spun at 600 g for 1 minute. Next, 40 μL of each of the phage dilution was added to each filter, followed by incubation for 10 min at room temperature. Filters were washed twice by addition of 400 μL PBST (0.05% TWEEN® (Polysorbate)), followed by centrifugation at 600 g for 1 minute. Next 50 μL LB was added, followed by incubation for 30 minutes at 37° C. Filters were spun at 6800 g for 2 minutes. Next, 30 μL of the filtrate was transferred to a LUMITRAC® 200 96-well luminometer plate, and a luciferase assay was performed in a Promega luminometer with injection of 100 μL Luciferase Assay Reagent (Promega, Inc.). Cell count was corrected according to the number of colonies in the parallel CFU assay. The signal to background ratio was obtained by dividing each well's signal by the average of signal from zero cell controls. FIG. 6 shows results demonstrating high sensitivity of the assay for detecting as few as 1 to 3 *E. coli* cells, via luciferase activity. FIG. 7 shows results demonstrating the very large detection range of the same method using serial dilutions of the starting bacterial sample. This shows detection from an average of 1.4 cells to 14 million cells.

Example 5

Bacterial Detection Via Indicator Phage Using 96-Well Filter Plates

*E. coli* DH10B was grown in LB at 37° C. with shaking T7SELECT®415-Luc phage were diluted to $4\times10^7$ PFU/20 µL in LB ($2\times10^9$ PFU/mL). Cells were counted and diluted to 500, 50 and 5 cells/mL (0.1 mL was added to each wells, giving ~50, 5 and <1 cells shown in FIG. 5). A CFU assay was performed in parallel with the following luciferase assay to determine the actual number of input cells per assay.

For each cell dilution, 0.1 mL was added to multiple wells in a 96-well filter plate: 9 wells for 0.5 cells and 3 wells for 50 cells, 5 cells and the zero cell control. The 96-well filter plate was spun at 1200 rpm (263 rcf) for 3 minutes. Next 20 µL of the phage dilution was added to each filter and incubated for 10 minutes at room temperature, followed by 30 minutes at 37° C. The luciferase assay was performed directly in the original filter plate with 100 µL Luciferase Assay Reagent (Promega, Inc.) injection using a Promega Luminometer, and plates were read immediately following injection and reread at 15 and 30 minutes thereafter. Cell count was corrected according to the number of colonies in the parallel CFU assay. Signal to background ratios were obtained by dividing each well's signal by the average of signal from zero cell controls.

FIG. 8 shows results demonstrating the use of the 96-well filter plate for detecting single *E. coli* cells in each well (0.5 cells on average were assayed, such that about one-half of the wells received single cells), and 5.4 and 54 cells per well.

FIG. 9 shows results demonstrating a very large cell detection range, using the 96-well filter plate system, from less than 1 cell per well on average (single cells) to at least 14 million cells per well.

Example 6

Filter Plate Assay Using JG04-NANOLUC® Indicator Phage and Low Cell Concentration

*E. coli* O157:H7 cells were grown in LB at 37° C. with 220 rpm shaking JG04-NANOLUC® Indicator Phage were prepared to $10^6$ PFU/20 µL. Cells were counted and diluted to 7290, 2430, 810, 270, 90, 30, 10 and 0 cells/mL. Aliquots of 100 µL of each sample were deposited into wells of a PERKINELMER® Optiplate 96-well Grey Luminometer 0.45 µm filter plate in replicates.

As illustrated in FIG. 10, plates were loaded into a swinging bucket centrifuge and spun at 2400 rpm for 3 minutes. 20 µL of JG04-NANOLUC® phage dilution was added to each well, giving a final concentration of $5\times10^7$ PFU/mL. Plates were incubated for 10 minutes at room temperature, 200 µL PBST was added to each well, and plates were spun down for 3 minutes at 2400 rpm to wash away excess parental JG04-NANOLUC® phage.

Next, 50 µL LB was added to each well and plates were incubated for 45 minutes in a 37° C. incubator without shaking Aliquots of 10 µL Promega Renilla Luciferase Lysis Buffer were added to wells, analyte was transferred to the wells, and luciferase assay was performed with 50 µL Promega NANOGLO® Reagent injection. Samples with cells were compared to 0 cell controls.

As seen in FIG. 11, the NANOLUC® Filter Plate results show statistically significant differences between the signal from 0 cells and 1 cell/assay (p value=0.034 by Student's t-Test), demonstrating the ability to detect single cells. More bacterial cells per assay show increasing signal in a dose dependent manner.

Example 7

No Concentration Assay with Low Cell Concentrations

In preparation for an experiment similar to the assay illustrated in schematic FIG. 12, *E. coli* O157:H7 cells were grown in LB at 37° C. with 220 rpm shaking JG04-OpLuc Indicator Phage were prepared to $1.2\times10^7$ PFU/20 µL, and 20 µL aliquots were distributed to wells of a PERKINELMER® Optiplate 96-well Grey Luminometer plate. Cells were counted and diluted to 10, 3.3, 1.1 and 0 cells/mL. Aliquots of 100 µL of each sample were distributed into wells in replicates (12× for 0.11 and 0.33 cells/assay and 5× for 1 cell/assay), giving a final phage concentration of $10^8$ PFU/mL.

Plates were incubated for 45 minutes in a 37° C. incubator without shaking Finally, 10 µL PROMEGA® Renilla Luciferase Lysis Buffer was added to each well, and the luciferase assay was performed with 50 µL PROMEGA® Renilla Luciferase Assay Reagent (coelenterazine) injection. Samples were compared to 0 cell controls.

As seen in FIG. 13, the No Concentration Assay with low cell concentration samples results show statistically significant differences between the signal from 0 cells and 1 cell/assay (p value=0.0024 by ANOVA test), demonstrating the ability to detect single cells. Thus the assay is surprisingly sensitive. Samples with fewer than 1 cell per well appear to show a proportional number of wells above the background signal.

Example 8

No Concentration Assay with Wide Cell Concentration Range

In a similar experiment with higher cell concentrations, *E. coli* O157:H7 cells were grown in LB at 37° C. with 220 rpm shaking JG04-OpLuc Indicator Phage were prepared to $1.2\times10^7$ PFU/20 µL, and 20 µL aliquots were distributed to wells of a PERKINELMER® Optiplate 96-well Grey Luminometer plate. Cells were counted and diluted to $10^8$, $10^7$, $10^6$, $10^5$, $10^4$, $10^3$, $10^2$, 33, 11, 3.7, 1.2 and 0 cells/mL. Aliquots of 100 µL of each sample were distributed into wells in replicates, giving a final phage concentration of $10^8$ PFU/mL.

Plates were incubated for 45 minutes in a 37° C. incubator without shaking 10 µL PROMEGA® Renilla Luciferase Lysis Buffer was added to each well, and luciferase assay was performed with 50 µL PROMEGA® Renilla Luciferase Assay Reagent (coelenterazine) injection. Samples were compared to 0 cell controls.

As seen in FIG. 14, the experiment for the No Concentration Assay with a very wide range of cell concentration samples shows statistically significant differences between the signal from 0 cells and 1.1 cell/assay (p value=0.000702 by Student's t-Test), demonstrating the ability to detect single cells. More bacterial cells per assay show increasing signal in a dose dependent manner, up to at least $10^6$ bacterial cells/mL, surprisingly demonstrating a very wide range of detection.

Example 9

No Concentration Assay with Vegetable Wash Samples

To prepare the vegetable wash, vegetable leaves (e.g., spinach or lettuce) were weighed and added to a clean plastic bag. One mL of LB (+/-0.01-0.05% TWEEN® (Polysorbate)) was added per each gram (g) of vegetable. Leaves and solution were mixed manually for a few minutes. Liquid was then extracted from the plastic bag and used as the "vegetable wash." Using this method, ~1 million bacteria were found by CFU to reside on a single spinach leaf (1-2 g).

E. coli O157:H7 cells were grown in LB at 37° C. with 220 rpm shaking JG04-OpLuc Indicator Phage were prepared to $1.2 \times 10^7$ PFU/20 µL, and 20 µL aliquots were distributed to wells of a PERKINELMER® Optiplate 96-well Grey Luminometer plate. Cells were counted and diluted into Vegetable Wash at 120, 60, 30, and 0 cells/mL. Aliquots of 100 µL of each sample were distributed into wells in replicates, giving a final phage concentration of $10^8$ PFU/mL.

Plates were incubated for 45 minutes in a 37° C. incubator without shaking 10 µL PROMEGA® Renilla Luciferase Lysis Buffer was added to each well, and luciferase assay was performed with 50 µL PROMEGA® Renilla Luciferase Assay Reagent (coelenterazine) injection. Samples were compared to 0 cell controls.

As seen in FIG. 15, the experiment for the No Concentration Assay using vegetable wash samples shows marked differences between the signal from 0 cells and 3 cells/assay, demonstrating the ability to detect single-digit cell numbers in vegetable wash. Using more bacterial cells per assay shows increasing signal in a dose dependent manner. The vegetable wash contains about $10^6$ non-target bacteria/mL, corresponding to about $10^5$ non-target bacteria in this assay (including the 0 cell E. coli O157:H7 control). The ability to discern as few as 3 target bacterial cells from $10^5$ non-target bacteria is surprising and again demonstrates the specificity of the assay.

Example 10

Specific and Quantitative Capture of E. coli O157:H7 Using Antibodies and Beads

FIG. 16 depicts an example experiment demonstrating that antibodies against E. coli O157:H7 and magnetic streptavidin-coated beads captured E. coli O157:H7 specifically and quantitatively from samples, but not E. coli B or Salmonella typhimurium in samples. In order to demonstrate specificity in capturing intact, viable bacterial cells from solution, polyclonal antibodies to surface epitopes of E. coli O157:H7 were purchased from KPL (affinity- and reverse-purified to minimize cross-reactivity).

Cultures of both E. coli species and S. typhimurium were grown in LB broth, harvested, and washed with phosphate buffer (1.1 mM $KH_2PO_4$, 5.6 mM $Na_2HPO_4$, 154 mM NaCl, pH 7.4). The washed cells were then counted and diluted to a concentration between 5-20 cells per mL.

A sample containing E. coli O157:H7 was combined with a solution containing BSA and biotin-conjugated antibody. Approximately 10 ng biotinylated, polyclonal anti-E. coli antibody (equivalent to about $4 \times 10^{10}$ antibody molecules) produced by KPL was added to each of the cell suspensions. A control experiment, where antibody was not added to the cell suspension, was also performed in parallel. The BSA concentration was ~1%, and the total biotin-antibody was 10 ng. The mixture was rotated end-over-end for 1 hour.

Following incubation with antibodies, $4 \times 10^7$ streptavidin-coated magnetic microparticles (Invitrogen/Life Technologies) were added to the mixture and incubated a further 30 minutes. The cell-antibody-bead complexes were then collected using a magnetic stand, and the unbound fraction (supernatant) was removed. The beads were gently washed with phosphate buffer with TWEEN® 20 (Polysorbate) (1.1 mM $KH_2PO_4$, 5.6 mM $Na_2HPO_4$, 154 mM NaCl, pH 7.4, 0.05% TWEEN® 20 (Polysorbate)). Both the supernatants and captured cell-bead complexes were then spread onto LB agar plates and the plates incubated overnight at 37° C. to determine CFU. Capture of E. coli O157:H7 with anti-O157:H7 antibodies, but not E. coli B or Salmonella typhimurium, was specific and quantitative.

Example 11

Hybrid Immuno-Phage (HIP) Assay

As illustrated in schematic FIG. 17, the Hybrid Immuno-Phage or "HIP" assay combines the benefits of bacterium-specific antibody capture with the benefits of a modified bacteriophage. The sample is first applied to the microtiter plate well coated with bacterium-specific antibodies (1702). The plate is then centrifuged to facilitate binding of the bacterium to the capture antibodies (1704). Following sufficient time to allow for complete capture of bacteria, a solution containing bacterium-specific Luc-phage is added to each sample (1706). Incubation with the phage results in the binding and attachment of a single or multiple phages to the captured bacterium (1708). Finally, the sample is incubated to facilitate phage replication and luciferase expression, which leads to cell lysis and release of soluble luciferase (1710).

In a HIP assay experiment, a white 96-well ELISA plate was coated with 300 ng monoclonal antibody (in 100 µL PBS) specific to the bacterium of interest at room temperature for 2-3 hours. Wells were washed with PBS (200 µL×3 washes), blocked with 5% BSA/PBS (300 µL) at room temperature for 1-1.5 hours, and again washed with 300 µL PBS×1. Test samples (100 µL) were applied to the wells.

The ELISA plate was centrifuged at 700×g for 30 minutes and then incubated at room temperature for 1 hour. JG04-NANOLUC® phage was added to samples (2-4×$10^6$ PFU in 10 µL LB) and incubated at room temperature for 10 minutes. Samples were washed with PBS (200 µL×2 washes). LB medium was added to samples (100 µL) and incubated at 37° C. for 1.5 hours.

NANOGLO® substrate (50 µL) was added directly to the samples, and the luminescence was measured in a luminometer. As seen in FIG. 18, the HIP assay was able to detect 100 and 1,000 E. coli O157:H7 cells in LB medium with approximately 2×$10^6$ PFU JG04-NANOLUC® phage. The average signal over a no-cell sample is shown on a log scale and ranged from approximately 50-fold for the 100 cell sample to over 1,000-fold for the 1,000 cell sample.

We claim:

1. A recombinant bacteriophage, comprising a genetic construct inserted into a late gene region of the bacteriophage genome, the genetic construct comprising:
   (i) an indicator gene; and
   (ii) a promoter controlling transcription of the indicator gene;
   wherein the promoter is a bacteriophage late promoter, and wherein the indicator gene is not contiguous with a gene encoding a structural bacteriophage protein, encodes a free soluble protein and does not yield a fusion protein.

2. The recombinant bacteriophage of claim 1, wherein the bacteriophage is derived from T7, T4, T4-like, JG04, JG04-like or another natural bacteriophage having a genome with at least 90% homology to T7, JG04, JG04-like, T4, or other T4-like phage.

3. The recombinant bacteriophage of claim 1, wherein the bacteriophage late promoter is a viral capsid promoter.

4. The recombinant bacteriophage of claim 1, wherein expression of the indicator gene following infection of a host bacterium by the recombinant bacteriophage results in a free soluble indicator protein product released into surrounding liquid upon lysis of the infected host bacterium.

5. The recombinant bacteriophage of claim 1, wherein the indicator gene encodes a luciferase, wherein the luciferase is one of Oplophorus luciferase, Firefly luciferase, Lucia luciferase, or an engineered luciferase.

6. A method for detecting a microorganism of interest in a sample comprising the steps of:
   incubating the sample with a recombinant bacteriophage that infects the microorganism of interest, wherein the recombinant bacteriophage comprises a genetic construct inserted into a late gene region of the bacteriophage genome, the genetic construct comprising a luciferase gene and a bacteriophage late promoter controlling transcription of the luciferase gene, wherein the luciferase gene is not contiguous with a gene encoding a structural bacteriophage protein and does not yield a fusion protein, and wherein expression of the luciferase gene during bacteriophage replication following infection of host bacteria results in a free soluble luciferase protein product; and,
   detecting the luciferase protein product, wherein positive detection of the luciferase protein product indicates that the microorganism of interest is present in the sample.

7. The method of claim 6, wherein the luciferase gene is adjacent to a major capsid gene.

8. The method of claim 6, wherein the bacteriophage is derived from T7, T4, T4-like, JG04, or another natural bacteriophage having a genome with at least 90% homology to T7, T4 or other T4-like phage.

9. The method of claim 6, wherein transcription of the luciferase gene is controlled by a viral capsid promoter.

10. The method of claim 6, wherein the luciferase is one of Oplophorus luciferase, Firefly luciferase, Lucia luciferase, or an engineered luciferase.

11. The method of claim 6, wherein the bacteriophage concentration for the incubating step to infect bacteria is greater than $1 \times 10^7$ plaque forming units per milliliter of volume.

12. The method of claim 6, further comprising a step for capturing the microorganism from the sample on a solid support before incubating with the recombinant bacteriophage to infect bacteria.

13. The method of claim 12, wherein the capturing step further comprises binding microorganism with a capture antibody.

14. The method of claim 6, wherein detection of the microorganism of interest is completed in less time than a time period required for increasing the number of microorganisms by 4-fold or 10-fold using culturing for enrichment.

15. The method of claim 6, wherein the method can detect ≤10 cells of the microorganism in the sample.

16. The method of claim 6, wherein the total time required for detection is less than 2 hours.

17. A system for rapid detection of a microorganism of interest in a sample, comprising:
- a component for incubating the sample with a recombinant bacteriophage comprising a genetic construct inserted into a late gene region of the bacteriophage genome, the genetic construct comprising:
  (i) an indicator gene; and
  (ii) a promoter controlling transcription of the indicator gene;
  wherein the promoter is a bacteriophage late promoter, and wherein the indicator gene is not contiguous with a gene encoding a structural bacteriophage protein, encodes a free soluble protein and does not yield a fusion protein;
- a component for capturing the microorganism of interest on a solid support, wherein the microorganism of interest is bound to the solid support such that a washing step will not remove the microorganism of interest from the solid support; and
- a component for detecting expression of the indicator gene.

18. The system of claim 17, wherein the indicator gene is a luciferase gene, and wherein expression of the luciferase gene following infection of host bacteria by the recombinant bacteriophage results in a free soluble luciferase protein released into surrounding liquid upon lysis of the infected host bacterium.

19. A kit for rapid detection of a microorganism of interest in a sample, comprising:
- a component for incubating the sample with a recombinant bacteriophage comprising a genetic construct inserted into a late gene region of the bacteriophage genome, the genetic construct comprising
  (i) an indicator gene; and
  (ii) a promoter controlling transcription of the indicator gene;
  wherein the promoter is a bacteriophage late promoter, and wherein the indicator gene is not contiguous with a gene encoding a structural bacteriophage protein, encodes a free soluble protein and does not yield a fusion protein;
- a component for capturing the microorganism of interest on a solid support, wherein the microorganism of interest is bound to the solid support, such that a washing step will not remove the microorganism of interest from the solid support;
- and a component for detecting the free soluble protein expressed from the indicator gene.

20. The kit of claim 19, wherein the recombinant bacteriophage comprises a luciferase gene, and wherein expression of the luciferase gene following infection of the microorganism of interest by the recombinant bacteriophage results in a free soluble luciferase protein product released into surrounding liquid upon lysis of the infected microorganism of interest.

21. The kit of claim 19, further comprising a component for washing the captured microorganism of interest.

22. The kit of claim 19, wherein the component for incubating may be used for capturing the microorganism of interest and washing the captured microorganism of interest.

23. The kit of claim 20, further comprising a component for determining an amount of the microorganism of interest in the sample, wherein an amount of luciferase detected corresponds to the amount of the microorganism of interest in the sample.

24. A method for preparing a recombinant bacteriophage, comprising inserting into a late gene region of a bacteriophage genome a genetic construct comprising an indicator gene and a bacteriophage late promoter controlling transcription of the indicator gene, wherein the indicator gene comprises a luciferase gene, wherein the indicator gene is not contiguous with a gene encoding a structural bacteriophage protein, wherein the indicator gene encodes a free soluble protein, and wherein the indicator gene does not yield a fusion protein.

25. The recombinant bacteriophage of claim 1, wherein the genetic construct comprises stop codons in all three reading frames of the indicator gene.

26. The recombinant bacteriophage of claim 1, wherein the late gene region is a class III gene region.

27. The recombinant bacteriophage of claim 1, wherein the indicator gene product is not incorporated into a capsid of the recombinant bacteriophage.

28. The recombinant bacteriophage of claim 1, wherein transcription of the luciferase gene is controlled by a viral capsid promoter.

29. A recombinant bacteriophage comprising a genetic construct inserted into a late gene region of the bacteriophage genome, the genetic construct comprising:
  (i) an indicator gene encoding a free soluble indicator protein product; and
  (ii) a promoter controlling transcription of the indicator gene;
  wherein the promoter is a bacteriophage late promoter,
  wherein the indicator gene is not contiguous with a gene encoding a structural bacteriophage protein and does not yield a fusion protein,
  and wherein the recombinant bacteriophage is purified to be free of the indicator protein product.

30. The recombinant bacteriophage of claim 29, wherein the free soluble indicator protein product is a luciferase.

* * * * *

SEQUENCE LISTING

<160> NUMBER OF SEQ ID NOS: 7

<210> SEQ ID NO 1
<211> LENGTH: 2196
<212> TYPE: DNA
<213> ORGANISM: Homo sapiens

<400> SEQUENCE: 1

| | | | | | |
|---|---|---|---|---|---|
| catatgagtc | ttgtgatgta | ctggctgatt | tctacgacca | gttcgctgac | cagttgcacg | 60 |
| agtctcaatt | ggacaaaatg | ccagcacttc | cggctaaagg | taacttgaac | ctccgtgaca | 120 |
| tcttagagtc | ggacttcgcg | ttcgcgtaac | gccaaatcaa | tacgactcac | tatagaggga | 180 |
| caaactcaag | gtcattcgca | agagtggcct | ttatgattga | ccttcttccg | gttaatacga | 240 |
| ctcactatag | gagaacctta | aggtttaact | ttaagaccct | taagtgttaa | ttagagattt | 300 |
| aaattaaaga | attactaaga | gaggactttta | agtatgcgta | acttcgaaaa | gatgaccaaa | 360 |
| cgttctaacc | gtaatgctcg | tgacttcgag | gcaaccaaag | gtcgcaagtt | gaataagact | 420 |
| aagcgtgacc | gctctcacaa | gcgtagctgg | gagggtcagt | aagtaatacg | actcactata | 480 |
| gggagaccac | aacggtttcc | tccctgtagt | cttttttgttt | aactttaagg | aggtcaaatg | 540 |
| gaagacgcca | aaaacataaa | gaaaggcccg | gcgccattct | atcctctaga | ggatggaacc | 600 |
| gctggagagc | aactgcataa | ggctatgaag | agatacgccc | tggttcctgg | aacaattgct | 660 |
| tttacagatg | cacatatcga | ggtgaacatc | acgtacgcgg | aatacttcga | aatgtccgtt | 720 |
| cggttggcag | aagctatgaa | acgatatggg | ctgaatacaa | atcacagaat | cgtcgtatgc | 780 |
| agtgaaaact | ctcttcaatt | ctttatgccg | gtgttgggcg | cgttatttat | cggagttgca | 840 |
| gttgcgcccg | cgaacgacat | ttataatgaa | cgtgaattgc | tcaacagtat | gaacatttcg | 900 |
| cagcctaccg | tagtgtttgt | ttccaaaaag | gggttgcaaa | aaattttgaa | cgtgcaaaaa | 960 |
| aaattaccaa | taatccagaa | aattattatc | atggattcta | aaacggatta | ccagggattt | 1020 |
| cagtcgatgt | acacgttcgt | cacatctcat | ctacctcccg | gttttaatga | atacgatttt | 1080 |
| gtaccagagt | cctttgatcg | tgacaaaaca | attgcactga | taatgaattc | ctctggatct | 1140 |
| actgggttac | ctaagggtgt | ggcccttccg | catagaactg | cctgcgtcag | attctcgcat | 1200 |
| gccagagatc | ctattttttgg | caatcaaatc | attccggata | ctgcgatttt | aagtgttgtt | 1260 |
| ccattccatc | acggttttgg | aatgtttact | acactcggat | atttgatatg | tggatttcga | 1320 |
| gtcgtcttaa | tgtatagatt | tgaagaagag | ctgttttttac | gatcccttca | ggattacaaa | 1380 |
| attcaaagtg | cgttgctagt | accaacccta | ttttcattct | tcgccaaaag | cactctgatt | 1440 |
| gacaaatacg | atttatctaa | tttacacgaa | attgcttctg | ggggcgcacc | tctttcgaaa | 1500 |
| gaagtcgggg | aagcggttgc | aaaacgcttc | catcttccag | ggatacgaca | aggatatggg | 1560 |
| ctcactgaga | ctacatcagc | tattctgatt | acacccgagg | gggatgataa | accgggcgcg | 1620 |
| gtcggtaaag | ttgttccatt | ttttgaagcg | aaggttgtgg | atctggatac | cgggaaaacg | 1680 |
| ctgggcgtta | atcagagagg | cgaattatgt | gtcagaggac | ctatgattat | gtccggttat | 1740 |
| gtaaacaatc | cggaagcgac | caacgccttg | attgacaagg | atggatggct | acattctgga | 1800 |
| gacatagctt | actgggacga | agacgaacac | ttcttcatag | ttgaccgctt | gaagtcttta | 1860 |
| attaaataca | aaggatatca | ggtggccccc | gctgaattgg | aatcgatatt | gttacaacac | 1920 |
| cccaacatct | tcgacgcggg | cgtggcaggt | cttcccgacg | atgacgccgg | tgaacttccc | 1980 |
| gccgccgttg | ttgttttgga | gcacggaaag | acgatgacgg | aaaaagagat | cgtggattac | 2040 |
| gtcgccagtc | aagtaacaac | cgcgaaaaag | ttgcgcggag | gagttgtgtt | tgtggacgaa | 2100 |

```
gtaccgaaag gtcttaccgg aaaactcgac gcaagaaaaa tcagagagat cctcataaag    2160
gccaagaagg gcggaaagtc caaattgtaa ctcgag                              2196

<210> SEQ ID NO 2
<211> LENGTH: 52
<212> TYPE: DNA
<213> ORGANISM: Artificial Sequence
<220> FEATURE:
<223> OTHER INFORMATION: synthetic primer

<400> SEQUENCE: 2
tatctgaatt ctaagtaact gataatacga ctcactatag ggagaccaca ac             52

<210> SEQ ID NO 3
<211> LENGTH: 40
<212> TYPE: DNA
<213> ORGANISM: Artificial Sequence
<220> FEATURE:
<223> OTHER INFORMATION: synthetic primer

<400> SEQUENCE: 3
aatgaaagct tttacaattt ggactttccg cccttcttgg                           40

<210> SEQ ID NO 4
<211> LENGTH: 169133
<212> TYPE: DNA
<213> ORGANISM: Unknown
<220> FEATURE:
<223> OTHER INFORMATION: bacteriophage JG04 sequence

<400> SEQUENCE: 4
gtggtaatgc tagttatgac gcgcctggtg gtgccggtta cacttcccaa ttcggcggtg     60
gtaatggtgg cgatgctggg ggtcggggcg gagatggatg gggtaatcac ttatctagat    120
ctggcggtgg tgctcctggc agagcagtat tcggaagttc accgtcatgg ggtgctacag    180
gcacaatcta cggctcctgg atttaaacga taatacctct caattataaa tattgataaa    240
tgggaggtaa tatggcagca ccaaaagtat cattttcgcc tagtgatatt ttatttgggt    300
tgctagaccg cattttcaaa gataacgcct ctggaaatat tcttatttca agagttgctg    360
ttgtagttct tttgttccta atggcactaa tatggtacaa agggaatatt tttatggatt    420
attacgtgag gtcgaaatat gatacttaca cagaagtaat tcaaaagaa agaaatacac    480 gatttgaatc tgcggcttta gaacaactac aaatagtcca cgtcacatca agggcggatt    540
ttagttcggt gtattctttc agacctaaaa atctaaatta tttcgtcgac cttattgcgt    600
atgaaggtaa gttacctagc acagtaactg aaaaatctat gggaggattt cctgtcgata    660
aaacgacagc agaatattcg gtccatttaa gtggacttca ctttacttct aaaacagatt    720
ttgctttctt acctaccaaa tcaaaaactc ctgaactggc gtatatgtat agttgtcctt    780
acttcaattt ggataacata tatgcgggaa ctgtttctat gtattggtat aaggggtcgg    840
atgtattaaa tgaagaacgc ttggctgcaa tatgcaacca agcagcaagg atattagggc    900
gggctaaata attagttgtt agaatacatc gtcaaatggc gataaatatt ttcaaaacct    960
tcattgaatt cactaatcag tgttttcttt tcttcggcag ttaaatttgt aattagtttt   1020
ctgaacgaat tctgatttag ctgccgacca tctttttaa ttccaatctc attcaagaat   1080
ccgatgaaat ttgctcggtc ttcaacaata tcttccctag agaatttaat caaaatagaa   1140
gcaaccgtaa taatttcacg tacaatttca atatctttat tcataacgtt ttattcattc   1200
```

```
cattttgttg atatgagtat agtaccatta tcagtgttga ttgtaaacag cttttttctac    1260 acttttaacg taatcagtgt agtcttcctg ttcatacgag tgtaaggcca agaacgtggc    1320
taatagttca ttatagacta aagcctcacg ctcacgttct gcctctacta cgttctgcag    1380
attatggctc atatcattcc ttataactat caatgtagtc ctgtatgtca agaatgaca     1440 tttcatattc tagggcatta agagcccgtt cttcagtata gtcagaacca aagacgatag    1500
tgatttcacc aggcttcatg tgattgaaat caacgctaaa aggaatacga gaacatactt    1560
cgtctgccat atctacgata acactacgat acacttctcg gttaacctga taaagctcta    1620
cgagttcttc gcaacgaata acaagttcag tggcaggatt ttctttgatt ttagtaagca    1680
tagtctttac ccttatgttt ttgtttgcgt ttagattgaa gttctgattt cttcttgtcc    1740
ttatggacag aagccttatt gaaatcgtgt tttgctacaa gattgttcat aatgatttat    1800
aacctcattt aaacatttat cggtaaaaga aaacttttta gccacagaac attcgatgat    1860 gtgttcttc aaatctttag agtcagtata acccatctca gtaataaagt ggcgaattaa    1920
agctttattc ttatcattaa cagaattaaa ataatctgct ttagaatcaa ttattctcat    1980
catctaattt ccttaattga tattgcaacg agctaataat ttcttcgttc attttaatat    2040
acatgtcacg caagaaaggt tttaacccat cacgaataat tgctaacgta tcacctttac    2100
ataaattaac caaataagga tgatctaaag cgtcccaacc aggctgatta gcatacatac    2160
catagttttc ttccatcata tgattaagac gtttgatatc ttggatacgt gattcaatag    2220
catctttctg gagttgttta atattcatta ataaggtcc tctgaataaa gttcttctc     2280 acttccgcca cgttcaatac gtacctgtcc agcatacgtt gcaataatca ttgcttcttc    2340
acgtgtccag taattagagt attggtcgat aaagccttgg tcatcaccac aaacttgttg    2400
cgagactaat tgaggaccaa ctatatcaag tacttcagcc atatctttag agtaatgacg    2460
aactccagga ataaccagag ttccaccgct cttcaattta aacctattag ctgcacatac    2520
tataacacgt tgaactttt ggtcattatt ccaatagcac gtttgccaac agatttcagg    2580
aacttcattc attatatcat cagcagaata atcataaccg taggactgaa attttttctgc  2640 tagactttca ggagtctcac gagacaaggc caaatctaat agctctaaac gttctttaaa    2700
tgatttcatt taaaccattc cttaatacgt tgccaaatag attttttgtgc ttgtttatttt  2760 acaccaatcg aacgaataac cggttgtgac tgctggtatt cttttataatc ttctttatag    2820 atttcgtaag ctgcatcaac aaatgaactg atcgcagcca tgtagttttt acgaaggcca    2880
aatggcgcgt cattattttc acgaataacc gtatattggc ctgctttaat ctttacaatt    2940
gtccctaaat aagcccgtg gtaccaaata tcccatcctt cctgagtagg ttctgcacat    3000
ttacgaagtt cgttaataat attcagctta ttcattatgt attcctcaca gtacgttagt    3060
tacaagggta atgatttctt tggacacatt agggaagtca atgtaagtat atttaccacc    3120
gatcttaatc ttaacatcat tttcaagaga agtaaacagc tttgattcag tttctgacat    3180
gttgtatgca aagattctaa gagcgccatc tcgacgaatt tcgatctgac gaatgcctag    3240
aactcgttta gcgaatcgaa cttctaagtt actacggttt tcaccaattt ctttaacttc    3300
aactttatct ttaatatttt caaaaacaaa gtttgctaat tcatgcattt caggagtaac    3360
tccacgtgct tttctggtgt tacgtttctg aagaagttct ggagcatttt cttgggcaaa    3420
gaggtctgca gcttttttgga taatatccat tgcttcgccg gttgccacaa gtccatcacc    3480
ggatttttcg actaaacctt tcttaatcaa tacaccaatg ttagagttaa caactgatgc    3540
gttgtattcc gcttccagag cttcacggac attggcagca gtggtgaagt tgttcttaat    3600
```

```
gatataaacc attattgcag cagttttttc attcagagcg ttttcagaag ctttgatgat    3660
gtaagtaact ttagacattt tatttctcca aattagtatt tgttttgata ggtctataat    3720
atcatgtttg aagcaaaagt aaactttatt ttgggctctt tttcaaaagc cctggtaaaa    3780
tttacaaact catttcttta ataaggctaa taagttttgc cttttagaa cgaagctttt     3840 ctaaatgata tccgtttgaa ccgcgaacaa ctaaagaatt gatttcaact tctaagaaat    3900
ttaattcttc aacaagtgct ttacgtggag cattcatacc aggttaact ttaccgaaac     3960 gagtagttgt gttttgggtt aatttcattt tagacatttt atttctccaa tttggttgtt    4020
ttgttttgat aggtctataa tatcatgttt gaagcacatg taaactgttt tgtgagaaaa    4080
aaatgcacaa aagggagccg aagctcccta atcatgtttg tccaaccaat acagccaaat    4140
cactagtgca gctattgcac cgagaaatcc taaggctagg gcactcaaag tgcctccaag    4200
tctttagtgt actctgtcac aacatcagta gacttccaat actcatttc ttctttctta    4260 gctttagctt cttctgctag tttacgtgct tcgtcagaag tgatatggaa gatgttaaga    4320
cctaccaatt tatcgatatg ttctttatac atttcgattt gtgctagctc ttcagtcaaa    4380
gctttacgag tcttgccttg aatcacaatt tcgccactga taacttttt gatgaagtgt     4440 gccttagcaa aagccagttt aaatgctttt tcagattcaa tgattttgtt atcaatacgt    4500
ttctgaacgt aagtcttacg gacttcaaca aaatctttga ttaagtccac tacgttatcg    4560
tagaccgtta atttacccctt tcattaatc actgtgatgt tttgtgaacg acgttcgatg    4620
agactaaaat ctttcatgat tttttcatga cgtagctctt cgtcatctgg aagcgagtac    4680
tctttacgga acttcacctt aaacccaaag ccgtgttcac cacaatcatc ttcccatgag    4740
attagacctt tgtcttccaa cgggtcaaga accttactca catacgtttc acggtcgaat    4800
ttatatggga tttcagttat ctgcatttga gtgcgagatg tgaacttata tgttccgtga    4860
atctcataac gcccatcaac ttcatgcact tcaccgcgga attccgggaa ttcaacttt     4920 ggtttagtga cattttacc ttgaagagct tgtaatacag cctttttgac cgatttaaaa     4980
ctatgaggca gaatatttgt tgcgtaaccg gttgcaatac cagagacacc gttcaaaaga    5040
actgtcggaa taataggaag atagaatttt ggtggaacgt gttctttatc ttcatgagct    5100
ggagcatatt cagtatcttt atatacgtta tagaaatttt tgcttacacg agcaaaaata    5160
taacgagatg ctgcagcttt ttggactgtt cgagaaccaa agttgccttg accatctaat    5220
agtggatagt tgttattcca tgtgttagcc atcaatgcac ctgcatcttg tgcagaagat    5280
tcaccatggt gataacctaa atctgcaaca ccgcctgcaa ttgacgcaag tttatgaaat    5340
ttttctttat taccacgagc caaatctaat gcacgatgaa ccacaaaacg ttgaaccggc    5400
ttaaatccat caatcatatt tgggattgca cggttttcaa cggtgtacat cgcatatgct    5460
aaggcttcgt tatcaataat acttttaaa ttacgagaat tcaattgcat attttcacca     5520
tattaatgaa cgaataacca ttataacatc tgaaatgaaa agcactactt ggattagtcc    5580
aaacatcaca ccgtagtaca gaatcgtaaa caacaacaag agcccgaagg ctcctgctaa    5640
gattttctta atcattactc gccttttaac acgttaagaa gagctaagac cgctaaggta    5700
ccttgtgata cggcctgttg aaataccgtt gtttcgcctg taactaaagt gttaacgaat    5760 aaaacgacc aacacaacaa tgcaataatc catgatacca ttttaattac ctcacaaata     5820
aattaaaggc ctaacttaat aggcctgtat aaattagtaa ctctgcagaa taaatttgaa    5880
attatcggcc agaagacggt tcatttcagt gagtgtttga tattctgatg tatggttgcg    5940
```

```
agtgaatgcc agagccaatt gacctttacc ataaccagta gtcagggggtt tcatgttctt    6000 ggctgaaaca aagattacgt catattcaat attattagtg cccatggtac gggctagttg    6060
cgaacggcct tgacgaatgt gagaaagaat tgcatccaac ccttgtttag aacgttgacg    6120
tcctacaaag aatcgtgctg ctacttgtcg ccagtcagat gaacctttaa caaagaagta    6180
aaaaccttca cgagaacgaa actctttaga aacttcagaa ccgtattcgc cattacgaac    6240
tactgcaaca acttcaccgc caactgccag aaggtcttta cgagttaaat atttggacat    6300
gctaatttcc tcaattgatt aatgtttttg taatccatga gagcattata ctctgctctc    6360
aagagtttgt acaattttat tcggctatat cagaacgttc aaaaagctct tcaacagtta    6420
aacattcagt gtcatcttca ataaagaatc gagtccaaca cgttggggcg atacagttat    6480
gagtttgtcc ggcgatagaa gctacacgaa taagctgctg accattattc agaacaaatt    6540
tttcaccaat ttcaacatct ttaaaaagct tagccatttt gtgttcctca tgtttcagta    6600
ggactactat accataatcc taccgtgatg taaacaatta aattacatta aaatatgtta    6660
aagccagcca tgttccagtg aacgaacatg caatgtaaaa aacagtatca caaattgttt    6720
ttagtacaat aagaagtgca ttttttcataa gtacctcaac acaattgaaa atattataca    6780
aatcattggg atactaagca accatattcc tatccacatt ttagagctca tatctcaact    6840
tccgcgagtt ccatatatcc tttgttgata acctctttaa ggtctttaga aagaataaca    6900
ttaaaatggt cgttcatatg cccgttaacc agacgagtta tttcggcttc agatgacata    6960
taaggcacgt ccgagtccca atgagataga cctaattgag tataaatcat cccttcgtca    7020
tctgcagtgt tgtacattga acaaactca ccagtcactt tatgttttgc gtagaaaaat    7080
ttaaatttca tgatgttatc ctcttttaga taggactact atatcatagt cctacttagt    7140
tgtaaacact tttatgaaat taagatgaa gataccaccc gttgtagttg ctcttgcgga    7200
cgattttctt taggtcttca tggtctccaa cgaactttat agaataagag aagacgtcag    7260
gtgatgtttc tttgacattc aatataataa tacagtcagc gactcgatga ttaaggaagg    7320
gccctatgtt gattccgttg ccacccggat aatcaccact gtatcctgtg gtaacagaaa    7380
tccatttcga atccatctga tgggtcttta cttctacgcg tagaccacag tacttaggat    7440
gagctaaaac gtcccatgca tacgtgtacg ggtcttctac gtcttcatta cctttattaa    7500
catatccgtc tagccaattt gctactacat actctgcaaa gactgcaacc ttacaacgtc    7560
gaacaacgtc ttcttttatt tgtcctggat cttgtttcaa cgagtaccga gcagtatcag    7620
cgatcttaac cttcatttcg ctagtcaaaa actcattcga caggataaat gtcggaagac    7680
tcttcagcct caacagtccc aagttcgtct ttaccataga tacctctaat gtgtagttcg    7740
ccaaaataaa tgcggtcacc ttcttcaaga tattctgcat ctaccggtgg gatttcaata    7800
acaacttcgt cacattctaa ccagccgtag tgtgcatcac ctgggtgttt taccaattta    7860
gcacaataaa cggatttaca cttatgatga ccacgaagat tagcaatttt ggattctgat    7920
acgtcaaatg gatgaatcat aattaccccct aaagaaaaaa aaggggaccg aagtccccaa    7980
ttattattct gcaaataatt cagtaacgtc tgaaattact tcataacggc aagtacgcat    8040
cttagcatca ccgtagtcaa ccgggatgga tacaacatcg cgtggatgaa ctttaacttt    8100
cacaacttta tctgagcttg aaccaaagtg gcgaatataa gatttagcac aaacatggag    8160
accgcgagaa caggtttgtg tatcatcatc gttaacacga gtacgaggca ttgaaacaac    8220
tttacctggt gagttatcaa atgtaccgct ataacaatct aaatagtctt tacgaactac    8280
tttccacgca tagaaatacc catcttcagt gatttcaata tcgtttgcaa ccaagaagtc    8340
```

```
gaataaacgt tgtacagctt tttcgcttgg gttttctaac aggttttcaa ggaacggcag    8400
atagaattta aagtcttcgc cttttccat  ggaatcaata atacgattaa ccagtcctga    8460
acgaatttct ataccttgat aaaataaact accaccttca atagtaacat taccatcaac    8520
aaacttagta atagctttct tgatgttaat aagttcgaca gctttactaa ggtttcctgc    8580
gaccagatta gctttaattt cttcaaaatt tgcatgactt gacggggtcg cattgtatgc    8640
tacgcgtcct tcaataattg aaataaattt agatgacgcg ttccatacga tttcaggacg    8700
atgtccgccg ataataggtt catcattttc tggaacttct tcgattacat aagaggcatc    8760
gtttgcttca gggacaacgc cttctgcttt aaaattctta acaatcttac gaagagtatc    8820
tgttgaaatg tcgaagtaat cggcaatttc tttacgagtc catttgcctg attcaaccag    8880
gccgtaagct tctaactgtt cttcttggga caagcatttg atattgtaca taatgtttcc    8940
ttatttggcc gcttccacgg ccttcatgaa tttaacgatt tgagcgacct gttctttaga    9000
aagagtacca cgtcgtccca tgtattctga cacaatatga taattggttt cgaattcaat    9060
aaccatttta tcatcattat cgtaagcatt atctttaagc ttatcgaaaa ttttagcaca    9120
caattctaac ttcttattca ggtctgtatt agtagcacct gcgaatcgat tccatcccca    9180
acgattattt actgttgaga gttttgcaaa atctttactg atttctttgt ttttagagct    9240
aaaatactta ctaaggaagt taagctcttc attacgagta atatgattca ataaggctg    9300
tgctctacga cttggtgata catactcatc ataatccact ttatcgatta gcgtaatata    9360
gtcattaatt gattttcga  acaagcattc tacttcacca agtttacgaa ctttcttagc    9420
aatctgtgga cgaactacag tgaactcttt aatacctgac aaatcagcaa tacgggtcaa    9480
gaaattggag tcatagttca accaaccttt atctgcgtca agacattcag cgttagaacg    9540
attacgaact atagcataac cttggatttc atctgcttca cttgccggaa taaagaggtc    9600
ttctgatacc caaacatcgt tttcattctt aaagaatcga tgagcacttg gcgatttagg    9660
acgaggctca ttagtccgtt tcctgacttc aatccatggc ttaacgattt gtaaaagctc    9720
tgaagtcttg tacatgttaa tgttgtcgcc atcaaagata actttaaggt gttccagaag    9780
tttcattgca tcttcgtctg tagggtcaac gaatagtacg cttttaccaa aaccacgtgg    9840
aactttaccg gataatttaa cctcgtcttt agacatttca attgaattaa gagctcgcat    9900
taatggaacg cgtcccttaa cgtcgtcaat aacaatttca acgttttaa  tgttaatgcc    9960
gatcaggctg ttaattgaaa tggttgatga tgagctacca ctttcacaaa tacgacgaag   10020
acgaggggat tcaacgatat cgtatacgac accaagatta caccactcag gtcccatttt   10080
aaaacgtttg tacagctcag aataagttag ttgttcttta gagtatttca gtgattcaat   10140
attagacccg gccttttcca tgtatttacg agcggtatag ccaagagaat caatttcgcg   10200
gaacacatga cgtgggtatt tacaatcaat ccatttctta gaatcttcag cgaacaattt   10260
agcatcgatt tctgcaacgc gtttatggat atttgctact gtacgtttat caaatgacaa   10320
tgcttcacga gacggagcta cgtctagttc acccataggg aatttaatat aagctgtagt   10380
gcatcgtgtc atcatccatg tttgttcttt aataacactt ccgattggat atacaatacc   10440
gccataaaca gccatgatat taccacgttc accccatgga gcttccttgg ccaaatatac   10500
atcatcaaat tctgggaagt atttaatatc tttaacacca cgaacttctg caatatcacc   10560
tagaggacgc ataacatatg caatttcgga tgcaaacttt tcaaaatctt ccgggttaac   10620
cggtacaact acttctacac ccgtacggtc atcaggaccc atcttatcta caaaggtcgg   10680
```

```
cttaatctgt ggacctgtgt catcttggta gattacgtaa ccacgaactt caccattatg   10740
ataagacgta aggttaaacg tatcagtata tgctaatgga gctttagagc cgagtccgaa   10800
tccaccaatg aaatcgttac tcgatgtttt agttgaagca aaatatgagt tataaattcc   10860
tggctcttcg tcattaccac gaatagtgaa atcactcata ccaggtccaa atcacgaac    10920 tacaaaacgt gggtctaaac gacctggagc ctgaacaata aacttatcag tgcaaccgtt   10980
aagaatttgt ccatcgatac agtttgtaat taattcacgt acacaagcta attctttgtt   11040
tgtataaagg tcattagaca aaatcttata aactttgcta ttgccttgaa tagtaaatgc   11100
tgtgctttta ccgcctgaac caataatcgt ttctttagcc gtttcaataa tcatattttt   11160
ctctcatcac aagttacgtt taaaaatttc tgctacttca agaagttctt ctttagtagc   11220
tgtgtcggtt tgtattttat atcgaatttc cttaaagcgt tctttaaagg actctgctga   11280
ctcgatatca aaaaatcttt ggataagccg gaattcccgg agcactgctt tatcaaaaag   11340
ttccaagtcc acgttatatg ttctcataat attctcttca gtagattcct agggcactat   11400
tactaaagac tatataatct atcatcttat gtgtaatagt gcctcaggcg attcaggatt   11460
tacgctgtga agattttatc ccacatcgca acaaccgcat ctcggttata cttcttccat   11520
actgcttcag cacgtttaac tcgagcttcg tatgtgtcag tgaattctaa tacagcttt    11580 gtgtaaagcg caactacttc tttcttagga gtagagggat caatttctac acgcacagta   11640
tctgggtcat attcgaatgt cgcgtgcgga taatccttaa aaactaactg aatcacaggg   11700
acacctttag agatggcttc aatagaacta ttctctaccg tacccgtgtc aggacacgta   11760
ttgataagtg ctttagctgt tttaagacgt tccatgattt cactgtgtgg agcatcaata   11820
ataacaggat acttagccgg tggtgcccat ttactaggac aataaccaat accattttcg   11880
cctagtgctt taatcgcttc aagagcaaca tcagtacgac gcattttagt gtcataacgt   11940
tgtgcactaa taatcagatc agtcgccgga agaacttcag gtttctcatt caaacaaata   12000
accggataat cttcagcttc aaacaacgga tttgctcgcc aataatcata atcaattttg   12060
tcagtcagac ctgaagtcat ataacaatat ttgcgttcaa attcacggaa ggctttagta   12120
ggagcataac tcttaccacc gttcttatga atttgaatag tctggtccca aatttgaaca   12180
atgccacgag atacaggttc aaatggtgtt gccataaaat tcttatgaac tttagaaaga   12240
cctgcgtctt taattgcctg aacggttagt ttggtcggtt ccattgtaac aacgaaatcg   12300
tactcattaa tgccggctag ttcaacaatc ttacgagcca tagtataact catacctaga   12360
ctgaatttag tcagatgacc aacaggatga tgattaacct tccaatcacc aaatgtgtca   12420
ttatcaaagc cgatataatc aatatcagca ccgatggaca caagatattt caacacattt   12480
aaatgtactg cttcaagacc accttgtaca cgttctgggt taaatgggac tgcgcgagat   12540
gggataaaca taactttcat aattaagcct tattaaaatt aaaatgaagc tcccgaagga   12600
gcttaggaca tccattcttt acgaagttct gaatcatcac ccatcagcat ttcaaagagt   12660
tctttccaat tttcaggaag tttaactacg tcgtacacag ggttctgaat catttcacga   12720
tactctgact tttcaaggga gcctaatccc ttaatgtatc gaatactatg cttaggcagt   12780
gtatctttaa cttcttcata ctcagctaca gtataaaacc atttttgagt tttaccaatt   12840
tgtgcaataa ttacaggcgt tttaacaaag cgaatacgtc cttgttcaaa caattcaggc   12900
caattactaa agaaagcaag caaagcagga taaatacttc caaggccgtc atgatcggca   12960
tcggtcataa ttgcaatatt acgatagttc gtattctctg cttttttcacc aagaataaga  13020 cccgtgatag cacagatatc aaagagctct tgttcttca tcatatcagc atatgacata    13080
```

```
ccccagctat tcatcacctt accacgtaat gggaatccac cgtgtagttc acggtcacga    13140
acatcaatga gatatccaat tgccgaatca ccttctgtta agaacaatgt cgtatctgca    13200
tctttaccac attggttagc tttaatatgc ttatgaacct tagctttagt tgcctttta     13260
gctgctttag tttctgcagc cttttctgct gccaatttac gagctaatgc tgcttcaaca    13320
ataggcataa tcaaggcttc gttttaaga  agtgcctgag caattttctt agcgtctaat    13380
tggatatgat tacgaatatc accatacgtt gacgttaaac gttctttagt ctgagaatca    13440
aaacgcatgt tgctcatgtc tctaataaac atcaacattg tgagacattc tttaacacga    13500
gctttagtga cttcaatacc cttatatttc tttttaatac ccggcaaaag atgttcgcag    13560
atatcgtcca ttacacattc aacatgatgt ccaccgtttt tagtatggat gttattcaca    13620
taagttaaat gacggaagcc atctggcgat gttgtgaatg ctatagagac tttatcattt    13680
tcttgaatga tgttatcttc gccaaattgt ttagcaaatc gtttaaaatt accatcgacc    13740
ttttaccat  taaatgtgaa cttgatatca ggataaacga ctgccaatgt ttgaagtcgg    13800
tctaaagtaa tatctaaata aatttgagat aaattatgct cttcaaatga agtgaaatca    13860
ggagtgaaga ttactttagt gcctttacct ttagatttct tagaagacca tgatttgttt    13920
tccattccgt ttgaacagtt aacagtgatt tcattttcgc catctgacgt gatgcctgta    13980
aacaacgtag agaagatatt agttaaacta ctcccgacgc cgttcatacc accagtcttg    14040
cgttcagagt catcaccaaa gttaccaccg gcctttggaa tagtccaggc tgctacaggc    14100
ccaggaattt gttcacctgt ttggtcggta actaaacctt gaggaatacc acgtccgtta    14160
tcttccaccg aaacttgatt atttttaatt tgcacatcaa ttttatttgc aaacttaaat    14220
gatgtacgaa tagcttcatc aaccgagttg tcaataatct catcgattaa tttaaccaga    14280
cctgaacat  attcaacttg ttgatatta  ccaaacaaaa aacgctcgtg gcttcttta    14340
gcagaagaac cgatatacat accactacgt ttcttaatat gttctacatc tgacaatacc    14400
ttaatttcat ttttaatcat gttgtctcct cgttatgaag gtattctatc atccgaaatc    14460
taaagcaaaa agggccgaag cccttattta aatttaattt tctgaagtgc atcaattgca    14520
gccaaacgcc cttgttcact tttaactgta atgaccacat cgcctgatac gatcaccgaa    14580
ccatcaacaa attctataga gccttttttg aaatcgacag ctgtatctgg ttcctgaact    14640
tcttcaaaga atttaaattc tgcaccataa agcagaatat caccttgcat actatgaata    14700
gttcggccat aatcgcctac ggcttctaca gcaatcattg aaacgccgta accaatcatc    14760
tcttccacaa taaaatcttt ggacaataaa gtagtatgca gattagtatt aagacgttta    14820
ccagtcgtat taagaattct caagaaatta tcttcttgac ctttgataat acgatatttc    14880
ttaccaactt caaaaccttt aaaagccata attaaccctt cttaagtaag tcgtaaaaac    14940
caccgttcac atgtttagga gcagaaaccc gacgagtaga cagacgatga cattcagggc    15000
aaacatcgtt ttctcgttca gaattctttt aattttttc atattcatga ccgcaatatt     15060
cagattggca tttatagtcg tataacggca ttattattcc ttaaaatgtg ctttcaacat    15120
ttgatacaaa gaccatgcct ggtcgttatt ttcgatagta attgtcatca ccggaaattc    15180
agacaattcg tcaagttcac cagaatcttg ctcttcggac gcttgatacg gatttccaac    15240
ttcgtcaaag aactctgctt cattcgtaga gagccagata aagttttcat caagaatatc    15300
accgcctgtt gcgtatccaa ccatgccagt agatgtcaca attttagtag gacgaccaag    15360
atggtcaaca tctaatactt taaatggttc catgccaaga cgtcgtgcat aaatcccatt    15420
```

```
atcggtgtgg tccttaataa actcttcttg ggcacgttta tctttaaatt ggtaccatga    15480
gttaacgcgg aatttattag ccattagtaa gtttccttcc aataagttgt accgttttca    15540
gtgatttcac ggaagatacc atagatgggc atttcatcgc caagtttttc gtaaacgtaa    15600
accacttcgt tgtagcataa aaattcggtc cagttttttct gtacaacaac taaatcagga   15660
ttaaacagaa catcttcaaa ctcatcgatg tttgaatcag tagttacgtt tttaatgatt    15720
tgacgtttca taatattctc ctcttgtttt gataggtcta tagtatcata gaccatagtt    15780
gttgtacatc attttagcaa aataaaatca acttgttctg ccaatgaacg tctaaacatt    15840
aattgacaac ttccgagtat gaaatcaggt gcttcataga ccgcgatgta gtatccttta    15900
gctttcaaga gttcaacatc cacttggtca tcaaaccatg cataaaccgc gtcaacactt    15960
tcaaatccaa aatagaaccc ttgagcccaa tcttcactca attcaaatgt gtactcaatt    16020
ctatggtatc ttaagatatt ttgttcaagg agtttgtctt catttactgt aggacgatta    16080
gggacattat agttgtcgcc gtgatggtag aagttacctg agagtattcc atgcttatca    16140
aggaactccc atgtttcttc agagttgtca gtgccagacc aaccgtaagg tgagcgaggt    16200
tctttattcc aagaggtttc ccaaattctg acggctttac cgtcttcgat aacaattcct    16260
ggtaatgatt cacgttgagt acaaaaacta cgttctacgc ggtaaactaa catattattc    16320
tcctctggtt gatatggtta taatatcaaa accagaggag aagtaaacaa ctttatgcga    16380
aagcagctgg gctatatttt ttaatttgga attcaggaac taccatgaac tgaccagcga    16440
aaacgatgtt ataaagctta acaccatctt ctacccaacg gtcgctaata aatccggcga    16500
tttgcttagt tttccatggc gttccatcag ttgccgcagc aatagtgaat tcatggtctt    16560
tttcaacaga aactgatctg catagtcccc atttgaacgc ttttcttct ggctcaatga     16620 actggcttga gacgtagcca atattaccat tagcatcacg aactttaact tggttacgac    16680
caaaaaccgg atcactcaca gaaagaactt caaccaactt cccggcaact ttagagcgag    16740
aagcaacaga tacatatacg taatcacctg tagagagatt tacaatattc ataataattc    16800
cttaagcttt acgaggagac acatagcgag tgatttcaga ttctttaaca actcggaagt    16860
cacctaagaa tacgatattg tataactttt caccatcttc aacccattgg tcactaatga    16920
agccgcacat aatatcagtt ttgtttggat aaccatattc gtcgatgaaa tcaaattctt    16980
tatcagtccg gaattcaacg cctttgcaaa gggcccattt gaactgtaca ttatgctctg    17040
tggattcaac ttttttctctt gaagcaaaag cactactcac aggcgtttcc aagaactttg    17100
cacgaacata agcaaatttg gtttcctgtg tcccaaaact aggaataata cgaacttta     17160 cctcagaatc ttcatcttta acgccttctt taagttgaat acttacaact tcaaccagct    17220
ttcctgcagc tttagaacga gatgcagacg atacacgctt aatttcacca atagtaatca    17280
taatttctct ctctttgttt aagttgaatt cattatactc catccgtcct tggatgtaca    17340
acattaatta aggatattaa ccacagcact acgtggaact acactaaaat cacctgcatg    17400
aacaacgttc agaagttcaa caccgtcttc aatccattgg tcagttaccc atccatttac    17460
tggacctgcg agcgggcgtc gaattgaaac atatttacac agcaaatcag taggctcaat    17520
aggcttaatc agagtaccgt acatacaagc gatatccata tcaatacaga tgtctttaac    17580
gggttctact tcttcaatca acagttcaaa gtctgtgctt ggaagggcgg tagtagaaat    17640
tgtaccatat gaatttttaa tttctaagaa taaccaaggg ccttcagctt gtttgatgaa    17700
gttaacaata gtgaaactat tgccttgagt ggcacctaaa atttcacaaa acttttcgta    17760
agctcgcact gaagcactgt accagttgat ttgtttttcg tctttcagga tgtaagtagc    17820
```

```
cgtagtattg atattcataa tgtttttcct gtttggttaa gatagaaaga ttatactcca   17880
accatccttg gttgtaaact gattttatcg ctgttttaca cttatcgggt caggattctc   17940
agggacatct tcaaggccaa gcgcataacg ctgagcatat tttaacatca aaatatcttt   18000
agcacaatca tgaatactat catgggcaac gaatcctttt agcgtaccca tcggtaatgg   18060
acacatactt aatcctcgtg tcaacgagta agcttcgatt gccgtacgaa tatcgcgttg   18120
agcccagaat ttaaccggtt ctaatttatc agtatcaatc tctggttcaa gaacaccttc   18180
atcacgatag agatcacgaa tcaaatcgac caagatcggg aagtcaaagc tcataccacg   18240
gcaccacatt tgcgatttcc attggtcaac tttattagct cgacaataat ctaaaaagat   18300
tttaatgcct tcaagcgtag tgacatcgtc ttcagacgga gccaggtttt tacgtgcttc   18360
tgctgattgt tctttccacc atttcatagt ggatttagcg aaaactcgct tccctttttg   18420
agaagctaaa ttaaatttaa ttcgcttacc tcgttgaaca agttcttcaa atgattcaac   18480
aacttcaggg tcggaattat atgcaataac cgccaggtca ataacagccg cttttgatgt   18540
attgccgaat gtttcaaaat ctataataac atcagtgctc ataattttct ctcaaataaa   18600
atggacgtca aaacgaccac gagttgtgcc gacatacaat agctgtttag ctaattctga   18660
atcggcataa tggatacacg gtgtataaac aaaggccgtg tcaacagaca taccctgagc   18720
cttatggaag gttgatactg gtagtgcctt caccttagtg aacatacgtt tagcatccca   18780
gaattcactc catggagctt taccaccttt attccagaat ttgtatgttt ctgctgtctt   18840
agccaaaaac aaattgaatt tataaagctc ttcttcagaa gaaataacct ttatatcctc   18900
gcggacgtat tcttcatcat ccccatatgt ttctactgta agattccaat atcgtatcat   18960
atactcgcct gaaacaccac gtgctttaac gaatgtagac gtttctacag catctcgaat   19020
acgaacgaat tgcccgttat tgaaaagcat ttcggtcata ttttttgccat ctaacttata   19080 cgtcttggta aacggctctt gtagaacaat gacttcatct ttaataaatg gcttttctgt   19140
ttcgagaagt tttcggcgaa taattgaatt taacttgtct actgacttat tgtgaatgc    19200 catcattcga ttttcgaaaa ggtcttcagg agttttaacg acattaaaat agttcatcat   19260
atatgattta aggtctgtat atccatgaac accgtgccca tcaactactt tatcataaat   19320
ccatttgcca ttacgaatat cagtcgcaac atcaataatt ggcgcattgc tacgtttaac   19380
ttctgtaagg ttgcattgca cgaagtcttt gtgagtgaag aaaggactta gatacgcagt   19440
ggattcgcct gggtctacag gtcgaatctg acatcggtca ccaattccaa ttactgtgca   19500
ccatttaggg atactagcta acattatttt aaacagagaa cggtcacaca ttgatgcttc   19560
atcaaataac agtacacgac acaaggctaa gtcgggaacc ttttctgtt caaataacac    19620 gttttcttcg tatgtagttg ggttgatttt aagaatgcta tgaatagtcg atgcttcttg   19680
acctgcaagt ttgcttagaa ccttttttagc agcgtgtgta gggctgcta aaataatacc    19740 tgattctcca gaagaaataa gggcttcaac gatgaatcta gtaagggttg ttttacctgt   19800
accggcaggc ccattaatag ttacgtgatg tttctttcct ttaatagctt tcataacaac   19860
gttgaaggcg ttttctggc cttcggtcaa atcatcaaat gtcatcgtaa agtccctgca    19920
attggaatac taacaatacg gccagtatct agaattcgtt gatacaatct ttgcgtctcc   19980
gcatctagtt taatgtgttt catttcaagc ttattaaacc agaacttacg cggagtttcg   20040
accattctta gaactcccat ttttaaatct gttttatact gtgttttcaa agtatcgaaa   20100
actttatctg caatatcctt tctaaaaaat actgcaggac gatgttcatc aagtggaact   20160
```

```
gggacagtaa atccttccat atctcgataa actattgcat atacataaac cataattaac    20220
ctttaatcag ttggaataat gatgcgctaa gtggtaggcc acgtttcaat tttaatttac    20280
caatgaaacc aatcttttca aaacgttgca gaccttggat aactttatca tatgtatcga    20340
aaagcgattc agcgtcagtt aatttagttt tagttttcca gtcagagcct ttaagaagaa    20400
cgttgagttt agtaagttca tgtccttccg cttgatgtga gccgttaatg cgtgctttca    20460
aagcaacaat tctaagttta gattcgttag ataaaggttg attttcatc atgttcgcca     20520 tatgcttaac acgattttca cgttttgctc ggattttaa aatagtacca taaacctttt      20580
tgatttgggc ccatttcttc tcgtcgagat taagtttctc tactttacgg gcagaaggat    20640
tagcgatacg tcttgcaatg gcatcacgtt tctcaataag ttcttctaat gttaaatcag    20700
aacgagccgt gttatatttt ttcttaactg ggataacatt accttaatg tagccgatat      20760 tgttatcaaa acgttctaag gataatttct caccttcaac agagttattg aaagattcac    20820
ctgagtaagc gcagaccttt tgatcaagaa tgtttttaag gtaattaaag tctaagttaa    20880
aatccttaga gcgtctcttc gcagaagctc tggtgtggtc aagacgacga tttatttgt    20940 taattttatt atttgataac ataatatttt cctctgtctt acggacgtta ggtcattag    21000 ctgataggtc tataatatca tgccctcagg tagtgtacac tcttttttc ataaaatgct     21060 ttaattttt atgtgttata atggttctga gttccatccg gttattccaa tccagtcagt      21120
aaccgacaat agacagattc cagattgtat aacgtccatc ttgaataata gaatctacac    21180
gcagtatagt ccctataggg agcataaatt cgcattcgtc agatataagt ctagcattag    21240
accgtcttgt tgcttcaggg aaagctccat tgaactcaca agatggcgca gccagaatca    21300
tgttaagcat atgttcacgg aagttgaaag caaatggtgc atctttgatg cagaacatat    21360
taaatgttcc ataaaaatta tatgaagcga agttacgtgc tacactgaac actgggatga    21420
agctcattac tctatcaaat ttaataatac taccaatgcc tttatcatcg agtgtggtca    21480
tagttttctt agagattcca cgatacattg tctcgggaac tgaagacgtc caatttctac    21540
gaacaattgc acttaaatct tgttgaatgc tatcaggctt gttttccata cattgccata    21600
gtacactttg ttcaatgtcg ctgaattgct catcgatttt gtactgaagc atatcttgat    21660
aatctgggca ttgagcacga cgaaccattt cttcaatttc acactcgtta tacggcataa    21720
acatttaggt ttctcctgtg gttgataaag gtatagtatc atcatcggaa gagtttgtac    21780
actaaaaatt caacattttc aaatgaatga ttttgtataa ccgagataaa gggtcatatt    21840
ctaagtcttc aatttctaca atctcaaatc tagagatacc tgagaccatg tattcttgtt    21900
cagattcaat catatctagg acgtcaacac gttttttcttc cataacatgc ttagggttct    21960
ttccggcgag tacaatgtta accatgtttt ggtagtaatc gaaaatgaac ggagcattcc    22020
tgagactaag aatagtgtac gtttgatatt cccaactccc agagaactgt ctggccgtac    22080
caaagtctgt tgtaaacgat gttactcgtc cgggagacca atgacatcca acagaaagaa    22140
gggaaagacg ttctacttct tctggagtta caccacggta gagttctact ggtactgtag    22200
aagtcatatg cttacgaaca agatggtcta attcatagtg gaaatctggg tcttccttat    22260
aatcagtgca gcccagaga atgttttgtt cttgtttagt gaatttatca tcaattagtg      22320
ctgcgagata ttcgcgttct tgaagttcag attgacatgt catgatagac ctccatttaa    22380
agataagcct atcataacac gagaggaggg aatgtaaact acttttaag ctttcctact      22440 aaaggcccat cagggccagg ttgttctaac atgaataacg atgctttaaa aagcaatgtt    22500 aacccttca ccattcgata ccatgtctca aagtcttttt ccttgatttc tagtaagaat     22560
```

```
ttctctttaa atttctcttt catttccaag gactccatgg tggagggtcg tcataataag   22620
aggcaaggtc tttcagggct tcaacaggta aactaaagcc gtgtcgttgt ataatactat   22680
ctagttcatc aacaagttca ctatgatgca ctttaggagc cttgacttca ggctcatcaa   22740
acatactcat aaggtccata ttattcacct aaataaaaac tagcaggttc agagaatgtt   22800
tctagcgcta cacctttgt cttaaaaaat ttccaaatag ctcgttgcaa atggattaaa    22860
tctgctaatg atgtaataaa gtattttttg gcaaaatacg tatggtctcg cttttcaaac   22920
aggtctaaac gcttttcagg attcacataa accgcatttt ctgtggattc atacctaag    22980
tcctttatgc cttcttcaag actaaacgga gaattttag aatgagtaat agctccaact    23040
cgctctacac gaattttgta acctttagga atctgcaatt tgcagaattc ttctacgata   23100
tattgcggat tatttagact tttgttaatg agaatagcta tttctagtgg agtcttatct   23160
tctactggta tatgtttaaa tgacttggct tcaagcaaat acattttaaa taacatagca   23220
tccattataa tttcctcgat ggttcaccca tataaagttt tacaatacgt tcgccttcat   23280
cttcgacgag cttttcttca tgtttctgga attctttagc catattctct tcaagaacat   23340
ctaaccaatc ttctggaccg acaccatcgt cccagctttt aaaccattta actatcttgt   23400
tcattcgcag ctccatgagc ttgaaccaca atcagaataa cttgacccag aatcaccagg   23460
ccaagacgat acgtatgaat gattataact tgaagagctt gaagcattaa cctgttttgt   23520
ttttggacga ataacttctt ccatcattcc gtcaccaata tattcccaac ttttttcatg   23580
tgtatcagga ataggcatca taccttcgcc tggtttaaca gcaaacaact tcttcagtat   23640
cgtaagcatt aattgttcct cgaacaaaac gaacaccacc atcatcccaa cggatttcgg   23700
cattaaattt gacgtcttca ccatccatca tgaatgagtg tacgactaca tcatcgtaat   23760
atccaagacc gtatttcaac gaaacttctt gagcaatcaa agcacctaat gtgttattag   23820
gtttaatcca acgatttaac atagtgttct cctcttgagt aagtaagaat atcttaacat   23880
agtttttagt ggatgtaaac tctagaaacg aaaaaaggaa tcccgaagga ttccttaaat   23940
tatttaacca cttactggtg tagggggtaaa cattgcagcg ttcttagttt tccagtcagc   24000
tgcatcagaa actacagtag aataagctgc cttttctgat ggaaagattt ggtaatgaga   24060
atctgcaatc cgatgttcgt ttgaataaat ctcaaacggc acagaaactt ccataccttt   24120
aacttcttta ccttcaccag caggatgcgt aaaggttttg atgtttacat aaccacccat   24180
aattaactcc tttgttgttt aattacaggt gtatttataa tgaattttctt cgggacaata   24240
aaatatccga atttagctaa tataacaaca ccaccgttaa ttattaccgg agaataatca   24300
tctggagtat taaatttcca gtggagtcta gtattatatc catcagagcc gaatgcttta   24360
ttagccggtc tcccggcttt ttgccatgca taaaaatcaa gtttcatttg caacccaatc   24420
aaccatatgt agatggtctg ataattgact aacatgctga agctgattag acaggagctt   24480
acaaataagc tcactgttat cattttttaaa tagttggtca atacgtttct tatgagcttt   24540
cttaagctga cgtttattta aacgagccat taataacctc ggtcttggcg agcgaagttt   24600
tcagcattct tcaggtaata cagttttaaag atttcttcag ccgaaagacc tagaccttgg   24660
aacatattca gaacgaaatg aagaatatca atcatctcaa atttaatttc aagctggtct   24720
tcaggagaca gttcatcgat acgacgattt cggtattcag catgttgtgc tttccaaggc   24780
ttccatacac tgctggcggc ttttttcacca ttgctcatac caccaagtga agtcagcagt   24840
tcacggaatt catcatcaat ataatctttc tgattacgca gccaatcaac aacatcacca   24900
```

```
gcagtggcca attcatcagg atgtttgtta tgttcaggct tgtcattagc cagacgaacc    24960
tgtaaagatt tctgcatatc aagcattacc tgcagtgggt ctttatcttc gtgaatcaga    25020
gcattaaaat aagcttcttc tgctttatca acaccagaaa taagttgtga acattcgtta    25080
aagtgtgcca ttattttcc tttcaattca gtataagaaa gttaattcta acattaattt    25140
tataaagcgt aataaataat aggtaactaa ggagatatta tgtttaaact tccatcgtta    25200
atcaacgcta ttaaaggcaa taaaagaaa actgctatcg ctgcaatagt tgtaggtggc     25260
attatttcat ggaacttcgg gattgcacca ttgttagttg cccatggtat tatagttcct    25320
tctgttccat tggatactgt agttgatttg gcctttgcta ttatagggct tgtttaaatc    25380
ttcgaataac gagataatct cattttagca tgcaacccac ttgaaatatt ctgtttcata    25440
tattctaaaa tttcttgtgg tgttgcattt tctttcatta ccatatcatt cacatccttt    25500
gatctccatg gagctcggtc ccagaacatg acacgttcgc ctgcatcaac taatcgcttc    25560
atacgagcta tagtatccgg atgcctaggt tcattatcca ttacccatac ccgacgttct    25620
ttaaatggta ccacatctaa atctatcgag ccgcctgtaa tagcgattgc attgggtatg    25680
aataaactat caatagggcc ttccattacc cagacgtctc cttccttaac acgttcaaca    25740
ccataaattt ttgttgcaga ctcaaacgct ttaatagtga tatatttctg aggagcatct    25800
ttgcgaagtg cacgtccttg aaatgactca gccttcccgt ctttattaaa aataggaatc    25860
actaaacgcg gttctggaat ctctttctta tacgtaccag gttgaatctt gttgaccaat    25920
ttaggccatt ctaatgtgaa ccataatctg ttccacgatt ctttaggaat acaccgagac    25980
ttaacatatt tcacaatagg atgctcttca ggcagcttgt ccagacgaga acaagacggc    26040
aaagaattta tagtcttttt ctccggttct ggtttatgtt caggaacctt ttcaatcttt    26100
ggttccattc tagcttttc tttacgaact tccattagat attcacgata aagctcttcg    26160
tcatactctt ttaagtatcc ggaaatcgta ttatgatatt gacagttata gcaatgcaca    26220
ttacctggag taccgccata ataccatccg cgggctttca ttgcatctgt ctgagagtcg    26280
ccacaaactg gacaacgaaa cgttaattta aatgtgcttg aattattgat ttgtctaaaa    26340
cgaggtaggt gagaaaacgc acgataagca aattcattat ctatccattc agccatagta    26400
ttctccagag gccttaaatt aataaggcca tcatatcaca acttattgat atttacttta    26460
attcgctttc ttttcttgga aggaatttgt tctggacctt tatttacgac tgcacctgta    26520
gttgttcctg atgcaatagc ttgagggctg ccacctgaat caccagccac catatcctca    26580
aataagggga gttctttaaa tatttctttc tgctgttctt ctgtaatgtt atagcgggat    26640
gctacagcac tccaggcaga catcattgag gccattccat taagtcctgg aacagtgctc    26700
atcattcgct tcattgaacg aactgaagca tgaaaaggtg tataagccgc tttctcttca    26760
ggagtagaag gacgtttaag aacacttcca cgttcgtcga ttattttggc ttcgtacgct    26820
ttccattctg taaaggtttt ttgcattagt cgaataaact tatatgcata aactgaatct    26880
attgcagtgt taataatacc cataggtacc tcctgagtat atttaatcaa tcacaaagat    26940
cgctttatca ccgttcgcat ctgtgacttc atatgtagtg tcttcatagt gtggaatatt    27000
ccaaattaca ccatcattag ctttttacgct aatatggcat tggtgttttg aaacaacttc    27060
ataatcttca aaacttgtaa aaacactaat tttagaacca gtgcaaattg cagtagtcat    27120
tttaacctcg attcataaat gcattaaata tttggtcatc aacagaaatt tctaattcga    27180
cttcaattgt ttcagtcttt tcttcaggtg gtaattcgta tccacacact acaattttt     27240 catcgatatc aaaatataca gaagcaatac gattaatgtt actttcagtt aagtctaaat    27300
```

```
caacatcaac atcttttga cctacactta aggataaact aatacgagtt attttattat    27360
ctttaacaaa gagtccacca acatactctg tactacgttt gaagtttaca cgtttccgaa    27420
ttgaaagata tgatacatct ttaccgtgag ctcggctcat aggacataat gaataactag    27480
aataagagat gtcaaatcct acgccttcaa catgtgctag agtatcatga gtaaaccaat    27540
tatagtcgta tgctaaatcc attaaattat aatatgtgaa aggcactgga ttaacatcat    27600
atgttgtacc tttaaaatct gcccaggcga cgatttcgtt atctttaaca attacaaaaa    27660
ttataccgat atggtatccg ttattatttt cattcggtgt tatattataa cattgtgcat    27720
taggaaattt accatattta aatggcgcgt ttttgtgcat ataataaatc atattattca    27780
cctgtgattt cggttacgat atctttgtta tcgaaattag ggtcacaata caaaacatag    27840
ttgtactgca tgataccgcc agacttaagt tgttcaacaa ctttattaac catattaggt    27900
cggtctcgtt tagtgatatt catgatatca gagaagattt gttgttcaac ctcttcttga    27960
tttgcagtca ttgaccactc acagaggtct ttatcataac ctgctgtaac tggagccggt    28020
gcacatgata ctgcaagtaa gattgctgcc aatgataact ttttcatttt aactccttag    28080
ttgatttgat aggactacta tactatagac catctataat gtaaacaagt ttattctttt    28140
tcgcgaataa taattacttg ttgaggctgc tgagcagatt tcttttcggc gacgatagac    28200
caaattaaag ttccaatcca accaatcatc gtccagttaa agagtaaaga tacaaagaag    28260
attgctgttg tgcttttttgt gccacgaata agtgcgatta cccaaggcaa catgtaaatg    28320
atgattgaac caatacctgc gattaaaact gctactgaac tagctacgaa taattccatg    28380
ttaatttcct cttgatttgt tatgtttata gtatcttatt ttaactttgg tgtaaaccga    28440
ttaattaaat ttgtttaaac gttcaataca ctggacgtag ttattcgcga tttgtttctg    28500
ggaaggctct ttaccagttg tttcaacata gcgaatgaat gcgatttcag tagcctgtaa    28560
gcaatgttct ttaacgcgtt gttcttttga caatgctaca gtatcagaat cacgataacg    28620
ttgagcatgg gcatcagctt gaatcattcg attacctaca gtaaccgggt cttccacttc    28680
aactttaggt tggttgtact gtttaacatt cgggttataa atcaattggc cgacattatt    28740
agggataaag ccatgagcac cacatccagt taatccaaat accattgcta aagtgattaa    28800
tttttcatt tcaatttcct ctgtagttga tagaaagata gtaacacagt atgtagtgct    28860
tgtaaacagc tattttaaa attatcgaaa atcagcttca aaactttct cgtcattaat    28920
aaatgcttta actaatgcat tgttcacttc agcaagttgt accgcaaccc actcgatttc    28980
ttcacgatca cctgataaca tgatatcttt agtgaacatc tcgccgcttt taaaccagcc    29040
aataaaagta actttagtta atttgctcat atttcctcgc aaaatgccca ttcagcgtga    29100
taaactgtag caccttttagt atcattcatt tgaactacat ctaccggaga aattactcga    29160
tagagacgtg gttcacctcc ataagagcgt gctgctcgtc ctgcataaat ctttgctaaa    29220
ccgatatctt cagtaaagaa tacacgatcc aagttttct tacgtccagt ttcagacaga    29280
actcctgttt cttcaggagg acaaagcatg ttttcgatgt tagctgaact acttgaaccg    29340
tgataaaaaa tcttaaattt tgctttacaa tcgatggttt tcattttgtt ctccagtagt    29400
tgataggtct ataataacac aactactgga gaagtaaact taaaaatgta atttagatac    29460
atctgcgttg atttcacttt ggtttgcgtc atatgcaatt aaacgaaccg ctttagatgg    29520
gtcattcaat gcatagaaat gatggaacat tgctcgaacg atatcaccat ttacgagttc    29580
tacctggata ggagaacctt tttcgagttg gaaatgttca taagctttga tggttcgcag    29640
```

```
ataatcaagt ttttgatttc cggctccaac gatttgtacg atacgtttgc ccatgttttc    29700
catacgagat acaatagatt taggagcaag aataacgtag gttgccagcg gagaaactac    29760
ttcaacagat gtgttttcgg tgattgcagt aaaaattgct tgagacatat tcataatgtt    29820
ttcctcttgg ttggtgtaag tacatcatat catgcctaga ggaagatgta aaccccgaaa    29880
ggagaccgaa gtctcctttt tattaaaatt ttaactcgtt ggctaagcta tctaggtcag    29940
cacgtgttgc tttggcttta cctacgcgtt ccgtacgatt cacctctgcc tgacgcatct    30000
gagcacctgc gttttcattt actgtgttag gtgtgttcat gccttcttgc tcaatctcaa    30060
tccatttctg gttacccttta cgtacaccca tcaggaattt attccactta ttcttatcac    30120
catatcgtga tttgatttgt ttgataagtt gttgttcagc ttgtgcaagt tcttcggttt    30180
caattacagc caacatgaaa tctgctgttg ctggtaaacc tgctgattct gcaatatcac    30240
tcatgttcat gtctgaagca tcccatgctg cacgtcctac ttgagctgca gtccatagaa    30300
ctgtttcaga ttctactgct aatgcacgaa gttcttctgc gatagcttta actaatgtgt    30360
agctattttc agtgtaaact ctgatacgac aagacccaca aatacctaag taatcaacca    30420
tgattacaga tggcacaaag ttcttcttaa gttttaactc attaagcaat gcacgaaatg    30480
tattagcatt agctccacca gtaggatact gtttaactac taaacgtcct aatgttgttt    30540
ttgaacgcca tttttccatc ttggctttat attcagcata agatacgtta ccatcatcga    30600
tatcatcgag tgatacgtca agcatgtttg catctatacg cttagcacaa acttcttcag    30660
ccatttccat ggaaatataa agaacattat gtcctgtttg aagataatct gcagcaagtg    30720
aacaaaggcc taaagattta ccaacgttaa caccggccat taaaacgttc agtgtacctg    30780
tttctgcgcc acctttggtg atttttattaa gaatgtttaa tttgaacggg accttacgtg    30840
ctttatttag ataagaaagc cagcgtgctt catagtcttc catccagtca tgaccaacat    30900
aactatcaaa cgaaattgaa agtgcttgac gcataatatc aggaatagct cctacgtcag    30960
gcattttctt gttacgttgt tctggaggta gttcagcatt agactgaatc tcaatgattt    31020
tggatgtagc attatacatc gcttttgct ggacatattt ctcagtttct ttaaccaacc    31080
attcgtggtc ttcaggagta tcagccaatt tttcaattag gtctgaagtt cctttatatt    31140
cggcttcagt taaagaactg ttatctaaag ccacctttaa tgcattgata gatggcattg    31200
cattatattc gttaacgtgg ctctttataa ttttaaagac attttttgcc ggtccacgct    31260
caaaatactc agaatccata taaggccaga ccttagaaaa ataagcctgg tcgtatacga    31320
gatgagacaa aataatttct accacgataa ctccttaaaa gaatttaaat tttttcttgg    31380
ttcgttcatt aaaagcttgt tgtacttgca ttgtaacaca tttttcaaca tgtggtgcaa    31440
gttctgcttt tctgtcctgg tcaagaactg caaagtccat tacgatttta ccatcaaccc    31500
agtctagttt tgtaatatag actatatgat gggaaccgtc ttcaagtgta atcagaatct    31560
cttgaatgac atttttccatt gctgaacgga taatttaag agattcatta aacactcgtt    31620
ctttgcgaat gtcttcccct tccgaagaag gggattcatc aacgatttct agatttaaat    31680
catcgagatt attcatcgaa atcttccatt tcgtcaaggt cgttttctat atctgctgca    31740
gacggagcat cagaagcttt aacaggaact ttagttgttg ctttgcaatt aataaggtcg    31800
ttaacagcgt catcaacttc tttaatagaa gagatagcac ctagtttata tttagtttca    31860
attgcatctc ggaaaggttt gtgtttaaac aacggtcccc agaattctac acaatcagta    31920
gctttagcac gccacgattt ctcttcacga atcatttcac ctgttcttc gtcaaggaat    31980
tcgcgagcat accaaccggc tttaggctta acaacaaatc caatttcagt tgccatttct    32040
```

```
aacaagccac tgaatggatc aataccgcca tcaaaattaa ccgtgattgg gaaagtagat   32100
ttctctttaa ctgtacgaga tttttctgct ttcaacgtga agtcataacc ggtcaattct   32160
gtaccttctt taacctgacg tttagagata aagaatacag tgttagcaga gtaaagaata   32220
cctgtaccac cacccataat ctctttagga tatagtccgc cgatttccat tgctgtatgg   32280
ttgattgcaa cacacggaat atctttaata gtcagataag gggtcacaat acggaacaga   32340
gatttaagtg ccttagcacg ggacatatca cctacgactt tctcgttcaa tgcatcttcg   32400
gtttctttct tagatgcagt attaccgatt gaatcgataa agataataac tttatcaccg   32460
cgttcaatag cgtcaagctg attagtcata tcaactttaa gttgttcgac agattgaatc   32520
ggagtatgaa ctacacggtc taaatcaaca cccattgaac gaaaataaga ttctgaagca   32580
ccaaattctg agtcatagaa caaacagatt gcatctttat atttcttcat atacgctgca   32640
accatagtta gtccaaacag cgttttaaag tgtttagaag gtgcagcaaa aatagtcaag   32700
cctgattgca atcctgcatt cagagcacca cctagtgcaa tattcaacat cggaatacga   32760
gtagggactt catcacgatt attaaacagc ttagacttag tcaagtctgc agtcatttta   32820
gaagtagaag ctttaatcag acgagatttt aaatcagaca ttgtattttt ccataggcat   32880
cattatattt tactcatgtt taaaagataa acgattata tactaagggt tatacagcat   32940
ttaaaacttt aaacaggctc ttaacgagcc catttgatga tttctgtaat caaaccatta   33000
cgttcgcttg cattaaatcc tataactttg ttagcaccat catgattaag taattgatat   33060
gtttggattt tgttatgaat tgcaaactct tcaaaatgtg aaatgactgt attaaaaccg   33120
aatgaagaca agtaataag gtcgtcttca aaactttcag tcatttcgtt acgtgttaaa   33180
ataattgtga acacatcatg gttttggcaa agacgaacat agtcctgttc ataaacgtca   33240
agaaccgagt ccgcatcttg tcgaatacgt ccataaaccc agttactaat atatccacgg   33300
tctaacagat aaatcttagt agggtctaaa taattcaaca tcgtttcgaa acagccaact   33360
tcatttcgag acttaacatc gaaacgccca tcaactgttc gtttagggaa atcaatcttt   33420
acatatcttt cactaatttc cattatgtca ttaatgaaag ttgttttacc agcattatcc   33480
ggcccgtcta ctaaaataat tttagccatt ttattcctcg attacgacat cttcgtattt   33540
aggtatatta tacggtgaag aaattaaagc attaaagtag atgaactcac caagacctgg   33600
atggaatact tcttcaggat tttcgaaata ttgaatcttc ggacgtcctt taagaatttg   33660
atagtactca gttttagttg gattaaaaat tcgaatcagc gcttcttcag gatacttatt   33720
tctgtcgaaa ctattatttg gatcagttat ataaagcggt tgacctaatt gaattgcgca   33780
ttcaaccact tgttcaaaac gatagcatgg gtcactaatt cgaaatggat gaaaaatacc   33840
atctagatga ataggagcca aatcacctac aagacgctgc atgatggaag gacgtataac   33900
tttatgcgtt acgataatct tattaccatc tgcacctgcg ttaaccagca cttcttttg    33960 acgttcattc aacacagtag tttgaagtga acgattaaca gacaacatgt cggtttttaa   34020
gaattcatca atataaaaac gtggtttatt agggtctgca gtgatattga aattgaattc   34080
tacatcaaaa gcgccgtcat atccagtgat atctgtgatt agaaaatcac aatcataata   34140
agcaattaat gaatcaacca caaattcatt ttcagaccaa aaatatttac gagtgttata   34200
cgcgttatct ttataccata atggaacaaa cttaaattct gggaaaagac gttcacattc   34260
tttaatatca gatgcattac gtggatatgt aatcacatca cccggattag cacggtgcaa   34320
atgaagttgg aagttgccat ccttaaggat agcatactgt ccagtttcat aagaccgcat   34380
```

-continued

```
actcaagata ggtacgcgga aaatagccat tagtcaagga atcctttaac ataatcaaaa    34440
tcacgttcaa acacatgggc acttaccatg gtatgagtat aatcaccaac ttctacacca    34500
cattcgttag cgatataatg aagtaatttt ccttggagat aaaaatccaa ctgcataaca    34560
acagcacagt tctgggaacg catatgacag tgggtataaa gcttaccgtc acgaatataa    34620
taagtcactg agtcagtaca tggatattca agcgtttcgt ccgaatcaag caaagcctga    34680
tcagaacttt ctagaatttg gaacacaact cttcgggagt taggcttctc tttaagttct    34740
tttagaagag ctggtaattg ggccgcaatg cgaggaccat agaaagtgtt gaagttcgcc    34800
ggcaaaacat ctgattttgg tttagaaata aatttagcga cattaggata tgccttaaac    34860
gcttcttctg cgttggtacc accagaaatc ataaacttcc agaagtcttc ggcatattca    34920
taagagatgc ggttaatacg tgggtcggtc attttgaatg atgatggagt gtcaacaact    34980
actgtcatag acccaatttc attacaacgt ccaatacgag aatcagttac gaattccggg    35040
ttttctaaaa tttcacgatt gactgcttta aatgcggttt gaaaatctgc ggctttgata    35100
tatttcattg tgttatgttt tcccatgttt acctcaatac aatttattat atactcaatt    35160
cgtaaagctt atttgaattt cttggcaatg ttgatataac gtaaagcttc agaatctata    35220
cttccaagaa cactatgaag gaatgcatca gtgtagtatt ccaattgaac aggttcttta    35280
atcactttag ccgctttggt ttcaaacagg cccataaggg cctttttaag aatttgttcg    35340
atagtgttca gtttcatagt caaaatctct tcgttaagtt tataattaaa acttttttcta   35400 gaaatcattc cgggtacctc aaagcgtcat cagagttagt tatatcaata atagatatgg    35460
agttttctgc taacccgttt ttagataatt gacgtttata ataccttttca caatatgtac    35520 acgttgaccc acagatttca ttagcacaat caaaatctgg atgtctgaac cacctttttt    35580
ctaaaaagcc atctaacaaa gaggtttcaa tatttactgt atgtgaaaac tcagtctcat    35640
tttcaagagt gaaaatagtc tctaaaggct tccacagttc taacaaatta ccttcaaact    35700
tttcagaagc gtatgcttca agaactttca aaatgtagtc tgtgctacct gtacgtcctg    35760
aaactttgaa ttgagtgata ccaatatcat tataaagttt caaatcttga ggacgaacaa    35820
aacgagttct cagccagtta aatgggtctg tatcacgagc tttaatacag tgctgcattg    35880
gatatccatt taaggattta gcatcatcag cggtaacatc agtactatgg aaaatatagc    35940
aagagtcacg atagctacaa tgtgttgtat acccctttacc agcattagaa cagaactcat    36000
ttacaagaac ttcaaatatt atattgttct tattgcaaaa ctctgctgca cgcttcagga    36060
aagaaactga acggttctta tgaattccgc aacagaccct tttgatgtta tattggtcgt    36120
gcaagtattt gatttgagtt acagcatcga catgtagaat tgttgaaact tcaatctcaa    36180
tgtctttatt gacttcacga acaatttcca taacaacagg gttagcgata gtaatacgcc    36240
atacgcctat tgaccaaaga tactgaacat aatcctgaat agctttcttc ttccactcga    36300
ctagttctct ttttgaacca ggatttatcg tgttgagtgt atagttaaag caaataccta    36360
attcgttaca acgtttaacg taatcttcta acatctttttt gtcaacgtca ggaagcctaa    36420
aatcaggtct ggctgctaca aaagccattt ctcttgtaga gccgtatact tcgtttatca    36480
agctattagg ataagttta ttgagctcta cgatttatc aagaagagct aaatcaaaat     36540
tcgttccgat tttaaaagta ttcattttt gcatctcgcg ttaattgatg cgatggtttt    36600
tgcaggtctt acttaaatta ttatagattc ggtttatatg atttaaatgt ttcgaattcg    36660
cctttattca taagagcttt gaattcgtca ggacgcatag ctttgtcgtc gataatccaa    36720
tcatatactg gtttatgtgt tagcaaatta tggtacttca agccaatgtt tgccaagttc    36780
```

```
tgaatcagac ttgggagaat gtcaattgct atacgaccag gacctactga cttcatacca   36840
cgagcagtgt aaagcgttat ggtatgccct gcatcataca gggcattaat ggcagacacc   36900
atttcgacgt ctggtttgaa gttcacgtaa tcacgattgt tattccactc tgttatacaa   36960
tcatcgacat caaaacaaag attaagcatg ttttctacac ggtgcattag attcgttccc   37020
attgatgagt gatatcgcca ccgattggac gataggaaac accagtttct ttatcagtta   37080
gtacccattt accaggattt tttgtaatca gagtagccgt tacaggttct gctacgtcat   37140
aactaataga gccgtcttga agtacacggc ccatgttatg taattgctta gtcagaagtt   37200 ccatacccttt ataatatgcg gcaaccgctt taagtggatt attcttgaaa taaccaccta   37260
atgcaatcca gataattgct actgccaaat gatgatactc gttaaacgaa ctcatctttc   37320
catatttgta aactaatgga ttgatgttaa tagtcacatt acaagttgtt tcatcaatag   37380
taaactgacc ccaggtcgga ttagcattga attcatcata acctgaaaca gcataaagca   37440
ctttagcttc atcatacaat tttggcccgt aaatcttggt ttcaccaaaa tatccacgag   37500
ggtcgataaa cttgacttcg ccgttatcgg taatcatagt attactgaag ttcgggtcac   37560
catgaataac agagtactgt ccctgagaac ggttatgata acgaataaga tgttctaaag   37620
cttgtttcaa cattggcttc agacgtccaa tcttagtgta gttcacatgt gtgattttac   37680
caaatgaatc aatcaatggt tgaatacttt cacaacgatc aataactttc gtatagaatt   37740
ctttagtgaa atcacggcga acagtttcag gacttacaaa ataagtgtct gtgctgaatt   37800
tcagtgcatc taaaattgca tcaacaattt gtggacgagc aagactcgat ttggatttaa   37860
tatattcaaa tgccggctta cctttaatgc gttccatttc aaagttattt tcattaacag   37920
aaactaactg aggaactgaa tctgatttca ctttaagata ccatgaaatc tcatctttct   37980
gaagagctcg gccctgttcg gttaatgcga atttagttac agtttcttca ccaatttcaa   38040
ctgcattaaa actacgatta agttcacgaa cttcatgagc tttttcaagt ttaggcatat   38100
cacctaaatc aattagattc ataagctctg atttattgaa tgcgctgccg taaaggaatt   38160
ctacgaaatc acgtcctttg cagtattcat gaatttcctc atcagtagaa cccatataga   38220
attcccagtc tttgaactga taaattccta caacattacc acctgttgaa cctacgttag   38280
tgatattttc accgtcgaaa ttatatcgac attcgtcacc cttaacatag attgcgttaa   38340
cattccaaga ccatgaacca aaatcaggaa taatatcaca ccagttaaca attacattat   38400
ggccatctaa atctttgtgt aatttagcaa gagcataagc agaaccatac gcttcatcaa   38460
ctgtacgaat agtcacattg aaccttctt gctcacaata agctcgaaca gtttcagcaa   38520
attttgaatg aactactaca ataatttcgt ctgcgccaag gtcagaataa attgtataca   38580
aattgctcag aatagtgtct tgtttatagt taacaagcac cttaggaata tggtgagtaa   38640
ttggatataa acgagttgct aatccagcac caagaataac agctttttc atgttgaagt   38700 cctcattggt aagtaggtgt attgtacact attctagtta aagcattcat actttgcctg   38760
tagaccaatc ataatccatc caattacaag tgttggaatc attaccggag ccgttaagct   38820
ccagtagata gtcatgacaa gcatcaatag taaaagtcct attgttattg ctttcattgc   38880
tcgcctcgta acatggcacc tagtgcaccg cctggatgga acttaaggaa atcattagag   38940
gtaaatccac gttcagatga aaggttgata gcgaacgtat cgataagcgc taacaacaat   39000
gtagtagaca tcgtcggagc taaagagttc tcgtcaactt ctaccgcgat accggtacag   39060
aacgtataat caaaagagc ttcgtattct tgtggaatgt cagggttaca atgtaacaga   39120
```

```
atctgtttaa cctgaggacg aatcatacga agatgtttag caacacctat catttcttca    39180
gtcttaccgg aacgactgat gtgaactaat acatcattag gtgcaataaa tcctgcgtca    39240
ccatgagaat aatgcccagt gttcaaatac atgctaggaa tacctagtga agcaaatgtc    39300
tcagaagctt tagttgcaat attagcattc ttaccaacac ctgtaataat tactcggctt    39360
tcataattac tcagtccagg gcgtcgaaga gtttctagaa tagcattata acgagcaggg    39420
ttttgactaa ttactttggc catagcggcc aaagaagaag cttgttttat gattgcgtca    39480
atagcgatag taataggagt agttttcata tttctctcat ttaattagtt tactgtccat    39540
gacattatat caaaaatcga acatatcgaa cagagatgct ttcttctcgt aatcgagttt    39600
cgctgctgat gtgaatcctt caagtggttt aataaatgtc ttctcaagga gaacagtgta    39660
gtccatccaa tgaagtacgt cgtctttaat taaatctgtg atttcagtac cagaaggcca    39720
tgcgatacat ttatcaccga atgggtttcc atcacgtaaa ggcagaacgt atacctttc    39780
gccttctaca acttgtggag catcaatatt acctttgata gctctgttat atgtcagaat    39840
tccacgaata tggaacgggc atttgggacc agggaatcca ccaacgtcat atttagcaat    39900
gttattcgca aagataccg acgcgatgct aatataattc aattgacgga attcttttc    39960
aaactcttta aatatcttt gtaatgattc ttcaccttct tgaagcatac gacgaataca    40020
ttctttaaga gctttctgta ctgctttagg ggtcgaagat ttctgagtct ctagacccat    40080
gattttgagt ttaggctcag cgtaacgagt accttccata tcccacacgt ttaatgcata    40140
acgtttctta ccagtccaga atccaccaat acctttagaa ccgagcggag gaccagcgat    40200
agcttctcgg tccatgaaca ttaagtgttg tttattgttc atgtattcgc acatttcacg    40260
gaaacctcta tcaatagcag gttccatacg ttcacgagcg aacttatcta agaagtctac    40320
ccaatggttg gtatcacgga atttagattc accaaccta tcgataattt tatcagcaga    40380
tacgtaaata gagtctgtat caccataaag aacgaaagct tcaccttccg taccacaaac    40440
ttcgttcaga tattcattaa ctttacgttc aatccactgt aaagccattt gcccaaatgt    40500
tgtgattgca gtagcattac gcaaatcata ataacggaac catacgttac caagtgcacc    40560
ataaagcgag ttgatgagca atttacggtt aatctgtgca gtcatacctg caacttcagt    40620
acgttgagct ctaaacaaca tttcgttaag agatttagca gacaactttt taatcttttc    40680
tttaatctca tcgctgaagt cgaaacgata atcaacatct aatggttcgt caacagaaag    40740
attaggatta tgtaaggctt ctttaattat ttcaccatta cgttgagctg caagcatgta    40800
acctttatgt tctttacgtt gattaaagac cttagtgatt tcagttggaa ctacaccgtc    40860
acggtcttta taatacatca tgccgttagg agagcaactg tacacatctg aaggacgttc    40920
agcgattgcg ttaatataat catgcaatgg agctacttta aacgttcctg ctattgtttc    40980
tgggctaata ttcacttggc gaataatact tggatacaga gatgtaaggt cgaaactcat    41040
tacatatttg tatcgatttg gaataggttc cttaacaaaa gcgccaggat aaggttgaac    41100
cgggtgagaa cgaccttgtg gaatcacctt gttctgctct ttaaggctat taaaaataat    41160
agcatcccat gttttaattg ggctaaacac agattgaatc tgtatcttag cataataacc    41220
catgtccaag ctcaagttaa tgaactggcg tttagcatca atttgcaata cacgatatac    41280
gtcgataatg ttataagaaa tatatcgttg gtgattgctt tcacgaagct tagaaatagg    41340
gccgtcatat ttcagtttac cgacattcaa ttcaaattct gaaatgtaat ccagagaata    41400
cgacggttga ttggtaaaag agaattttt gtaaaggtca atgtaatcaa gaacagagat    41460
accgaacaat gtaatgattt cacgagaacc atacatgttt tcgataactt taacacgagt    41520
```

-continued

```
tttacgatgt ggcgacaacc gtttcgcagt agattcgcca aaaatattct tgattcggtt    41580
atacacatat ggaatatcaa atgactcaac gttccatcca gtcaaaatga caggagtttt    41640
ctgttgccag aagttgagat attccatcaa caattctttt tcgttatcga acggcatata    41700
aatgatttta tcgataattt cagatggaac ttcatcacca ccttgttctt gaagcttagc    41760
cgcaatttcg atagaccatt cttctacatt gccatatgga gaattcaata gatcaaatac    41820
gtagaacctg tcgtcaattg agtcataatg ggtgatagca tcaatcggat gttttgcttg    41880
tgacggctca gggaacccat ccggggatgt tacttcgatg tcgaagttag ccacacgaat    41940
ttttgtatgg tcgtatttga tttcatagtt ataagtgtca gacaaatacg ccaatttgaa    42000
atcgtccatg ccaagtgctt caagtccgat atcttccatg cgtttaatcc attgggaggc    42060
atcacgcata ttagcgaaca acttacgagt acaaggttta ccgtagatat cgaaatattt    42120
agtagcctga ctttctggac aatgagcaaa cagtgatggt ttatattcta cttcacgagt    42180
acgttcacgg ccattagaat cgatgtaacg ttcaaaaatt gaatcaccaa tctgttcaac    42240
cgttaagtaa aattctttca tttaatttcc tttagacgag ttattgtctt tgtttgttg    42300 atgaacttat tatactccaa atgggaccga agtcccattg ctttaattac caattgtata    42360
ttttgctttc aaagtccagt catctttctg tttaaaagag ataacacgga agttattagt    42420
caggccaaac agatcttcac gagcagagtc ttcaataaca atcaatcccc agtcttcaag    42480
caactgagca atcgaatcac gtcgctgata gtcttcacca tcaatatcaa cctgacgtcc    42540
gtccatacgc aacatttctt taaagtggac aatatagtac ttaccttgct tttggaggat    42600
atgacaagac tggtaaagga ctttatcttt gttattagcg atgcccatac gggtcaaagt    42660
ctctttgact ttaagaaaat cttcagggtt cttcaattta atttcaatca tttttaccat    42720
tccaatgcta atttttttaaa ttgttttttgt tcttttacgt tttagtaac ttctttgaga    42780 aattcatcag tgaccatggc cttcagttct ttaaggacta ttggcaactt gttattttt    42840 tcaaggagcc gcttatactc ggtagcatcg ttcatgttga ttgtgtaatg tttcatcaac    42900
agtttgataa ctagtaactc tgaagtgtct tcgactagtt tagcccattt agagaatcga    42960
cgaccacgtg gaattgccgc catcatatag ttgaagtgcg cttcatcact taattcagaa    43020
ccgactaagt tcatcatgta aacggctggc atacattctg ggaactggga taatgagttc    43080
tcaaccataa attttgagta gtcgacctga gcaattgaca tagatttctt ttcattaata    43140
gcattaatga tttaaagaa ttcattctca ggttttct taaacatatc agcacatttt    43200
tgaatcgcat cagcgtcatt agacttccat gcaatttggt gctcgttaag ctggacgtca    43260
tcatcgaata agttcatatt atttccaagt cagttcacag gtcagttgaa gaagcatata    43320
cataacatgt aattcaatat tacttgctag tccatgaaac ttattatttt cgcctgcaat    43380
ttcgtaaagc gaaataatac ttttaccagg tgcaacttgg tcataacatt ctgaaactaa    43440
tttatcgatg aaccatgaat aatctgcagc atattttgga gctaatgcac gaagctgttt    43500
gatatctttg ttcttcattg cttcgataac atcagagact gtgccacggt cattagttac    43560
gatagacaga atacctgcat caagaacacc tttagacgag tactggtcta attggccaat    43620
tgtacgacga aagtctggga agttctttt aaccagagct gcaacaactt tcatatcagc    43680
gatttcgata ttttcgttct tacagatttc aaccatacga tgaatcattt tcttcatcat    43740
cgagatttta tcttcttcag tcggacgacc gaattcgata actctacaac gactacgtaa    43800
tggttcaata attccatcaa tattgttagc agtgataata atagagcagt tactagagaa    43860
```

```
ttcttccata aacgtacgaa ggtgacgttg tgattcggca aggccactac ggtcaaattc   43920
atcgataaca ataactttag gcttgccttc cattgagact gaacgagcga atgcagttaa   43980
cgggccacgc acaaaatcaa tcttacaatc agaaccgttg acgaacatca tttcggcatt   44040
gatatcatta cataatgctt ttgctacggt tgttttacct gtaccaggag aaggagagtg   44100
caaaataata tgaggaagtt ttcctttaga tactaaagac ttgaatgttt catggtcata   44160
cgcaggcaga atacattcgt caatggaaga aggacgatat ttctgttcta gaatgtgttc   44220
tttggaattg atagtaatca tgtaattttc ctcattatca ttaatctgga ggatttctcc   44280
tccataatcg tactacatta aacgtaaagc tttgacttag aagtcgtgag tagaatcggc   44340
ttccattgca ataacataac ttacttgaga gctttcaaac ttggctgcaa ctttatcacc   44400
agctccccac aacattactt tatagttacc tggctggatt ttcatattag ccatattgat   44460
tacgaagtta aagttgttag aaccatcata atcggtaaga gtcaaagaat acttaggacg   44520
agttagtcca gaatcttcaa ctttattgta accattgata acaattttac catctttatt   44580
tgtaatagca attgtatcaa tctggagacc acgtgaaact cgaagcaatt gttgaaggtc   44640
ttcagcttta atttcagtaa tcacagaagc caccgggaat tgaattggct tattaggaaa   44700
aacaatggtg ctcttgtcgg cagcaggcca ataaaccgtg gaacgtgtat ctgcaatttt   44760
aatattgcca tcagtgtgca ttgaaatttc agcatcgtca gacactagac tcaaaatgct   44820
taagaagcta ttcaaatcat aaagtgctac gtcaaaatca atttcatcag agatatttgc   44880
ttccgcataa gtggtgccat taactgcacg ggtcataata aatttacctt gactcagcag   44940
aataccagag ttaatagagg caaagttttt cagaatagcg atagtatctt tagacagttt   45000
cattttattt cctttcaaga caattcaaag tttataacaa atttattatg cagcaaccat   45060
ctgcttttta atagcttcag gcagtgattc aatatattct ggaattttag aagcaacaat   45120
ttcgccagct gcaattaatt gttcgtcggc atcaacacag tagaaatctt ccagacgctc   45180
agaaccatct ttatcaagaa cgattttttcc acctgcttca atagaatctt tatagtgctt   45240
acgcatcaga tgaatccaca tatcagatac atcgttatca ataaaaccat aaatcataaa   45300
acgagtttct tgtggcaaag attgaagctt tttagcactt gcgtcatcac aatgcaggac   45360
ccatgcttta cgaacacgat tatggttatg tgggttagag tcagtacgga tagaagtaac   45420
tttcagatca gcagcagtga aacctttagc agtagtaaac atattatttc tctcttattc   45480
gtagaagtca gtaactgtcc atgcggaatt gcgattagac attattttat tatactcatc   45540
tttaaaagca gatttgagca tttgttcagt aacaatatgt tcttcacctg aaaacgtatt   45600
ggtcaaaaca tatttttttaa tttcaggaac aacgagaaga tgttgtccgg ttgaatactc   45660
catgttgttc tccatttaat ttgatgtggt cattataacc acatcgtgtt aaagcgttta   45720
tgaaacagtc atcacagtaa atcgtccaac tttactcatc tgaagatgtt gtccataacg   45780
ttgagggtca tggtctcgat gagagataat gaacacatta gtattttgta aacttccaag   45840
aatggtatct atagccttaa cagcttcaga atcaactgcc ccatcaaaaa cttcgtcaag   45900
aataagagtg ttgatttttaa caccagaaac ttttttcagca atatctcgcc atgtaaacaa   45960
caatgcgata tctatacgtg cctttttcacc ttgactaaat gaagcataac taaaatcttc   46020
acgaccacgt gattttatag attcattgaa ttcttcgtca atagaaaaca cgtaatcggc   46080
ttccatgatt ttaagataat ggttaatctg cttgttgaac agaggcacat atttttttaat   46140 gatagcacct ttaataccag aatctttttaa catatctgtg ataataccac gatggtattt   46200
ttcaagaacg atatccgatt ttgttttaat gattttatca agttcttttt gaagcaaagc   46260
```

```
tatctcatcg gcatggttga taaattccgc tgaggcttgt tctattgcag ctttaacttt   46320
cttagcttta tcaatagtgg caatcattgc ttgtttcttg gtacgaatat cagatgcaag   46380
gtcctgttta gtcttaacat tagctcgata ttcgtccact aggacactca gattatctct   46440
gtggcaggta agttgctcga atgagtgatt acattcatga agcttatcgg taatcttaga   46500
gacaataggg tcaccctggt gcaactgtga tgcacaagta ggacatgtac cgccatcatg   46560
atacatctta ataactttgt tatatgagtc aattttagat ttaatcaaga atgcttcttg   46620
tcctatcttg ttgaatgcct cagtagggtc ttcgtcaaga acgatattaa gtagacgctc   46680
gttagcttct tcaatttctg cttttaatga ccgagcttct ttggctaggt cgtcatacat   46740
attctgtaga cgcgctacat tatcgccaga taatttcttt tgacgttcga tattctcatt   46800
ataaatctta atttgttgga taataccatc tttcttggca tcaagaactt gcccctggga   46860
attaagttct cgaacttgag acttattgat tttatccatt tcagcgagtg ttccaacttc   46920
taataagtct tcaacaagct ttctgcgagc aggggtgcta agagccatga aaggggtata   46980
ccctgccgtc ccaagcacaa cgatctgttt aaaagacgcg tatgacattc cgatgctacg   47040
ttcaaattct tcttggaagt cgcgactgct ggcagattca tcaagacgaa caccgtcaac   47100
ggagatttcg aaaatattgg gcttttggcc tcgtttaatg aagtattttt tatcatcgaa   47160
ttccatccaa agctcaacta agagctcttt cttgttcgtg ctattaatga tttgtccttt   47220
cttaacatca cgaaatggtt taccgaaaag tccgaaagta atggcttcta acatcgtaga   47280
tttaccacca ccatttttac cagtgattaa tgtcttttgg actttatcta attggatatc   47340
aataggattc ccacctaccg acatgatgtt ttgataacga cacgattta atttaaatga   47400 tttcatatgt attctcttcg aatgaagtcc tctacatatt ttaacatgtc atctctatca   47460
gcaaaatatt catctagttc tgcatacata acaacacctg gtgcgtactc acaggtaaca   47520
tacattgttc caaagaaacg aggagttgtc tcctcgtaat tctcagtcca ttcaacgata   47580
ccaatataac cgtcaccaat actaaattca tgacgatgga tttcatagtc agtcttcgtc   47640
attatacgca tcctcgatac atgcttcagc cattttaaga atagagccag gagtatcgtt   47700
gtccattata ttaaagctaa attcaatagc ccagtcggta cagacatgaa cggctttaac   47760
ttcattgcct tcaacgcgta atggctcaat ccaatacttg atagtgttct cgaatccatc   47820
atcatcttta acgtctattt caacttcaag cccaagccca gcattgttaa attcatctaa   47880
agtcattgtg ttgcctcaat ataaagttcg ttggaatatt tgaccagcgc ttctctgtct   47940
tcgtctgaga tatctggaat cgcgtcaata tattctttaa tgatatcttg aagtgattta   48000
atctcgattt cctggtcgtc atcagattca acactgttat caactttaga aaccatacga   48060
agagagtgaa ctactttttc aagttcagat tcaaatttag tcaactctga atcaattct    48120 gatactataa cacgtacggc tagattagta taatcagaat aattgatttt gcctttaaac   48180
ggataagtga ttcgtcgatg ccatgtcgtt tcattaggaa taaattccat acgttcaaca   48240
tcagtgtcaa atacccagaa tccacgtggg tcgttctcgt cacctgcagt aagggtccat   48300
ggtgtcccaa tatatttgac gttagcagct tcagagattg tgtggaagtg gccggaccag   48360
acttgtttat aggtctttaa gaaatcaggt tcaagcccat gagacttcat tcctttatag   48420
aaataaaagc cattcagttc ccagtgccca acacaatacg cagcagaaga agtcttgata   48480
tgctctaaga tttcacctgt attttcttca cacatccatg gaacgatatc aatcagacat   48540
ccatcaaaat ctacagtagt tggatgttcg taaatagtaa agttttcaaa ttgagttaac   48600
```

```
aattcagaaa cagtgttagg tgttattgta ttcttaaacg ccatgtcgtg atttcctatc   48660
gtgacatgaa cgtgaatgcc tgctttagaa atcatatcaa cgatttcacg attgaattcc   48720
attgtacgat gtgtaattgc tttacggacg tcaaaccaat caccgtattg aatccaagtt   48780
ttaatcccgt gtttcttaga gtattcaatt gcttgacgaa taccatcacg ttgaatatct   48840
tgaacccatg ggtcgtcttg tttgactccg atatggaagt cgcctaagtg caaaattttc   48900
atattatttc ctcattagtt aattcattct atcatccgtt tgtaaagcaa aaaggaact    48960 ccgaagagtt cctatccaca tagtacaccg tacagaggct catttggact tttaaatcga   49020
atgggcttgt acgtaatagt tccttcggct ttagctttat cataagactc tttaaaacgt   49080
ctcattcttt ctgctttgcc tttacggatt ttatcgaaat tttcagaagt cgggatgttc   49140
atcatgcata agcacctctc ggaaaatgcc taaatcgatt tctctcatcg tttccaccat   49200
ttcttaactt gaaatgaatc aacccacacg agttgttttg ggtctgcctt tacaataggc   49260
ggacaaattt ctgtaataga accatcgtga tattccttt cagaaatttt aacacaaaga    49320
ggaccaccca atttaacggt gaaccctgcg ttcagcttca gacgtttaaa ctttgtttga   49380
actagcgcca ttaatgatgt cctcaatagc ctgacgagta gtaacccact ggattttaat   49440
taacttgtca ttatatggtt gtcgtagaat atcccgagat ttcttaatag cgtattcgta   49500
agcttcgaag ttgttttgaa ttgctgcttc ttgagcatgt gcataaagac ggtttagttc   49560
aaaacgattc ttttttaagaa tcttttcgga ttttttacgt gcttcagctt catttttctt   49620
ttggatttct tgtagcattt tagctactgc atcttctgct tctttatttt caataatctc   49680
ggtagtcata ttatctcatt aaattaaaat aaaaacgtcc gtcctcttca atacagaact   49740
cgtactcaac tggagtccca tttatcgaaa atgacacgtc atgtgggttc aaagggtcga   49800
tgtcaaaatt aattttaaat tctcgaccca acagttttac caaataaggg attgcttcgt   49860
caaaaggttc ttctaagtag ttagagatat caattgtcat cctcatataa aaaatccaaa   49920
ctaggcgaat cgctaacaac ttccttcttt tcagccccag gagctttata agcggattct   49980
tcataatgcg tcattttatc gtagatgtct tgaataaacg tttcatctac caacgctacc   50040
atatcatcgt catgactgtc gtagacatta tgaacgaagt aactatattt ctttgcaact   50100
tccttacgtt ctttttttgat acgttggaca aaagcattaa aacaagctcg agttatgtat   50160
gcatgtgggt tattgtactt agtttcgtcg aaattatgaa gtcccttaat agaggcttca   50220
atcccatctg caatcatctc ctgcttccaa gactgggtat atcctgaaaa gttgaaacgt   50280
ttggacaggc cttcggcgat aagcataatt gctaaaccga tggtatcatt ctgacgaata   50340
attttgtttg ggtctttatt atttaagagc tccttttttcc actcgattat agcagcgaga   50400
agctctttat tattcacata gttattttta ggttttgtt cagtcataag tacctcttgg    50460
ctcaattcat aggtctatta tatcataata tttagagacc tatcttaaag cacgagatac   50520
tatcggagca acaataagc ctggaatact ttttccatta aacgtttgaa ctcatagata    50580
tcgatataaa gctcggttaa tccagctcca taaagaaaat ctaaaaagtt ctcatgtgtt   50640
tcgttatagt cgccttcgtt taattgagat acatgagttt cccaaaaacc aacacctta    50700 acgaatggaa aatacgtgac tttcatgtat tcatcaacat aaaaattcgcc cagcttttct   50760 tcagttatgc tgattcgagt taatttcatt ctagttcctt tgctgcttca agagcaacat   50820
ccagcgaatc aaattggtca acgaaatcaa tattcaacgc atcgtcaacc gtagcatata   50880
accaccattg tttgaattcg tattctagaa taaatccagg cccttcaatc tgaggaagac   50940
ctagactatt tgtaccaact tcgtaaccag ctagacgcag gtcattaatc aaagtttctg   51000
```

```
ttaatacgct cattttgccg ccttaacaat tttcaggtca acgaattttt tcttacgttg   51060 attttttcata cgacggatag tcttttcaga gatttcatgt ttctgataag ctttagattc   51120
aacaccaaat gcagcaacgt caaattcaga aagaatatat tgcactagaa tttcacgaat   51180
agaattacgt ccaattttct ggtcgtgttt ttgcatgatt tcataaagac ggaattccca   51240
tgcgtcaaga acttgaggag taacaatatt gccggattcc agaagagcaa caactttatc   51300
gaaagcgaaa gaattaacta cgttttgat tttagtagac atattatttt cctcggttat   51360
tttattatcc gatgagagaa ttatactcat ctctcaagag tttgtatatt attttaagc    51420 atgaaaagta agtaatttgt atcacgtgga gtaaatcaa cacccatatc aaagatgcct    51480
ttatagattg ggtatttgtt ttcggttgta tcgaagctga aactatttcc atcacaacta   51540
acagtaatag catctgttaa aatgtcatac tcaatcctaa caattgaatc cccaattta    51600 acgtcgaggt gttttttgaa tttgataaaa tctaattctt gggccatgat attttcctca   51660
ttttaagacg ataggaagat aataacatgt cttcctatcg ttgtacatta ttaaccgaac   51720
tttttagcgc ctttccagcc ttcgtacata gctgcacaag tcaatagtac agcgtgctgg   51780
cattctttgt atttgtaaat ccagaaccag cgtaagaagt cttcatcctc aacgccgttg   51840
agtttcatat tggcaaagaa ttcggcacgt tcttcacgaa gcttttgcga taacatagat   51900
tcaggattca ttttgtattc cacgccccat tttcatcgat gaacttaatc cagtcattta   51960
cagaccattt agttgtatca ccctttggat taacatttaa agtatataat ccttgcttaa   52020
aaagcattcg tttaatattc ataatttcct caactgtaac gataacattc gttagcttta   52080
cgtttggctt cagtatgaga agtattataa tcatactctt ctttactgta aacatctttt   52140
ttcaacttac gaacctcttt gcggagttgt cgattcattt cattcttgac ttcagaatca   52200
acacctttca tacgtttcca tttatctgag cggaagatgt tttcaaccat gtctttgtgg   52260
ctaacaccgt caggagcttt acgcttacca aaatagtcgt aatcgcgaac tttcaaatct   52320
ttacgacgat atgttttacc cataagtacc tcagaggttg attgatacaa tgcgtttgat   52380
aaaattcact tcacttactg aaaggtctt aagaccgatt gattctaaac gctgagtaag    52440
cgtcaacatt gggatatagt cccattgagt tttagacgtt tgataagtac gaacgccatt   52500
agcaatttca acatgcaaat ctgaaatggt aacgaatacc ggtcgctcat cattaacttt   52560
aagggttaga acaactttct ttgaatctaa actaatcata gtttaatttc cttcgcgatt   52620
gaacagaaga taccacggtc acaaagcatt tcaccaattt ctggatattt gattgaacga   52680
taccaaacat ccaggcttga aattctggtt atccgtactg cattaccatt gacagaataa   52740
tactggtcaa ccttaatttc tttatcttca attgtcattt tgttttcctc tatagcagat   52800
ggtttaatct taacatatct atcgaggatg taaactgttt tatgaaaata ttttgattt    52860 gagaggggca caaggagata gtgaagtgaa gattccaatg gattatatta gaaatgagat   52920
aaagaagacc aggcggcacc tggtcaatct tctatgatat cagagtcgta tcctaatgaa   52980
atcaaggact ttttaaactc tgcaatattc ttttgtttct tatcatttaa aaatatgaca   53040
ggataacgaa tattaagtga agtgaatcct gcacgtttag caagagatac gattaaagga   53100
cggtcatatt caatcttacc attattagtg aggactttat aaaatgtata aggagcattg   53160
agctccttta aaagttttgt aacagtataa catcctggac aacgtcctac ttcttcaggg   53220
atgccgtaga tttcaatctt attctttaag ttcgagtttt gttccacgag aaataattcc   53280
ttgataagcc caataaggag gattaacaga atcctcaccc gagttttctt caggaaaata   53340
```

```
aacctggata caaatccag atgcatcaaa ggtaaaataa accgtaggca gttcacctaa    53400
caattcggca cgagcattaa tttcttcgag atctcgttca cgtccagccc aaaaactagg    53460
atttagacta cattcgtaaa aataatagtc attaccgaac atatcaaacc ccttccaact    53520
ctctaccacg taccgctcaa aactaatcat aattaagcct ttttatcaag aacagaattc    53580
agtttgttag taattttgtc cagacgctca ttgaactcac tagaagataa gcccttttct    53640
ggagaaatta aactaatcac gaaaaataca ccagtaaaag gaataagaaa aatagctcca    53700
actgccataa acaaaaagaa cgttacagtt gtaagaaaat cagctaaacc tttacgaaat    53760
ttatacatat ttacccttaa ttaattaacc aagcgttgat aagcaaacca tattgcgaat    53820
aaaattctgg accaaaatga aaaatcatat catttatagt atccataatg tagttcaatt    53880
taatcatgtt tccacacccc atcggtattt gaccaaagtc gctgattatc tgatcctcgc    53940
cacagctttt tggtcggaag attttttctca tacttcccat caataataac atcaacatat    54000
ttaagcattt ctagctgttt aatatcttca aacttatatc ctgtccacaa ccaaatgctt    54060
ttattaggat aaagattttt aatagtttga actacagagt gaataacatc tcggttgtca    54120
ggatagagag ggtcaccctcc ggttatagtc aatccttcta tataatcatt attcaaacat    54180
tcaattaatt gttctagtgt tcaccagtg aatggaacac catttctagc attccatgtt    54240 gattattat aacacccttc gcatttatgc aaacaccctg taacgaaaag aacgaccta    54300 caaccagggc cattaacaaa atcgcaagga taaaatctat cataattcat tggtgtttaa    54360
ccctatgcat gatttctta ttttaccga gattaaatcc gcgttcgttc ggatttccca    54420
aatagccgca tgttcttctt atggtgttca tcttttagg atcagtttct ccacaaactg    54480
aacaaacaaa tccgttttca gtaggagtca tttcatgagt acttccacat gtaaacatt    54540 tatctactgg catattaaca ccaaaataat ctaaatgttg tgcagcataa tcccagacag    54600
cctcaagtcc ctttaaattg ttttcatat ctggaagttc aacataagaa atgtgaccac    54660
ctgtcgcaat gaaatgatat ggcgcttcac gagaaatctt ttcaaacgga gtaatatttt    54720
cttctactga aacatggaaa ctattagtgt accagccttt atcagtgaca tcttttacac    54780
ttccatattt ttctgtatca agtttacaga agcgatagca aaggttttca gcaggagtag    54840
aatacaagct aaaagcaaaa ccggttcttt cggtccactg cttaagacga gcattcattt    54900
tagttaaaat ttcttgtcca atatcacgac cgacaagaat attcaattcg tgaataccga    54960
tgtatcctaa agacactgaa cttctaccgt ttttaaataa ctcaattata tcatcgtcgg    55020
gtttaagacg aaccccgaat gcaccttctt ggtaaagaat aggagcaaca gtcgctttaa    55080
ctccttttaa ggaactaatt ctacacatca aagcttcaaa gcacagatcc attcgttcat    55140
tgaataattc aacaaatttc tgttcattga actgtgttcc aatataagaa tctaatgcga    55200
tacgaggaag attcagtgtt acaacaccga gattattacg tccatcaaga atttcattac    55260
cagtcgaatc tttccatacg ctcaagaaac tacggcagcc cattggagaa actgaaactg    55320
aagaaccggt aatagcttta ttattcttaa cagaaataat gtcaggatac attcttttgc    55380
ttgcacactc tagagcgagt tgcttaatat catagttcgg atcgtcttta taagattaa    55440 cgccttcttc aacaaacata acaagcttag ggaaaatagg agttattcca tcacgaccaa    55500
gtcctttaat gcggtttta agaattgctt tctgaatcat tcgttcagtc caatcggttc    55560
ccgtaccaaa tgtaattgtt acaaaaggcg tttgtccgtt tgaactaaag agagtattta    55620
cttcatattc ataagcttgg aatgcgtcat agacatcttt ttctgttttg gattgagcat    55680
aattcagaat gtctggtatt tgccattttt ctgcatcttc aacatgttta gcgtatgtac    55740
```

```
gtttaacata aggagaaaga actttatcga cattcgcaaa tgtagttccg ccatactgat   55800
gtgaagcaac ttgtgcagta atttgtgcca taattgcagt agcaacacca atcgatttag   55860
gcgtttcaat ttgagcattg cccaatttaa atccgttctc aagcatcccc tttaaatcga   55920
ctaaacagca attggtaaac ggaagagcag gagaataatc aatatcatgc atgtggataa   55980
ttccactttc atgcgcattc ataataaaag acgggaccat attttggca atgtgcttag    56040 acacaatacc agccataagg tcccgttgag ttggaaaaac acgagaatct ttattagcat   56100
tctcgttcaa aagatcttta ttagttttat aaattaatcc ttcaatttct ttttcaattt   56160
tcattttaaa ctcttttctaa gctgctttt gaatgaagct attaattgtg ttttagtatc   56220
agattcatta tattcaaatc ctctttgaag catctcagtc atcatttcct ctttacctag   56280
tcttgagaac tctttagttt tgtctggaac aaaattagga tggatattat tatcagaata   56340
atcttgtttc aaataagcaa gaagagcttc aagccattcg aggtagtcga catcacgacc   56400
tttaagacca gaacggttga acttatgctt catttggcct tctgctgcgt tgcacagatt   56460
acagagtaat ccacgaactc taccggcttt tggcccgttt aactcgtggt cgtggtcaag   56520
atggttacct tgaacatcag ggtctaattc acggtggcaa ataggacact taccgttctg   56580
tgcatcataa aattttgtt tttcttcttt atattttgcg cctgataata acatgataaa    56640
cccttacctt aaatagataa gggtatttat aatttagtaa atgttataaa agttacgatg   56700
agaacgttta gctttgcgaa gctgacgttt agtaggacga actgtaaatg gttgtccaga   56760
gaaaaaattc ggatcggttt taataagcaa ataccaatca cgcttgccat ttttttaataa   56820 acggtacaat aatttaactt gcataataat ctcttcccat ttccatatcg attaattcat   56880
ttattgaagg ttcatcataa catggttctt cgtcgttgta aactgtttcg acgtctggct   56940
cgacagtctc ccatcgagca gaataccacg gtttaacccc ggagtttatt gagctcttca   57000
taatcaatcc aggattctag ccctgacggc aggtcacatt caatgttcca cagaagctct   57060
tcaatggctt gcaggcgatt atattcttca acggtaatgg taaccattgg tgcaaccggt   57120
tctgcctttt taaccatcat atcgttcatc aggacgtaaa ggtcatcacg aacgacagtg   57180
tcgttccaac cccatgattt ggcttcgtaa gctaatgatg aagggagcac atttaaaact   57240
tcaataatag ttggagcatc aggaccaagt tcattggcac aaacttcgta tacatcttgg   57300
aaatctttaa gatttaatga atatgtcatt taaaatattc tcgcagttta ttgttctacc   57360
caggcacagg aaacttcgaa atcaggacca ccgtattccc agtgatattc accaacagga   57420
atccagtcac cgtgctcgtt ttcttcatag tcctcagcct caaggccaac gaatcgccat   57480
tggacaccga tgattcgatt acccattaat atatgaaatt caccccatgg attatcgata   57540
gcatattgga tatcgttctt agcacgagaa cacatttctt gatataacaa agcttctaat   57600
tcgccctgat cataagggcc cgggaaagtt aaatcaatac tcatttaaaa tattctcgta   57660
gttggtcaaa tccaccaata tgacttccat caggagcaaa tacttgaggc atagtcaatc   57720
caacttgtga ttcacgtcca agcttaacaa gaagctcagc aattttctca tcatcaaaaa   57780 caccttttc tggcataaca ttaatgaatt cgaatggctg tttcttaaca gtcagcaatc   57840
gtttcgcatt atcacaataa atgcatttat gaatagtaga gtcatacccg tacactttaa   57900
acattatttt tcctttcatc gattaaatat gcaatgccaa atacaataca tgtaataaaa   57960
cctgtgatac agatagaaac caacaacact gtaccaaaga accaaatcaa gttatcttta   58020
gtagtttgtt tgatatccat ctcacgaatt tctatagcta tcgtatcacc tttattcaga   58080
```

```
agcgtataaa acgacggtga tacacgcctg tcaaaactc gtccttgctc atctttatag   58140
actgcaataa attctaattt agaatatttt cctgtagatt ggcctgagat taattccact   58200
acctccacag gaattacttt agtttccatg taagtattct gactgttcca aatgaatgga   58260
ataacggcaa aaactaaagc tgcgataaaa caacgaaggc tatatctcat tataatattc   58320
tctcaaattt gtggaagcat ttacggcatt tcaatttcaa gttatcagtg gtccagttaa   58380
ccagttggac ttggatagtt ccacattccg ggcatggatg ttttgctgct gatttggcag   58440
cattttcacg tcgttcaacc attttcatta tttcgttcca tgctggagga acgaactctt   58500
cttcaccgtg gattttatct cgctgaacaa attcaatctt tgaactatcg tcaataaact   58560
taaccaagcc atgattagtg ctcatatcaa tatcctctaa aagacgtagt ttcattataa   58620
cacctcaatg gcatttcgta aaccgtccgc tttcgcattc agagctttta acgatttagt   58680
ctgttcttta atctgggctt cgacttcttt cagacgagat ttgagatatt cacgttcttc   58740
gctcaagttg tcaactttt ctactttagg ttctttaata gtcttaagtt tatactcgtt   58800
agggttcttc agcttaattc gggtgcgaga actgtataac attgaaccgt tatcttcgga   58860
ttcgtcgaac gtttcaacaa catccatagt ctctaacaat gtaataagtt tataagacaa   58920
tgaacgaacg gttttgttat gcttattaat ttcttcagct ttcatggtac cgagattacg   58980
tgagtagtaa taaggaacct ggatatcaat tgataatgat gcgttaccat taccggtcgg   59040
tttgaatact gcagtaaccc aatctttaac atgaacttta tttgtacgac catcaccgcc   59100
cgtgaataat ttacgagaat gtttaaaaag catattcact tggttattga attcacaagc   59160
aaatttatca gcgaatttag tttcaggaat ggtagagaac caatcagcta aatgagtctt   59220
tttaacatca ttaacaatag tgaattcaac caaatcagtt ttagatgtca cagatttaat   59280
aaagctcggt ttcataaagt ttttaatgtt atcgcgagct acagtagaag ataataaacg   59340
agaacgttta aaccattgaa gcagtgtccc taatgaatga gaatacgcat tctgagtatc   59400
tttacagata tgattttctt ggcctgtgta tgtaccaaaa tcgcgaagaa taccacttac   59460
tacatctcgg tgtggaacat caaatcctag tgcaccaaca gcgcgctggg catgaacgtt   59520
agcgataaga ccggcaaagt attcaacgta atgtgaacgt gtcataatat tttcctctcg   59580
ttaagataga tttattatac tccaaccatc cttggttgta aactgattta tgattttaac   59640
gcattcattg cgttaaaaag tttagagtac tgcaactgga gattcgttac aacactttga   59700
gcatcacgaa gcttagcttg tgctttgtca agttcaacgg acagttggtc tacagtagcc   59760
ttgatttggt tgtaatgata atcttcggcc ggaagaaggt cattagaaac atttagtttt   59820
actgccgaca gtttgcacac atttggcaaa cctttaaaca taccgggttg tgtcggagaa   59880
tatgcgctta gaacctctgc attaccgact ggtgttgctg tgatattgcc ttcgaacgtt   59940
gcattttcct ttttaagatt ttgatagtat tcagagtctt tgtgccacca tggcgcagga   60000
acctttttac caatagatac acgagcctgg atagcgatat ggcccttatt cttgataggg   60060
tcgataatat taagctcacg agaataaatt gctttaatct ggtagatatt atcacctaaa   60120
acttctaacg cttggtggaa tacacgagca acgttatcgt tcttaggttt atacgtgaga   60180
gtgaactcgt tctcactgat aaccatgatt tccaacttat cgtaagtata tttcaaatgt   60240
ttcatgttaa ttgcttgagg acgaatacga gaagcaatgg ccatcagatt gttaaggtta   60300
ttccggaact gcttagcgaa atattgtcct tcaccgccaa tacaaaaatt acgaagtttc   60360
tgtttggcta ataacggct gaactcacca tttttaatga actctttaac gggcgtgtta   60420
gtaacacatt caaattgagt aaacatacga gaagtaatcc cataatacga acagatttcc   60480
```

```
tcaatctctt caggagtctt tacaggcata cggataggat taggtcctgg agtatatgcg   60540
ttcgaggtaa attctttgat aagttctcta cgtgtaatag ccattttata ttcctcatgt   60600
tgaaaaattt attatactcc aaccatcctt ggttgtacat cattccttaa gaagttttac   60660
tacttgaata agattagctc gttctgtttt attttaccg tttaagcctg ctaatcgtga    60720
gatttcatcg tcagtttgtt gaatagttac attaagttca ttaatcaaag cttcaaagta   60780
tttgatttgc tcagcatgtt ttgattcaaa tttctgaacc ggataacgt cttggttcag    60840 ttcatcaata aggtctttaa gagcatcttc ttggttgata tcatattcaa cttcttttat   60900
ttcttcaacg agctcgtctt tatatctaac gtctttagt cctggagctg gtcctgaaat    60960
ctcttcttta agagtacaaa catacccaat acggtatcca atgccgtctc gcttgatatc   61020
aacttcgtcg ataaatccac aatgtttaag accagagccg attatgtcaa aatatccttg   61080
acgtcgtcct tcaaacgtta cacgaactac taagacagtt ttaccaccaa ccttttgaag   61140
ctcacattta taaagtctg ttgaacctga ataacgtgga tgagttttaa agttcatctg    61200
acgatctagg cccatttgta aacgtgctgt tacggccata aaacgtgttt ggttctcgtt   61260
aagatgagca acaatccatt tcaaaggcat tttacactgt tcatgaccga acaaatcagt   61320
acgtcctaga ttacgcagga tattgttaga gttaatcatc gacagaacgt taagtttatt   61380
cagcgcgctg aagattccat cagccattga ttttccataa cctttacacg ctttaataag   61440
tgctcgcggc agattagtat agatttcaga cggcatatga aaatcaaatt tactagtcag   61500
taattgatga acttggatag caatttgctc ataattaagt gctctgcgat cgttatggtc   61560
tttaaaccac actttaatct gtgaagcaca taaaccgtta atttcatgtt ttaccgcatc   61620
agatgtaatg ctcataacta tttcctcaga ttgaattgga actcaaaacc attataaccc   61680
gtccttgggt aaagcgttta tgcgtgaacc gtctttaaac gttcttcaaa tttccgaaga   61740
gtactaatac gttctgcttt ctgttttgta tagtttgcaa tacgttctga agtgagagcg   61800
tatcgttcgt ttactgtttc tttcatgaag tcagggattt cacgagaagc tttaatttca   61860
tcaaacttgt cgagtactgc ctggtcttca gcgattaaat tttcatacat ctcgatatct   61920
ttcttgataa actcgatatc ttcctgagtt actttggata aacgagatgc tttatccttt   61980
ttgtactgct cgttagtttc acgagaccag aataatgtac gttttttgtt agtgttttg    62040 tagacttcca caattccaac tgaatcgatg ataacaatcc aattccagcg agatttgaaa   62100
atctgacctc catccacggt aatctcgtta ccataagcaa cgtcattaaa gaacttgctc   62160
tgtgcttcag atttaaattt accgtcgtta taatttacca ggttgaaaat atctttagcg   62220
ttcatgtttt acctccagta gttgataggt ctataataac ataaccatag accttgtaaa   62280
caactaaaag aaacttttt cggtattttt tccactgaac caaacagact tcgggatttt    62340
ttgtaatttt tcagatttaa gtttctcttc ctgttctttc ttatatacac tcttgtcgta   62400
ctggagcatc tctatggcat tcttttgcaa atgatctaag gtaattaagg ctttagtttt   62460
tcctttcaag gaagagtcct ggcgaacttc ctcgctatat ttcatcgtag aactaaccat   62520
acgatgtgca tagagttcga ctgcggcttt aattttttgc ataaaatcca taacatatcc   62580
tctttgattt gtacatcatt attttaaat atttctatgc cctcagtagg ttcctggtgt    62640
ccttctttga ggtaagccat atgattattc atctttatgg cttttgttac ctcagaactt   62700
cctataagct tatttcagta aagtaacttc cgagatttct tcccaaccat ctttatcagt   62760
tgaaataaaa tctgctacat aaagagccgt acgtaatgat acattgcgaa gacgagatac   62820
```

```
gttagccttc atccaggaca atgctttata cgtttctgca tccgtcagac cacgtttctg   62880
catcatgtca gtagataata ttacatcttc aactcgaacc ataatctctt cattagagtg   62940
tactccaagg tcgagataca ctgaacgaga tactaaagct tgaaggtgtg gagcaagttt   63000 cgaacccgt tctaactctt tatcgatatc aacgtttgta atgaaaacga tagtaccttc    63060
aaactcaaat tctttatcaa taccttatc ctcgagataa gatgacgcag tgctccaaca    63120
aactttgcgt ttatctccgg tatctaatgc tgctttaaga aggttcagga tgtccatatc   63180
tgagaatacg tcaacgtcat cgattaagag aacgctgtct tcatcacggt tgagccaaag   63240
ttgttcgtaa aggccaatac tggagatttt accattaatg cttttgtatt tgatgaaacc   63300
attatcatta gcattattaa gtgctttatc cagagaatac gtcttaccaa taccagctgc   63360
acctgaaata atgagtgaac gaattttgcc atcaataatg ccattcgtca tcatgttcat   63420
tactttaaag cgtttgttga tacgagtttt catatcttca gtgctttcaa caactgcaac   63480
tggtgacgtc tcaactcctt ccattacgat gtctgatttg aagacccata ctccacgttc   63540
agaaccatca atcataacga aaattttacc gtcacctaag tgggaacatt caggattaag   63600
ctttgccggg aaccatgtct ttgtggcaac ataagaacca gagatttcgt tattacgata   63660
gatacctttt ttgatttgaa cgttaacat tttattctcc aaatttactc atttcgtttc    63720
gataggtcta taataacatg tttaaagcaa aagtaaacaa ttatttgcga cgagattttt   63780
tggtaagagg ttgaaagaac actgctttac cggcaggagt caaagtgact cgtaatgcat   63840
taccgattcc caaggatgct ttaaccagac ctttagattt cagttcaccg aatgcttgac   63900
gttggtctgc attacgagtg ttaaccataa gacctttatc accagcttca cgaatcattt   63960
ctaacatttt ggttttcatt ttgtttctc ctcttgtttt gataggtcct ataataacat    64020
atcctaaaag catgtacact acttttaaa aatattttga cccctaaag ggcccgaagg     64080 cccttatcat ttatagtatg aattgtggtt ttctaagtag acttgctcaa ggaagtcatc   64140
ccagaaactc atatctactt tttgctgcat accgttctta gcggcttgtt ctgcggcatg   64200
ttcaacttgg tcaacgatat cttctaagaa ttcctgtacg gttttaaacg tatgtttacc   64260
aagcttaaca tcgagaataa atggagcatc ctgaagcggg taaaccaggt cgccggtttt   64320
gtaaatttct aagagctgaa gtccaccacg gcatgcatga ctcaatgctt tccaatcaat   64380
accttcgtta gcttctgcct tacgagcacg ttcaccatag ttctcttcca gtttaaccag   64440
gatggcattg aactctttat tggttaacgt gtcttggaat ttacggtcta acagattata   64500
gaatgtttgc ttacctgttt tctcgttttc ggtttcaatc cacgaagcaa attcacctat   64560
aggcagaaca ttcttcatat gtgataaacg aattactgca ccgttgacaa agtattgtcc   64620
ccattcatta gaacgtttaa gggcttggcg gagaacagcc agacgagaac ccttgacgcc   64680
atatttagaa gcttgcttac ggacataccc taaataagat ttcatgttag tggtatagaa   64740
acgagatctg ttatcttgaa tatacttcca tacatcaggc aaatcagatt taactactag   64800
actcggtgga gtgtgaagca tatctaatgc gacggtttca ccatctgcag ctagtttaaa   64860
gaaatatttg agactataca actcatggtc tacgtcgtct tttgtgttct tagaagatgt   64920
gttattcgtg ttcttgctca tatgttcttt aacgttaccg gtcaaaatat cacgagcatg   64980
agggacataa atttctttaa aatcaacgtc agattcagga gtagacgttc cataaaggtg   65040
gctaccaaag taagccttaa caatcgtttt cattatttag ccttatattc aagagtagga   65100
cagacttttt ctttacgagc tttaaggtat tcacctatta atgatttctt acgttcaata   65160
ggctcaagtc catttttaat tcgttcttgg ttttgcgcaa tgagctcaat ttctttataa   65220
```

```
tacttccgct ctctatataa gtcgattagc cacggtatgc ctaatactaa aactatagaa   65280
ataccaacac ataatgcaat gaataaaaca cctacaccaa ttgaggccgg aaccaatgac   65340
cataaactac taaagacaaa gaatttagtt aaaatttcat ggccaacgat tgtggccgct   65400
gctaaaatcg caaatccaat aatcgaaaca aacaataccg ggagaaacgt tttccaaaaa   65460
taagcacaca acgttttcgg acgattccat gtactattaa acgcggcata aattttaaag   65520
tgccaagagt tttcattgat aatcataata attccttatt tcaaagttgg gataatagaa   65580
tcgagataag ctttaagagc aactgcttca tctttgtcta atgtaacgat atgttgacga   65640
aggtcatcaa tttggcgaat aactacaaca tcgccatctt cataagaagg attaacgcct   65700
aggaccgttg tatagtcagg gcggtcctga tttgtaataa aagcattacg gcatttagcc   65760
cattgaagtt tggccttttt ggctgtttca gattccatta attctttcac cttagtgacg   65820
aatgttttcc aattattaat agaaaggcat tcatcttctg tttcgatatt aaccccgcta   65880
taaagaccgt gataaaaacg aacttgaagg tcttcatcga tgttaattac agatgcatgg   65940
ccgggcggat tgagtttcaa atcttgtcc agttccatag gaagaatagt aacagaatca   66000
tcttcttgtg tcagaacata cacataacca cgttttttcga tacataaatc accaaacaac   66060
tcggttgttt caattacaat tttcatatta ttccaccaatt aaagtttcaa caaaattcac   66120
caaatcattc agacaagcat caacctgttt ttcataaaag tcttcgttat catttactgc   66180
atgataagct acatcattca aatctgaatc ggcttcacgt aaatcacgga taggtccat    66240 caatttatta gcttgttcac gggtcatttt accatactcg tttcaataag attcactatg   66300
ccgtttacca tgttataagt aaacatcgga taattgtatt gtactacaac ataagcgata   66360
agcaaaagtt tcattttgtt ctccgttcgt tttggtagga ctactataac ataatcctac   66420
caagatgtaa actaccgatt gtgttttaaa tgctgataaa gttcttcaac ttgtttaggg   66480
tccaaaacaa ttaggtcatt ttcttggcga agataaatcc atcccttatc accagggcca   66540 ttttttacaaa acatcaccac catatcatca tcttcagcgc tttcaggtaa aagttcaagt   66600
acaccgtctt cagatttttcc agtataatcg taaagcataa tatcctcaca taatctcgtt   66660
aacatacgtt tgcaattctg tgtgggcgtc agccatcttt ttcattgcct tattgatatc   66720
aatatcgcca tcttcgcacc catgggcatt ctcccaatca gatacggcat tagcgtactc   66780
ttcaatcaaa aacattaact tagaaatttt ttcctttacgt gacataacgt tctcctctag   66840
taagtaaaga ctactataac acaacctgcg gagaagtaaa ctgatagata caaaaaagcc   66900
ccaaccataa ggaaggggct agtaaattag atagatgtag gctctaatttt tattttcatg  66960 aactcagcaa attgtctggc agttttatg ccttgttcct ggcattcaaa tgcatcatca    67020 cagggggctat ttttgtaatg ctttgccata tacttataaa atttttcaga attctcaaca   67080
ttttgaattt cgaacaaagt atatacgttt ttaatccctg attccataaa gttatcaaag   67140
tatgggtcaa catatgcagt gccaacaata ggagtcgttg ctgcaaaaaa ccccagcatc   67200
gccacaatgg ctatcgctct taaggccata taggcctcct gttaattttg gccagtattt   67260
atttttcgcc tttggacggc cttaacatct gcgaggtatt tttccagctt tcgcttgcgt   67320
gtataatcag ctttagaacc agtttgacga atatcctcgt ttaaatgaga aatagaatgt   67380
cctaattctc ttcggatttc gtccaattgg gttacagtaa gattacgaag ttgtctttcg   67440
tttaattgct gcatatatat acctcttggt tagatattag tatttataac aaccctgtca   67500
aatcgttcca atgcttccgg cataatgaca cgtatctatc ggtatcacca atttcaattt   67560
```

-continued

```
gtccaccatc tgtaattgga agtccatctt ccgtgactct agctaccatt gtggcttttt    67620
taccgcaatg acagacacct ttaagttcaa caagcttatc ggcaatagcc attaatgctt    67680
gagaaccttc aaatagatta cctttaaaat ctgttcgtag tccgtatgcc attaccggca    67740
cattgtatac gtcaacaata cgactaagtt gatacacctt ttcagtagtt aagaactgag    67800
cttcgtcaac aaatacacag tgaatatcct tttgtgctgc agcccattta taaaattcaa    67860
agatatccat gtcttttgta attatattgg catcctgacg aataccaata cgggagacta    67920
tttcaccttt tgaatcgcga gtatcaatag ccggtttaag aactaataca cccatgccac    67980
gttctttata gttatgtgcg gcagtaagta atgaagcaga cttaccagcg ttcatagcgg    68040
cataggtaaa aattaaacta gccataagag tcccttatag tgaattcacg tagtcaatga    68100
gttcttgttc tttcctgtca aatgattcca tcaatgcttg atattcttcg tctgttaaag    68160
gagcatattc atagtacgca ttagtggctg cttgctcatc caataggtca tggataagtt    68220
cgaacagttt agttttctct tctttagtca atttcattta ggttcacctt ctttaacgaa    68280
atctgggtaa gggtaaaatc ctgagtaaaa cccttcacct ttatgattgc tacaaccttt    68340
gttcgaacag taacaccaat aatcaaaatc acaagccatt tcgtcattgc ataaagcaaa    68400
aactacaggc cattcgcatt tttcgcattt agcacctgta agaattttg tttgactcat     68460
aaccatttga cctgcatgca atattcttcg acatgctttt tacgaccttt cttatcaata    68520
aagtatatt ccataaagcg tccatgataa cgacgttcaa catcgtgagg ggtgttaata     68580
ggacacttag tctgacgaat ttcttcccat tcacgaataa taactgcttt attctttggg    68640
tcatacgggt gaggataatg cacattcata acaatggttc ccaatcaaca atcacaattt    68700
ctagtttagt ggaatacgta tctaaaatct cttcgatgac atcccagttt ccaccaccaa    68760
tacctgcacc aattcttggc atataaatta caggctttgt tatcttattt tttccgaatt    68820
catttaattc tattatacaa ttcattaaag cagagtactc aaaattaggt cccggctcaa    68880
actgtgtata aagattaaag caataagctt tattggtctt aaaatatttt tcataaaccg    68940
aataagtccc gagtttagac tcgtctccga attcggtttg aagtttatcg gcttctaaaa    69000
tttttggata agccttttgcc aattgacctg ctacaccggc acccattgta tgaaaacaat    69060
tgcacccatg agcaatatta ttacctttag aaaacagggc gacaatatcg cccttgatat    69120
agttttaat cacttgctac aagtcctcta gtataagagt caactagacg gtccaccata     69180
gaattgcatg ctgccttatc tttaggttcc gccaccgagc attctaatat ttgccatttt    69240
ttatagtatc ttttaattaa ggtagacgcc ttgaacctac tagacgcccc atcttttttct   69300
ccgtctttat acgcatataa caattttttgt gaaaaatcta ctttacactc ttgacttta    69360
ccacaataat cagacgccgt tctgtttgta tactccgtta catcagtata tgtagtatta    69420
gcaagagcgt taaatgaaac caagccaact attaaagcta acattttggt cattctttta    69480
tttccagtag tttatttgat ttaaggtaat tagccttttc taggacttca gaagcatatt    69540
tacttccagc acttgtcttc caccccgcat tatatgagga tatagctttt cttatatccc    69600
cgttatgtat atttaaccaa taagaaaatt cgatataagc ccatctggcc gaattagacc    69660
gcttagatag catttttctta atttgggcat cagacatatt ataaccaagc tggttaattc    69720
ttgccctcat tgttggtaga tagttttgga acattccata cgcatggtga cctttcttat    69780
ctttaagatt aataccggca gatgattctt gccatagtat tgcggccatt atgtatccaa    69840
gtcctttctt atgcatattt tcatgcgttt taaattttcc gtccttagaa aactgttccc    69900
caaactgata agcataattc aagttatcga gttggacatt actaaaagta tgctcggagc    69960
```

-continued

```
tatgtgctga taacgaaaga gcaaatagac cagcgagtag tgcttttctc atgtttacct    70020
ctagatttta atcactgctt tagaagcttt tcctggtagt cgtttactgt taataatagc    70080
cattctacat tgaagagtct tcattttgaa tgttggattt tcgcgacaga ctgtaagtcc    70140
taaccaaaga tttccatcag ttatttctaa acggcctggg cgatattcga caccttcgac    70200
aaaatcttca tcaacatctg gacgtgccgg cattgataaa aattctgcaa cttctttaac    70260
atgattttt actttatgaa ataattcaaa aacgtaattc tcatctattt ctctctggat    70320
ggcacgatct aagagatgtt gagaatactt gatatgaaag cctggtagtc caagagactt    70380
tgcagcatct tttataccgg catttatttt gcggaactcc gtttcaaaga ttcgacggag    70440
tttattacgg cggataaaaa cttccgaatt gatagtcatt ttgatttctc ctctagttga    70500
caggtctata gtaacacaac tagaggagaa gtaaactact ctttgaaagg aattaacttt    70560
ttaactgctt tagatacttc gtcacgaacc tgatggaagt tcttgagctg ttcaaggcgt    70620
tgttcgtaat acgcaatctc atcttcttca agacaatcgt cagcgtcttc tttcagatat    70680
gccttgtact cattaaagag ggcccatagg cggttctcaa agtcatcaag gctttgaatt    70740
ttcttgtgct tcggaacaag gccaaaagga ttgcttttcag ttatgcgtct agatgcttca    70800
taatgagttc caaagcctga taggatttga gccattagta ttttttcctca ggtcgaaata    70860
ctgcacgaca ggcccacatg ctggcttctt ttagatgttg cttagcatac ttaagagcct    70920
gtactgcatc catatcttct ttggtttgtt gctctgtttc attttctttc aagatatatg    70980
cttcttcaat cagagcatca aacaacaatc caagacggac ttctgcatct ttaatagcgt    71040
tcactttacc gatttatcg tcggtatgtg gcttgtagcc tttaatatct tcaatcgaca    71100
taaggaattt cctcatcggt ggcaaggtca tattcgacca attggatagg ctcattaata    71160
ccatatccac gtacagtgat atcagttgcc ggatagtttc cagtaatatc acccattcta    71220
aatgcttcaa tgaatgattg ctcgcctgag caactaaacc aggcggcaaa acattttaaa    71280
acatcttcag acccttctat aatcaattta gccattatag actctcagta aaggtacgag    71340
cgataacgtc acgctgctgt tccggagtca gagagttaaa gcgaactgca taccgata     71400
cacgatggt cagctgcgga tattttccg gatgcttaac tgcatcttcc agagtttcac    71460
gacgcagaac attaacgttc aggtgttgac caccttcaat tttaacttta ggttgatgtt    71520
caatttcaat ttcacgggca ttcaaaccgt agaaatttc cgggtctaca atagcgtctt    71580
ctttaaaagt cttagaggca ataatccggg cttgagtacc gtcttcaaaa taaatagtgc    71640
ctttgtgtgt gccttcaaga atttgatatg ctttcatata acctcaatta gaaataaat    71700
ttatccaagt tttttctta atcaaaaatg ggtcggaatt aaacgccatt aaactttgag    71760
tgattaatcc cttaaatggc ccatcaataa attccatttt gaaatgcgga atactagtca    71820
taaaccgtgc attaggagca gtacaaagaa cctgctgccc tgcgaacggg cctttagtca    71880
aacgatatcg tttaggttta aaatggtaaa tctcataatt ttctacaaga gcccttttat    71940
tgcatactgg gctgttataa caatattcaa aaacttcaat agtggtcatc attgcattcc    72000
aatcacaaaa aattgaggac gagcattacc gccgatgcaa tatttgcttt tgcaacagtg    72060
ttggactgtt ttaatatgga cattgtaaat cttatccata tcaggagctt taataggctc    72120
gtcaattatg tacagaatac gagaaagcgt taatccacgg aatttagaac cttcattgcc    72180
aataaaacta cggacagaat cggtaaataa acggaatcga atatcatcgc tagaataacg    72240
agaaaattct ttttttaatgt tgccagcaga aatttttagca taggctgaag tattagaaag    72300
```

```
aacaataact gttccaccgt catacagcca attaacagca aaattagtta ctgcagtcga   72360
tttacctgat tgtctgccgc cgtctaaacg aagtgtacag tactgcttga gtacgtcttc   72420
aaatggtggg gcataaccgt tcttacaaat ttcttctact ctagcatcag aatggtgtgt   72480
aaaagcattc atcagggata gataaggacc agttaaaaat gttctcattt agtttctctt   72540
ttaggttggg ccattccgtg gcgcatgaat tgtccatttc tgtatttacc cctctaagta   72600
attatgaata tactatcaca attctaggag aaagtaaact gttatttacc tttaattact   72660
ttagctgctt cgatagccgc ttgctgaagg tcatccatag acataccgaa tttagaagca   72720
aagttatcaa ttttcttttc gacagcattc aaaggcttgg cctgtttacc ttcattagcg   72780
ccaggaagag cgagaatacg ctctttgtca atataaaggc ttacaagttt cttacggtct   72840
ttatcggaca atcatgaaa tgaatgggcc tttttattta tagcggcttc taatttacct   72900
gcactcactc gcgcttcagt aataaattct tgatatgttt tcatttttg tttccttgtt   72960 gttttgatag agtaattata ccatattaat acttaagcgt aaacaattta agctttaccg   73020
ccagaaataa ttccgaagtt gttaaaatcg tatccaatat cgtcaacatc tactttagga   73080
tttactacaa cataagcaat ttcactacgt tttgcatagg tgttgatttc tttaccatcg   73140
ccacctaaga aagaataccc attacgtttt aatgagccaa agtcttcggc atcaccaatg   73200
aaagctttaa cttaaatttt aggacctttg gcatctgctt caatgataaa ttcttgatac   73260
attttcattt ttccttagta aattgattta ccatagtatt tgtaccaagt aggacgttga   73320
gcaatttttt catctaagcg tgcttgactt atcgcaacgg acgcttcgga cgggacataa   73380
ttattacgaa attcggcagg gatgtcggaa atatcctgga ctgtcgtgtc cttgattttg   73440
aaaccacgtt tcaagcattc agcgattagc tcgatttgtc gtaaacgtaa aaattcaagt   73500
ttgtcgtaaa agaatgttac gtgacctgtg cctaagataa atgttggaga gattttaaaa   73560
tcctttacac gtttaccgtt ttggacatgt ttacggactg cactaaatac gcgtggtaat   73620
tcacgatact cagccataag atgttgatcg gtcagttcag aaacaagtgt taaattgata   73680
cgagtcataa tttcctccaa gtagttgatg aatgtatagt atcaaaaccc ttggaggaag   73740
taaacactat ttttctgaag cgcctgaaat atatttttca agacgttgtt tcatcagcga   73800
gccgttctta gcgatttctt ccggtttatc gcacatacgt aacaaggctt caagcttagc   73860
gatatcgctg gtacgttcaa atttgcgagt atctatctta ctagcaagtt cagaaatacg   73920
tgctaataga ctttcggctt caaccaaagc tgcacctagc ttagttgcaa atgtgtcagt   73980
agcttcgtta agaatagatt ctgataaaaa ttcactatat gttttcatat atacgctttc   74040
caagttcctg ttttaaatgt tgagattacg cgtttcgcgc gattaggtgt ctgacgatac   74100
catttagatt gggcgagatt tactgccgct tcatcccaac gtttctgttg aagcatacga   74160
agagaattag taaaaccagc aacgcctgct acacccattt ggaagaccat attgaccaat   74220
gcacatcgac gaaccgcgtc taagaatca tataccggtt taagtttagc attacccaag   74280
attccgcgaa cggctttatc gacgtcttca ttaaatagct tttcagcctc atcaagggta   74340
attgtaccgt tgcatttacg accgatcatt ctgtcaagtt cagctttagc tacggctaaa   74400
gacgggttct tgttactaa atggcctatg ccaatcgtcc aaaagccttc agtgtctttg   74460
tataaagtca gtctaagacc ttcgtcatta cgaagcattt caaatatatt cataatacct   74520
cccacgttta taggaggtat ttattactta taggatggta gtgagcacct tatataatga   74580
tttgcccatt acatattccc attgagaagg tttaattaaa gcgaatgcat caaattcagg   74640
aatctgtcgt ccgtccggga atgtatgata tgaattacaa acactgtttc tgaattgctc   74700
```

```
gtgctctaca gggatggtat ataggaacag atgaatattc ttattgtctg agtaatgatg   74760
ttcacctagg tctttcagga aggcagggtc atattgtgta aacccagttt cttcttcgca   74820
ttcacgaata gcggcttcga taggagattc gccaggttcg acacggcctt taggaatatc   74880
ccaccgatga gctaatgcac ctttaggacg agaaccagtt acacgaccca tgaataattc   74940
tttatctttt gtcatgaaga taataccggc tgatagttct ttcactttat ttttcttact   75000
catcatctcg gtcccatgat ttggccatta attcggacat aaattcttca atacgcgttt   75060
ctttagatgg actttcacta ttagagaccg caagtttgta atctgcaata ggactgaaca   75120
aatcaaggtc catattaaga tcgtctttga ttttttcttc tgacacatct ttatcatatg   75180
tgtacagata actatcacat gattctgatt taatgtaaat tgctatactc atctcaaatt   75240
cctgcattcg gtaataaaac gttcaacttc attattcttg gcctttatct tgtctttacg   75300
ttcctgtaaa ctacttttaa caagattaat aatgatgcct atagtacctc caccaataat   75360
accaccaata atacttacga tagtagatgc taataagata gcgataatat ctggtatggc   75420
aaaggcactt actttagtac taaaaaacca taccgacggt acaaatataa tccatcctgt   75480
tatccattga cacttattga aaaacttttc aagatcagct tgagttgttc gtattacttc   75540
atcgataggt tgatatccat taatgtatct gttcacgata atacctgctg gctggtcgat   75600
tttaaattct tgacaaatac gtttcactaa gtaggatgga catcctgtcc aatctactga   75660
atagtatgaa ataccttcat tgccgtcgtc aatattagac caatatgttt tgttaatcat   75720
taccagcctt ccatagggaa ttccagataa acttgggcat tgacacgaat tcattggta   75780 atcttttaa ctcggtctgt attacgagat acacgtccga accaacgcca tccattacta   75840
attgcacgag aaccagtgtg ccatgtttgc caatcaaact gaagaagagt acggtctgga   75900
gcttcccatt tctctagttc accttttca attttttcga ggacttcttt gtgccattgg   75960
cgatagataa gttcgccatc aggaatctga ctgaactctg cagttcctgt tgcaaaatga   76020
gtaggacaca cgtcagcgtt aacaagacca agaatatgtt cagaatggta acgagggtta   76080
tcatagtcag gttgtcctgc agtaataaag tgttggccga ctggaatatc agggcgagga   76140
acatcgtcat ggtgatatcc aggaatagca ggataccaac caggcatcag catatgaacc   76200
cgagaatcaa atacaacatg ttgattagtc caatcaattg ggagattggc aataaagcta   76260
cgagtaatag gaccgccgtt atcccaagca aaactcaaat cacagttaaa gaacattggt   76320 tcattttttga tttggtcatt ttgtacgtta tgagcaaaac cacctactgc acgagcttga   76380
ctattaaaca ctttagaact attcatatta ttttcctcga cattctttaa tgaaattttc   76440
tagattggta gattcaatag cttttttacg agcttctgcg tgttcttctt cagacaattt   76500
acatttataa ttaacccaga cgttatggtc aaaactagtc gtggcatata ataacaaagc   76560
cccgacgaat aataaaaatg gtgataagaa tacaaaacca ggaacaccat ccatatcgta   76620
agccttttgt aatactgcaa cagaaagagc tacgtaaaaa agtgatacaa atatagttaa   76680
aagaccaatt cggttggttt cgcctaattt cataatattc tcctcatgtt ttaataggac   76740
tactataaca tagtcctata attgtgtaaa cagttttgcg aaattatttg aaaggtttta   76800
ccatatggaa attttgttta aaacgttta cataatcgtc atgtcctaag ctttggtaca   76860
tacttacaac tttgctgtag ttttcccaag cgtattcacg gaaccagcct gacgtgattg   76920
aagtacagac ttttctctaat gccatcataa aactatcacg tggatggatt tcaaagttat   76980
taggaatctg agaacgttct aacgctagta cacatgattc ttcgtatacg ccggctaatt   77040
```

```
tgaccatttc tggtaatgat tcgaacttct cgcgtgaggt catgacttca gaaccatctt    77100
tcatataaaa tgtatacgct ggacggtctg ttagtgcaat ggcttcgtga atagtatcat    77160
ggtcatacgt atagatgtca tctttaaaga atgcgctttt agaagtgtca agaactgggt    77220
gagcatagtt caaggtttct ttctggcgtt tcagcataat ttcagtaagt tcatcgttca    77280
gtgtaacacc tttaccacga agatactgaa tatggttcat agtctttaaa aagaatggat    77340
tatttttctt gaaacgatga gacatcttaa ttgcaagaca catctcagga gttgcccagt    77400
aaaacccgtt caaacggtct ttagtcaaat ttttcttggc gtattttaaa aggtcataag    77460
aagacgtgaa atcttcagga gtgagttcac cgactaattc acggacatta gtgattgccg    77520
gaacaatata tgcttcaaaa tgagtttcgc gtccattatg gaagcatttg aaaacttgga    77580 catcaggggtt atcttggtga acatatacac ccatcatttg attttgaat acattccaag    77640 aaccttggtc cgcaataaag tcccagtcac tattttgat agcgctagaa tcaataagac    77700
cgtgatagtg aagtgcacga gaaccaataa ctaacatcat aatattttcc tcgaatttag    77760
attacttaaa tttcgcgaca tgcgatatta tattcatccc agaggtcgtc atgtgaagcc    77820
tctactaatg gaacgattgt gccgtttatg tcttcattat aagggcaaat tgtacagtgc    77880
gcatcttcga atcggatgcc tttgtgttca gatttttttat aacgcatatc gaatatcttt    77940
gcaaactttt cacgagtaat agttttagca actacttcgg ttcctatact ttcgtaataa    78000
accattgttg tctccattta atttgatagg actactataa catagcccta tcttgttgta    78060
aactgtttta gcaagaataa ctagatgata cccagccttg aacagtaata ctattatttg    78120
ataacgagat tgcgtcctgg agattcagac ctgcattatc ttcaatccac aatgtaactt    78180
cttcacgctc ttcggttgca atctggaaca ggttttctag agcagctacg gccgtacgta    78240
cagcacaatc taattcacga gacatatgat ttccttaaca agtgtgagaa gatgcaaccc    78300
aaccaccatc ttcaaggctc aagttgtagt cgtattggta aacgtcggcc cattcagcat    78360
aaccgttttt tgtacaacgt tcaagatcgg ctttaagatg tcctggtgaa tgataggttc    78420
cacccatgcc ataagctgga tacaagttga atgttgtgtt ttgtttatta gcaatttctt    78480
tggcagcctc aatagctgca tagatttttg ctacagcttc agccagttcg gtttgttctt    78540
tagacataat gattccttag cacaacgcag aagacgaaac ccaagcacct tcagtaataa    78600
cgtaaccatt accttcacgc ttaacatcgc caccattatt tcaatttca tctttcatcc    78660 actgggatac gatttcaccc ttaggataat aagtacgacc gctaccataa tcacctacag    78720
aaaatgatac tgcatattgg tctgcgatct ttgttgcttc ttcttcgatg cgttcagctc    78780
gattcagaag tttataaatt gcatctgaag cggatttggc atcattaaac tctggtactt    78840
taatttcaat aatcttactc attttctaca ttccttaata aagttttcga ttgtttcatt    78900
ttcactttag ctaggagttc attataacta atcatttgag aagcgtaaac agcataaatt    78960
cagttaaggc ttttgcatct tatttcctta acgaattcca tagcttcttc atattcatac    79020
tttttaacag cttcatcata ctgagcttgg gcttttgcgc actgaacttt ccattctctt    79080
aatcgggctc tgtgatgacg tccttggtac caatatccca tccagttaat aggcattaat    79140
aaaaacggta caataagtgg tgcgacgaac attaatgaaa atgctgcatc agacgatata    79200
acttcactag aatctaaaac ggctcctata atcataaaga ttaaaaatgc taaagctaaa    79260 ataggggccaa atagtacttc atttgggatt aatttacgct tgtattcata cgcccagggc    79320
ttacttggca tgtatagggt tggctttgac atattctcta cattccataa taaattgctc    79380
aaggattaaa ttgttagtga aattaggact aacaaccata gtttcataaa gcgcatcaat    79440
```

```
agcacttaaa gcatcaactc tcttaagcaa aggcttgcct tcatacatag tttcagaatc    79500
gacgattaac gtaaagtagt atttttttatt atcgactaga acttctgtat cgatataaaa   79560
catattagac ctcagaagct tatctctaaa accataataa tcttcagagc gttcgctgat    79620
atattcccat tcagtgttta aacaacaaac agaccacgta ggagcaacga aatcagtgaa    79680
tctaatatca tggtctgcaa ctagtttagc aatagctccg atatcatgaa tcataatacc    79740
tggggctaat aaagattttc tgctatggct agccgttttc tcggtggtct cataagaaga    79800
cgaccagtac catttacgtc cggttgcaac atatcgtaat gaatcaacta agacgtagg    79860 tggatttacc ttatctcgga actcttcgaa cattgagtca atatcattat tttggtttcg    79920
catgttaact cctttattat ccaaaaggag gaccggagtc ctccgtatta ttttatttca    79980
aagagttaat atattcttgt acatcagcag aagtggtttc gacgccggct ggagtgccat    80040
tgaacgtttc aacacgagtc agagtgtctt cgatatcaac cttagtcagt gcagcaattt    80100
caatcacatc atcagccgta gagataccaa gggcattggc tgctcgagtt tcacgaatgt    80160
attcgagttt gattgccaga ttctgacgag catcatcaag ttcaacaacc ttacgagcaa    80220
tttcaattcg catagcggca taccgtcag ctttttgtatt aagttgttcg gcagttcgac    80280
gatacagaag accaagctta gcatgcatgg taacatcttg tccttcagcc aggagcttac    80340
gaatttcacg ttccttagaa gcggcttgct tgttcttttc attaacaagt tcgcgaatac    80400 gttttctcttc attaatagat ttaacagaag ccgttttttag ttctttgatt tgggtaatca    80460
acttatctgc agctgcgtta tactgttctt cgacagtcag attttttagcc atagcagtac    80520 ccagtttagt gcggatgaat tcaacaagtt tcttcagtgt gttcatatta ttacctttca    80580
attggtggtt tattatccaa tgagagcatt atactctgct ctcaagagtt tgtaaaattat   80640 ttttttaatca aattgacata aaacttggcg tcttccgggt gcatgccttc gcagtattct    80700
tcaaccatga acttcttaac agcttcataa ggaccactca gattaagctc agttgtccaa    80760
aacttggaat cttgggctga atcgatacga acttcagggt gtcggttgcg aataacttct    80820
tcggtgtatt cataatcaac gacatcaata ctaactttag ccattttgtt tctcctctgt    80880
agttgataag tcctatagta tcaccatcat tggtgtttgt acatcattat ttttaatttt    80940
tccaacttaa caacttgtag tgtccttcat tcatacgcgg tttatcccaa gaaatactaa    81000
tatatgattc gccatcaata gaagtcgccg ggttttttctc taccgtaaga ccttcacttt    81060
ccagccattc aatagtattt gcgcataaat ctgaagaaca cctcatcgga aactggcaag    81120 attttttcacc tttagatgca gcgttataca tcttttctaa aatacgcttt tgcacgtttt    81180
taaaaatggt ttcagcagat tcttcagatt ttttattcag atcagtataa agactcataa    81240
tattctcctc attaatggg ctcataatat ctcaatcata agcccatgta cgcatttatt    81300
tcatattatc gaaatattct tcagcgattt cgacattatc atggtaaact ttagaagaca    81360
gtttaacata accttctgcc gcgaacatat taatcacaac ctttacagta taccattgtc    81420
cgtcttcatt acccattact gcgtaagttt caaacatcgg atggtcaggt ccaataactt    81480
taatatcatt caccgtacgt ccgaaatctt ctggaacgca tttcataaag aagttgaaca    81540
gttcaccgta attatccatt tcattctcca aggttttttct gtatcggtag ttgatagttt    81600
tatagtacca cggaagaaca gggatgtaaa cagttttttgt gaaaaaaaaa ttttttaaaaa    81660 gttttgtgga attctagggc agggagggga aatcaaagga tatgataata tattataaag    81720
ggcagaaact aaatgatgcc tagagaggtc gggaaaggcc tagataccaa aaagccctat    81780
```

-continued

```
catttagata gggctttaaa attatttacc tagtttagtt attatagctt cggcagcagc   81840
ttttagctta gatgcagtgt taatacgatt tttaatttca gtatacgcat cgccaagaac   81900
atcaaggcta tcagaataaa cacttacact attgcgttcg ctatttgaaa tagaaccttt   81960
agttttacga tcaaaatcag tgtacacgtc ttgaagatca cgggctgcct tctttgcatc   82020
atccaatgca tcaagagctt tattcaaagc attgacgtat ttttttagtg tcaaacatat   82080
tcttagaaat tttaacaggt gcacgttcag gagtagctaa ggcggattta ggaacctgtg   82140
tgccagatgc cagtttctta gaaattttga aaaatgcttt attgaaacta ttttcttgac   82200
tcatcgtaaa agaactagta tcgatgttat acatttcaat agcttagct ttccacttaa    82260
gaaaatcgcc acggtctttt ggatccaagt ggaagaatac tttagtaaga tctgcttcag   82320
atggtaattt tgctgcttcg gttaaaaatt cggcgtaggt tttcatttaa aatccttgaa   82380
ataatttatc ggttggttat taattattta ttactttggt attatcagta acagcattct   82440
ctgagagatt caaactaaaa agccccaacc ttttggctag ggctaagaat gttatttgat   82500
ttgtttagca gaccaaatgc ggtctttaat aagttttttgg atatcttcaa catactcaag   82560
gctatgagcg tgaggattat cttttgaagct atgtgctcgt gccagtttct ggccttcagt   82620
tttgattacc aaaagttctt taagaattgc ttcatactta gaaataattc ctttggcgat   82680
atttttttct tgagctgctt tagggcccgc ttttggtgct ggtgctttac ctgtagcttt   82740
ctggaacaat tcacctgatg cagctaggct tttaaaaact cggctaacag tattagcatt   82800
agtaaaacct tcggctttaa aatctctaat aaaacggaaa cgttcttcat cagaggcgtc   82860
tttgtaagaa tatttacctg cttgaattgc tgcaatcgca gcggcttttta catctgaact  82920
agattgttca gtcaaaaatt ctgcatatga tttcatgtta cttttcctaa gttaattaac   82980
ttatctattt attattatgc aaaaaagccc caacctttcg gaaggggcta agccttgcgg   83040
taaccttgtc ggggttccac ctgctaaggc aagtgtttgt acgaaacgcc gggattcgaa   83100
cccggttatt aagcagttga cgctactcaa tattttttaaa aggccatatc tcgaccatat   83160
ccgaacgttc cgtcaaaaac gctactcggc ttacggcaaa gatatttcct cgaatcgata   83220
attctgtgcg ccgtttctgc tgtgatgtaa gggatatta acgaatcata aagatttatt    83280
aagaccagtc cttactcagg gaacatcagt ccgacgactt accggtagcg acccggcttc   83340
ttattttggc atatcatcaa tttgctctcg acgccgacgc catagattaa tcgcttcatt   83400
aacacattca gcgtttggta tatgacggca ataatataat gattcacgtt tctgaaaccg   83460
atgttgcaat gggatttcgt ttaaaaggtc tttacgatca aagtattcaa aactagttaa   83520
ccctgaacgg ttttttaatga acttccaatg tccgaattca ttttgaacat agatgtaatc   83580
ggcatgctga tacagcgaat taatcaatcg atgagaaata actgtatcat attcgttaaa   83640
ataaaacgtt aaatcatgaa ctaccagata aatattgcct ttcatatttt cctcacttaa   83700
agttggtcga gacagaagga ttctaacctt caacctacgg attagaagtc cgttgctcca   83760
tacaattgag ctatgcctcg aatatatggc ccagaccaga ttcgaactgg taaccttttcc  83820
cttatgaggg gactgctgct aaccattgag ctacagggcc taaataactt tctattatga   83880
aaggcacttt agagcacctt tggtaataga gggtatgaat taataataac acataattct   83940
taaagcaaat caatcatttt aacggttggc aaaacgattt cttcttcaat ataagcaaat   84000
tcgacacgtt caactacacg caagaaatcg taatcatagt attcagaagc atagccaaga   84060
atatcaataa gtccttgaga tatctcatcg ccttttcacaa agaacaggtc gaatacgcgg   84120
gcttcgtctt cttcagattt atcaccaagg tctacttcga tgccaaagac cttttttaata  84180
```

```
aattccggtt ggagttggtc tgagaacagt ccttcaacca gatattcgta gataataagc   84240
gagcaacgac cgaatggtgt attaccgcaa taacgttcgg ctttggtgct agaatgacgg   84300
ctcttaaatt tcttcaagag atatttaaac tgttggagct catgctcttc cacttcaaac   84360
aatgttttgg ttttatagtt gtcaccatca ctttcatagg tagtgacatc aattacgtag   84420
cccttaggaa ttgtactgcc taatcgaata ttcatttaat caccgtacca tattaatgta   84480
attatattca atgcaacgta atttcaaagg attcttgaaa atatcatatt caagagggcc   84540
tttttctgtt tcaataaaga aatcaaagtt aactgtgtta aatttatcat cttcacagag   84600
taatttaacc tgtgaagacg aacggtcaat gtaaaccttt tcaacttcaa aatatgttaa   84660
aatgccataa tcatcgatca atgctttagc tgcacgttga tcgctttcgt atccattctc   84720
gacagatttt actttagcat aaagaatcat gagtgttcca ccacttcaaa agtatgtgca   84780
tttacaatct ggtaccagtc aaaatttctct tcagcatttt tgtagatttc acgaagagct   84840
tcaacagttt ttcctgtagc aacaagatca tcaataccac caagaggata acagtcataa   84900
ccagcaaaca gaaggaaatt aatagtttct gtaggttctg gatgcagtgt accattgtca   84960
tcgactactt caaagaacat ataaccaggc gatttagatt taatccaagc ccatgcttga   85020
gccgctgaat caaatggttt gcgtatcaaa cgacaatcag ggtctttaga aggatttgct   85080
tcaaaatccg catatacacg atatttcatt ttactcacct tttgcaattt tatccataac   85140
gatagcgatt aagccgatta gaaatgctac taccaatgag atagaatttt ctgttgttgt   85200
cagtagtcca caaatgaatc ctacaaacat cgaaaaacta aaagccattg aagcaattac   85260
tacagcaaca ttacgaatca gttcagcgcg tttcatttta ttctcctcag tagttgatag   85320
ggtaatagta tcaccaccct atctaaaagt aaacggtttt ataaactatt ttattccgcg   85380
tgatgcaatc gtattctgcc gtttaacacc agtttgttta aagtcatgac tgtcgatttg   85440
atcggtgcga gcaactccga atgatgattt aatcttagct ttagatcctt tagttataga   85500
aataaacatc tcggaagacc ctttcttaaa gtctgatgca gatacttcaa caccgttctt   85560
agcaagtgac ctcagaattg catccgcgta ctcatcatca agactcgctt gagtattaat   85620
aacaaatgtc tttggtgcag ccgcttcatt gataaattct ttataggttt tcattttatt   85680
ttcctaatta attttgatag gactactata acatagtcct attagcatgt aaactactta   85740
cagaagggtt tttgcaataa ttttaagctg agctacagaa atatgcttag ctttaaacag   85800
tgcagtctct tcagccggag agataacaat agtagcgcca tctttcttag cagaccatcc   85860
atcccctaag taaacagtac cttttacttc ttcgccgtca accagactaa tcatcggttt   85920
accctcacgt cctttatttg ctttaataac ttcggaagta agggttgctt cagtcagagt   85980
agaaacgtta gcatcaggtg atataaattc tttataggtt ttcattttat ttccttgagg   86040
tcgtttattt gataggatga tagtaacacg ccatcatcct tatgtaaact gttttgtgaa   86100
attattttag atcttcggcc caatctagtt ttaagggttc tttgtattca cggtcgagaa   86160
taaccggaat agctacatca ccactgaatg atagttggcc aacgttatat gataacgtta   86220
tatgtggagt gtagtcgtcg aaatcatgag tagcacctaa agctcgtgcg tactgatgac   86280 gacatcaag atattcggaa tcaagaacta aaaccagtac agcaccgtcg tcagttttcc   86340
atacctcaag gtgtcctgat tcggcaacag aataactacc actagatgta gtatatggta   86400 tgttacacg tgaataacaa attgttgaat gaagcttttc acgtggtact ggattaggaa   86460
ttcttaattt gcgctggagg tcttccagcg catcaagtgt taattctgaa aacttagctg   86520
```

| | |
|---|---|
| cgacgtagag gccttgtgaa aagtcctcaa atttcattat tcttcttctg tggtttcagc | 86580 |
| tttaacaagt tcacgtactg cttctaccag gtcttccagt ttaacagatt cacttgtaat | 86640 |
| accgaccagt tgagcaatct gagctagggt attctgaaga agtttagaat cgtcagaaat | 86700 |
| acgagcggcg gcatcttggg tatcaagaat acgagatttc agaattacga tttcagactg | 86760 |
| cagttttcca atagtttcat tggacatttt attaccttaa gatttttca attttagaat | 86820 |
| aaagctcttc taacgagccg tcgtttgtaa taactaagtc gccttcttca ataggcaacc | 86880 |
| cagcttctgt aatatgttta tcagtggatt ccgtaccaga gcgaaccaca tgaataactg | 86940 |
| tagcacccat cgctctagca gtttccattt catggacttg gcgcgtatcg gtcacaacgt | 87000 |
| agtaatcgaa atcacttcca atataatcca tatagtttaa tgcaaaaagc ttaacccaat | 87060 |
| acatacggtc aaataaatta acgacaacat ccgtaccgag ggcttgcata agacggcgga | 87120 |
| tcgaccatgt gtcgttgata ttatttatag cttcacgcag ggcttcatat ggtttaatat | 87180 |
| ctagatatga atatccacct tctaacgatg ataaatacttt aacattatta attggtaaat | 87240 |
| attgactttg taaataaatt agcgcttctt ccaataattc aataacatcc aacttattga | 87300 |
| gatttaatgg tgtttcacgg tcgtatccaa tgccttcaaa gtattcgtat ttcaactctg | 87360 |
| tgaatacatc aggattttca gcatgtctac gtccccaggc tattgctaga gcgtctttaa | 87420 |
| ttggatatgc taattggtat tttacggatt taaagtttga attgatgtaa tcagcagtag | 87480 |
| tgtctttacc actacgtttg atgccactta aaaagattag ctccataggt tttcctcata | 87540 |
| taatttataa gtgattataa catacggagc tagaagcgat taacgcaagg aagggtgtct | 87600 |
| agaaatggat ttagattcgg ctgcttgacg aggctgttga gatacaatga cttcgccgtc | 87660 |
| tttttctatc gtcatatacg cgtagtgaat agttgctacg cacgtaacgg caggatcaga | 87720 |
| atcttcagtg taactaaatt caatttcgct caaatcagaa atccatggtt tatagaaatt | 87780 |
| tgccgtcaaa acgacttcag tcttattgtt gtttaaaatg tgcaaagtaa caaactcagg | 87840 |
| accatcggca tgggctgtat tatgaccggt tatatagtta ttagtgctga gcatccattt | 87900 |
| atacatgttc atccaggacg tcatgtcttc gtcaactata aatcgtacaa taaaagggtc | 87960 |
| atattcaaat gtggtgcctg cacgcattgc acgacctagc cccattgtgc ctgtcacagt | 88020 |
| ttcaacaaca ggaattctca cacctggcag tggagccgtt tgggcattga gcacaaaacc | 88080 |
| tgaagttcgt gtactatccg ggatatccac aacaaagttt gttatatttg tttggttaaa | 88140 |
| aatctgtctc gctggacgag tcataagcac ctcaaaaacg ctttaataaa aatgcagtat | 88200 |
| aatggtttta ggtctcttcc attaatctgg ttcaacagaa tatcagaaga acggaagaga | 88260 |
| atagaattaa gatttccaaa cagtattcgc agagaaacgt tttccttttg acataaattg | 88320 |
| ctgagtaggt aacatgatta tgttagccca gtctttagga gcgatttctg ttattgttcc | 88380 |
| tctaatgtgg cctggcaggt atgctttaat cattttgtcg gcaccttgaa atcctttcac | 88440 |
| cttgctccag tctatcttca actttgtgtt attagtaata gtagttgtgc tagcatattg | 88500 |
| cttcagcaat tcttcaagaa actgttgacg tgctttaggt gggatatagt gcaagtttaa | 88560 |
| cccgtacatc aaattatgtt tacctaatcc taaataaata atcaaaggat atcggtccca | 88620 |
| gtatggcaga gtatctttat gtttagcatc atacacgtaa gtataaattt tgcctggcgt | 88680 |
| aggcttgact actttatgac cttttacact tttcttaatt gtttcaacaa accacttaga | 88740 |
| tgatttgttg tttactgctg cgccttcatt tctaatcttt tctcgtattg aactgcgaaa | 88800 |
| cgagtttatc atcagaagtt gacgttcttg cttattgagt ttattttag gtttagattc | 88860 |
| aagcgtttca attttctgtg cagtcttaat agatgatgca tatctagaca ttgcagatgt | 88920 |

```
aaacgacgag tattttattc cttttgattc tgcaaatgct tttgcagtga ttcctttctc   88980
tttagctttc ttgtattcta atcctatctc aatccatttt ctttcattca tagactgagc   89040
aatcttaggg gcttgtacgc cttcagatat aatttggaat atgctcataa ttaccccttg   89100
tatccgagtt tcctaagtcc gtcttcggtt agaactcgaa attttatatt tctcttttct   89160
gcgacagcag aagcagcttt ccatttgtcg cagttcacag accaggtgta tatttcgttc   89220
atataacgtt tctttgctgc ggtcgtaaga tttacaggct taataggcgg ttgagtttct   89280
ttctttggtt ttatttctac aaagaactct tgacctgatg catctttcat ccatatgtcc   89340
atatagtatc gacgtttctt accttcagca ttacaaaaat atggaattac ggctgtttca   89400
ctaccccatg caataatttc cggattttta tccaaccatt cgaaaaagaa tttttcccag   89460
tttgaacgat acgttatttt ggtatggtct ccacggtatt ttttaaatt ttttgggacc   89520
catttaccag agtaggccat gttgtcctcc ttataaatag tattattatt tataccaatt   89580
tcatattgga aggagactat cttgttattt acattcttcg acccaatagg atatagtgct   89640
aaaaccatta ataagaacgc acctactatt cctatgacag acatatttcg taactataaa   89700
gagtacttta aacgtgttgc gaccaactat agattacaaa cttattatat taaaggttct   89760
ccacgccctg aagaactagc aaacataatt tatggcaacc ctcaattata ctgggtcctt   89820
ttgatgtgta atgacaatta cgacccgtat tatggttgga ttacatctca ggaagcggcg   89880
tatcaggcat ctattcagaa gtatgcaaat gctggcggag accaaattct ttaccatatt   89940
aacgagaacc gtgagaaatt ttacaattta gtttcatatc cagacgagcc tttagtgtgg   90000
tatgataaag gtgatgaagc tcgtaagtat ccgcaatata aaggaccttt agctgcagta   90060
gatacttatg aagcagctgt actagataac gaaaaacttc gtaaaataaa aattgttgca   90120
aaggaagata taaactcgtt tatcactgat ttgattcgtg agatggagat tgcataatgg   90180
aaatgattag tagtagcctt aattggttcg ttggtgttgt tgaagacaga atggacccat   90240
tgaaacaagg gcgtgttcga gttcgagtcg taggacttca tccagcgcag agagcacaag   90300
gtgacgtaca aggtattcct accgaaaaac ttccatggat gactgttatt caacctatta   90360
cgtctgcatc aatgtcaggt attggtggtt ctgttacagg tcctgttgaa ggaactcgag   90420
tatatggtca tttcttagac aaatggaaaa caaacggtat tgtactcggt acatatggtg   90480
gaattgtacg cgaaaagcct aatagactcg aaggttttc cgaccctaca ggtcaatatc   90540
cacgacgttt aggtaatgat acgaacgtat taaaccaagg tggtgaagct ggttattatt   90600
cgaattctaa cgtaattcaa gacaacaact tggactatgg tataaacccg gatgatacag   90660
atttagcaaa tattccagaa gataatgacc ctaattttac aataacagaa atgttacgtc   90720
gtgatgaagg tcttcgtgat aaagtgtatt gggaccatct agggtatcct acagtaggta   90780
ttggacacct tatcgtaatg gaaaagaccc gagacatgac tcgaattaat aaattgttat   90840
ctgatcaagt agggcgtgaa gtaacaggaa atcccgggac tattcatta gaagaagcaa   90900
cagcgttatt tgagaaagac cttgctaaga tgcagaaaga cattcgttct aattctaaag   90960
taggtcctgt ttatgctaaa atgaacaggt ctcgtcaaat ggcattagaa acatgtgct   91020
tccaaatggg cgttggtggc gtagcaaaat tcaatactat gcttaaagcg atggccgcag   91080
gtgattggaa aactgcatac aaatctgggc gtgattcatt atggttccaa cagactaaag   91140
gacgtgcttc acgcgtaaca acaattattt taactggtaa catggaatca tatggcgttc   91200
ctgttaaaac accaccttca ccaggagtcg gtgccgattt agttactaga aataccgatc   91260
```

```
cagaagaccc ggccggtcct cctgttccat tagattcgcg tatccttttt aaagaacctg    91320
aatcaagtta tcgtggtgaa tacccatatg ttcatgctat ggaaacagaa agcggtcata    91380
tccaagagtt tgacgacact ccaggtaacg aacgttatcg cttagttcat ccaacagggt    91440
catatgagga agtttctccg tctggtcgtc gcactcgtaa aactgtagaa gacccttttg    91500
acatcactaa tggtgatggg aatttcctgg tttctggtga taaacttgtt aacgttggtg    91560
ctaacgaaat atattataac atggcggacc gcctccatca aatagatggc agcgacacaa    91620
tctttattcg tggcaaccaa gttaaaactg ttgaaggcga tggaactctt tacgttaagg    91680
gcaatatcaa aatagtcgtt gacgggaatg cagatattct tgttaaaggc gatgctaaaa    91740
ctcaagttga agggaatcat gactatactg tcaatggtaa tgttaaatgg actgtcaatg    91800
gtaatgttga tatgactgtt gctggtgatt ggtcggagac aatgactaca atgagctcaa    91860
tagcttcagg acaatatact gttgacggat ctcgtattga tattgggtaa tatatggcac    91920
aaatacttcc tttaaatacc gacttaggag aagacatgga aggggcgtct attgacgtcc    91980 ttttttactcc gcagttagaa actaccgaaa ctttggtgtc aataaatata atagattatg    92040
aaccaacaca aggcattaca gttgacggta atcacttata tggaacatat gaaagcgtat    92100 ttagctttc ttcagatgca ttgaaatatc gattaaacga tgattttaaa actgcatctt    92160
catgggaaga tttaccacaa gaccaaagca ctcaactata tttgtggaga gctcctcaga    92220
atcttcgtaa agtgtttagt tatacggttg aaatgattta taactaccaa gaagaaagtt    92280
catcaggcgg cacaagaagt gactctggta cagaacctcc accggctcca gtacaaaaaa    92340
ctcttactaa ggtttataca aaaactatag taggaaattg gagcaaatgg gctcaacaat    92400
tacgaaacta tgtttatgcg aggccataaa aatgtctgga ttaagttacg accagtgcgt    92460
tacaacaggt catgaagcat ggcctcctac agtaattaat gcttctcaat ctaaagtatt    92520
caccggcggt attcctgttc ttgtagcagg agaccaaata acacctcata cagaaattaa    92580
aaaaccgtac gagactcatg gtggtgttac tgaacctcgt acatctaaag tatatgtcac    92640
cggtaaaaag gccgttcaaa tggctgaccc aatttcatgc ggggacactg tttctcaggc    92700
ctcgtcaaaa gtctttataa ataggaatt aaaatggcaa acactcctgt aaattatcag    92760
ttagtcagaa cagcgaatgc tattcccgaa atttttatcg ggggcacatt tgccgaaatt    92820
aaaacaaata taatcgaatg gctcaatgga cagaacgaat tcttgatta tgattttgaa    92880 ggttcacgtt taaacgtatt gtgtgacctt ttagcatata atactcttta tatccaacag    92940
ttcagtaata gtgcagtgta tgaaagcttt atgcgtactg ctaacttgcg cagttccgtt    93000
gtacaagcgg ctcaggataa tggatatctg cctgcatcta aatcggcagc acaaacagaa    93060
attatgctca catgtacgga tgcgttaaat agaaactata tcactattcc gcgtggtact    93120
cgtttcctgg cgtatgctaa aggtacttct gttaacccgt ataactttgt ttccaccgaa    93180
gacgtcattg tagttaaaga caaaaataat caatatttcc cacgtcttag gttagctcag    93240
ggacgtattg ttcgtactga attaacattt gataaattaa aacctatcat tattcgtgat    93300
aagaacattg accgtaattt ggttaaattg tatgttgacg gagcagaatg gattaactgg    93360
actcgcaaat cgatggttca tgctggttct acttcaacca tttattatat gcgagaaact    93420
gttgacggga acactgaatt ttattttggt gaaggtgaaa tctctattaa cacgtcagaa    93480
ggtgctttaa catctaacta cattggcggc cttaaacctg tccagggttc taaaatagta    93540
attgaatata tttctactaa tggtgctgaa gcaaatggtg cagtaggatt ctcttatgct    93600
gatacattag ctaatatcac agttattgga attaatgaaa acccaagtaa taaccctgac    93660
```

```
ttcgttggtg cggatggcgg tggcgaccct gaagatattg aacgtatccg tgaattaggt    93720
acaattaaac gtgaaactca acaacgatgt gtgactgcga ccgattacga cacattcgtc    93780
tctgaacgat ttggttctat tattcaagcg gttcagacat ttacggattc atctaagcct    93840
gggtacgcat ttattgctgc taaacctaag tctgggttat atttgacttc cgtccaacga    93900
gacgatatta aaaattatct taatgagtat aacttaggga cgataactcc tgttgttatt    93960
tctcctgatt atttgtttat taaaatgaat attcgcgtta cgtatgcatt gaacaaatta    94020
caggaatctg aacaatggtt agaaggccaa attattaata aaatcgaccg gtattatatt    94080
gaagacgtgg aaattttaa  ctcgtcattc gcaaaatcta aatgctaac  gtatgtcgat    94140 gacgcagata tttctatcat tggttcgtct gcgactattc aaatggttcg cgaggtacag    94200
aacttctaca aaacacctga aacaggtatt aaatacaata accagattaa agatagaaca    94260
ttagaatcta acgtgttttc atttgatagt ttacgcgttg accctgaaac ggaagctact    94320
attaaatacg acgttcgcat tgtaggttca gatagaaatg accgtggcat tggacaagtt    94380
atcattggcc cgttttgcaga tggcgacgtt atagaaaatg cttatattca accatatact    94440
ggtgacgatt taataaaact tcatgttacg gacggaagaa acaaatatta ctctataggt    94500
gaagtaaatt atccggctga ttcaatttat tggaatatag ctaaaattga tttaacttct    94560
gataggtttg aagttcaaac tattgaactc tattcagacc cagctgatga tgttatcttt    94620
actaaagacg ggtcattaat tgtatttgaa aatgacttac gtccacaata tttaaccata    94680
gatttggagc ctatttcaca atgacagtaa aagcgccagc agtcacgagt ctcagattat    94740
ctaaattgtc cgcaaaccaa gttcaaattc gctgggatga ggttggcgct aatttctact    94800
attttgtgga aatagctgag accaaaacag ctaacgggga agcaattccc cgtaatagct    94860
atagatggac taatttagga tataccgctg ataacaattt ctttgagtct ggtttaaatt    94920
cattaacaac atatatgatg cgtgtgggcta cagcagcgga gggatttgag cagtctgatt    94980
ggagatacac cgaagagttt gaaacatttg aaataaacgc ttacacattc caacatatga    95040
ttgaaatgca attagctaac gagtttattt ctgaaaaatt tacaaaaaat aatacaaact    95100
acgttgattt taataatgac acgatcatgg cagcactgat gagcgagtcg ttccaattca    95160
gtcctgcata caccgatgtg tcatcgatta gaaattttat aattggtgaa atcagtatc    95220 atgaaatcca ggggcatatc caggatgtat gtaaagatat aaatcgagta tatctaatgg    95280
aatctgaagg aattctttac ctttttgaaa gattccaacc tattgtaaaa gtgtctaatg    95340
ataaaggcca aacatggaaa gcggttaaat tgcttaatga ccgtgtagga tatccacttt    95400
cacgaaccgt atattaccaa tcagactata cgacgtattt gctcggctat gataagattt    95460
tttacgggcg taaatcatct gatattcgtt ggtctgctga tgatgttcgt ttcagttcac    95520
aagatgtaac atttgctaaa atcggggacc aattaaattt aggttttgat gtagagattt    95580
tcggtacata cgcgtcatta ccaggaaacg tatcacgtat tgcagaagct attacttgta    95640
atgatgacta tgtttatatt gcggccagag ataaagttcg cttcgttaaa accagtaacg    95700
ctcctattga ttcagatcca ttatctccga cctattccga acggttgttt gaacctgaga    95760
cgtttacaat aacaggcaac cctaaagcag tttgttataa aatggattct gttggtgaa    95820 gaatattcgc tcttattatt ggtgaagttg aaaacgttaa tgacgaccca agaacaaagc    95880
ctattttgga ttccgttgat aaaggtgtat acgttttaga ccatgacgct ggaacattta    95940
aaaggatatt tggtaatacc gaagaagaac gccgtcgtat agaaccggct ttcaccaata    96000
```

```
tgtctactga tggtgttgag ctttatatct cttctagtaa ttttaaattt ttagaatctg   96060
atattgttga cgacccagaa acgcaatcta agtacggact tttgggagca gttaagtatg   96120
aatatcctag agaatggctc gcagataaac attaccatat gatgattttc gcatcaaacg   96180
aagaaagtaa ttgggaaact ttttcaccaa ctcctatgca gtattatgcg gaacctttct   96240
ttagttattc tagaaaatca ggcacacgtt cttggattaa taactctgat agagcggtag   96300
tgatttattc tgatttgctt tacacaaagg tagtggaaag ctaccctagc acttcacctg   96360
atcgtaaagt tcacgaatac tggaatgatg gcgattgtaa gattgttatg ccgaatatag   96420
aattcactgg atttaaaaaa tacgcatctg gtatgttgtt ttataaatca tcaggtgaaa   96480
taatttcata ttacgatttt agttatcgtg ttagagataa cgtttctata atttggaagc   96540
ccactaacgt atttttgacc gcctcattac aaaaccaaga aaagaaact tcttgggttc    96600 ctgttgaaga gacaggtcta gctgacccgg atttacgccc attactcact acaatgatgc   96660
cggagtctta tctgttggat aatacaaact ttgaagcatt ttgtgaagcg tatattcaat   96720
atctttctga tggatacggg acccattata ataacttatt gaatttgatc aaaaataaat   96780
acccacgaga agaacacgca tgggaatatc tttggtctga aatttataaa cggaacattt   96840
atttgaatgc tgagaaacgt gatttagttt ctaggttctt tgagtccaga agttatgatt   96900
tttattctac taaaggaact gaagcgtcgt ataagttttt gtttaaagtt ctttataacg   96960
aagacgttga agtggaaatt gagtcatctg ctggaacgga gtacgatatc ataattcaat   97020
ctgattctat aagtgaagat ttggttggac aaactatata caccgctaca ggtagatgta   97080
atgttacata tttagaaaga agctattcta aaggtaaatt acaatggact gtgactattc   97140
ataacctttt aggtaggctt ttagtcggtc aagaagtaaa agccgaaaga ctagcagatt   97200
ttgaaggtga aatagttcgc ggtattaaag gtaagaact tgcccaaaac actatcgatt    97260
attttaatcg tggtagagct tattacgtca tgaaaataaa gtcaaatctt ccatcctctc   97320
gttgaaaatc tgacgtacta cgttttgtac atccggtagg attggattt attgcaataa    97380 ccttattaac aatgtttatt aatacaggat taacgcttaa acatgttgaa actattatta   97440
ataaatataa aaattataag tgggattccg gactgcctac ggaatatgca gaccgcgtcg   97500
ctcgtttaga ccctcaaggt aatgtagaat tcaatcctgt tacaggtgaa gtaattatg    97560 atgctggtcc ttatgccggt atcgaatacc ctttacctgc aaattataac gaagaaaatg   97620
ataactctat tttccaagga caattaccgt ccgaacgacg caagccaatg agcccattat   97680
ttgatgcatc aggtacaacg ttctctagat ttagagagct tgttaatgaa agattgttag   97740
ataacgtggg aaatcctaga gacccgatta atccaccaca ggttaaatta gatgaatgat   97800
tcaagtgttg tctatcgttc gatagttact tcaaaattta gaactgaaaa atgttgaat    97860 ttctacaatt caataggtga tggtgataat aaaaacacca tctttataac gtttggtcgg   97920
tctgaaccat gggctgctaa tgaaaatgag gtgggcttcg ccccaccgta tccaacagac   97980
tcggttttag gtgtaacaga tatgtggact aacatgatgg gtttagttaa agttatccca   98040
tctatgttag actcggttat tcctagacgt gactggggag atattcgtta tccggaccct   98100
tatacgttca aaataaatga tatagtcgta tgtaatacag ccccatataa cgccactgaa   98160
gtcggagctg atggttagt ataccgttgc gtagatgttc ctgatgttgg gatgtgttct    98220
attgagtctc tcgacaacaa agaagaatgt cttaaattag gcggtaaatg gactccatct   98280
gttaggtctt taaccctcc tgaaggccgt ggagacgctg aagggattat cgaagttggt    98340
gatggatata tatgggagta tctttatgag attccaccg atgtgtctat aaaccgatgt    98400
```

```
actaatgaat atatagtcgt tccatggccg gaagaagtta aagaagaccc tgctcgttgg    98460
ggatatgaaa acaatctaac ctggcaacaa gatgattttg gccttgtgta tagagttaaa    98520
gcaaacataa ttcgttttaa agcctattta gactcagttt atttccctaa tgcagcactg    98580
cctggtaata aaggatttag acaaatttct attatcacaa acccgttgga agctaaactc    98640
cgtcctaatg accctaatat aaaagctgaa aaggattatt atgacccag agatttacag     98700 cgtcattcgg gtgaaatgat ttatatgaaa accgtccac ctattattat ggcaatggac      98760
caaaccgaag agatcaatat tttgtttatg ttctaattta gggagacttc ggtctccctt    98820
tcgtgtataa atagtataaa ctattaagga ttagccacat gtatattcaa actccaaaac   98880
aattgattga cgttggcgaa attggtaacg cttctacagg cgatatcctt tttgacggcg   98940
gtgttaaaat aaacaatgat ataaatgcta tttacaatgc gtttggcgac caacgaaaaa    99000
tggcaactgc taatgggaca ggaccaaatg gacaaataat ccatgctact ggatactacc    99060
aaaaaggagg tcctactgat tatttcaccc ctgttccagt aggaagtaga cacgacatag    99120
atgcttccac cggtggtgtt attgttactg ttgctagagg tgaactcggt gattccgtgg    99180
aatttataaa ttcaaacggg tcaatttcgg taaacaaccc attaagtatc caagcattag   99240
attctattaa aggtgttgca ggtaatttag ttataaccac accttatact aaagttactc    99300
ttcgttgtat ttcttctggt acaggcggct caatatggga ttattctaca gaaagtatgt   99360
ttagtcatac cgaaattcct gtagacggga catggaatat tatttcagac tatgtcaata   99420
ttcctctatt ttataaaact gaatataatg ctgctaaact tttggttaca tgccaatctg    99480
ccaatggcag aaaaattaaa tcatgcgaaa taaatattct aatagataca attaattcaa    99540
gagttatttc aaccgaatac gcagtgatgc gcgttggtaa tgataacgaa gaagatgaaa    99600
ttgcgaatat tagttttttcg ataattaaca attttgccac tatgacagtt tcttcacata   99660
taaatggtct tcgagtggca gctaaagtta tttcaactca gaaaattagg gtcgctcaat    99720
aatgaaacaa aatattaaaa ttgggaacgt cgttgatgac ggacaaggcg attaccttcg    99780
tcgtggtggt gcaaaaatta tgaaaaactt tgatgagttg tattatgaat taggcgatgg    99840
cgaagttcca tattccgctg gtgcctggaa aacataccat tcttcagatg gacttaattt    99900
agctgctgaa tggggtaaat catacgcaat tgatacttca acagggcgtg tttctataaa    99960
tttacctaaa ggaacagtgg aagattataa taaagtaatt agagcccgtg atgtattcgc   100020
cacgtggaat attaaccctg taacattaat tgctgccagc ggtgatacta ttaaaggttc   100080
ttccagccca gtagaaatca atgtgcagtt ttcagactta gaattagttt actgttctcc   100140
tgggcgctgg gaatacgtta aaaataaaca aatagacaaa attactagtt ctgatattag   100200
tagtgtagct cgtaaagaat ttttagtcga agttcaaggt caaactgatt ttcttgatgt   100260
atttgggtct gtttcttata atgtgaataa tatccgtgta aaacatcgtg gtaacgaatt   100320
atactacggt gatgcgttca gtgacaatag cgactttggt tctccaggag ctaatcccgg   100380
agaaatcgtt gcattagatg gtaaaaacat ccgtttaaga caaccatgta atattggcga   100440
caccgtacaa attgaaacct ttttggatgg gattacacaa ttacgcagtt cttattctcg   100500
ccgccaaata cgtatttag attcaaaatt aacaacccgt ccttccttag aaggaagtgt   100560
atatgtcgct gatttgtcaa ctttgaaatc tattcctttt tccgcatttg gagttaatcc   100620
ttcagaaccg gtcaatacca attctttaga agttcgtttt aacggtattc ttcaagaatt   100680
agctggtact gttggtttac ctatgttcag atgtgaagga gctgacgcag aaacttctac   100740
```

-continued

```
tgagtgttca gctttaggtg ggacttgggt tacatctaac acagattatt ctattgaata    100800
tgatgataac gatgcaacta tcgcacgtgc tttagtcttt gaccgtaagt ttgaagacca    100860
agacattatt gatattacat ggtttaataa cgatttaggc actttattaa gtatcgatga    100920
cattttagat acaactgatg aaaggtatgt cgcacaaggt gcaaccgtaa atgtgacagg    100980
cgatgtggct ttgaccgatt tcaataatat cggatggcct aatgtagaac ctgttccgac    101040
atatagcagg gaattctcgt ctattgcaaa tatttttaac actatttacc ctgtcggtac    101100
tatttacgaa aatgcggtga accctaataa cccagccaca tatttaggat ttggctcttg    101160
gaaattatgg ggacaaggaa aagtattagt tggatggaac gacgatatta gcgatcctaa    101220
ttttgcatta aataataacg accttgattc tagcgggaat cctacacata ccgccggtgg    101280
aacagtcgga acaacgtcta acacactaac taattctgat ttacctccta ctcaaactga    101340
cgagaaagtt cttatttccg atgagaacgg tacaattatt attggtggtt gtcaatacga    101400
ccctgatgca gaaggtccta tatacaccaa ataccgtgaa ggccacgcca caacgaatag    101460
tacacacgta ccgcctcaag ctgtaaataa tattcaaccg tcaattaccg tataccgttg    101520
ggtaaggatt gcataatgac catacttagt actaaagcgg gagtaatatc ccgcgaagca    101580
gatttttttag gatttagaaa aaatcctact caaattgata tttttaaacaa ccaaggcgta    101640
ggttctgtaa ctatttctca attggcaaaa ggattctatg atgataacgt agaatctgca    101700
ataaacgatg ttcataatat tgctagagca gatgtaggaa cagttacaat taacacctca    101760
ggtgtatctc ctgaaggaac ttcacaggta gattattggt cctttagtgg aagtgtaact    101820
gaccctagtt tgcccgatgg aagccctgtt attgtaaaag tttatggact tcctgttaat    101880
gctactgtag gtatgaccgc cgacgaattt gttgtacaat tacgtactac tctccggaat    101940
gcgatttccg accaattggc tattgcagag tataaagatg acccaactgt tgggactaaa    102000
ttacaaataa catatttaga taaccaaaga cacgtactcc caacgtattc ctcttatggt    102060
atcacggttt ctcaagaaat agtgtctcag gctaagtccg ggtacggcac ttggaattta    102120
ctaggtgcgc aaaccattac tcttgacaac catatttcac ctacaacctt ttattatttt    102180
gtgagaaccg catgagtaac aatacatatc aacacgtttc gaacgaatct gtatatgttg    102240
aatttgaccc ggtagggtca aattttgata gttcaataac caatgtccag gcagccttag    102300
cctcaattag cgcgtatggt gttaaaggtg ttccggacgc aagtgaagca gaaaaaggtg    102360
taattcaatt agcgacagaa caagaagttc ttgatggatt taatagtact aaagccgtta    102420
cacccgccac attaaatgca agacttcagt atccgaacgc gtcagaaaca caatacggtg    102480
taactaaata tgcaacacaa gaggaagcca ttgccggcac tttagacact gtttctatta    102540
ctccgcttaa attagaccaa actattgata acacgttctc tactcgttat tccaccgaaa    102600
caactaatgg tgttattaaa attgcaactc aaaccgctgc acttgccggg tctgatgata    102660
ccacggcaat gacaccgctt aaaactcagc aattagcaat aaaattaatt tctcaaatag    102720
ctcctaataa cgacccggct tcagaatcta ttaccggtgt tgtgcgttta gctacggtgg    102780
ctcaaacacg tcaaggaact cttcgcgaag gatatgcaat ttccccatac acctttatga    102840
attctgttgc aacacaagaa tataaaggtg ttatacgtct aggaacacaa gcggaaatta    102900
atagtaattt aggagatgtt gctgtaacag gtgaaacgct aaatggtaga ggagctaccg    102960
gttctatgcg tggagtcgta aaattaacga cgcaggccgg tgttgcaccc gaaggcgata    103020
gctctggagc attagcatgg aacgcggatg taattaatac acgcggtggg caaactatta    103080
atggttcttt aaatttagac catctcacag caaatggaat ttggtcacgt ggcggaatgt    103140
```

```
ggaaaaacgg tgaccagccg gttgcaacag agcgatatgc atctgaacgt gttcctgttg    103200
gaacaattca aatgttcgca ggtgatagcg ctcctccagg ttgggtttta tgtcatggcg    103260
ggaccgtttc tggagaccaa tttccggact atcgaaatgt ggttggaacg agatttggcg    103320
gtgattggaa taatcctgga attccagata tgcgcggcct ttttgttaga ggagctggta    103380
caggtagcca tattttaaat aatcgcggac aagacggcta tggaaaggat agattaggtg    103440
taggatgtga cggcatgcat gttggcggtg tccaagcgca gcaaatgtca tatcataaac    103500
acgctggtgg atggggcgaa tatcaacgtc acgaggcacc attcggagca tccgtatatc    103560
aaggttattt gggtactaga aaatactctg attgggataa tgcgtcatat ttcacaaatg    103620
acggcttcga attaggtggt caccgtgacg caacaggcac tcttaaccgt gaaggactta    103680
tcggatatga gacccgtcca tggaatatat ctttaaatta tattattaaa gtccattact    103740
aagggtaaaa aatgatcgaa ttaaaaagtc taccatacgt tgatggccct cctgatgagg    103800
gtcaaaaacg tttaaactgg attaaaaatt cagaagaaat aactggcgct gatacgttat    103860
acggttctga aggagtaatg aaccgtccaa taacagaagt tcaacgaaat gtagaaacaa    103920
ttaacgataa cgttaagact atcgcagaat ctttagatac cgctaatgcc gatattgtca    103980
caattaaaag tatcttggat gtttctggtg acgtagatgc tttagcacaa attggacata    104040
acactgatga tattgaagta ttaaaacaca ctgtaaattc acacagtgtt gatattttaa    104100
acactgaaga aaaactagat gatactattg ctaatatcgg agtagttaat ccagaaacag    104160
attcagtgta tcgtactgtg cgtaacgacc ttctttggat taaaccgaa ttagggcaat    104220 atactggaca agatattaat ggtgtcccga ccgaaggtaa tgaaagcacc gggatgaaac    104280
gacgtattat tactaacagc tcagtgttgg ttgaccaagg cgttcgttta accgagttag    104340
aaaataaatt tgccgattct gatgttgggg ctctgacaac cgaagttgaa aacctccgtc    104400
aagaaatagg tcctagacca tcgttaacag taccggttta cactcgttta tccggtattg    104460
attcatccat ttctatccaa actagagata ttgcggcatt aaaagatttt gttggatatc    104520
ctaattcaac cgctattaaa actcaagtcg aggccaatcg tctttctata tcaacaataa    104580
attcagacat taactcgcct ggcggtatta agccacgttt gacaacgtta gaaactacta    104640
taggctctcc agatttacca actactcttc agggtaagat caaattaaat accgattcca    104700
tttcaggtat taacacagtt ttaggtgttg attcttctag tggtttacgt tttaatgtag    104760
catggcttaa tcaggtggtt ggcgttgatt caaatggtgg acaacctgaa ccggctggtt    104820
cacttttata taggactcgt attcttgaaa ctggtgttac cgacctaggc aataacattc    104880
aaaacgttca aactgaattg ggaactaatt cgtctggtat taaggacaa gtaactagtt    104940 taaataaact tataagcggc accaacccaa acggtcaaac catagaagaa cgtggtatat    105000
tgccaacagt taaaaaccac gacacgacaa ttacggattt aactacgcgt gttaccactt    105060
tagaaacaga ccttgctgca gcagaagcag aaattcaagc ccttaaagag gctggatata    105120
tcaaagatgc tccttcagac ggtaaattct atgttcgtaa agatggtgct tgggttgaac    105180
ttcctacagc ttaatgaaaa gggccttcgg gccctaaagg atttatatgt caggttataa    105240
tgcacaaaac cctaaagaat taaggatgt aatattacgt cgtttaggcg ctcctattgt    105300
aaatgttgaa ttaactacag accaaattta tgattgtatt tccagagcat tagaaacttta    105360 tggcgaatac cattttgacg ggttgaataa aggtttccat gtattttttg ttgatgacga    105420
agaaaaatac cgtcacggcg tatttgatat gcgtggttct aatgtatttg ctgtaacaag    105480
```

```
aattataaga caaacgttg gctctattac ttcaatggat ggtaatgcaa cttatccttg    105540
gttcactgat ttccttttag gaatggcagg tgtttctggt ggtatgggta gtaattgtgg    105600
taaattctac ggtccgaacg cttttggtgc cgacctcggg tattattctc aattagtatc    105660
ttatatgggt atgcttcaag atatgattgc tcctcttcca gattttggt ttaactctgc    105720 aaacgagcaa ttaaaagtaa tgggtaactt tagacagaaa gatgtcatta tcgttgaatc    105780
gtatgttcgc tcttatatcg agacccataa gatggtagga aatacagtag ggtacggtca    105840
ggtcggtcct cgtgattcat ggtctatttc tgaacgttat gataatccag accataattt    105900
agtcggacgt cgagttggtg aagatcctgc aaccaaacaa ggcgcatata caaccgttg    105960 ggttaaagat tatgcaactg cattagctaa agagcttaat ggacaaattc ttgctaaaca    106020
tcaaggtatg atgttaccag gcggtgtcac tgttgatggt gttcgattaa ttgaagaagc    106080
tcgtgtagag aaagaagctt tacgagaaga gttatattta ctagaccctc ctgcaggtat    106140
tttggtaggt taatatggca acttatgata aaaatctttt cgccaagcta gaaaatcgtg    106200
gtgggtattc tcagacaaat gagaccgaga ttttaaacaa atacgtgaac ttcaacaaat    106260
acgaaaatag tcaaacccta gccgatgttc tagtggcaga aagcatacag atgcgcggta    106320
ttgatgtttt ttatgttcca cgtgaatatg ttgccgtgga ccttatcttt ggtgaggacc    106380
ttaaaaataa atttactaaa gcatggaaat ttgctgcgta tctgaactct tttgaaggtt    106440
atgaaggagc gaaatcgttc ttcagcaact tcggaatgca agttcaagat gaagttacat    106500
tatctattaa cccaggtctt ttcaaacacc aggtcaataa tcaggagcct aaggaaggtg    106560
atttaatata cttcccaatg gacaacagtt tgtttgagat taactgggtt gaaccatacg    106620
acccgttcta tcaagtaggt aaaaatgcga ttcgtaaaat tactgcaggc aagtttattt    106680
actctggtga agaaatcaat ccggtgcttc agaaaaatga aggtatcaat atacctgaat    106740
ttagtgactt ggaacttaat cctgttagaa atcttgacgg tatccatgac attaatatcg    106800
atgaatattc tgaagttgag caaatcaatt cagaggcaag tgaatacgtt gaaccatatg    106860
tagtagttaa caaccgtggt agacaaaatt caccatttga cgatgggttt atgaattaat    106920
aaataaataa gataaagcaa acaccggtcg aaaggccggt taggagaaat gatgtttggc    106980 tattttaca actcgtcgtt caggcgatat atcacaatga tgggcgattt gttttcaaat    107040
atccaagtta accgtcaatt gtctacaggc aataaattaa ttagagttcc tattacgtat    107100
gcatctaaag agcactttat gatgaaactt aataaatgga cctctataaa ctcacaagaa    107160
gatgtggcta aagtcgaaac tattctacca cgtataaatc tccaaatggt agatttcgtt    107220
tataaccgca cttttaaaac gaatatattg aataactctc ttttgagtaa atcgactaag    107280
gatattgtag accaatacaa cccatcacca attaaaatga tttttgaact gagcatcttt    107340
actcgttacg aagatgatat gttccaaatc gttgagcaaa ttattccata ttttcagccg    107400
cattttaata cgactatgat tgagcaatat gggcaggata ttccatttga aagggatatt    107460
aaagtcgtat ggatggcagc agcaatggat gaacaaatag acggtgataa tttatctcgt    107520
cgacgtttag agtggtcatt aacatttgaa gtaaacggat ggatgtatcc tccggtaggc    107580
gcagctgaag gccttattaa aacgactttc cttgattttc atgctaatga acgagacctt    107640
caaacagccg ccagtgtttt tgaatcagtt gatacagaaa ttaaaccgag agacgttgaa    107700
gcacaagatt ggaacggtga agttgaacaa acttatactc atgatattcc aatcccgact    107760
ccaccaaccc ctcctggtcc tagaaaacaa taagaggtaa atatgaaagg tctagatatt    107820
aataagcttt tagatatctc tgacctccct ggaatatctg gggaggaagt agaggtatat    107880
```

```
gctcctttac aattggtgga agttcagagt aatcctcaaa accgcacccc ggatttggaa    107940
gatgactata gcgttgttcg taagaatatg cacttccaac aacaaatgtt aatggacgct    108000
gccaagattt ttcttgagac ggctaaaaac gccgattctc ctcgtcacat ggaagtattt    108060
gcaactctta tggggcaaat gactacgacg aacaaagaaa tactgaagct tcataaagat    108120
atgaaagaaa tcacatctga acaagttggc actaaaagtg ctgctccatc tagccagatg    108180
aatatccaaa atgctacagt gttcatgggc tctccaacag aattaatgga agaagtagga    108240
gatgcttacg aggctcaaga agctcgtgag aaggtgatta atggaacagc cagttaacgc    108300
attgaatgat aatcacccat tgaatgaagg tgacaaagtt gttattctac cgcctcattt    108360
agctgaacgt aaagaagaag atggtatcta ttggattaaa tcccaatggg atggtaaatg    108420
gtacccggaa aaatttagtg attatctacg tataaacaaa atagttaaaa ttcctaataa    108480
ctcagataag cctgaattat ttcaaacata caaagataag aataataaac gtacacggta    108540
tatgggttta ccaaaccttta aaagagcaaa tataaaaact caatggacct atgaaatggt    108600
cgctgagtgg aaaaaatgcc gtgatgacat tgtatatttt gctgagacat attgtgctat    108660
tacccatatc gactacggta caattaaagt acaacttcgt gactatcaac gtgatatgct    108720
taaaataatg tcttctaagc gtatgactgt ttgtaacttg tcacgccagc taggcaaaac    108780
gactgtagta gctattttc ttgcccattt tgtttgcttt aacaaagata aagcagtagg    108840
tattcttgca cataaaggct caatgtcagc ggaagtatta gaccgtacaa aacaagcaat    108900
cgaattactc cctgattttt tacaaccagg tattgttgaa tggaacaaag gatctattca    108960
gttagataac ggttcctcaa ttggcgctta tgcttcatca ccagatgcgg ttcgcggtaa    109020
ctcattcgcc atgatttata ttgacgagtg tgcatttatc ccaaacttca tcgattcgtg    109080
gcttgctatt caacctgtta tttcttcagg gcgtcgatca aaaattatta ttacaaccac    109140
gccaaatgga ttaaatcact tttatgatat ttggactgca gcggttgaag gtaaatcagg    109200
ctttgaacct tatactgcaa tttggaactc ggttaaagaa cgtttataca acgatgaaga    109260
tattttgat gatggatggc agtggtctaa acagactatt tcagcctctt cattaacaca    109320
gttccgtcag gaacacacgg cggctttcga agggacatca ggcacactta tttccggtat    109380
gaaattagct atattagatt atattgaagt tacacctgat agccatggat ttcaccagtt    109440
caaaaagcct gaggaaggtc ataaatatat tgcgacgtta gactgttctg aaggacgtgg    109500
acaggattat catgcaatgc atattattga tgttacgaca gataaatggg aacaagttgg    109560
tgttctacac tctaatacta tttcacacct tatactccct gatattgtgt ttaaatatct    109620
aatggaatat aacgaatgtc caatttatat tgaattgaac tcaacaggtg tttctgtcgc    109680
taaatcgctt tatatggacc ttgaatatga aaacgttatt tgcgattcaa tgaatgattt    109740
aggcatgaag caaagccgta gaactaagcc tgtaggttgc tctacattaa aggatcttat    109800
tgaaaaagac aaactcaaaa taaaccatag ggctactatt caagaattca gaacgtttag    109860
tgaaaagggt gtatcttggg ctgctgaaga aggttaccac gacgacttag tgatgggtct    109920
tgttattttc ggatggttgt caacgcagca gaaatttgca gactatgcgg ataaagatga    109980
catgcgcctt gcatcagaag tattctcaag agaattacag gatatgaatg acgactacgc    110040
cccggttata tttgttgatt gtgcaagtaa ttcggcagaa tataatccat cagcacatgg    110100
cctgtcaatg gtataaataa aataaagcaa attaagagga attaaaatgg cacttctctc    110160
tccgggcgtt gagctcaaag aaactaccgt acagagtact gtagttaata actccactgg    110220
```

```
taccgctgcc ctggctggaa aattccaatg gggacctgca ttccagatta acaaatcac   110280
cgatgaagtt gcgttggttg atatgtttgg tactcctaac acagacaccg cagattattt   110340
catgtctgct atgaacttcc ttcaatatgg taatgacctt cgtgttgtac gcgctgttga   110400
tcgtgatact gctaagaact catctcctgt ggcaggaaac attaatttta ctatttcttc   110460
ggctggcaca aactacagag tcggtgataa agttgtagtt aaatattcta cagatgttat   110520
cgaaccagac ggtgaagtta cttcagttga ttctgacggt aaaattttga atatctttat   110580
tccttcaggt aaaattatcg ctaaagcgaa agaaatcggc gaatatcctg aattaggttc   110640
aaactggact gccgaaatgt ctgggtcttc ttctggtctg tctgcagtaa ttactattga   110700
ttcagttgta atggattctg gtattctgtt gactgaagtt gaaacttcag aagaagctat   110760
tacttctcta actttccaag aatctattaa aaaatatggt gtcccgggtg tagttgctct   110820
ttatccaggt gaacttggag accagctcga aattgaaatc gtatctaaag cagactatga   110880
caaaggtgct tcagcccagt taaaaattta tcctgatggt ggcactcgtt attctactgc   110940
taaagcaatc tttgggtacg gtccacagac tgatgaccaa tatgcaatta tcgttcgtcg   111000
caacgacgcg gtagtccaga gcgtagttct ttctactaaa cgtggtgaac gagatattta   111060
tggtagcaat atcttcattg atgatttctt tgctaaaggc gcaagcaatt atattttcgc   111120
tacggcacaa ggttggccaa aaggtttctc tggcgtaatc aaactgaatg gtggcttatc   111180
atctaatgaa acggttgaag ccggtgattt aatgaagct tgggatttgt ttgctgaccg   111240
tgaatcggtt aatgcacagt tgtttattgc tggttcttgt gctggtgaat ctttagaagt   111300
tgcttctaca gttcagaaac acgttgtagc aattggtgat tctcgtcaag attgcttggt   111360
tcttgctcg cctccacgtg cagctgtagt tggtattcct gttaatcgtg cagttgataa   111420
tctggttgat tggcgtacag cgtcgggaac ttacactgat aataacttta ataaagttc   111480
tacttatgct gctattgatg gtaactataa atatcaatat gacaaatata cgatgtgaa   111540
tcgttgggtt ccattagctg ctgatatcgc cggtctttgt gctcgaacag acaatatttc   111600
tcagccttgg atgtctccag ccggttataa ccgtggacaa attcttaacg ttattaagct   111660
tgcaattgaa actcgtcaag cacaacgaga tcgtttgtat caggaagcta ttaaccctgt   111720
tactggtacc ggtggtgatg atatgttct gtatggtgat aaaactgcca cttctgttcc   111780
ttcgccattt gaccgtatta acgtacgtcg tttgtttaac atggttaaaa cgaacattgg   111840
ttcggcatcc aaatatcgcc tgtttgaatt gaacaacgca ttcacccgtt cttctttccg   111900
tacagagact tctcaatatc tacagggtat taaagctctt ggtggtgtat ataacttaa   111960
agttgtttgt gatactacca ataacacccc agcagttatc gaccgtaatg aatttgtagc   112020
tactttctac ttcaaccttg cccgctcgat aaattatatt acgttgaact ttgtagcaac   112080
agcaactggt gctgatttcg acgaactgat tggtgctgta ggtggctaat aagacgcctg   112140
atgggcattt tcggtagccc ataaaatat actatatcgt ttaaaaatta attctatggg   112200
catccggtta atcctaagcc catattacta cagaggctaa tatgtttgta gatgacgtaa   112260
ctcgtgcctt cgaatctggt gatttcgctc gccctaacct gttcgaagta gaaatctctt   112320
atcttgggca aaactttagc ttccagtgtc gtgctactgc tcttcctgct gcgatcgttg   112380
aaaaggttcc tgtttcttat atgaaccgta aaattaacgt ggccggtgac cgtacattcg   112440
atgattggac tattcagta atgaacgacg atgctcatag tattcgtcag aaattcgttg   112500
attggcaagg tattgcagca ggacaaggta atgaaattac cggtggtaaa cctgctgaat   112560
ataaaaagac tgctatcgtt cgtcaatttg ctcgtgatgc taaaactgtc actaaagaag   112620
```

```
ttgaaattgt tggcttgtgg cctactaacg ttggtgaagt atctcttgac tgggattcga 112680
ataacgagat tgaaacgttc gaagtaactc ttgctcttga ttggtgggaa taatctggtt 112740
ggggagaaat ccccagcttc ccgtgatgac ggagaagtcc atataaatat aactataatt 112800
cccattcgga gaatacaatg aaatttaata tcttaagttt gtttgctcca tgggcaaaaa 112860
tggacgaacg tgattacaaa gaccaagaaa aagaaaattt agaatcgatc accacaccaa 112920
aattagacga cggcgcgaaa gaatacgaag tatctgaaaa tgaagcacag caaacatata 112980
atgctatgtt tcagagaatg ttcggtagtc aagaaccagg gctcaaatca acccgtgaat 113040
taatcgatac gtatcgaaat ttgatgacga actatgaagt ggataatgcc gtctctgaaa 113100
tagtttccga tgctatcgta tatgaagatg atacagaagt cgtttctata aatttagaca 113160
acacaaaatt tagtccaaat atcaaatcaa tgatgttgga tgaatttaac gaagtgttaa 113220
atcatttatc tttccaacgt aaaggttcag atcattttag acgttggtat gtggattctc 113280
gaattttctt ccataaaatt attgaccctc aacgccctaa agaaggtatt aaagagcttc 113340
gtcgtttaga cccacgtcaa gttcaatatg tccgtgaagt tattacaacc actgaagctg 113400
gtgttaaaat agtcaagggt tataaagaat atttcattta tgacacatca cacgaatctt 113460
atgcttgtga tggtcgcata tatgaagctg gcacaaaaat aaaaatccct aaagccgcga 113520
ttgtttatgc ccattctggt ttagttgatt gttgtggtaa aaatatcatt ggttatttgc 113580
atcgggctat taagccggcg aaccaattaa aacttcttga agatgctgtt gtaatttatc 113640
gtattactcg tgctcccgat cgtcgtgtat ggtacgttga tacaggtaat atgccttcaa 113700
gaaaagcagc agaacatatg caacatgtta tgaacacgat gaaaaaccgt attgcatatg 113760
atgctaccac aggcaagatt aaaaaccagc agcatattat gtcgatgacc gaagattatt 113820
ggttacaacg acgtgatggt aaagcagtaa cagaagttga tacattaccg ggtgcagata 113880
atactggaaa tatggaagat gtacgttggt tccgtaatgc gctttatatg gctttacgta 113940
ttcctattac ccgtattcca agcgaccaag gtggtataca gtttgatgct ggtacttcta 114000
ttacacgaga tgaattgaca tttggtaaat ttattcgtga gctgcaacat aaatttgaag 114060
agatattcct agacccgctt aaaactaatt taattcttaa aggaattatt acagaagatg 114120
agtggaatga tgaaataaat aatattaaga taaaatttca tcgggatagt tatttctcgg 114180
aattaaagga tgctgagatt ctggagcgtc gcattaatat gcttcagatg ccgaaccat 114240
ttattggtaa atatatttct cacagaacag ctatgaaaga tattcttcag atgtctgacg 114300
aggaaattga acaagaggct aagcaaattg aagaagagtc gaaagaggct cgtttccaag 114360
accccgacca gaacaagag gattttaat ggacgattta attcaagcta ttaaatcaaa 114420
cgacctcgtt gctactcgaa agttttttga aagtgcaatg gcagaaaaaa cggttcgttt 114480
gattgaagca cgcaaagcag aaatcgcttc tcaattttg attgaaggcg aagaacctga 114540
agaagaagaa aagaaagcta aagcttcgga agacgacgct gatgaaggcg atgacgaaga 114600
cgaagatgat gaggacgatg aataatgtat cttatccctg aatcttatga attggtactc 114660
gaaaatgtcg aagcacttat tcctgaagca cagggccgaa tcgatgcatt gtcttctgct 114720
ctcgatattg acgatataaa tactattatc gagaacatgc ttgaaactga aacggattta 114780
gctgttgcaa tggcttccat tattaatgaa gagcagttaa atgagtttat cgttaaacat 114840
gtttcttctc gcggtgaagt cacccgcact aaagaccgta aaactcgtga acgtaacgcg 114900
ttccaaacaa ccggtctttc taaagcaaaa cgtagacaaa tcgctcgtaa ggtcgttaaa 114960
```

```
gctaaaaaag ctaacccttc aggccaagtt aaaggcatgc gtaagcgtaa aaagctctt  115020 aaacgtcgta aagcattagg attaagctaa tgaataaacc cgagttactt attgaaactt  115080
ggggtcaacc cggtgagatt attgatggcg ttccaatgtt ggaatctcat gatggaaaag  115140
attctggctt aaaaccaggg ctttatatag aaggtatttt tcttcaggca gaggttgtta  115200
accgaaataa acgtttatat cctaaacgtg ttttggaaaa agccgtaagc gactatatta  115260
aagaacaagt cgcaaccaaa caagcccttg gagaattaaa tcatccacct cgtgcaaatg  115320
ttgaccctat gcaagccgct atcattattg aagatatgtg gtggaaagga aacgatgtat  115380
atggacgcgc tagaattatt gaaggcgacc atggtcccgg cgataaatta gctgctaata  115440
tacgagctgg ttggattcca ggtgtttcct ctcgtggtct tggttcttta accgacacca  115500
ataaagggta ccgtatcgtg aacgaaggat ttaaattaac cgtcggtgta gatgccgtat  115560
ggggaccttc tgctccagat gcttgggtta ctcctaaaca aatatcagaa tcagaaaatt  115620
cggtggaaat caccaaaaac agtgctgatg aagcatttaa agctctcgca gagagtttaa  115680
aagcattata aataataatg taatctaaac cacaggacac taaaatgatc aaagaacaac  115740 tttttgaaaga agctcagaat atcgagactt cagttgctct taatagtgtt ttcgaatcag  115800
tagaactgtc tccggacgtt aaagctaatt tcagcactgt attcgaagcc accgttaagc  115860
aggaagcagt caaactagct gaatctcata tcaaagctat cgccgaaaaa gccgaagaag  115920
aagttgaaaa ggctaaagaa gatgctgaag agaaagctga taaaaaattg gctgaacaag  115980
cttctaaatt cctggaccat cttgcaaaag aatggctcgc agaaaaccaa atcgcagttg  116040
ataaaggcat taaagctgat ttgttcgaat ccatgcttgg tggtctgaaa gaactgtttg  116100
ttgaacataa cgttgttgtt ccagaagaat ctgtagatgt tgtagcagaa atggaagaag  116160
agctggccga acataaagaa gaaaccgctc gtttgttcga agaagttacc aaacgtgatg  116220
catatatcaa ttacgttcag cgtgaaaccg ctattaatga aagcgtaaaa gacctgactg  116280
aatctcagaa agaaaagtt attggcctgg ttgaaggtat ggattattct gacgcatttg  116340
gtactaagtt aactgctatt gtagaaatgg ttaaaggttc tactaaagaa gaagccgcta  116400
ttaccgaaag tataaataca gttgacaatg acgctgccgg tcttaatttt gttgccgaag  116460
cagttgacac taccacaact caggtagaac agaattctaa tgtaagttta tatgcgaaag  116520
tcgcatctcg tttctaattt aaaggttaac acaaatgact actatcaaaa ctaaagctca  116580
gctcgtagac aaatggaaag aactgctgga aggtgaaggc ctgccggaaa tcgctaatag  116640
caagcaggct attatcgcta aaatcttcga aaaccaggaa aaagatttcg aagtatcccc  116700
tgaatataaa gacgagaaaa tcgctcaggc atttggttct ttcttgaccg aagctgaaat  116760
tggtggtgac catggttata atgctcagaa catcgcagca ggtcaaacct ctggtgcagt  116820
aacccagatt gggccggccg ttatgggtat ggttcgtcgt gctattccta atctgatcgc  116880
ttttgatatt tgtggtgttc agcctatgaa cagcccgacc ggtcaggtat tgctctccg  116940 tgcagtatat ggtaaagacc ctatcgctgc tggcgctaaa gaagctttcc atccgatgta  117000
tgccccagac gcgatgttct ctggtcaggg tgctgctaag aaattcccag ctctggctgc  117060
tgacactact accgttgtag gtgatgtcta tactcacttc ttccaagaaa ctggtactgt  117120
atatctgcaa gcttctgctg tcgtaacact tgattctggt gcaactgatg cagctaaatt  117180
agatgcagaa gttaagaaac aaatggaagc tggtgcactg gtagaaatcg ctgaaggtat  117240
ggctacttct atcgctgaac tccaggaagg tttcaacggt tctaccgata acccatggaa  117300
tgaaatgggc ttccgtatcg ataaacaagt tatcgaagct aaatctcgcc agctgaaagc  117360
```

```
tgcttactct atcgaattag cacaagacct ccgtgcagta cacggtatgg atgctgatgc    117420
tgaactgagc ggtattctgg ctacagaaat tatgctagaa atcaaccgtg aagttgttga    117480
ttggattaac tactcagcac aggtcggtaa atctggtatg accctgactc ctggttctaa    117540
agctggtgta tttgacttcc aggacccgat tgatatccgt ggtgctcgtt gggccggtga    117600
aagctttaaa tctctgttgt tccagattga taaagaagca gttgaaattg ctcgtcaaac    117660
cggtcgtggt gaaggtaact tcattatcgc ttcccgtaac gtagttaacg tactggcttc    117720
agttgatact ggtatttctt acgctgcaca gggtctggct tccggtttta ataccgacac    117780
tactaagtct gtatttgccg gtgtacttgg tggtaaatac cgcgtataca tcgaccagta    117840
tgctaaacag gattacttca ccgttggtta caaaggcgct aacgaaatgg atgcaggtat    117900
ctactatgct ccttacgttg cacttacccc actgcgtggt tccgatccta agaacttcca    117960
gccggtaatg ggctttaaaa ctcgttacgg tatcggtgtt aacccgtttg ctgaaagttc    118020
cctgcaggcc ccaggtgctc gcatccagtc cggtatgccg tctatcctga acagccttgg    118080
taagaacgct tacttccgcc gtgtatatgt aaaaggcatc taatcttaat tgattaaatc    118140
ttattttggg agacttcggt ctcccatttt tggttttatt tctgtgcaat ttcgatgtaa    118200
gttttcaaaa tattttgcca attaggcata ccttcttgga catatgccgg agaaccgtct    118260 ttgttttttga atgatgcaag tttatcagtg gcccaataac ctttagctcg agcttcagaa    118320
taaactttca tccatacttt gttgaaggca ttaccattaa cttttgcacc atatttttct    118380
actaacttaa ctgcttcagc ttccagaact tttaaagtat ctcgtaagaa acgtgcttta    118440
gtcattttgt ttactcctct gtagttgata agtctatagt atcacatacc aaatacgttg    118500
taaacaatct ttataaataa tctatatcac ataaggaaaa aatgcaatga gtaaaatcca    118560
aaaattattg cgtgaatcta caacgtctac tagcaactca atcggtcgcc caaatctcgt    118620
tgctttgact cgcgctacga ctaaattaat atattctgac attgtagcaa cacaaagaac    118680
taatcaacct gttgctgctt tttatggtat taaatatctt aacccagaca cgaattaac    118740 gtttaaaact ggtgctactt atgcaggtga agctggatat gtagaccgag aaaaaattac    118800
cgagctcaca gaagaatcaa aagtcacact aaataaaggc gatttttttca aatataataa    118860 tatcgtctat aaagtgctag aagatacacc attttgcagat attcaagaaa gtgatctaga    118920
attagctctt cagattgcgg tcgttcattt aaaggtacgg ttatttttcag atgcagctgt    118980 gacaagcaaa tttgaaagct ctggtagcga aatttctgat gcaagattcc agattaataa    119040
atggcaaact tcagtcaaat ctcgtaaact aaaaccggc ctcacggttg aattagcgca    119100
agatttagaa gcgaatggat ttgatgcccc taacttctta gaagatttgc ttgctactga    119160
aatggctgat gaaattaata aagatattct tcagtcttta attactgtat cgaaacgtta    119220
taaagttact ggaattactg acactggatt tattgacttg agctatgcgt ctgctccgga    119280
agcaggtcgt tcgttatatc gaatggtgtg tgaaatggta tcgcacattc aaaaagagtc    119340
aacttatact gcaacgtttt gcgtagcttc agctcgtgca gctgctattc ttgctgcttc    119400
cggttggtta aaacataaac cagaagatga taagtatctt tcacaaaatg cttacgggtt    119460
cttagctaat ggtttaccgc tttattgcga tactaacagt ccattagatt atgtgatcgt    119520
tggcgtagta gaaaatatcg gtgaaaaaga aattgttgga tcaattttct atgctccgta    119580
tacagaaggt ctcgacttag atgacccgga acatgttggt gcatttaaag ttgtagttga    119640
tccggaaagc ttgcaaccgt ctatcggttt attagttaga tacgctttat cagcaaatcc    119700
```

```
ttacacagta gcaaaagacg aaaaagaagc gagaataatt gatggcgggg acatggataa    119760
aatggcagga cgttcagact tgtctgtttt acttggtgtt aaattgccta aaattattat    119820
agatgaataa aaaaaaaagg gaccgtaagg tcccttttt cgttatgata ctaattcaat     119880
ccatgcagga cgcaatacat cttgcaccat tcggactaat tctttcttaa caagattcgg    119940
attatcagat gatgttaata caataccttc acgagaagtt tcttccagaa tatcttgaac    120000
agtcaatccc atcactttgc caaaatcttt cggagttact gtcccaatct tagaaatcac    120060
attgttaaca cgatttaatg taacataaca agctagaaca tcaagtaagt ttttgtcaat    120120
ttcggttaat ggaacctgag ttttaatagg cttatcagac ttttctttt cactgaattt     120180
agagttcttg cacttaatcg ctacacgagt accgtttggc agccatttag ggaaacaagg    120240
cttcagaaca taaccttctg cagtattatc accaataaca ttagcatcaa atacgcaatt    120300
atttgcttcg acaaggtctt ccgatgccgt agcgttataa gcggctaaga cggaatcaag    120360
gtcgtttgga atcgtgataa gagcatcaaa tgttccacgt ccaagcattg gtgccatttt    120420
aaaaccaaac gtattacaga aatcttgcat ttcgtaatca ctcatgtaat aagtatcacc    120480
gctttcagtg tttatgatga tatcgaatac atagaaatct ttttcaccat agtcaacacc    120540
tttctgaatt ccaccaccag cgaattcacc aaagacttga tatgtcaccg gcactgaagt    120600
tgaaatactg cccatgactt cctgaacggc tttaatagct ttatcatact tcttgagtac    120660
gatttcgtaa ccataaaaat cttctgctgg aagaataggg cctgtgcgct tggcgcatgt    120720
gacgttgtca cgttcaataa ttaaactaaa gttggtcccg tggattttct cacgtgctac    120780
ccaaacacca gtagtcaaac cattagtgta gagttttca ataaacttag agttgtagtg     120840
gttttcaaga ctgctgtatt tcttaaacat aaatcaccat tataaataat aatatcaaaa    120900
taattagcag agactctatc tccgacccga tgtttaattt gaatggatag aacctagatt    120960
cattatacca tcaaaaaatg taaagcatat tagaacttga tttctatcca atgcccgtca    121020
cgttggtcat gattaatttt gtactgaaag ccgttatcac gaagccattg accgacttgc    121080
tcggtgatag ttaaatcatt ctttgatgga tagtacgtga attgtgtctg gcctttgtca    121140
gcggctttct ctgccatcac agagaagtta gtaataaaat cactcaacaa attagcttta    121200
atggccagag cccttctctc taattcctgt gcaaaactca tttcttcacc tttttattaa    121260
tcaaacgttt acggtataca acttttttctt ttgctttaaa ctttgaccga gctgtctcgg    121320
ctttagtcca tagtaatcca acttctttag gttgtaaacc aattttttga gcaatttcta    121380
cgaatgaaaa tcccgcctca tgtaatgtat aaacttcaac ttcagctctc ataatcaatc    121440
ccgtattatt tggtttgtgc cattatatac atcaatctca agttgtgttt tgtatgcttt    121500
aaaaacgaag aaaggggccg aagcccctta cgattatgga tatgtataga tgataccagt    121560
ttccaaagca gttttatgga tgatgtatcc attacgtgat tcttgaacat caacttctgg    121620
atagtctttc atcatcttct gaagcgtata acgatgcaag taatacttac taccaggatc    121680
gtcaattttc caatctttac cttcttcagt cattttttgg atttcatcca taacccacaa    121740
accgcaccag atgtaagctg aagtacgatg tggaagagga tgaacataag gtagttcacc    121800
ttctggctca attggagtct gttcagcaat aacaacttca gcggttgaac taattgtctt    121860
tgaagtataa ttatcttag ttaatactgc ttcaacttta attgtatgag tacccgccga     121920
ggaggtatca atactgtaag tattagtaga attactttct gctacgttgt ctttcttcca    121980
agaatacaca atattagtat cacctggagc accagtaaca gatgctgtta agttgcagt     122040
tccaccaaca gtagtattaa ctgatggcgg agataaagaa atggtggcac tattaaatga    122100
```

```
cgcattatta gttactactg ttgcttctgc tgaaatttct tttgtaacat aatttgttgc  122160
agaaacagat acagtgcatt taagagtttt acttccgacc tcggttggag tgaatttata  122220
cgtagcagaa gttgcatccg gaatattact gtcatccatt gaccactgga atgatgtagt  122280
agcacctgaa ggtgcaccag agacatttgc agttaaagta ataggaacac caaagaccgt  122340
agtcggagac tcaggcgtaa ttttttagtgt tgaagaatta gccttttttat ttacagtcaa  122400 agaaaccgct gatgattcta ctgttttatc aacgtaatca gttgcagtca ctgtgacgga  122460
gcaagttata gacttagttc cttcggatgt tggcgtatat tcaaaggttg attgcttttg  122520
accatcaaca gcaatcccgt caactttcca tgtataagca atagcagcac cactaggttg  122580
attgcttaca ttagcagtga atgttgttgc tgttccaatt tctactgccg ccggagaagc  122640
cggagtaaca gcgacggtag aattattttc tttcttatta acagtgatag ttgttgacgc  122700
ttcagctatt tccggatctc ctgcggaaag tgtattagtt gcaaccactt taattttttt  122760
ttgttcctgc cggagaagca agagtataat ccattgtagc agcctagac tcctgtgcta  122820 tatcatctac agtccagacg tatgtaatag taccatctgg agtttcacct gcaggtgtag  122880
cagtgaatgt ttgtgaacct ccaataaccc ctgtaggagt taaaggagat aacgtgacag  122940
tgaatgtcat aagttatcct tattttaatg ttatgaaaga agaattacga gtttcacgaa  123000
ttagaactga tccatcgcga ttaatataat aaattaagct aaataatgtt tggtgagcag  123060
aagcgtgcac aaaactagtt gggcgagatt tccaatctgg ggtttcggct atccattgat  123120
aaatccacca aggaacagta acatatcctg ggcctttgcc taatttaatg agtgtaggac  123180
taaaattttc aggcagaaca aattttactt ctttatttac ctctgtctca ggctcttttt  123240
cagattcaac aacctgagta attgcttctt cgaatttatc atggtcgaat tctttttctt  123300
gttcgacaac ttctaatact tcaacttgtt ctgttggaga atcaaacaac agaatagctt  123360
cttctttaac ttcttcgttg gtgaaattaa caccgtccac atcatctgcg gcagtaatta  123420
aatcggtgat agataatcca tcagtttcag gtaatggttc atcagccagt gcgttaagag  123480
cttcttcgat atcaataaca atattatcga acgattttgt tttcttaaca ctaatgccaa  123540
attgttccgc atattcaaac agtttagctt tggcttcctt tttatcagaa agagcacgta  123600
actcttcaat atagtcttta tcgatcatgg tatttcctca ttataaatat aactatattt  123660
attacatggt aatttgacat gactgacatt aaagtacatt tttatgattt tagtcacgtt  123720
cgcattgaat gcgacgaaag tacgttttac gaacttcgtg acttttttag ctttgaagcc  123780
gacgggtata aatttaaccc aaaatatcgc tatgggcaat gggatggtag aattcgactt  123840
ttagattaca atcgtttgtt accatatggt cttgtaggac aaataaaaaa gttctgtaac  123900
aatatgagtt attctatatg gattgaccct aaaatctttg agactgaaga ccttaccagg  123960
gaagattttg acgcgtggct ttctaaacaa gaaatttatt caggcaacgc caaaatcgaa  124020
ccacattggt atcaaaaaga tgcagtatat gaaggtctag ttaatcgtcg tagaatttta  124080
aaccttccga catcagcagg taaatcacta atccaagcac ttttagctcg gtattattta  124140
gagaactatg aaggtaaaat tctcattatc gtccctacaa cagcattgac aacccaaatg  124200
gctaatgatt ttgttgatta tcgcttgttt agtcattcga tgattaagaa aattggcggt  124260
ggtgctgata agccgacaa atctaaaaac gacgctccaa ttattgttgg cacatggcaa  124320
acggtagtta agcagcctaa agaatggttc tctcagttcg gtatgatgat gaacgatgaa  124380
tgccacttag caacaggcaa aagtatttct tcaatcatct caggattaaa taattgcatg  124440
```

```
tttaaattcg gtttatctgg ctcattaaga gacggaaaag ccaatgtaat gcagtacgta   124500
ggtatgttcg gcgaaatctt ccgtcctgtt agcacgtcta aattaatgga agacggacag   124560
gtaactgagc ttaagattaa tagtattttc cttcgttatc cagacgaatt cgccaccaaa   124620
ttaaaaggta aaacatacca agaagaagtt aaaattatta ccggactaaa acgtcgtaca   124680
aagtggattg ctcaactttc agtcaaattg ctaagaaag acgagaatgc ctttgtaatg    124740
tttaaacacg ttacacacgg taagaaaata tttgaagcta ttaaagagct tggatacgaa   124800
aaagtttatt acgtatcagg tgaagttgat actgaaacac gtaacgcact taaagtcatg   124860
gcagaaaatg gtaaaggcat tattattgtc gcatcatatg gagtattctc taccggtatt   124920
tcagtcaaga atcttcatca tgttatttt gcccatggtg ttaaatcaaa aattatcgta    124980
cttcaaaccg taggtcgcgt gcttcgtaag catggttcta aagctgttgc tacagtttgg   125040
gatctcatcg atgacgcagg tgtaaaacct aaatcattaa atactaaaaa gaagtatact   125100
catcttaatt acttgttaaa acacggtatt gatcgtatcc aacgttacgc tgatgagaaa   125160
tttaactatg taatgaaaac aattaattta taagggcttc ggcccttagg agataaaaat   125220
ggtacttgaa tttaaacaat ttttatacga agcatctatt gacgaattca tgggtaaaat   125280
tgctagttgt catacccctag aagggcttga agaattggaa gcttattata agaaacgtat  125340
aaaagaaacg gaattaaaag atacagatga tatttctgtc agggatgcct tagcaggtaa   125400
gcgtgccgaa cttgaaggcg acgatgagga tgtggaagaa gacttctaat taaaaaaag   125460 gcccgacctt tttggaaggg ccaaaaacca taggcaaaaa aggtaacact atagtaaaag   125520
ttgggtttcg ttcaattgct cttctgaact ttctgaaacc ggcaattgtt gtacataatt   125580
ataacaagga ccaggatgtg ctggacctt gtctgtttca acaaccaatg cagaatcgat    125640
tggagtttta cagacaacac aaatcttatc tgacatgatt gcctcctaag ttgaaattac   125700
atatctattt ataccactcg catgcacata tcgatacca tatcttttgt ataaaaatac    125760
tcgtcgatat acccagcaaa cttcccttta atataaagga cgtcttcacc acaagggtgg   125820
tctgccagga tacgaatatc ctgacgtcgt agacgatact ttccattaa gaatttaatt    125880 tctgtttcaa attcttcatc attattaaag gcatcttcaa ttgaataacg cattattgcc   125940
ccgcttcaaa ttctcgcata tcctggatat gtttaagtgc aaaactacga gacttaactg   126000
cgtcaagtgc accactacag aactcaagta aaattcccca gtattgtaaa gtagtctcta   126060
ttttaagcac atctttatct gcggccagga cagttttcat ttcagatttc tcatatcggt   126120
ccatactgaa ttcatcacca tcacctcgtc ccgagtagta gtctaatctt gcttttagag   126180
cagttttctt ctgagtctct atacgcaaca tttctttacg aataaatgag tgtttacgca   126240
gccatttgct gtataactta acattattcg ccgtctcata ttgcaacttt gtcatatcaa   126300
tagctaagtc tgcgtctaac tcttcctgta aatcttccag cttcataata ttctctcttt   126360
taactaataa tctcccggct gtatcggaag gacctaaaac cattatacat aggttgcctt   126420
gaagcattac actctattgc ttgacgctaa ctgaagtttg atttgttcga tatcatcagg   126480
gttatctacg actgaaaatc taatctctac tataactgta tagtcatcat atactggcgt   126540
tacacttaca gaaagtttgt cgatgcgtgg ctcatagtta cgaacagctg cctggatatt   126600
acgctcaata gtatcggctg taagtggtgt catgttctcg aaaagttcat caaccaaatc   126660
gcatccaaat tcagggtcga aggggcgtga gcctttcta gttgtcacta tgccaagaag    126720 actatttta atagaacgaa gtcctacaga acgagcaacg tccttgttcc aatccatacg    126780
catttctggg tcgatatctg aataaagttt attgatatta gacattatag taactcaaag   126840
```

```
aattctttga ggcctcgtat tgtgtgaacg tgtgacgccc cgcatttggg acatttaata 126900
ggggttgcca gataaattga tggcgacacc aaaagatttt taatattgat catgtcatct 126960
tctgttataa ggccataaag gtcgtttatt tctgcttcag ttaaatcttc aacagggatg 127020
gactctccat tgacaaaaac agcctcaata catgaagcaa tcattaacgc gatattttta 127080
tcatcaaata atttaggttg acggaactta attttaatac cactgaacga ataccaggga 127140
tcggcctgtt catctaattg agtgtgcaat aaattcatat agacttgaaa tgaatgccca 127200
caggaacaat tccaggtgtg ttcttgattc acttcaccta atgaatgtgc ccacagattt 127260
accaacaata actcggcttc ttgtttagtc aagtttttag cgttagagca attagtgata 127320
atattgttca ctgctgattc aatagtaccg gtagcccgag cacctataag tcctaaatat 127380
tcttttaaag taaaggctct acaattcact tctttatcgc ctaaacgtac ggtaaacgta 127440
tatttgtaca tgttaactcc tttattgtgt atttataaat aatagaaaag gagtaattat 127500
ggctaatata attcgttgta aattaccgga tggtgttcat cgtttcaagc cgttcaccgt 127560
ggcggattat agagactttt tactagttag aaatgatatc gaacatcgtt cgccacaaga 127620
acaaaaagaa ataattgctg atctgattga tgattatttt ggcgagtacc ctaaaacatg 127680
gcaaccattt atattcctgc aagttttgc aggctctata ggcaaaacaa aagttccagt 127740
tattttcact tgccctaaat gctctaaaga aaaaactgca ccatttgaga tatatcaaaa 127800
agaactagtc gaacctgaac ttgatgttgc tggtataaaa atacgttttt ctttccctga 127860
aaagttttat gacaacaaag cattaatgat aagtgaaaac ataaaagaaa tatattataa 127920
tgatgaatgg tacccatgga atgatttgac tgaagagaac caaatccaag taatagaagc 127980
aatagacatt gactcgctcg agaaggttat tgcttctatg aaccctatta atttgaccct 128040
tagattaggt tgttgtgaac gacatgttaa aacatatact gatatcttag aggttttttaa 128100
attgttagtt aaccctgatg agattttttac attctatcag ataaaccatt cactagtaaa 128160
gagtcaatac acattggatt ctattatgca aatgattcct gttgaacgtg gtattgcttt 128220
aacattagta gaaaaggacc ataaaaaatg acagtattcc aacgtccagg atatcctaac 128280
ttaagcgtta aattatacca agattattcg gcttggcaag aaaatagata cgttgaactc 128340
gcagcaacaa taacaacttt aaccatgcga gattcgctat atggaagaaa tgaagggatt 128400
cttcaattt atgacactaa aaacatccac actaaaatgg acgtagaca gatagtccaa 128460
atctctgttt caaattcaaa cacacctctc caagttagaa ctcgaattta tggatgtaga 128520
cattattctg tgtctgtgga ctcaaaaggt gacaatatta ttgcaattga gcttggaaca 128580
atacattcta tagagaacct taaatttggg cgtccattct tcccagacgc aggcgaatct 128640
atacgtgaaa tgttaggtgt catatacaaa gaccgtacgt taattactcc gccaataaac 128700
actattaatg cttatgttcc tgatattcct tggacaagca catttgatga ttatttggca 128760
tatgtcagag aattaggact tgctacagcg agtgataagt tcgtattcgt atggcaagat 128820
attttaggcg taaacatgat tgactacgat actcttattg gtcaagaagg cattaagatg 128880
attgtaggtg agccaaatac tgtaggtcag tatattcaag agcttgagta tccattagta 128940
tgggatttta cctggatgac taaagccaac caatttacaa gagaccctat taaaaacgcc 129000
acgatattcg cccattcatt tttagataca tctattccgg ttattgttac aggtgatggt 129060
gataatgcta ttcttgtgtc aagatccggc ggatattccg aaatgaccta tcgtaatgga 129120
tttgaagaag caagtcgtct tcagacaatg gctcaatacg acggttatgc taaatgcact 129180
```

```
actacaggta attttaacat aacgcctgct actaaaatta tatttgttga ccaaaagaac    129240
caattcaaat ccgaatttta cgtggatgaa gttattcatg agttatcaaa taacaactca    129300
caaactcatc tgtacatgtt taccaactca atggtgttag aacctgttaa cccagttaag    129360
gttaaaaatg aacttaaatc tgattctacc tctaaagaaa ataattctac cacagtctaa    129420
taaaaaggta atgattccca aattagggct caaacattat aatcttttaa aggatgttaa    129480
aggtcctgat gaaaacatga aaatcttagc tgattctatt tgtaaaaata tgagtcctgc    129540
tgattttgat tttgcatgtc tacatatatt ggaatttaat aacaaactta agtctgaagt    129600
tgaaaaagac ggattcacat ataaactaga tgacgtctat gtatgccaac gaacagaatt    129660
ccaattccaa ggcaatactt tttattttag acctccaggc aaatttgaac aattcgctac    129720
aatcagtgaa atgttatcaa attgcttaat aaaagttaat gacgaagaga aagaaatttc    129780
tttccttgag atgcctgctt ttgtaatcaa atgggcagaa gacctttcga caactattgc    129840
tattccaggc cctaatggtc ctattaaggg tatagcagaa attattggat tgcttgaatg    129900
aaacctgaag aaatgaaatc catgcgtaga ataaggtca ttgccgataa taaaccacaa    129960
aaagtagctg caacagcagc taccgattca ttagaagcat tgaatgatat ttcatcaaaa    130020
ctagacgatg tccaagccgc gtctgaactc acatcgcaaa gtgtagaaga taaaggcaat    130080
ggaattattg aatcaattgg agacttaaag aattcgacag ataacactgc tgaaggcaca    130140
gagcttatcg cagaagttat tgaaaaacaa actgaagtca ctaaaagtat aaacgaagtt    130200
tctagtgcaa taagctctaa gttagaccga ttagctacat tattagagca aaaattacaa    130260
acatctaccg ctattcaaaa tacaggaggc acctctcttg aagtaattga gaacgcgata    130320
cctgttaaag tggttgagaa cgaaacttct gatgagttgt ttaaagcatt acctacacct    130380
gaaaagatta taataagcc agacgaagat ttcttcccgg tcccggttca agaaagtgct    130440
aattctactt ccgattctaa aggcggtatt agctttaaat tgagcgataa aattgcaatg    130500
ctcactaaaa cagttcaaac cgggtttaat aaatcaatat caatttcaga cagaattgct    130560
ggaatgcttt tcaaatacac tataacggct gctattgaag cagcaaaaat ggccgcactt    130620
attcttggta ttgttatcgg tattgattta ttgatagtcc atttcaaata ttggacagac    130680
aagttcactt ctgcctggga tttatttgat gaaaacttta ctaaattctc cgatgaagct    130740
aaagagtggg gtaaattctt aagcgatata ttcacttcta ttgactcgat aaaacaattg    130800
tgggaagctg gagactgggg tggtttaacc gttgctattg tcaaaggtgt aggaacagca    130860
ttaatgaact taggtgaact aattcaatta ggaatggcta aactctccgc gtctatattg    130920
cgtgctatag gttttggcga taccgcggac gaaatagaag gacgtgcttt ggaaggattc    130980
caagaaacta ctgggaacaa attaaagaaa gaagaccaag agaaagtcgc taaatatcaa    131040
atgaagcgtg acgatgggga attaggaacc gtttctaaag gtcttgatat gttacaacgt    131100
ggcaaaacat tcgttactaa ctgggttcgt ggtaatgaca ataaagaaga gtttagtaca    131160
agcgatgagc gtgctgcgga atcagcaaaa ttaaagagt tacctgaaga ggagcgtaaa    131220
gaggcgtata taaaagctaa tgaaactcgt gcggcactag ttagatttga ggattatatc    131280
gataaaatcg atatgactaa tccggaaaat gctaaaaacg tcgagaagtc ttatgctgat    131340
ttaagtaaac ttattaaaga ccctgaactt aataaaactc ctgttgttaa aaaggaaata    131400
gatgctagat ttgaaaagct aaataataaa atggctgaag ccaaaaaggc tcagacaaca    131460
gttaagcctg aatcttcgac taaatctcca gaagcaaaac aagttcagtc aatagagaaa    131520
ggacgtgctt ctgaatctaa acaacagcaa ccggtagcgg cgattagtaa cacaaataat    131580
```

```
gtcgtcaaaa agaataccgt agtccagaat atgacccctg taacaagtac aacggctcct   131640
ggaattttcc atgccaccgg tgttaattaa ggattattat gattagtgta aaagaaatag   131700
tagtagatgc aaaggattta aataaagcaa tcccagtctc agaaagtgct gggcaaagca   131760
ctaaaaccga acaactact aaaacttatg ttgctcaatt tcctacagga agagcagccg    131820
gaaatgactc cacaggagac ttccaggtaa cagaccttta taagaacgga ttattattta   131880
ccgcgtacaa tatgtctgca cgcgattcag gatccctcag gaatttacgt ccggcatacg   131940
ccgggacttc atctaatggt atcatatcag atttaactga taacgtgaaa gatgcagtga   132000
ctaaattctc aaatggattg cttcctgcca gagctaataa gtctactata aataaaactc   132060
ctgttgctaa tatactttg ccacgttcca aatctgatgt tgatacaact tcgcatcgtt    132120
ttaatgatat cggtgatagc cttattacta aaggtggagg tactgctaca ggtgttttaa   132180
gtaacattgc ttctactgca gtctttggtg cattagattc tattactcaa gggcttatgg   132240
ctgataataa cgaacagatt tatacgactt ctcgtagtat gtatggcggt gctgagaacc   132300
gtactaaagt cttttacatgg gatttaactc cacgttcaac tgaagacctt atggctatta   132360
taaacattta ccaatatttt aactatttct catatggcga gaccggtaaa tcacaatacg   132420
cccaagagat taaaagttat ttagacgaat ggtaccgttc aacgtttatt gagcctatga   132480
caccagacga tgctgtaaaa aataagacgt tatttgaaaa gattactgca tcattaacaa   132540
atgtattagt tgtaagcaac cctacgattt ggatggttaa aaactttgga cacacatcta   132600
aatttgacgg gttaactgat gtatttggcc catgtcaaat tcaaagcgta cgttttgata   132660
aaactccaaa tggacaattt aatggtctcg ccgttgctcc taacttacca tcaacattta   132720
cgttagagat aacaatgcga gaaattatta cattaaaccg ttcttcactt tatgcgggga   132780 cttttctaatg tactctttag aagaatttaa taaccaagct ataaatgcag atttccaacg   132840
aaacaatatg tttagttgtg tatttgctac tacaccgtcg accaaatcgt cttcactaat   132900
ttcgtcaatt ggtagttttg cttataataa cttagggttg gattccgatt ggctaggatt   132960
gactcaaggt gatatcaatc agggcgtaac aaccctgatt acagcaggaa cacaaaaatt   133020
aattcgaaaa tcaggtgtaa gtaaatatct gattggagca atgagtcaac gtacggtaca   133080
aagcttgtta ggtgagttca cagtaggagc ttatctgata gacttcttca atatggcata   133140
taataataca ggtttaatga tttattctgt aaaaatgcct gagaaccgat tatcttatga   133200 aacagattc aactataact caccgaacat ccgaattacc ggtcgtgaaa tggacccgtt    133260
agtaataagc tttagaatgg attccgaagc atctaacttt agagcaatgc aagactgggt   133320
aaactctgtc caagaccctg taacaggtct tcgtgcttta ccacaagacg tcgaagcaga   133380
tattcaggtt aatttacatg cacgaaatgg tttaccacat accgccgtca tgttcactgg   133440
atgtattcct gttagtgtct cttctcctga gttaacgtat gatggtgata atcagataac   133500 agttttgac gtaacatttg cttatcgcgt tatgcaatca ggtgctgtaa atagacaggc    133560
cgctttagaa tggctggaat caggacttat tagtagtgtt tcaggaatgt ttgggaataa   133620
tcaaaatgat tctgggctag gaagtgcagt atcaagactt tctagattag gtgggactgc   133680
tggaggtgtg tctaatataa acacaatgac aggtatggtg aattctacat caagagtttt   133740
aggtctataa gaaaaaggga gacaacgtct ccctttaggg gtttatttac ggaatgaaag   133800
aaatgctggt gctcggaatg gagtatcatc tttagagtat ttaactaata cgaccattgg   133860
tacctctgtt tctaaatgac ctgtcagtac accgataaaa atttgatcag tgtgttcagg   133920
```

```
gtcacgaaag tttttaagag gttccatagc aatatggaat gcacctggga atactcgatt   133980
caattcgtca atcacagctt cgttaaaaac atcatccgct gggatagcat cttcaactac   134040
tagttcttga ccattaaagc gaagcataga tttcataacg ttttcctcat gttgttgata   134100
ggatgatagt atcacacatc catgtgcttg taaactatcc ttgaacaaat ttaaacggaa   134160
ccgattctaa atccattaaa gatgctaaca gtttcaatcc tttaggagca ctagttttttt  134220 ctacaaatga ggagaacgat accggctcat ccgattcgat ttcaccagtc atagcaacca   134280
cctcgcctgt ttccatgaga acatcaccat cgtaaatgac agcttcatcc aactggtctg   134340
aggacatgac ttcagcttga ataaatttaa ggttggattc taaacctgca ccagtgtcag   134400
atgacgcatc tgtaatttta tttatctgca agagaatgcc tctaggcaaa ataatttctt   134460
gctcattagg gtgattactc aactgtcctg gataaatcac gttaacttta tgggcgccgt   134520
caatagccca tccaacgtta acacggattt gttctggtgc atgcatagct gttcttactt   134580
gactaggaga aatagtaaca ccttcgtcat tattgtcaat gttaagctct ttgcgaactt   134640
cttcaggagc aagtccaagg gcaacgttct cttttaaccc gccgaaaata ataggagcta   134700
gtgaagtaga aacatagttt ctgaagtaga ataccttatt tttaaccatt gcttcgtaaa   134760
taggcattct gatagactga gctctataca acgttagtcc ttcaggtaaa cggtctccat   134820
ttaaaaacgc cgaatcaaga ccatcaatag cgcgtttaac ttcatcttca tctgcaacat   134880
cataaaaatc cggtttataa cgtcctaaca acatattatt gatatcagta tatgcagaag   134940
aggcatattc acgaatagct cgttttttcgg caatagagta ttgtttaggg tcccgattca   135000
ttgttatatt aaaggtgcct ctggccgatt ctcgtgcata agtatacatc acattagaca   135060
agaacgctga tttacgttgt ttccaagttt tttcagatac ttcagctaaa acgtcatcag   135120
ccagttggaa attatctcgt ctaaaatctt caaaccattc gtctctaata gagtctgcaa   135180
tttcgtttgc agcttcaaca aaagcagcta atgctttaac agatgttgtt ttttcggttt   135240
taattttctt agcaaacttt tctaaagtcg gcttaataac actaccataa gaaacttcat   135300
cagcaaatct aaaggattca tcaatacgat tataaatctt attttcgata tcagcaacta   135360
aagtgccttt tgctgtagac gatgcttggg ctagtacgat ttcatatgct tcaggaagta   135420
attcagctgt agctgggcca ctaacttctt tagcagaatt ttcgtatttc tggaatagct   135480
caccttcttg gcggtcagct tctaaagatt gacttgcggc aatagcgcga cgagaaattt   135540
tagtacgagc aataacaggc ttatctttac gttttttcttc tacagcagca atagaaccag   135600
cgatagccgt ttctttggtg acctttttcgc cagtcttttt actcacataa acttcaccaa   135660
catcagaatc tactttcgtg tacaactctg tgttaatgtt agggatgcct ttaatatctt   135720
caatgttggc attttttacga accatcatca catatgtgtg tttacctgtg aattgataca   135780
ttgcagacaa tactttaaaa cgaccaccag ttttagtaga aactaaacga gcaagaagag   135840
tttgaagttg ttgtccacgt cctttcaatt tcttggtagg gaatcggaac aaaactgcat   135900
ccatacgaag agctttaacc tgttcataca ctgtattgaa aatggtgttg attgcatcaa   135960
taggagcagg accaagacca ttttttcaatt cagcgagatt acccttttca gaaagactca   136020
taataacgac atgagcgtat ttgtcgccaa gtttaacttg ttttacagca tcgccttcgg   136080
aaaggtaaga gaataaacga actacgatgt ttgtatcgat atcaccaatt ttccagactt   136140
gtggaacttt agctttaggg ttcaaattga cgacaggaag actgccttca gattcaaaca   136200
cttcatttaa ttgttcagac atagtgtttt ccttttagta ataatttata tttatgccaa   136260
aaagagcccg aaggctctta atccacaatc ggaagcaaag tacgataaac ttcaaaatta   136320
```

```
gggcctttt  cgtacttatc  aaaattgtcc  ataaaaatat  tataggaatc  gttattagga  136380
aaatctaata  caatttggga  acaagaggtg  gaaacatcac  caccatcttt  attagcgaca  136440
actactgttt  ctaaataagc  tttcattata  aacctgtctg  ggaccacggt  ccaaatacgt  136500
cttcaaatga  atccgcttct  gttttatcaa  aacggaaccc  tttaataatt  ggaaggaaaa  136560
tacctacagt  accttcacgg  cctttagaat  gaacccaacc  attacattcg  caatcagcaa  136620
tacgtccaat  caatttacct  tcacgagctt  cagccattaa  tcgttcacgg  tctaaatcat  136680
gacgctcatc  taaaggaata  agaatcttta  caccatcaac  tgttttatga  gttgtatctt  136740
taaaccctga  accacaatcg  gttgtaatac  gacgacaacg  tgatacgagt  tcgacaccac  136800
ctaatttgtt  agggtcttta  gagtgttcat  agtatcctac  aacttctaaa  gcgatatcaa  136860
taacttcttt  aaatttaatt  aggttcttag  agcgtttgtt  ttcccaatat  gaatcacggt  136920
ttttaaggat  aataccttca  agaccttggt  caacatattt  tttataaacc  actttagctt  136980
cgtcaagatt  acgaactaac  tgattttcaa  ttggctcaat  tcgattaaag  ccttcagcca  137040
tattttcaag  agcagcaaaa  cgaacatcgt  atttctgacc  tttaattttg  ccatcagaat  137100
agacttcatc  taaaggaaca  tagtcccagg  cttgaagaac  cataccttcc  gcttcttttag  137160
gagaaatagt  cccttgaaga  gatttatttg  ctaaaccgtt  tgaagtgcta  cggtctgcaa  137220
cttgtacttc  ttcggattct  tcattatcgc  caaataagaa  cgacaggtca  tttcctgagc  137280
tcacagcctt  tttaatatca  aatgaatgat  aaactaattc  gccgtcgatt  aaaacccat  137340
tagggtgtct  ttcacgggct  tctttagtca  tttccattag  ttcatccgct  aatagagtaa  137400
gaccatggta  ttcgttacca  gcacgagaaa  agaattgaac  accatcatca  cgaacttcag  137460
cgaaacaacg  agcaccatct  gcttttaatt  gggcgaatgc  cggccattta  atattttag  137520
taatcaattt  ctcatcatat  gcagatgcta  acatctgtgg  ttgcaattga  ataagtccag  137580
gccacacctt  attcgcgata  gacactgaag  cacctacttc  aaggtcgcgc  atcattacac  137640
gacgaaggac  ttctacatca  tcaggtttac  cgtcagcgat  ataacccatg  agctctttaa  137700
ttgcagcatt  accagtgagt  ttacgagtgg  ctaatgtgaa  ctcaataaaa  tccaacatgt  137760
catctaattc  aagaagacca  tacgcttgag  acctttcacc  tggcccaggc  catttcttaa  137820
tataatactg  gataccacgt  gcatacgtta  aacgatacac  acgttcaagt  aatttgttgt  137880
ccttattttt  cttaaggatt  tcctgttttg  ttttagtaga  accgatcgca  gctatttggt  137940
ttaaaatatc  taaatcatt  tgatatcctc  gattttggtt  acggttctat  tataagccac  138000
ttcatctaga  agcgatttca  gcgttttctg  ataagtggta  atccatttac  cgagtccttc  138060
aacataatat  tctgaaatgt  agatgaaccc  ttgttcaaca  cactctttaa  atatttctgc  138120
gtcttttact  gaacgaaaca  ccggccagtc  tcgaaagaac  atgttaacat  ggccgtagtc  138180
acgtgtggtg  tttttgccat  ctgtaatatc  atgaactaca  aacataatta  gcccttaaca  138240
atttatagac  caagtccatt  tagacgaatc  taaaggaaag  ttttgaatcg  tccaccatgg  138300
ctgcatatcg  gttggtcctg  gggttcgcca  ggtatatgga  gtacgtgttg  tcgaggggcc  138360
accaatttga  ttaggccatg  cacctggact  tgttgcacca  gattcttaa  gcaaatcggc  138420
caatcgtttt  aaaaggtctt  cacgatctga  atttgaatta  tgctctggcg  gaaccaatcg  138480
agattcaata  tcatcccacg  tgtgtacacg  ttgtgcagtg  cgaggaatat  catcacgttc  138540
accacgagcc  aaccaataaa  tcggtacatt  aagaatttct  gccgcatggt  cacagtgatg  138600
agctaaatcg  tcaacgtaac  aaatcacgtt  atattttgtt  ttagctagtt  cgaataattg  138660
```

```
ttcctttgaa gaatcatgac cacacatcat tacttcagag aaagcgcctg ggaacaaagc   138720
attcaaatta aattgtctat tcaatcgagc atcaattgaa tcacctagcg ccgtcacggc   138780
tacaaaatta tagtcttctt ttagtttatt gataactcga agagcatctg aataaggcgc   138840
taagtaacga ataaaatcag agctattata tttttctatt aattgtttac caaggttatc   138900
gtcggtattg aatagtttac caggagaaat aaattttcg tcctgaatca ttttttaaaat   138960 atgttctaat ggaagattat attttttgggc aaaataagga agtccggatt gccaacttaa   139020
acatacacca tcaatatcag tcaaaatagt aggcttcata aagagtctct taataggttt   139080
aacacatcaa taaattcagc ttcagttagt attgtatcat cttttgttag gtggctagcc   139140
atgctgtgct tcaaaatttt tcctttagag gcttgtaagg catcacgaaa ccccttattt   139200
tggatcgcgg cttcaaaata tgcatttgtg tataattctt tccacgcttc ggagtatctt   139260
gaaaacggaa ctcctaacca gaagagagtt ccacggtcct gagctcttgc ataagacctt   139320
ccagcttgct gtgcagccaa tccagacaac ccaaatatac gtctttgttg ttcaacattt   139380
ttcaccttac atccttggag aaatccttca agacctccga attgaatacc atccataaca   139440
aaaggccatt gagcaaagtt acttaatgca catgacggcc acttgaaatt acttcttatt   139500
tctaattcag acatctttaa cacttataat ttcaacatca gcccaatggc cgtaactagg   139560
cagacggtct tcaatagata aaccaccgtc attttttaagc attttaattg tcttgataaa   139620
tggttcatcc tgtggatgaa taggcgagca gtcagttaca cgataagtaa cttcgatcat   139680
ttctgtacca aacaatttct ggattagttt attcaacatg tttcaaccct taataggag    139740 ataactcttt acccatacgt atgtcagaag tcccatcaac ccattgaaca gcatacgctt   139800
cattgataat tacggcggcg gttttaaatt catggagaac tttaaaaatc atcccaggga   139860
ttccaacacc ttttaattgg actgtttgtg ctattaaaaa tttcatattt ttccacttgc   139920
taaagaaatc attatactct aatccgtcct tggatgtaaa ctacttaacg aaattaattt   139980
ccaccggatg aacaacaggt tgagcagtga tatattgagt aattgctttc atgactagag   140040
cttcagaacc aggatttttc tcaacgaatt cacgtgcttg gttatgagct tcgagttcac   140100
tcaataatcc ggaacgttgg catccacggt cttgagtacc ctgttcagat aaaaagacga   140160
cgatgtattt ttcatcgtca tacggtttag acggttgagc aaatgttcct ttacttccaa   140220
aaggagagtt atgacgccac atcacgccgt gaggagtttc aaccttcgta tattcgtgcg   140280 ggccatttt cttaatttct tgatgtggaa cttcatagac cttagggtta ggacattcaa    140340
taaaatgctc atctaaatcg gtcgagaata ttaaagtaaa acaattactg aatttaccaa   140400
cacctgcctg ataaattta ccttcagaag ttctaatttc acaaaccgag ccagcatcag    140460
taacttctaa aacttcaaaa ggctcgataa ggtcatatga aacatgtttt taaggcgtg    140520 gagtaatatc cccattttta aaattcattt tataaaaagt attaacttta aacataattt   140580
cctcactggg agcttcggct cccaattaat ttagatatca aattcattaa gaactacatc   140640
aaagattgct tcgagatgtt caggtttagc tcggttactc aggatatgac gaatccaggt   140700
tttaaccaga agtttacgat taacaccatt ccagcaagga tgagtaccta atcgcgctg    140760 acggaaatca tcatcttaat gcaattttaa aatttgaacc ttccatcgtg attgaaaccg   140820
tgatgccatt ttcaaatcgc atataaacat aattaggagt catgcactgt tcgatttcac   140880
aaactgtacc gttttcgtgt ttccataagc aaataacttc agaagaacca gcgataccgt   140940
tagaaacata tttacgttcg aagttgatgt agttcatttt attctccaga tgtttaagtt   141000
gtttgttggt acaggtatat aataacatat cctgtaccaa agtaaactgt tttatgcaac   141060
```

```
tttaatccaa ttgtctaaat ttaaaacacc tttggctttc atttttttcg atcaggttat   141120
ctgctgtaat gcgtccattt tgataccatg taacatcttc agagtaacca gtttcttcgt   141180
caacatatgt ttctgagcga attttaccgg taataatagt ttttaattcg tatgtgtcac   141240
ctgtgaaaaa gtttgctaac acaatttcc aagagaaatc atttgaagga ccttcagggg    141300
tcatacaact tacgaactca aattgctctt tgtataacat ccactggaat tctttaattt   141360
cgatagcttt ataaccgtcg tggtctttac atttgatgta tgagtttaga ttgattttca   141420
ttttattctc cagtttgttt tattgattag gtggtacaag tctatagtaa cacatcctac   141480
aggagagtaa acatctttt aaactttttc tgccctaaac gcacaaaagg gagaccgaag    141540
tctccctaaa attacgcaac aacctttcca aaacgagaag catcatctcg aagaactgca   141600
cgtgctctgc gcatgatctt ctcaactgtt tgattaatac gagagttcga cccacgcttg   141660
tatccagcgc gtttagaggt accatcaact ttcttttcaa ctgctttctt tgctttagct   141720
tgttttgcca ttataaattc tctttaaatg aaaatgcagg acttattgac attgcctgcg   141780
caagccctca tgggaacata ggttttggat atttaacgac aggataacca taaacccgtc   141840
atcataccaa ccacgactta gacagataac ctttttctga cgcgtgatag tacaaaatac   141900
attcaagagg tacaccgtaa aactgccggg gtcttaaaac tataatgatt cgcaaatcat   141960
taatcagaca attcgacggc tcctcgattt aacttacttc agggtaataa caaaatgacg   142020 tactgctttta cgagctgctg aagccaaagg cttagcatat ttcagttcat cttttgcttc   142080
cagttcagca gccagagtag cctgagcagg attcagatgt ttgaaatatc gcaggatttc   142140
cagtgcttcg gcttcaacat caattgaagc gccgtagttt tcgtgaccgt tattccatgc   142200
gttgcgttgc agatcaagag cgtgttgtag ttgtttaatc attttaaatt ctcaattcga   142260
gataatattt agtagccacg ttcgtctgaa tttcaccttc tttcgacaag tctctcagtt   142320
gtaggctacc gcttagaaga gtgttctctt catatagtta tttatatcac ttataaagac   142380
acggaatagc tttatagtgg catgttacga atttctgttt aatttcttta ggttgtttaa   142440
gtcccaaagc cacaaatgga tgtggaacat ttcgaatttg tccaactggt agtggagtca   142500
aatcaccgac ttcaacaaaa ccttcaggaa catcaggacc tacagaatga actacacata   142560
gttcaggaac ttcaccttga acacgtttac caatcacaag tcctgattcg gtaacttctt   142620
catcacctgc ttgagcgggt tcagaaacca gaatgacata ttcaccaaca gcacgaattg   142680
ggagttgtac ttcagacatc ttatttcctt gttgtttgac gatagattaa taataccata   142740
ctattcgtaa agcatattac ataagaagca aacgttcgac cggagtacca tcaaccgaaa   142800
ttactttatc aaggcggaaa gaacgccact gacctaactt ggtatcgaat gctcgaactg   142860
attcacgagg ttcataacga acttctgttg ccggattgtt attttcatat ttgacttcaa   142920
gttcatcgcg cgaagcaaac atagtgcgta catcaccgtt agccttttca aatacaacac   142980
aatgaacgcc tacagacaga atagttttaa tacgttcacg aagaaccata gtttcttgtt   143040
cagttaaaat catattattc accacaaaag tttcggattt gttcccaatt cagagaacga   143100
agattattac gagagtactg aattacttca ataccagctt gttttagaat gtctgcccaa   143160
ttttcaggag atctgtcgta taattctgcg tatacgacct ttttaatacc tgactgcgta   143220
atagctttag tacaatcagg acatggagaa agcgtcgtat ataacgtagc accttcaata   143280
gaattacctt tacgagcggc aaacaaaatt gcattcaatt ctgcatgaat ttcattatta   143340
gcagaccatg cactatgagc agctcgatgt tctttggcta aaacaaaatt atctacccgt   143400
```

```
ccaaatgctg tagtgccttc tttatgtcca gcaacgatga ctgggattgg tttattcttc   143460
aaccaaccat tttcagatgc atgttcgcaa cagttaacgc cacctgcagg tgaaccgtta   143520
tatccagtag agataatgcg tccatctttt tcaatgacgg caccaacttt ccatgaacaa   143580
cattttgatt cttgagaaat cagatatgca atctgaaggt atgtgctagc tttcattatt   143640
gaaccttatt aatataagtt aacagctctt tagtttgttc ccaactgatg cacgcatcgg   143700
taacggaaac gccataggac atattatcag aaatttttg atttccttca tgtaggaacg    143760
attctatcat aattcctttg accaaatcat tagctgctaa attttttacca ataccaattt  143820 gattgctata atgcccatca gcgtttgcat ggctacagtc aaccattaca taatgattca   143880
gacctactgc ccttgctttg ttagaagctt cttgaatatc agaagaatga tagttcgggc   143940
cgttggtccc gccacgcaat acgatatgcg tattctgatt accttcagct tcaacaatgc   144000
ctacagtacc atcgacgtcc atacccatat accgatgagg ccaggcggca ctatacatcg   144060
cgtctgtagc tactttaata gaaccattgg ttgcgttctt gaagcctacg cacatcggta   144120
gacctgaagc aatttcacga tgtgtctgac tttcagtcgt acgagcgcca atagcaaccc   144180
atgagaaaat accagaaaga tacttaatcg tgaatgggtc taatacttca gttgctaatg   144240
gaagtcccat acgtagaagt ttacgacaca atgttcgtgc aactataaga ccgtggttca   144300
tatcaaaact tccgtcaaga tatggatcat ttacaagacc tttccaacct acggtagttc   144360
gaggcttttc aaaataaacg cgcatcacta acagaacatt aggaagacga gtttgaagtt   144420
cagccagacg tttgccgtat tcaaccgcag caatagggtc atgaattgaa caaggaccta   144480
caacaataag tttgcgtggg tcttcaccgt tcataatcga attaacttgt tcgcgatgag   144540
aagccacttg tgatgcgtaa gcttccgaca aaggaataat ctcagccagt tctttggag   144600 aaataagttt tccgacgaca ggtaacataa caatccttag gagatataaa cagattctga   144660
ttcaacaata cctttaaccg gattagacag gctaagttgg tagtgctcag atttatgacc   144720
attctcgata gtaatgagat agctctcatt atagtgttcc atatactcga gttgcttcaa   144780
caagaccatc actgcctaat ttaagattag taatttggtc accatcttta ggattaacga   144840
ttatgagaaa agaacgtgga gattcttgaa taactcgtaa tgttgcatcc tggaaacgtt   144900
cagacacttt attgatgagt gcttgagcaa attctttac tttaatctga aattcgtgta    144960
ctgtaattgg atttcactt agcatttcaa tttcctcatt tgttggtaga gttatagtat   145020
cacaactcca ccatgttgta aacttaaatt gcaaaacatt taatttcttg tgaatcgaaa   145080
tcaacttcac actgaattac tagttcagca tcaagaccaa acacaacaat cacatgagcc   145140
gagctgggca acaatgtaac agacacagaa tccacttggt caggcaccag agtattcaaa   145200
acgtagagta gttcagagtg gaccttaagc tcggtagcag tatccagctt atcaaagaaa   145260
tgatttgcga taatctgact aaaaacgacc tttacaattt cagaatattt agggaacata   145320
attacctcag tgtatagtat ttactttaac tcgaacaaca aattgctcgg tcggttcgcc   145380
tacaggaaca aactctacat gatattcgcc tttgtaacga gtattcaggt cgttacgaat   145440
ttcggtaagc ttgttgatta atgtagaact catattaagt ccaactagtt tacgaagcat   145500
tttgtatgct tcatcttcga tttcatgatg tttatcgtac atagttttca tttaaccatt   145560
caattgcctg gtcgacgtta tcaaatatac caccgtccaa acgttcttca tgctcatagt   145620
ccagcacatc aataccgaac tgtccattta ctaaaggcca ggctacaaac aaatattctt   145680
tatgctgttc gatggcctca atcacttcat ataatcgttt cattaaaaat caccatggtt   145740
aacttgccaa cactctaaac caatacgacg ccacatttcc acaacctggt tacggtcatc   145800
```

```
aacggccaat ttcacatcat aatacggagc aatacaattc caaaagagtt cttccttaac    145860
aacatcgtcc ttacgagtgt caccttgatt acgttgaatg tgcatttccc atggaataga    145920
aaccgtgtcc atccattttt tagttgcttc gtaataacac attgaatctt ctttagttcc    145980
agattcacga ccacttacag taataattgt atacccggcc tgatgaagca tcttaacata    146040
ttcgacaacc atagggttcg gggcatctgt ggatagttta tccaactcat aaggtccacg    146100
agctacatgt agagctaaag tcccgtcaag gtcgaagata accgctttag gtttacccgg    146160
agttccttta taaaccggaa gtcctttgta ttcacgcata cgagaataca tcgaacgtag    146220
aacatcaata ggaacggcct ttgtgccacg tttggcatta cgtttaacca attcagtcca    146280
tggaacatcg aacacttgat atacaacttc atgaccccac tccttagcgt attcttccca    146340
gacaagacga cgttcaggat ttaagttggt gtcagaaata ataacaccct tagttccgtc    146400
ttaacagaga atcatatgtg ccgcgtcgtg ttgcatataa gttacgatac tttctttctt    146460
ctttgtgtat ttgtactcgt cgcgttcttc gtggcccatg acggattgac gataatcgtc    146520
gcggttgata ttaaagaacc caggattctt agcaataaat tcacgagccc aagtgctttt    146580
accagaccca ggacaaccta cagtcaaaat aatctttttc acagttttac tacctcttca    146640
gcaaattcaa attgtccacc aagaatttta gcaatttcac gtcctagttc agcacctttc    146700
ttgcaatctt gcatagtcca agactcacca ttctgtgatt tacgaagagc ccgtgtattg    146760
atatctgcta caagcgtatg gattaactta tcaattttgg cttggtccat tattttattc    146820
ctaagaaaat ttcaagaata cgaatgttat gctcgcgccg gtctttatta atttcagcaa    146880 cgttttatt aattgacgta cttctaacgt ttgaagaaat aaatttaatc atatgacttt    146940
tgagttgttg caaatccaac ccttttttctt tagcagcttt acgaagagct ttacctgctt    147000
catctagtgc ctttgctgca tctttgtcat aattgccaag tgacattcca cgacagatat    147060
caatatactc atcagaccgt ttgatgtaat tctctagtaa tgttttcatt tagatttcct    147120
caattatcca taggagcatt ataatctgct cctgagagtt tgtaaactat tttactaaag    147180
attcaatata ctcgtgaaga gctttagtcg ctactgccca cttattctga tattcatttt    147240
tcagattagc acgagactga actaacaatc ggtcattagt cggaggcaaa gattctaatc    147300
gttgaatctg cgcccataa atcatagccg ccatttcaga ttcatagata agccctttaa    147360
tgtattcatg ctgttcttta gtcattggca ttttttcctct tttaaactac tacgataata    147420
acataacata gtcttctggt catgtacata tctttttacg tcgtttaacc agatacgaaa    147480
ttcttgagag tcttcaaatg gcattccaac ccatggatta ccatcaataa cctttacttg    147540
ccatttctga ttatattcaa caatagattc aggccatggc ggatgtaaag tttctttagg    147600
gcttaagggc acatcctggg cacatccagc caaaatgcca atagataata caactgcagt    147660
taatttaatc attctgagag cttcctgagg tcttctgcaa aggaatcgaa ggacctgttg    147720
atttgttttt cgaccaatcc tggcttactt gccaccacgt tcttcttctt cgaatcctga    147780
cggagctttt cattttcagc cttaagttgg tcaactaaaa cacggttctt ataagtcatt    147840
tcttcgattg actgatattg aactttgaag tcgtctaata ctttagcatt gttttttagca    147900 gcctctttaa cagaagctaa ttcagtattc aacgaatcaa ctttgttgtt taagacaact    147960
attgttaccg tagaaactag agcaaaagct gctactatag cataaatcgg atttacttta    148020
agcatgtttg aataatctca atgatttcgt ctcgggataa tccattgata agaactgttt    148080
taggcccatc agtttggatt ttgtaggtct caaacattac acacaactct tctgctgtat    148140
```

```
gatatggact tgagattccg aggcggttga atttgtcggt aagagggtcg caaataatgt   148200
agaattttat acctgcgata tgtacgtttg gttgactaat attaatgaac acattagcgt   148260
catatttagt caaattgttt tgaagaaatt ctaccatagc attaactgct tccggcattg   148320
cttcacgttt ctcttcggtg taacgtgttg aatattcctt ttgctttaac ttcttttttag  148380 cattttttcgc tagagtagta cgaaggtctg taagataacc gactgcacgg cctttcttaa  148440
agactcggat tccatctgta gaatcaccaa atgctgccac aaccatatcg ttagtaatca   148500
attgcatatt cataattttc tcctcgtgtt gttgataaaa gccatagtaa caccatcctt   148560
ggtgtttgta aaccattaat atccttcagg gatgaaattt ttatgatttt taataaaagac 148620 tgattctaga gcagtcataa tttgctcttt tgaaccacct tggtaaagat tcataatgat   148680
gccaaataac caaggtgtct gtgcacccct acaaacagcc tgagcttcta tagcatacgt   148740
tttacgatct tttcctttgt gcttatcata tgtatctaga cagatataaa atgagcggtc  148800
taagaaatcg agatatgctt tttcgaagag ctcgaccttt ttaaatgaaa actcatcatc   148860
tgcatacatc gctttaaggt catctgaagc accgttcact atagcaagaa acaacttttc   148920
tgggctagag attgagtctc gagtcgtatg aagagcaaca taccaatcag tcttcaattt   148980
gaaatgagac ccgtctttca ttacggccac atacccttca atatttgtag aagacttaac   149040
atctgatgtc cagtcacctt ctggtacttc aaatcggtct acaagatatt tacgaaaaac   149100
agggtctaga taaatgtcat catactcgat gtattcacct gtgttgttat cgcgaatatt   149160
caaaagaatc aaacgttttt cagggtatgt taaaacaatt ttatttgttg gagcaacgta   149220
ttcgaagtta gcagtgaacc cgtcattaca aagttctaat aaacgatcag ccaagttttt   149280
atggtcgatg tctaacaaaa tactcgtggc cgatacagcc tggtcggatt tgattgaccc   149340
tttagatttg aaacgaacag tcccaccatc aagatatgtc gagactaacg aaccgtcttc   149400
tttagtcatc agatatttta catcatcaag gttaattgac aatgtaaacg ggttctcatt   149460
tagattaaag aatttttcca ttggacgaga agcaatacgt ataggagttt caccatccat   149520
ttcgaacata ataccacgac actctaacgc gtcaggcaat aaccaatctg aatatgaagc   149580
aaagttatat gagaaaatac gatactttt accgattgga cttacatcat ccgagtagaa    149640
aaatttacgg tcggatgacg atttacacag agataacaga ttataataaa gcttttccat   149700
tttgtatcct cagttagttt ttttaaatt gtaccacaat ccttgtggta tgtaaactac    149760
tttttcttat gttggatatt ccaaggcggg ttgaactttt tgataaaaag tggttcttca   149820
aggtccattg ttgcgatggt cattgaacca agttcgttgg tgactgaaag gtcaaaacat   149880
tggcgggccc agaattcaac cttttttgcct tgcattaagg catccaaaat cataagtgat  149940
tttcttgaat ctgaagtctg gtcttttcga tttatggctg ttcgataata gttaatgcgt   150000
ttctttaaat tcttggtttt accaatatac acaagttcgt catctatagc aatagcgtat   150060
atgacatttt tcttattagg ggcatcaatg gtttttaattg ttgcatcttc taatagctcc  150120
aattctatat atttaataaa ggaatattcg gcggcaatat ctttcataat aaagtgggac   150180
cgaagtcccg tccttagaaa tatttttttgt atgaatttat tacattttgg tctacatcat  150240
tatcaatttg tgcgacaaga taagaactga tttcaacttc ctgaggagct gcttgaacta   150300
aatcagagtt cagatattca cgaatccaag gatacggatg cttggtcgga gcatcagtga   150360
ttgggcatgg caaaccacac tgtttcatac gagacacggt caagtaatca acaaaagcac   150420
acatactctg cgtattgata cctggacatg taccatcttt aaaaaggtgt gcagcccatt   150480
ccttctcttg actatttact tccataaaaa tgtcaactgc ttcttgttca cattctttag   150540
```

```
caatttgaac ccactcatca ccgtcagtac cagattgaag ttgacggata atgtactgag  150600 taccctttgag atggagttgt tcgtcacgag caatgaactt cataatctttt gcattgcctt  150660 ccataatttc catattttta tggaagttga aagtacatgc aaatgatacg taaaaacgaa  150720
tagcttctaa ggcgttgata acatgcaaac agagataaag agacttcatt aggtcatgtt  150780
tacattcttc catgtgcata agactatttg aatatgcatc taaatcatat tcattttcgg  150840
aaaaacactt aaaaatttct ttagcatttt cccattcacg ggttttaatc agaacgtcat  150900
cataataacg tccaatggat tcagcgcgtt tcataatagc ttcatctaat acaatttcat  150960 caaataccttt cgatggatcg gtataaagat ttcgcataat atgagtatac gaacgagagt  151020
gaatagtttc actgaatgtc catgttgcga cccatgtatc taatgaaggg tcagaaatca  151080
gtgccataag taccgcagat ggggccctgc cttggataga atctaataat gattgatact  151140
taagattgtt tgtaaagatg tcctgttgga actgaggaag cttattgaac tgcgcagagt  151200
ccaacatcaa gttacctct tctgggcgcc agaaaaacga caattgtttt tcaataagtt  151260
cttcgaaaac tttatgacgc tgaatatcat accgtgcgag gccaagacca gaaccaaaga  151320
acatcggttc attcaaaaca tcgacttgtt gtgtgttaaa aactgtactc attatatttt  151380
ctcacttagt tattaactca tccatgagta aattataatc aaaagtctta aagcttacaa  151440
gcagagcaat cttcagcttt aggtgtttct aattcatagt catctgtacc tgacccatca  151500
cgagtgttat gatagtagag gttttttccg ccaaagtacc agaagtaaag cagatcgtca  151560
agcattactg acattggcac tttacctttc tcaaatactg cagggtcata gtaagtatta  151620
gcagaagcag attggcacac ccatttcaac atgatagcaa cttgggtcaa ataaggttta  151680 ttaccttttct tagcaagttt ccacgcatag tcataaagac ccatgttgtg ttcaatatta  151740
ggaactactt gacggaaatt accttcttta gattctttaa tacttactgg gccacgaggt  151800
ggttcaatac cgtttgtgct atttgagacc tggctgcttg attcgcatgg catgagtgca  151860
gacaacgttg agttacgaat tccgtgttct ttgagttcag ctcgaagttc ttcccagtcg  151920
cagacgtagt tcggggctgc gatttggtca atcttttttat tgtaccagtc gataggtaat  151980
tcgcctcgag accatttagt gtctgaataa tactcgcaag gtccttttc tttggcgagt  152040 ttgattgaag ctttgataag gctatattgc aatctctcaa acaattcatg agtcaaatcg  152100
ttagcgtctt catatgaagc aaagttagaa gctaaccatg cagcatagtt cgtcacacca  152160
acaccgagat ttcgacgctt tttggctttt aaagcttctg gaaccggata gtcttgatag  152220
tctaacaggt tatcaagtgc acgtacttgt acttcagcaa gttcattaat tttatcttgg  152280
tcttgccaat caaatttatc taatacaaaa gcagataacg tgcataaacc aatttcagca  152340
tcagggccat tcacatcatt agttggaata gcgatttcac aacataagtt actctgacga  152400
attggagctt tttcacgaat aaatggagtg tagttattcg tgttatcaac aaactgtgga  152460
taaattcgag cagtaccaga acgttcagtc atgaacaatt caaagagttc tagtgctttg  152520
attcttttct ttctgattgt tgggtctttt tcagctttct cataaagctc acggaattta  152580
tcttgatctt caaagaacga gtaatatagt tcgcctgaca tttcgtgagg gctaaataaa  152640
gtaatataat cattttttgcc aaggcgttcc atcatgaggt cattaatctg aattccatag  152700
tccatatgtc gaatacggtt ttcatccacg cctttgttat ttttcagaac taataggttc  152760
tctacttcta agtgccacat cggataatac gctgtagcag caccaccacg aataccacct  152820
tgagaacaag attttactgc agtttggaaa tgtttccaga atggaataac acccgtatgt  152880
```

```
cgaacttcac ccataccgat cttagaacct tctgcacgaa gcataccaac gttgataccg 152940
ataccagctc gtttagaaat atattcaata attgatgctg aagttttgtt aatagatttt 153000
aacgaatcac cagcttcaat aactacacaa ctagagaact ggcgagttgg agtacgagca 153060
cctgccataa ttggagtagg caacgaaact tgatgagtag aaacggcatc ataaaaacga 153120
ataatatgtt tcaaacggtc atgagtttcg tcttgatgta aggccatacc aatggccatg 153180
atagcaaact gtggagtttc ataaatcttc ccagttgttt tatctttaac caggtatttt 153240
tctttaagct gcatggcacc agcataagtc agatcaaaat ctcgctcatg tttaatccga 153300
gaatcaagat aaatgatttc ttctgcagaa tatctagaca caactcagg atcatatttg 153360 ccttcattaa cacaatacga gatatggtcg ataaaagcag gaggttcaaa ctgaccatac 153420
acatctttac gaagtgcaaa cattaatcct ttagcggcaa catattgata atcaggttct 153480
tcgacagaaa tcgagttagc tgcaacttta atacaaatct tctggatatc tttggtgctc 153540
atcccatcaa ccagatgagt cttaatttct tcatacaatt cgtatgggtc gatttgtgtt 153600
ccttcacact gccaagttaa gacttgaata atttttctgtg catcaaaatt tgggatacc 153660 ccactgctct tagttacttg catatattcc tcagtatagg ttgatagaca ttactccaaa 153720
cgggatagta ttatcccgtt aatttattat acacttttaa actgaagcgt taattattct 153780
tagcaataat ttctttgtat tctttaggtg tcaagactgt gatattgaaa taaaccaacg 153840
gttctttttc cataccgtaa ccaccacaaa attcacgata ttcataaatt cgttcgtgtg 153900
aatgacaaat gaatcgttca cctttaactg tgatttcact atttggtgaa gggatatcca 153960
gttcggtagg atttttcatt tcaaaaattg tggtgccata tgaattaata aaacgtaaaa 154020
tcatttatac cgccatttta gctttgatag ttggatgaga ttcgtaattt ttaagaatga 154080
aatcactcgg attcatatgc tctgttaccc aatgaagctg taatgtcgtg ctccaatcag 154140
agaatccttc aggccaatca attttaagtt cacacagttc tttaggctca cgacgaagaa 154200
cttctttgca ctgctctaca tggttgctgt agatatgcgt attgccgcct gagaatacta 154260
aatcacccgg gataagatta cacatcttag ccacaatatg cgtcaaggca gcgtacgagg 154320
caatgttgaa cggcaggccc aagaaaacat ctacactgcg ttgataccat tgtaaatcaa 154380
gatgaccatt acgcacatta aattgataga acatatgaca aggaggaaga gccatttggt 154440
caatttcggc agggttccag gcagaaacaa tttgacgacg atcagttggt aattttttaa 154500
tacggtcgat tgtttcaact aattggtcca caccaccgaa atcacgccat tgtttaccat 154560
atataggacc aagttcacca ctatgataac caaggtcttt tgcctgattt tcgtaattat 154620
cgtcccaaat agttttacct tcaattagac taccatgagt acgaagacgt aattcattaa 154680
cattagtaga accggacatg aaccacagta actcggcaat acaagctttc catgctaatt 154740
tcttagttgt tactgcaggg aatcctttag tcaggtccca acgtaattta gttccgaaca 154800
gggcaattgt tcctgtgcct gtacggtcgt ctgtttcgta gccatttttct aggatatcat 154860 taatcaggta ttggtattgt ttcatttata tacgctctca gtaatttcgg tgagttcatc 154920
gattctgtag taatgagatt ctaccataga acgttgaagc ataatatctt ggatgaaatc 154980
tttatcaagt tgaacatcgg aattaacacg acatttctta atgattttag tcatcacaat 155040
ttcatcggca taaggcagtg cttgttttaa taaggcagga ccgccgataa cagatacatc 155100
aacatgttca gtagaaagtt taaacggtac gtctgttgaa gggctgaaca agttaatttc 155160
actaccagtc accagggtaa taaattctgc ttgggtgata tagaaccgtg caagttcatc 155220
agttttagtc ctaggcagtt ttctggccat atcagcgaca accacatgag tacgatctgg 155280
```

```
tagtagacga ggtaatgatg caaaagtctt agcacccata accattacag tgtttttagt   155340
gcgagcaaca aagttactca tatcttgttt gatatgcttc catggtagtc catcacctaa   155400
tccaaaagca tattccagtt tatcatcgac tgttttagat ggtgcgcatg cgaatactaa   155460
tttaagcatt tttatttcct cagatttttc ttaacaactt tccaatcagc tttgaacgat   155520
tcaacgtcag agtggcaaat ccagaatcct gcactttcac catcttcgta gagtggacat   155580
ccatcacatt cttcgttcca acccatttca cgtaaagctt cttcagcttg ttcaaggagt   155640
tcagcgtctt taccaacgat gttgaagtac catttacctc taacttcaga atctttgatg   155700
ctctggcgtt gcaatctcat tttattctcc ttcacttttg atttgatagg gctactataa   155760
catagcccta tcttgttgta cactacttt  taaaagtttt ttgcaaaagt tcgatgattt   155820
cgtcgacgtt ggtttcatct acgatacaat ggattttgt  tacacctaaa gttatacctt   155880
cgttagtagg ttgaggcttt actaaatcta cctcagtaaa gtatttgaac tcgtcaggat   155940
aaatctcaaa atatgtttca atttcaccac cggcagaaca tacagtacca tcttccatag   156000
ttacacttac tacgtttgac gtatcgctat cataatcagg ttccattccg tttacaacaa   156060
aactaggtcc gtggagttca atcaatttta acatcttagc gttattgtgt ggtgcttctt   156120
gaacaaagtc atctttaaat aaagggttga tgatataaga ttttccgatt tccatttga   156180
tttcctcatg ttgttgatag gtctatagta acacatctag ggaagaagta aacaactttt   156240
tcggcaattt acagatactc aaaagggaga ccgaagtctc ccgatttatt atagaccagc   156300
taacaggtca tcgaggtcgc catcatcaga ggatgaggta gagctcatga agtcatcttc   156360
agttttgca  gaactaaagg cttccatgtc tttatcaaaa tcgtcaaggt cagaagcaac   156420
tttatctgca acagaagctg ctgcggctgc tgcaccacca agagcggcag taccaagaac   156480
cttagcgaaa gattcattta attttcaaa  ggatttgaac tggtctttag ccgtcaaagt   156540
agtaaggtct accatctggt catatagttc tttctggaat gcttcgtcat taatacgagg   156600
aatttcagat tgacccaaga atttagattc gtcgtagttg ctaaaaccag aaacctgctt   156660
agctttcaga acgaagttgg caccttcaaa cgggcaagta acatcaactg gagtttcacc   156720
catttcggta tcaacagcaa tcattgcatt gatttgtcc  caaatctttt taccgaaacg   156780
atatttaaat actttacctt cgttatctgg agcttgaggg tctttaacaa ccagaatatt   156840
agcccaataa gaagttttac gtttcagttg agaatattca gttttgttgg tattgtacag   156900
gtcattttta ctaatgtact gacatacagg acaagagtcg taatcaccat gtgtagaaga   156960
gcaatttca  atataccatt taccattttt cttgaaaccg tggttaacaa gaattgcaaa   157020
tggtagtgcg tcatcagttt ttgctggcag gaaacgaatt accgcttgac cattacctga   157080
tgcatctagc ttcagcttcc attcgccttt atcttctgaa gagaaacctt tgttaccgtt   157140
cagtttagcc atttgagcag cgaggtcagc agtagattta cgtttaaaca ttatatttac   157200
ctttatttag attatttaat ttatttacag ttggttgcta cgacacttat acctcgtagc   157260
tggtatgatt tatttataaa gtaattttaa cacacaagaa ataaagctta atacttacat   157320
gatttgattg tttctatgaa caatttctta gcagcatttc catcgatttg aagtatttt   157380
cgatatgcct ttaatttggt agaataattt tgccagacta aattgtcggt gagttcgtcg   157440
tgcttatcta taatattcaa gaatgaatcc aacaacaaga aggtttcaaa tgaaattata   157500
ttgctttgta gcaatttaaa tatgtagctc gactgaactt tattattata atcaaatatc   157560
tcttgaagcg cactaacttc cactttctta ctgaaatagt agatgttacg tacatcttca   157620
```

```
gcaaacgtct ccttggcttg tttgagacgt ccaatatatt ccctatagaa aactaatgca 157680
tcagcgtctg atatctcacc aatccacgca tcttggttag caactaagtt actgatgaat 157740
atcaaggtga gttcctttaa cttatatttc tctgctagtt tctcaaagaa atatttatct 157800
cggcgttttt gatacgcatt atccgaaaca cgcatgcacc agttatattt gattacgtca 157860
taccgaccat taaaatgttg tttgcacatc aagtatagtt tgtataccga ttttccgtta 157920
atataacgtt ctccatcagg aggcatgcgt atttttaatca taataagaaa tctaacgtat 157980
tagttttttc accacgagca actgatgggc gaagcatatt ttcgtcaatt gcttcgcttg 158040 taatttttc aacaattcct gtaggaataa atttagcaaa ttgtgtttct ggaatagaat 158100
tttcttctaa gaaagcagtt gttgcttcta aataagacat accaaattgt tcaaccatag 158160
attcgataat gaatccgttt tcttggcggt caagcaattt agcgatatca tctttatcat 158220
gttttactgc taattcttgt tcagataaac cggcctcatc aaccggttta atatcactta 158280
gtgaaaactg tgtcataaag ctcgactacc tcttcgtttt cagcttcaaa ttggtcacga 158340
gcatctttat gataaagagc taacaaacga ttaaacattt ttccatcgac accaagctct 158400
tctttagcac gagtacgaat gtctttaatc agttcattat aaccagaaat tttaagtttg 158460
ttatcggaag cttccttgac tagtttagcc agttcttcac catgcacatc ttgattaaat 158520
tcaactgctt ctttcttagc catgtttacc tcagaattca ttaattacac ttgttaattt 158580
agaaagaccc gattttacaa agtatgaata aatcttgcct ttaggttgtt gtttatatga 158640
gttataatac tctataatgg ttgaagcaat attatcaggg atataatcaa aatcaatgag 158700
aaccaaattt tcttggtacc gtttatattc ttctgcactt aataatactt cagcttgaga 158760
acggtcatta gcaattgctt caataatcgt tgttttcata ctcggagttc gttcgccttc 158820
aactcgagta aaccagaaat caccacgaac tcgaacagac gcaacaccgt ctttacggtc 158880
gcctttaaga attttagtca tgcaatcaat ttcggcagaa ccattcttaa ttttaaccca 158940 tttttctgc ggcggcgacc actgtttaac gttagggtat ttgtgtaatt gtgtaaagtc 159000
accatctgat gcaacaatac acaccttatg accggctaat gacaaatatt tagttaatac 159060
accgatatgg tcatctgctt cgtatttgtc aatatccatt acaacgtatg gcatatattt 159120
cttaatctca tcaacgactt tatggagtgc agtaaaatat ccttcccaat cccactttga 159180
agcttcacga tcggttttac gattttttctt ataatagtaa gcaaagtcac gacgccaata 159240
tccagaagta gcgttatcca tgcacaatac aaattttgta taaccttgct tacggaacat 159300
cactacgttt ttacgaattg aattcaagac tacatgacga accatcggaa cagtaatttt 159360
atcaccatct tcaaagttgt ttaatgcagc tgccaatgca atgttactaa agtctgcaag 159420 cgcaataccct tctttgtaat cttcatccaa catcatttct aaatccatat gaacctcttg 159480
ttcagttagt caacttagac catagtaaca tactagttcg aaagcgtaaa tagtcttta 159540 ctcatttata aatagtaaaa tagaacacat aatgataaga ggactaccat ggttgacatc 159600
aaacgtaagt tcagggccga agatggtctt gacgcaggcg gtgataagat agttaacgtt 159660
gcgcttgctg accgcacagt tggcaccgat ggcgtgaacg ttgactttt ggtgcaagaa 159720 aacaccgtac agaattatga cgatacgcgc gcgtatacaa aagatttat tgttcttat 159780 gataatcgtt tttatcaagc tttaaacgat attccagctc cggcaggccc tttctctttg 159840
gctaaatgga aggcaactcg tacagatgca gaatggacta cagttcaagg cggagatttc 159900
caattatcag taggtaactc tattgcggtt gatacttcag ctggcactga tattaatttc 159960
actttgcctc aaaatccttt aaatggcgat acagttattt tgtctgatat tggcggtaga 160020
```

```
gtaggctatg taaaagttca aattactgca gaggctcaaa gtattgtaaa ctttagagga  160080
caacaggttc gttcagtttt aatgacgcac ccaaaatcta aaatggtctt catttttagc  160140
aaccgcctat ggcaaatgta tgtttctgat tacgaacgta atgcagtcac agtaactcct  160200
gctaagccat atcaggcgca acctaacgat tttatcattc gacgttttac atcagccgct  160260
cctattaata ttacattgcc tcgcaatgct aataatggcg atattattaa tttagttgat  160320
ttagacaaat taaacccgtt atatcacaca attgtcaaaa cttacgatga tacaacttct  160380
atacgagaag ccggtgttca tgtagcagaa ggacgtaata ctgcggaagc attctttgtt  160440
tatgattctg ctaatagctt atggcgtgtt tgggaaggtg accagaaatc tcgtttacgt  160500
atagttcgta atgatactga tttacgccct aatgaagaag ttcttgtttt tggaactaat  160560
aatgatacaa tctcgacggt aaatcttact ttgcctacag atattttgtc tggtgatact  160620
gttaaaatat cgttgaatta tatgcgtaaa gggcaaactg taaaaattaa agctgctgaa  160680
ggcgatacaa ttgctagcag tatttcttta ttacagttcc caaaacgttc agagtatcca  160740
cctgatgcac aatgggtttc tgttagtgag ctggaattta atggcgatac ttcgtatgta  160800
cctgtacttg agttagctta tatagaagat tattcatctg aaacaaaata tgggtagtt  160860 caacaaaaca ctgtaaccgt agaacgagtc gatgcatcga gcaatacaac tcgagctcgt  160920
ttaggtgtta ttgctcttgc ttctcaagcg caagcaaatg tcgatttaga aaatgctcct  160980
ggtaaagaac ttgctattac tccggaaaca ttagcaaatc gtacagcaac tgaaactcgt  161040
cgtggtattg ctcgtattgc aacaactgca caagttaacc agaataccga ttttgcattc  161100
caagacgact tgattatttc tcctaagaaa ttgaacgaac gtacagcaac tgaaacccgt  161160
agaggtgttg ctgaagttgc aactcaggat gaaactaatg ctggcataga tgataccact  161220
attattactc ctaagaaatt ggatgcccgt caaggttctg aagttttatc tggtattgta  161280
aaatacacat ctacgactgg tactacagcg gctactgttc gtggtaatgc tgggactaac  161340
gtttataaca aagccgtaga taatttaact atttctccaa aggctcttga ccagtataaa  161400 gctacccta ctcaacaggg cgcagtaatt cttgctattg aaagtgaagt tatcgctggt  161460
gaatcacaaa ccggttgggc taatgctgta gtgacccctg aaacactaca taagaaaact  161520
tctactgatg gacgtattgg tttaattgaa attgctacgc aagcagaaac taacactgga  161580
actgattata ctagagcagt aacgcctaag acgttaaatg ataggaaagc tacggaagga  161640
ttatccggca tagccgaaat tgctacgcaa gttgaatttg tactggaac tgacgatact  161700 cgtatctcgt ctccactgaa aattaaaact cattttgatt cttctgaccg taccagtgtt  161760
aattctgatt ccggacttat tgaagaagga accttgtgga accattatac tcttgatatt  161820
tctaaagcaa atgaaacaca acgcggtaca cttcgcgtag cgacccaggc agaatctaat  161880
gcaggaactt tagatgatgt tcttattact cctaaaaagc ttttagggac taagtccact  161940
gaaacgtctg aaggcgtaat taaggttgct actcaggctg aaactgtaac aggaacttct  162000
gctaatactg ctgtatcacc taagaattta aaatggattg ttcaatcaga accatcatgg  162060
actgctacta cggcaattcg tggattcgtt aaaacttcat ctggttctat tacatttgtt  162120
ggtaatgata cagttggttc aacacaatct ttagaatcat atgagaaaaa tagctatgcg  162180
gtatcaccat atgaattaaa ccgtgtactt gctaactact taccgttgaa agctaaagca  162240
gctgatagta atttgttaga tggtctagat tctcttcagt tcatccgtag agacatcgac  162300
cagacggtta atggttcttt aagtcttact aaacagacca acctgagtgc tcctttagta  162360
```

```
tctacaagca ctgcttcttt tggttccgaa gcatctgtta ctcgtagatt aactcttaat  162420
gattctagcg gttctgaaat aattttcact aaaggaaccc aatctcttag taataaagag  162480
aatttcgttg ttagagcatg gggtaatagc gctacagatg gtgcccgtga tacagtattt  162540
gaagcgggtg acgaaaccgg ataccatttc tattctcagc gcgctgctga taatagagta  162600
tcatttaata ttaatggaac actttattca acaggtattg tttctacaaa tggattaaat  162660
gttacaggtg tttctacctt tacagggcct attagtgcta caggcgaaat tgtttctagt  162720
tctcctattg cattcagagc tattaatggt aactatggtg ttatgcttta taatgctggt  162780
aacagttctt atattgcatt aactaactca ggtgaccaga ccgggacgtt taataactta  162840
cgcccgatca cgattaacaa cgccacaggc ttagttcgtc ttgacaatgg tgttcaaatc  162900
acgagtggtg caacaataac taccgtgggg ttaactgtaa atagcagaat tatttctaac  162960
ggcgttaaaa cagccactgt ttataccgat aaaccaacag cttctactgt aggtttttgg  163020
tctattgaca ttaacgattc tgctgtatat agccaattcc ctggatactg gacgcgtgat  163080
aacaaaggta accgtgacca agaaattaaa tatcctggta ctttgactca attcggcaat  163140
agcttagatt cgctttatca ggattggatt tgttatccta caggtgcaaa tggtggtagt  163200
attcgttata ctcgtacctg gcagaaaaat aaagatgctt ggacttcatt tgcaatggta  163260
tttgatagtg gcaacccacc ttcacctagc gatgtcggtg ctatcccatc tgataatgct  163320
gttattggaa accttactat tcgagacttc ttacaattag gaaatgtgag aattgttcca  163380
gacccggtta acaaaacagt taaatttata tgggttgaat aagaggttat atggaaaaat  163440
ttatggcaag gtttggacat ggatacgtcc aaacgccgtt tttatcggaa agcaattcag  163500
ttagatttaa gctaagtata gcgggttcat gcccgctttc aacaactaat ccgtatattt  163560
tgttccaaaa cgagccttta gggttgcagt cttttggtat tggactaaat gttagggtga  163620
taaatccgga aaatggaact atagttgata gtaaattata caattttgcg cctacaaata  163680
atgcaacttc agctgcattt atttcgtttg ttaatacata cgcagataat ttcatttcg   163740 catttatttc taataacaaa tttaatttgc caccggaaat aattgaatgg tttaaagctg  163800
ctgggagttc agttataccg tcaattgaag ttgctagtct tgttgatatt tcatattcag  163860
cgttttatgt ttcaggtaaa aatactattg cattagaaca cataaaatac agtaataaga  163920
aaacaatttc tgattacgca actccattag atattgtata tgactctatt gctgatatag  163980
gtgctaccgg ctatcctaga cgtacatatg aagctctaga aacgttttta tctcctgttg  164040
gaggaactaa caatgaaata aaaaggatgc ctacgtcatc ccttgttact cctatcgcaa  164100
actatggatt aaagcctaca gattttcttt atttgaaatt tcaattaatg gctgatgaag  164160
aattattaga ggaaggaacc acaagacttt caattcgttt ctttaagtct ccatctagct  164220
ctcctatatc atctaaagat ataaactttg atggaactgc cggggagtgg aagctatatg  164280
aagaatacgt tgaaatacca gctgaagctg atggctttac agtatattgt taccgtacgg  164340
cctcagtcgg tcaaggtgga ctaagaaatg ttattttcac tgaagtatca tgtaacggaa  164400
gtatagcaaa acccgctgag tttggtataa atggtattcg tgttaattat attgatgaat  164460
cgttaaccgg taatgatata atggacttgc ctactcagtt atctaacgac acaggtaagg  164520
tatttgggca ggaatttaaa gagtacacag aataaaggag acttcggtct cctttcgcg   164580 tataaatact ttaatattaa taaggagaca cgaaatggcc gatttaaaag ccggaagtac  164640
agttggtggt tccgtcatat ggcatcaagg caattttcct ttaatgccag ctggcgatga  164700
catcctatat aaaacatttta aattatacac cgaatataac aagccaaaag cggctgataa  164760
```

```
cgatttcgta tctaaagcaa atggtgggac atatctcaaa aaggtaatct ttaacgaagg   164820
tattgcagtc aaaacagcag atgaccaaac gaatggtatt ttttctggtg gtggtgacgc   164880
cgcgacattc gaccaaacaa acatggatat tgtttcgtgg tatggtattg ggtttaaatc   164940
atctcaaggt acaggtgaaa gaactgttgt aattgatact cgcaccggta atataagttc   165000
taaaggcgtt attgaagcat ctcaattcag agccacaacg ttagcacctt taaataatta   165060
cgaccttact cgcaaagatt atgttgatag tcaaataaat acagttaatg ctaatgcaaa   165120
cagtcgtgta ctccgttcag gagatacgat gaccggcgcg ctgaccgccc caaacttttt   165180
ctcacagaat cctgcatctc aaccctcgca tgttccacga tttgaccaaa ttgttattaa   165240
ggattctgtt caagatttcg gctattatta agaggactta tggctacttt aaaacaaata   165300
caatttaaaa gaagcaaaac tgcaggagca cgtcctgccg cttcagtatt agccgaaggt   165360
gaattggcta taaacttaaa agaccgtgta ctttttacta aagatgacca aggaaatatt   165420
attgatctgg gttttgctaa aggcggtagt attgacggga atgttattca tacaggtaat   165480
tataaccaaa ccggcgatta tactttaaat ggcaccttca ctcagacagg taattttaat   165540
ttaactggta ttgctcgagt aactcgtgat attattgccg ctgggcagat tatgactgaa   165600
ggcggtgaac ttattacaaa aagttcaggt acagcacatg ttcgtttttt cgatggcaat   165660
agccgcgaac gtggaatcat ttatgccccg gctaatgatg gattaactac acaagtactt   165720
aatatcaggg ttcaagacta cgccgctggt agcgaaagca tttatgcatt ttcaggcaat   165780
ggacaattta tttcacctga gtatcggca cggaaatcta tgtcaactcc tcagattttg   165840
actgacaaag tcattacaga cgggaagaag gccggtgatt atgacatcta ttcattagca   165900
aataataatt ctaacacaga taaaaataat ttacgtgtcg tacgtaccga cccggcggcc   165960
gcaatgctcc atgaaatttg tgaaaataac ggcatcagtt ggtattctgg ttcaacccct   166020
actgattaca tgttgtcatt ttcttattcc ggtgggcttc aagcaggcca ttcaattgca   166080
gtaggtatgg aatcaagtcc tatgacatat tcagccttag gtaaaggttc tattgctatt   166140
ggcgataatg acaccgggtt aaaatggcac caggatggat atttccatac agtaaacaat   166200
ggaacaagaa ctttcatcta cggccctgca gaaacacaaa gccttagaaa atggttatg   166260 ggttattctc cagatgggct tcttatgaca cgccaccga cagaaaacta tgctttggct   166320
actgttgtta cttaccatga taataacgca tacggtgacg gtcaaactct tttaggatat   166380
tatcaaggcg gtaactatca tcattatttt cgcggtaagg gtactacaaa cattaatact   166440
cacggcggtt tgttagttac tccaggtaat attgatgtta ttggcggttc tgttaatata   166500
gatggtagaa ataattcttc tacactaatg tttagaggca acacaacagg atacagctcg   166560
gttgataata tggatattaa agtttggggt aatacgtttg ttgatccaag cggaggtatc   166620
cgtaaaaaca ttatggaaat ttctgatgca actagctgga tgagctatat tcaaagactt   166680
actactggcg aagtagaaat gaacgttaat ggttcatttg aatcatctgg tgttactgct   166740
ggagatagag gagttcacac aacaggtgaa atttcatctg gagcagtgaa tgctcttcgt   166800
atttggaacg cagattatgg agccattttt agacgttcag aaggaagtct tcatattatt   166860
ccaactgctt atggcgaagg caaagatggc gatattggtc cacttcgccc atttagtatg   166920
gctttagata ctggtaaagt tactattcca gatttacaat caagttacaa tacgttcgct   166980
gctaacggtt atattaaatt tgttggtcat ggagcgggtg ccggcggtta tgacattcaa   167040
tatgctcaag cggctcctat tttccaggaa attgatgatg atgctgtaag caaatattat   167100
```

```
cctattgtta aacagaagtt tttaaacggt aaatctgttt ggtctttagg taccgaaatt   167160
gaatcaggta cattcgttat tcatcatctg aaagaagatg gttcacaagg ccatacatca   167220
agatttaata tggatggtac agttaatttc cctgataatg ttctggtcgg tggtggtgaa   167280
gctgctattg ctcgtaatgg taatatttc tcggatattt ggaaaacgtt tacttctgca   167340
ggcgacgtaa ctaatattcg cgatgcaata gctactcgtg ttgccaaaga aggtgatacg   167400
atgaccggca ctctttggat taataaagat gctgctggaa tagttcttaa tcctccttg   167460 gccagtgatt catcatttat tcgttccgat acggccgggg tcaataattg gtatattggt   167520
aaaggcggtg ccgacaatgg tctaggtttt tacagttatg ttacacaagg cggtgtatat   167580
ataacaaata acggagaaat atcactttct cctcaaggcc aaggaacatt taatttaat    167640 agagaccgcc tccatataaa cggtacacaa tggaccgcac accagggagg tggttgggga   167700
aatcaatgga atcaagaagc accggtattt gtagattttg gtaatgttgg taatgatagt   167760
tattatccta ttattaaagg aaatccggt attactaatg aaggatacat atctggtgta   167820
gattttggta tgcgacgcat tactaataca tgggcacaag gtattattcg tgtaggtaat   167880
caggaaaacg gttacgaccc acaagctgta tatgaattcc atcataacgg cactttttat   167940
gctccaagct tacttaagag cagtagagta tcagctggtg gtggtgaccc tgcatggggc   168000
gggccgtgta ttgtacttgg agataacgat accggtttgc tttgggaaaa cgatggtatt   168060
ttcaacgcat atgcaaacgg ccaaggtgtg tttagttta gacctggttt agctcagaca    168120
ttcggtgatg ttaacttcca ctgtaatgca ggtatgtatg ttcgtgataa cattgatgtt   168180
aacgacgttt atattcgttc tgatattcgt tgtaagtcgg aaattaagct tattaagaac   168240
gctcaagaga aatctaaact attgggcggt tatacttatc tgcttaaaaa ctctgttaca   168300
gacgaagtta accgtccgc aggtttaatt gctcaggaag ttcaagaagt attacctgaa    168360
cttgtttctg aagataaaga gaccggactg cttcgtttga actataacgg tattgttggt   168420
ttaaatacag ctgcaataaa cgagcataca gatgaaatca aggaattgaa atctgaaatt   168480
gccgaattga agcattaat taaatcattg ataaaataat aaaagggcct tcgggccctg    168540
gaggtttata tggcagtagt aggaatccct ggttggattg ggacttcagc cgttgctgaa   168600
acggggcaaa gatggatgac ggctgcttca agggaacttc gtttaggaaa cccttcatgg   168660
atgtcccaat tcgcgggccg ttcaagagaa ataattcaca cacttggagc agaccataac   168720
tttaatggtc aatggttccg agatagatgt tttgaggcgg gtagtgcgcc tatagtgttt   168780
aatatcaccg gaaatttagt atcatatagt aaagatgttc cattattctt tatgtatggc   168840
gatacaccaa atgaatatgt tactttgaat attcatggtg gagttcatat gtggggacga   168900
ggtggtaacg gtactgtaaa cggaaaccca ggcacaaatg gcggcgatgt aatccaaaat   168960
gatatcggcg gaagacttcg tatttggaac tatggcgtta ttgcatcagg cggtggcggt   169020
ggcggtgcag tgtcattaca gaatagctgg gcgccaaatg ttacagcagg tggcggcggt   169080
ggtagaccat ttggcatcgg cggtggcggc gttaattggc cgggtggtaa tgc           169133
```

<210> SEQ ID NO 5
<211> LENGTH: 5213
<212> TYPE: DNA
<213> ORGANISM: Artificial Sequence
<220> FEATURE:
<223> OTHER INFORMATION: synthetic pUC57.HR.Fluc plasmid sequence

<400> SEQUENCE: 5

```
tcgcgcgttt cggtgatgac ggtgaaaacc tctgacacat gcagctcccg gagacggtca      60
```

```
cagcttgtct gtaagcggat gccgggagca gacaagcccg tcaggcgcg  tcagcgggtg    120 ttggcgggtg tcgggctgg  cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtaagct tagattgata agaagcagt    420 tgaaattgct cgtcaaaccg gtcgtggtga aggtaacttc attatcgctt cccgtaacgt    480
agttaacgta ctggcttcag ttgatactgg tatttcttac gctgcacagg gtctggcttc    540
cggttttaat accgacacta ctaagtctgt atttgccggt gtacttggtg gtaaataccg    600
cgtatacatc gaccagtatg ctaaacagga ttacttcacc gttggttaca aaggcgctaa    660
cgaaatggat gcaggtatct actatgctcc ttacgttgca cttaccccac tgcgtggttc    720
cgatcctaag aacttccagc cggtaatggg cttttaaaact cgttacggta tcggtgttaa    780
cccgtttgct gaaagttccc tgcaggctcc aggtgctcgc atccagtccg gtatgccgtc    840
tatcctgaac agccttggta agaacgctta cttccgccgt gtatatgtaa aaggcatcta    900
aacgcgttat aaataaatac tagtagataa ggaggatttc gaatggaaga cgccaagaac    960
atcaaaaaag gcccggcacc gttctatccg ctggaagacg gcaccgcagg cgaacagtta    1020
cacaaagcca tgaagcgcta cgccctggtt ccgggtacaa tcgcctttac cgacgcccac    1080
attgaggtga acatcaccta tgccgagtat tttgagatga cgttcgtct  ggccgaagcc    1140 atgaaacgct atggcctgaa caccaaccat cgcattgtgg tttgcagcga aaacagcctg    1200
cagttcttta tgccggtgct gggtgccctg ttcatcggtg tggccgttgc ccctgccaat    1260
gacatctata acgaacgcga actgctgaac agcatgaata tcagccagcc taccgtggtt    1320
ttcgttagca aaaaggtttt acaaaagatt ctgaatgttc agaagaagct gccgattatc    1380
caaaaaatta tcattatgga tagcaagaca gattatcaag ctttcagag  catgtacacc    1440 ttcgttacca gtcacctgcc gccgggcttc aacgagtatg atttcgtgcc ggagagcttc    1500
gaccgtgata agaccatcgc cctgatcatg aacagcagtg gtagtaccgg cctgccgaaa    1560
ggtgtggccc tgcctcatcg caccgcatgt gtgcgcttta ccacgcccg  cgacccgatc    1620 tttggcaatc agatcatccc ggacaccgcc atcttaagcg ttgtgccgtt ccaccacggt    1680
tttggcatgt ttaccacccct gggctatctg atctgcggct ccgcgtggt  gctgatgtat    1740 cgcttcgaag aggagttatt cctgcgcagc ctgcaggact ataagattca gagcgccctg    1800
ctggttccga cactgttcag cttttcgcc  aagagcaccc tgatcgacaa atacgatctg    1860
agcaacctgc acgaaattgc aagcggcggc gcaccgctga gcaaggaagt tggtgaagcc    1920
gtggcaaaac gcttccacct gcctggcatc cgtcaaggct acggtctgac agaaaccacc    1980
agcgccatcc tgatcacccc ggaaggcgat gataaaccgg gtgccgtggg caaggtggtt    2040 ccgttttcg  aggccaaggt tgttgacctg gacaccggta aaaccctggg tgttaaccag    2100
cgtggtgaac tgtgtgttcg tggcccgatg atcatgagcg gctacgtgaa taacccggag    2160
gccaccaatg cactgatcga taagacggc  tggctgcata cgcgcgatat cgcatactgg    2220
gatgaggacg agcactttt  tattgttgat cgcctgaaaa gtctgatcaa atacaaaggc    2280
taccaggttg ccccggccga actggagagc atcctgctgc agcatccgaa catttttgac    2340
gcggggggtg cggggctgcc tgatgatgat gcaggtgagc tgcctgccgc cgttgtggtg    2400
```

```
ctggagcacg gtaagaccat gacagagaag gagattgtgg attacgtggc aagccaggtg    2460
accaccgcga agaagctgcg cggtggcgtt gtgttcgttg acgaagtgcc gaagggcctg    2520
accggtaaac tggacgcccg caagattcgc gagattctga ttaaggcaaa aaagggtggc    2580
aaaagcaaat tataagccgg cttatttctg tgcaatttcg atgtaagttt tcaaaatatt    2640
ttgccaatta ggcataccct tcttggacat atgccggaga ccgtctttgt ttttgaatga    2700
tgcaagttta tcagtggccc aataaccttt agctcgagct tcagaataaa ctttcatcca    2760
tactttgttg aaggcattac cattaacttt tgcaccatat ttttctacta acttaactgc    2820
ttcagcttcc agaactttta aagtatctcg taagaaacgt gctttagtca ttttgtttac    2880
tcctctgtag ttgataagtc tatagtatca cataccaaat acgttgtaaa caatctttat    2940
aaataatcta tatcacataa ggaaaaaatg caagtcgacg gcgtaatcat ggtcatagct    3000
gtttcctgtg tgaaattgtt atccgctcac aattccacac aacatacgag ccggaagcat    3060
aaagtgtaaa gcctggggtg cctaatgagt gagctaactc acattaattg cgttgcgctc    3120
actgcccgct ttccagtcgg gaaacctgtc gtgccagctg cattaatgaa tcggccaacg    3180
cgcgggagag gcggtttgc gtattgggcg ctcttccgct tcctcgctca ctgactcgct    3240
gcgctcggtc gttcggctgc ggcgagcggt atcagctcac tcaaaggcgg taatacggtt    3300
atccacagaa tcaggggata acgcaggaaa gaacatgtga gcaaaaggcc agcaaaaggc    3360
caggaaccgt aaaaaggccg cgttgctggc gttttccat aggctccgcc ccctgacga    3420 gcatcacaaa aatcgacgct caagtcagag gtggcgaaac ccgacaggac tataaagata    3480
ccaggcgttt ccccctggaa gctccctcgt gcgctctcct gttccgaccc tgccgcttac    3540
cggatacctg tccgccttc tcccttcggg aagcgtggcg ctttctcata gctcacgctg    3600
taggtatctc agttcggtgt aggtcgttcg ctccaagctg ggctgtgtgc acgaaccccc    3660
cgttcagccc gaccgctgcg ccttatccgg taactatcgt cttgagtcca acccggtaag    3720
acacgactta tcgccactgg cagcagccac tggtaacagg attagcagag cgaggtatgt    3780
aggcggtgct acagagttct tgaagtggtg gcctaactac ggctacacta agaacagt    3840 atttggtatc tgcgctctgc tgaagccagt taccttcgga aaaagagttg gtagctcttg    3900
atccggcaaa caaaccaccg ctggtagcgg tggtttttt gtttgcaagc agcagattac    3960
gcgcagaaaa aaggatctc aagaagatcc tttgatcttt tctacggggt ctgacgctca    4020
gtggaacgaa aactcacgtt aagggatttt ggtcatgaga ttatcaaaaa ggatcttcac    4080
ctagatcctt ttaaattaaa aatgaagttt taaatcaatc taaagtatat atgagtaaac    4140
ttggtctgac agttaccaat gcttaatcag tgaggcacct atctcagcga tctgtctatt    4200
tcgttcatcc atagttgcct gactccccgt cgtgtagata actacgatac gggagggctt    4260
accatctggc cccagtgctg caatgatacc gcgagaccca cgctcaccgg ctccagattt    4320
atcagcaata aaccagccag ccggaagggc cgagcgcaga agtggtcctg caactttatc    4380
cgcctccatc cagtctatta attgttgccg ggaagctaga gtaagtagtt cgccagttaa    4440 tagtttcgc aacgttgttg ccattgctac aggcatcgtg gtgtcacgct cgtcgtttgg    4500
tatggcttca ttcagctccg gttcccaacg atcaaggcga gttacatgat cccccatgtt    4560
gtgcaaaaaa gcggttagct ccttcggtcc tccgatcgtt gtcagaagta agttggccgc    4620
agtgttatca ctcatggtta tggcagcact gcataattct cttactgtca tgccatccgt    4680
aagatgcttt tctgtgactg gtgagtactc aaccaagtca ttctgagaat agtgtatgcg    4740
gcgaccgagt tgctcttgcc cggcgtcaat acgggataat accgcgccac atagcagaac    4800
```

```
tttaaaagtg ctcatcattg gaaaacgttc ttcggggcga aaactctcaa ggatcttacc    4860
gctgttgaga tccagttcga tgtaacccac tcgtgcaccc aactgatctt cagcatcttt    4920
tactttcacc agcgtttctg ggtgagcaaa aacaggaagg caaaatgccg caaaaaaggg    4980
aataagggcg acacggaaat gttgaatact catactcttc cttttttcaat attattgaag   5040 catttatcag ggttattgtc tcatgagcgg atacatattt gaatgtattt agaaaaataa    5100
acaaataggg gttccgcgca catttccccg aaaagtgcca cctgacgtct aagaaaccat    5160
tattatcatg acattaacct ataaaaatag gcgtatcacg aggccctttc gtc           5213
```

<210> SEQ ID NO 6
<211> LENGTH: 4162
<212> TYPE: DNA
<213> ORGANISM: Artificial Sequence
<220> FEATURE:
<223> OTHER INFORMATION: synthetic pUC57.HR.NanoLuc plasmid sequence

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtaagct tagattgata agaagcagt      420 tgaaattgct cgtcaaaccg gtcgtggtga aggtaacttc attatcgctt cccgtaacgt    480
agttaacgta ctggcttcag ttgatactgg tatttcttac gctgcacagg gtctggcttc     540
cggttttaat accgacacta ctaagtctgt atttgccggt gtacttggtg gtaaataccg     600
cgtatacatc gaccagtatg ctaaacagga ttacttcacc gttggttaca aaggcgctaa     660
cgaaatggat gcaggtatct actatgctcc ttacgttgca cttacccccac tgcgtggttc     720 cgatcctaag aacttccagc cggtaatggg ctttaaaaact cgttacggta tcggtgttaa     780
cccgtttgct gaaagttccc tgcaggctcc aggtgctcgc atccagtccg gtatgccgtc     840
tatcctgaac agccttggta agaacgctta cttccgccgt gtatatgtaa aaggcatcta     900
aacgcgttat aaataaatac tagtagataa ggaggatttc gaatgaatag ctttagcacc     960
agcgcctttg gccctgttgc ctttagcctg ggcctgctgc tggttctgcc ggcagcattt    1020
ccggccccgg tgttcaccct ggaagatttt gtgggcgatt ggcgccagac cgccggttat    1080
aacctggatc aggtgctgga acagggtggt gtgagcagcc tgtttcagaa tctgggcgtg    1140
agcgtgaccc cgattcagcg cattgtgctg agcggcgaga acggcctgaa aattgatatt    1200
catgttatta ttccgtatga gggtctgagc ggcgatcaga tgggccagat tgaaaaaatc    1260
tttaaggtgg tgtatccggt ggacgaccat catttcaagg tgatcctgca ttacggcaca    1320
ctggtgattg acggcgttac cccgaacatg atcgactatt tcggccgccc gtatgaaggt    1380
atcgccgtgt tcgacggcaa gaaaattacc gtgaccggta cctgtggaa cggcaacaag    1440 atcattgacg agcgcctgat taacccggat ggtagcctgc tgtttcgcgt gaccattaat    1500
ggcgtgaccg gctggcgtct gtgtgaacgc atcctggcct aattaattaa ttatttctgt    1560
gcaatttcga tgtaagtttt caaaatattt tgccaattag gcataccttc ttggacatat    1620
```

-continued

```
gccggagaac cgtctttgtt tttgaatgat gcaagtttat cagtggccca ataacctta      1680
gctcgagctt cagaataaac tttcatccat actttgttga aggcattacc attaactttt      1740
gcaccatatt tttctactaa cttaactgct tcagcttcca gaacttttaa agtatctcgt      1800
aagaaacgtg ctttagtcat tttgtttact cctctgtagt tgataagtct atagtatcac      1860
ataccaaata cgttgtaaac aatctttata ataatctat atcacataag gaaaaaatgc       1920
aagtcgacgg cgtaatcatg gtcatagctg tttcctgtgt gaaattgtta tccgctcaca      1980
attccacaca acatacgagc cggaagcata agtgtaaag cctggggtgc ctaatgagtg       2040
agctaactca cattaattgc gttgcgctca ctgcccgctt tccagtcggg aaacctgtcg      2100
tgccagctgc attaatgaat cggccaacgc gcggggagag gcggtttgcg tattgggcgc      2160
tcttccgctt cctcgctcac tgactcgctg cgctcggtcg ttcggctgcg cgagcggta      2220
tcagctcact caaaggcggt aatacggtta tccacagaat caggggataa cgcaggaaag      2280
aacatgtgag caaaaggcca gcaaaaggcc aggaaccgta aaaaggccgc gttgctggcg      2340
tttttccata ggctccgccc ccctgacgag catcacaaaa atcgacgctc aagtcagagg      2400
tggcgaaacc cgacaggact ataaagatac caggcgtttc ccctggaag ctccctcgtg       2460
cgctctcctg ttccgaccct gccgcttacc ggatacctgt ccgcctttct cccttcggga     2520
agcgtggcgc tttctcatag ctcacgctgt aggtatctca gttcggtgta ggtcgttcgc      2580
tccaagctgg gctgtgtgca cgaaccccc gttcagcccg accgctgcgc cttatccggt       2640
aactatcgtc ttgagtccaa cccggtaaga cacgacttat cgccactggc agcagccact      2700
ggtaacagga ttagcagagc gaggtatgta ggcggtgcta cagagttctt gaagtggtgg      2760
cctaactacg gctacactag aagaacagta tttggtatct gcgctctgct gaagccagtt      2820
accttcggaa aaagagttgg tagctcttga tccggcaaac aaaccaccgc tggtagcggt      2880
ggtttttttg tttgcaagca gcagattacg cgcagaaaaa aaggatctca agaagatcct      2940
ttgatctttt ctacggggtc tgacgctcag tggaacgaaa actcacgtta agggattttg      3000
gtcatgagat tatcaaaaag gatcttcacc tagatccttt taaattaaaa atgaagtttt      3060
aaatcaatct aaagtatata tgagtaaact tggtctgaca gttaccaatg cttaatcagt      3120
gaggcaccta tctcagcgat ctgtctattt cgttcatcca tagttgcctg actccccgtc      3180
gtgtagataa ctacgatacg ggagggctta ccatctggcc ccagtgctgc aatgataccg      3240
cgagacccac gctcaccggc tccagattta tcagcaataa accagccagc cggaagggcc      3300
gagcgcagaa gtggtcctgc aactttatcc gcctccatcc agtctattaa ttgttgccgg      3360
gaagctagag taagtagttc gccagttaat agtttgcgca acgttgttgc cattgctaca      3420
ggcatcgtgg tgtcacgctc gtcgtttggt atggcttcat tcagctccgg ttcccaacga      3480
tcaaggcgag ttacatgatc ccccatgttg tgcaaaaaag cggttagctc cttcggtcct      3540
ccgatcgttg tcagaagtaa gttggccgca gtgttatcac tcatggttat ggcagcactg      3600
cataattctc ttactgtcat gccatccgta agatgctttt ctgtgactgg tgagtactca      3660
accaagtcat tctgagaata gtgtatgcgg cgaccgagtt gctcttgccc ggcgtcaata      3720
cgggataata ccgcgccaca tagcagaact ttaaaagtgc tcatcattgg aaaacgttct      3780
tcggggcgaa aactctcaag gatcttaccg ctgttgagat ccagttcgat gtaacccact      3840
cgtgcaccca actgatcttc agcatctttt actttcacca gcgtttctgg gtgagcaaaa      3900
acaggaaggc aaaatgccgc aaaaaaggga ataaggcga cacggaaatg ttgaatactc       3960
atactcttcc ttttcaata ttattgaagc atttatcagg gttattgtct catgagcgga       4020
```

```
tacatatttg aatgtattta gaaaaataaa caaatagggg ttccgcgcac atttccccga    4080
aaagtgccac ctgacgtcta agaaaccatt attatcatga cattaaccta taaaatagg    4140 cgtatcacga ggccctttcg tc                                            4162
```

<210> SEQ ID NO 7
<211> LENGTH: 5163
<212> TYPE: DNA
<213> ORGANISM: Artificial Sequence
<220> FEATURE:
<223> OTHER INFORMATION: synthetic pUC19.HR.OpLuc.KanR plasmid sequence

<400> SEQUENCE: 7

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attcccttt      240 ttgcggcatt ttgccttcct gttttgtgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc atttttaatt taaaaggatc taggtgaaga    1140
tcctttttga atctctcatg accaaaatcc cttaacgtga gttttcgttc cactgagcgt    1200
cagaccccgt agaaaagatc aaaggatctt cttgagatcc ttttttttctg cgcgtaatct    1260 gctgcttgca aacaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg atttttgtga tgctcgtcag    1800
gggggcggag cctatggaaa aacgccagca acgcggcctt tttacggttc ctggccttt    1860
```

```
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt agattgataa agaagcagtt gaaattgctc gtcaaaccgg    2280
tcgtggtgaa ggtaacttca ttatcgcttc ccgtaacgta gttaacgtac tggcttcagt    2340
tgatactggt atttcttacg ctgcacaggg tctggcttcc ggttttaata ccgacactac    2400
taagtctgta tttgccggtg tacttggtgg taaataccgc gtatacatcg accagtatgc    2460
taaacaggat tacttcaccg ttggttacaa aggcgctaac gaaatggatg caggtatcta    2520
ctatgctcct tacgttgcac ttaccccact gcgtggttcc gatcctaaga acttccagcc    2580
ggtaatgggc tttaaaactc gttacggtat cggtgttaac ccgtttgctg aaagttccct    2640
gcaggctcca ggtgctcgca tccagtccgg tatgccgtct atcctgaaca gccttggtaa    2700
gaacgcttac ttccgccgtg tatatgtaaa aggcatctaa ggcgcgccta taataaata    2760 ctagtagata aggaggattt cgaatgttta cactggcaga cttttgttggt gactggcagc    2820 aaacagccgg atataaccag gaccaggtgc ttgaacaggg tggccttttcg agtttgtttc    2880 aggcgttagg tgtgtcggtg accoctattc agaaagtggt gctgagcgga gaaaacggcc    2940
tgaaggccga tattcatgtt attatcccgt acgaggggtt atccggcttc cagatgggtc    3000
tgattgaaat gatcttcaaa gtggtttatc cggttgacga tcatcatttt aagattatcc    3060
tgcactatgg caccctggtg attgatggcg tgaccccgaa tatgattgat tatttcggcc    3120
gtccgtaccc aggcattgca gtatttgacg gtaaacaaat caccgtcacc ggtaccctgt    3180
ggaatggtaa taaaatttat gatgaacgtt tgatcaaccc ggatggcagt ctgttatttc    3240
gcgtgaccat taacggagta accggttggc gtctctgtga aaacatttta gcttaagcga    3300
tcgcataact tcgtatagca tacattatac gaagttattt gacaggctct gtattacgtt    3360
tctataaata aggaagagta tgagccatat tcaacgggaa acgtcttgct ctaggccgcg    3420
attaaattcc aacatggatg ctgatttata tgggtataaa tgggctcgcg ataatgtcgg    3480
gcaatcaggt gcgacaatct atcgattgta tgggaagccc gatgcgccag agttgtttct    3540
gaaacatggc aaaggtagcg ttgccaatga tgttacagat gagatggtca gactaaactg    3600
gctgacggaa tttatgcctc ttccgaccat caagcatttt atccgtactc ctgatgatgc    3660
atggttactc accactgcga tccctgggaa aacagcattc caggtattag aagaatatcc    3720
tgattcaggt gaaaatattg ttgatgcgct ggcagtgttc ctgcgccggt tgcattcgat    3780
tcctgtttgt aattgtcctt ttaacagcga tcgcgtattt cgtctcgctc aggcgcaatc    3840
acgaatgaat aacggtttgg ttgatgcgag tgattttgat gacgagcgta atggctggcc    3900
tgttgaacaa gtctggaaag aaatgcataa acttttgcca ttctcaccgg attcagtcgt    3960
cactcatggt gatttctcac ttgataacct tattttttgac gaggggaaat taataggttg    4020
tattgatgtt ggacgagtcg gaatcgcaga ccgataccag gatcttgcca tcctatggaa    4080
ctgcctcggt gagttttctc cttcattaca gaaacggctt tttcaaaaat atggtattga    4140
taatcctgat atgaataaat tgcagtttca tttgatgctc gatgagtttt tctaaataac    4200
ttcgtatagc atacattata cgaagttatt tatttctgtg caatttcgat gtaagttttc    4260
```

```
aaaatatttt gccaattagg catacottct tggacatatg ccggagaacc gtctttgttt    4320
ttgaatgatg caagtttatc agtggcccaa taacctttag ctcgagcttc agaataaact    4380
ttcatccata ctttgttgaa ggcattacca ttaactttg caccatattt ttctactaac    4440
ttaactgctt cagcttccag aacttttaaa gtatctcgta agaaacgtgc tttagtcatt    4500
ttgtttactc ctctgtagtt gataagtcta tagtatcaca taccaaatac gttgtaaaca    4560
atctttataa ataatctata tcacataagg aaaaaatgca atgagtaaaa tccaaaaatt    4620
attgcgtgaa tctacaacgt ctactagcaa ctcaatcggt cgcccaaatc tcgttgcttt    4680
gactcgcgct acgactaaat taatatattc tgacattgta gcaacacaag tcgactctag    4740
aggatccccg ggtaccgagc tcgaattcac tggccgtcgt tttacaacgt cgtgactggg    4800
aaaaccctgg cgttacccaa cttaatcgcc ttgcagcaca tccccctttc gccagctggc    4860
gtaatagcga agaggcccgc accgatcgcc cttcccaaca gttgcgcagc ctgaatggcg    4920 aatgcgcct gatgcggtat tttctcctta cgcatctgtg cggtatttca caccgcatat    4980
ggtgcactct cagtacaatc tgctctgatg ccgcatagtt aagccagccc cgacacccgc    5040 caacaccgc tgacgcgccc tgacgggctt gtctgctccc ggcatccgct tacagacaag    5100
ctgtgaccgt ctccgggagc tgcatgtgtc agaggttttc accgtcatca ccgaaacgcg    5160
cga                                                                  5163
```